United States Patent
Wang et al.

(10) Patent No.: US 12,071,415 B2
(45) Date of Patent: Aug. 27, 2024

(54) CARBON MONOXIDE PRODRUGS FOR THE TREATMENT OF MEDICAL DISORDERS

(71) Applicant: Georgia State University Research Foundation, Inc., Atlanta, GA (US)

(72) Inventors: Binghe Wang, Marietta, GA (US); Xingyue Ji, Atlanta, GA (US); Ladie Kimberly de la Cruz, Atlanta, GA (US); Xiaoxiao Yang, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 0 days.

(21) Appl. No.: 17/233,171

(22) Filed: Apr. 16, 2021

(65) Prior Publication Data

US 2021/0238155 A1 Aug. 5, 2021

Related U.S. Application Data

(63) Continuation of application No. PCT/US2019/056591, filed on Oct. 16, 2019.

(60) Provisional application No. 62/825,677, filed on Mar. 28, 2019, provisional application No. 62/746,410, filed on Oct. 16, 2018.

(51) Int. Cl.
| | |
|---|---|
| C07D 291/06 | (2006.01) |
| C07C 69/757 | (2006.01) |
| C07C 311/19 | (2006.01) |
| C07D 207/36 | (2006.01) |
| C07D 231/20 | (2006.01) |
| C07D 239/62 | (2006.01) |
| C07D 275/04 | (2006.01) |
| C07D 285/01 | (2006.01) |
| C07D 307/60 | (2006.01) |
| C07D 333/32 | (2006.01) |
| C07D 401/06 | (2006.01) |
| C07D 403/06 | (2006.01) |
| C07D 409/06 | (2006.01) |
| C07D 417/06 | (2006.01) |

(52) U.S. Cl.
CPC .......... *C07D 291/06* (2013.01); *C07C 69/757* (2013.01); *C07C 311/19* (2013.01); *C07D 207/36* (2013.01); *C07D 231/20* (2013.01); *C07D 239/62* (2013.01); *C07D 275/04* (2013.01); *C07D 285/01* (2013.01); *C07D 307/60* (2013.01); *C07D 333/32* (2013.01); *C07D 401/06* (2013.01); *C07D 403/06* (2013.01); *C07D 409/06* (2013.01); *C07D 417/06* (2013.01)

(58) Field of Classification Search
None
See application file for complete search history.

(56) References Cited

U.S. PATENT DOCUMENTS

| | | |
|---|---|---|
| 4,638,045 A | 1/1987 | Kohn et al. |
| 4,806,621 A | 2/1989 | Kohn et al. |
| 4,946,929 A | 8/1990 | Amore et al. |
| 4,983,593 A | 1/1991 | Miyajima et al. |
| 5,010,167 A | 4/1991 | Ron et al. |
| 5,013,557 A | 5/1991 | Tai |
| 5,019,379 A | 5/1991 | Domb et al. |
| 5,019,400 A | 5/1991 | Gombotz et al. |
| 5,399,665 A | 3/1995 | Barrera et al. |
| 5,456,923 A | 10/1995 | Nakamichi et al. |
| 5,512,600 A | 4/1996 | Mikos et al. |
| 5,514,378 A | 5/1996 | Mikos et al. |
| 5,543,158 A | 8/1996 | Gref et al. |
| 5,576,025 A | 11/1996 | Akiyama et al. |
| 5,578,325 A | 11/1996 | Domb et al. |
| 5,696,175 A | 12/1997 | Mikos et al. |
| 5,710,182 A | 1/1998 | Reunamaeki et al. |
| 5,716,404 A | 2/1998 | Vacanti et al. |
| 5,723,269 A | 3/1998 | Akagi et al. |
| 5,736,372 A | 4/1998 | Vacanti et al. |
| 5,770,417 A | 6/1998 | Vacanti et al. |
| 5,792,883 A | 8/1998 | Harada et al. |
| 5,795,913 A | 8/1998 | Lehmussaari et al. |
| 5,804,178 A | 9/1998 | Vacanti et al. |
| 5,837,752 A | 11/1998 | Shastri et al. |
| 5,858,411 A | 1/1999 | Nakagami et al. |
| 5,869,103 A | 2/1999 | Yeh et al. |
| 5,902,599 A | 5/1999 | Anseth et al. |
| 6,007,845 A | 12/1999 | Domb et al. |
| 6,095,148 A | 8/2000 | Shastri et al. |

(Continued)

FOREIGN PATENT DOCUMENTS

| | | |
|---|---|---|
| FR | 6788 M | 8/1967 |
| FR | 2945713 A1 | 11/2010 |

(Continued)

OTHER PUBLICATIONS

Database Registry Chemical Abstracts Service, Columbus, Ohio, Accession No. RN 1334612-00-8, Entered STN: Oct. 7, 2011.*
"[(2R)-4-Methyl-5-Oxo-2-Tridecyl-2H-Furan-3-yl] Formate", Pubchem CID 89308269, Feb. 13, 2015, 5 pages.
"1,1-Dioxo-7-Propylsulfanyl-3H-1,2-Benzothiazole-2-Carbaldehyde", Pubchem CID 117061250, Jan. 30, 2016, 4 pages.
"1,2-Bis(1,1,3-Trioxo-1,2-Benzothiazol-2-yl)Ethane-1,2-Dione", Pubchem CID 101834713, Dec. 18, 2015, 4 pages.
EP19872797.6, "Partial Supplementary European Search Report", Jun. 24, 2022, 13 pages.
Ji et al., "Strategies Toward Organic Carbon Monoxide Prodrugs", Accounts of Chemical Research, vol. 51, No. 6, Jun. 19, 2018, pp. 1377-1385.

(Continued)

*Primary Examiner* — Samantha L Shterengarts
(74) *Attorney, Agent, or Firm* — Kilpatrick Townsend & Stockton LLP

(57) ABSTRACT

The present invention provides new compounds and compositions thereof that release carbon monoxide for the treatment of medical disorders that are responsive to carbon monoxide, for example, inflammatory, pain, and dermatological disorders.

7 Claims, 35 Drawing Sheets

(56) References Cited

U.S. PATENT DOCUMENTS

| | | |
|---|---|---|
| 6,123,727 A | 9/2000 | Vacanti et al. |
| 6,221,338 B1 | 4/2001 | Staniforth |
| 6,254,889 B1 | 7/2001 | Kigoshi et al. |
| 6,287,588 B1 | 9/2001 | Shih et al. |
| 6,303,148 B1 | 10/2001 | Hennink et al. |
| 6,395,302 B1 | 5/2002 | Hennink et al. |
| 6,413,539 B1 | 7/2002 | Shalaby |
| 6,495,164 B1 | 12/2002 | Ramstack et al. |
| 6,497,903 B1 | 12/2002 | Hennink et al. |
| 6,506,577 B1 | 1/2003 | Deming et al. |
| 6,582,678 B2 | 6/2003 | Staniforth |
| 6,589,549 B2 | 7/2003 | Shih et al. |
| 6,632,671 B2 | 10/2003 | Unger |
| 6,632,922 B1 | 10/2003 | Deming et al. |
| 6,686,446 B2 | 2/2004 | Deming et al. |
| 6,706,289 B2 | 3/2004 | Lewis et al. |
| 6,818,732 B2 | 11/2004 | Deming et al. |
| 6,948,496 B2 | 9/2005 | Eason et al. |
| 6,989,155 B1 | 1/2006 | Ganderton et al. |
| 7,060,296 B2 | 6/2006 | Hennink et al. |
| 7,078,057 B2 | 7/2006 | Kerkhof |
| 7,383,837 B2 | 6/2008 | Robertson et al. |
| 7,404,828 B1 | 7/2008 | Nicola |
| 7,455,855 B2 | 11/2008 | Kuwano et al. |
| 7,541,022 B2 | 6/2009 | Staniforth et al. |
| 7,585,517 B2 | 9/2009 | Cooper et al. |
| 7,744,855 B2 | 6/2010 | Staniforth et al. |
| 7,845,349 B2 | 12/2010 | Eason et al. |
| 8,101,160 B2 | 1/2012 | Staniforth et al. |
| 8,137,657 B2 | 3/2012 | Staniforth |
| 8,158,728 B2 | 4/2012 | Desimone et al. |
| 8,192,408 B2 | 6/2012 | Nazzaro et al. |
| 8,202,912 B2 | 6/2012 | Curatolo et al. |
| 8,205,611 B2 | 6/2012 | Olsson et al. |
| 8,257,741 B2 | 9/2012 | Curatolo et al. |
| 8,263,128 B2 | 9/2012 | Curatolo et al. |
| 8,263,129 B2 | 9/2012 | Desimone et al. |
| 8,268,446 B2 | 9/2012 | Desimone et al. |
| 8,277,830 B2 | 10/2012 | de Juan, Jr. et al. |
| 8,298,578 B2 | 10/2012 | de Juan, Jr. et al. |
| 8,337,899 B2 | 12/2012 | Curatolo et al. |
| 8,367,097 B2 | 2/2013 | Mudumba et al. |
| 8,399,006 B2 | 3/2013 | de Juan, Jr. et al. |
| 8,409,607 B2 | 4/2013 | Hughes et al. |
| 8,420,124 B2 | 4/2013 | Desimone et al. |
| 8,431,159 B2 | 4/2013 | Curatolo et al. |
| 8,444,899 B2 | 5/2013 | Desimone et al. |
| 8,465,775 B2 | 6/2013 | Desimone et al. |
| 8,465,778 B2 | 6/2013 | Hughes et al. |
| 8,481,069 B2 | 7/2013 | Hughes et al. |
| 8,486,960 B2 | 7/2013 | Kleinman et al. |
| 8,512,738 B2 | 8/2013 | Edelman et al. |
| 8,580,306 B2 | 11/2013 | Staniforth et al. |
| 8,580,311 B2 | 11/2013 | Armes et al. |
| 8,623,395 B2 | 1/2014 | de Juan, Jr. et al. |
| 8,628,801 B2 | 1/2014 | Garreta et al. |
| 8,632,809 B2 | 1/2014 | Asgharian et al. |
| 8,663,639 B2 | 3/2014 | Dor et al. |
| 8,663,674 B2 | 3/2014 | Wen et al. |
| 8,691,750 B2 | 4/2014 | Constien et al. |
| 8,715,712 B2 | 5/2014 | de Juan, Jr. et al. |
| 8,795,712 B2 | 8/2014 | de Juan, Jr. et al. |
| 8,808,727 B2 | 8/2014 | de Juan, Jr. et al. |
| 8,889,193 B2 | 11/2014 | McDonnell et al. |
| 8,905,963 B2 | 12/2014 | de Juan, Jr. et al. |
| 8,910,625 B2 | 12/2014 | Mullinger et al. |
| 8,911,768 B2 | 12/2014 | Whitcup et al. |
| 8,927,005 B2 | 1/2015 | Mudumba et al. |
| 8,939,948 B2 | 1/2015 | de Juan, Jr. et al. |
| 8,957,034 B2 | 2/2015 | Hanes et al. |
| 8,962,577 B2 | 2/2015 | Hanes et al. |
| 9,022,970 B2 | 5/2015 | Dacquay et al. |
| 9,028,870 B2 | 5/2015 | Appel et al. |
| 9,033,911 B2 | 5/2015 | de Juan, Jr. et al. |
| 9,060,938 B2 | 6/2015 | Miller et al. |
| 9,066,779 B2 | 6/2015 | De Juan et al. |
| 9,095,670 B2 | 8/2015 | Briant et al. |
| 9,211,261 B2 | 12/2015 | Appel et al. |
| 9,265,731 B2 | 2/2016 | Ray et al. |
| 9,358,478 B2 | 6/2016 | Dobry et al. |
| 9,387,252 B2 | 7/2016 | Babcock et al. |
| 2003/0202944 A1 | 10/2003 | Staniforth |
| 2004/0234611 A1 | 11/2004 | Ahlheim et al. |
| 2005/0009910 A1 | 1/2005 | Hughes et al. |
| 2005/0152849 A1 | 7/2005 | Staniforth |
| 2007/0043030 A1 | 2/2007 | Morton et al. |
| 2007/0071756 A1 | 3/2007 | Peyman |
| 2007/0149593 A1 | 6/2007 | Ghosh et al. |
| 2008/0166411 A1 | 7/2008 | Shah et al. |
| 2008/0305172 A1 | 12/2008 | Ahlheim et al. |
| 2009/0203709 A1 | 8/2009 | Steinberg et al. |
| 2009/0269412 A1 | 10/2009 | Staniforth et al. |
| 2010/0215580 A1 | 8/2010 | Hanes et al. |
| 2010/0285142 A1 | 11/2010 | Staniforth et al. |
| 2010/0330188 A1 | 12/2010 | Staniforth |
| 2012/0052041 A1 | 3/2012 | Basu et al. |
| 2012/0114709 A1 | 5/2012 | Staniforth et al. |
| 2012/0121718 A1 | 5/2012 | Lai et al. |
| 2012/0269894 A1 | 10/2012 | Ahlheim et al. |
| 2013/0071349 A1 | 3/2013 | Robinson et al. |
| 2013/0122064 A1 | 5/2013 | Ahlheim et al. |
| 2013/0164343 A1 | 6/2013 | Hanes et al. |
| 2013/0183244 A1 | 7/2013 | Hanes et al. |
| 2013/0236556 A1 | 9/2013 | Lai et al. |
| 2013/0272994 A1 | 10/2013 | Fu et al. |
| 2013/0287854 A1 | 10/2013 | Morgan et al. |
| 2013/0323179 A1 | 12/2013 | Popov et al. |
| 2013/0323313 A1 | 12/2013 | Suk et al. |
| 2014/0031408 A1 | 1/2014 | Edelman et al. |
| 2014/0037737 A1 | 2/2014 | Staniforth et al. |
| 2014/0107025 A1 | 4/2014 | Wirostko |
| 2014/0178475 A1 | 6/2014 | Figueiredo et al. |
| 2014/0248358 A1 | 9/2014 | Figueiredo et al. |
| 2014/0249158 A1 | 9/2014 | Figueiredo et al. |
| 2014/0276482 A1 | 9/2014 | Astafieva et al. |
| 2014/0294986 A1 | 10/2014 | Liu et al. |
| 2014/0329913 A1 | 11/2014 | Hanes et al. |
| 2014/0352690 A1 | 12/2014 | Kolb et al. |
| 2015/0050350 A1 | 2/2015 | Staniforth et al. |
| 2015/0086484 A1 | 3/2015 | Hanes et al. |
| 2015/0165137 A1 | 6/2015 | Mullinger et al. |
| 2015/0174343 A1 | 6/2015 | Muellinger et al. |
| 2016/0045505 A1 | 2/2016 | Jiricek et al. |
| 2017/0157168 A1 | 6/2017 | Rodrigues et al. |

FOREIGN PATENT DOCUMENTS

| | | |
|---|---|---|
| JP | 2010534236 A | 11/2010 |
| JP | 2017528416 | 9/2017 |
| JP | 2021518359 A | 8/2021 |
| WO | 0059902 A2 | 10/2000 |
| WO | 2005044186 A2 | 5/2005 |
| WO | 2005072710 A2 | 8/2005 |
| WO | 2006033584 A1 | 3/2006 |
| WO | 2007024323 A2 | 3/2007 |
| WO | 2007056561 A2 | 5/2007 |
| WO | 2007081876 A2 | 7/2007 |
| WO | 2007133808 A2 | 11/2007 |
| WO | 2008030557 A2 | 3/2008 |
| WO | 2008100304 A2 | 8/2008 |
| WO | 2009051837 A2 | 4/2009 |
| WO | 2009132206 A1 | 10/2009 |
| WO | 2009132265 A2 | 10/2009 |
| WO | 2009145842 A2 | 12/2009 |
| WO | 2010009087 A1 | 1/2010 |
| WO | 2010065748 A2 | 6/2010 |
| WO | 2010088548 A1 | 8/2010 |
| WO | 2010099321 A1 | 9/2010 |
| WO | 2010132664 A1 | 11/2010 |
| WO | 2010141729 A1 | 12/2010 |
| WO | 2011008737 A2 | 1/2011 |
| WO | 2011037908 A1 | 3/2011 |
| WO | 2011050327 | 4/2011 |
| WO | 2011050365 | 4/2011 |

(56) References Cited

FOREIGN PATENT DOCUMENTS

| | | |
|---|---|---|
| WO | 2011068955 A1 | 6/2011 |
| WO | 2011106702 A2 | 9/2011 |
| WO | 2011140203 A2 | 11/2011 |
| WO | 2011153349 A1 | 12/2011 |
| WO | 2012019047 A2 | 2/2012 |
| WO | 2012019136 A2 | 2/2012 |
| WO | 2012019139 A1 | 2/2012 |
| WO | 2012019176 A2 | 2/2012 |
| WO | 2012039979 A2 | 3/2012 |
| WO | 2012061703 A1 | 5/2012 |
| WO | 2012065006 A2 | 5/2012 |
| WO | 2012068549 A2 | 5/2012 |
| WO | 2012109363 A2 | 8/2012 |
| WO | 2012145801 A1 | 11/2012 |
| WO | 2013022801 A1 | 2/2013 |
| WO | 2013038170 A2 | 3/2013 |
| WO | 2013040247 A2 | 3/2013 |
| WO | 2013040426 A2 | 3/2013 |
| WO | 2013082111 A2 | 6/2013 |
| WO | 2013090804 A2 | 6/2013 |
| WO | 2013110028 A1 | 7/2013 |
| WO | 2013116061 A1 | 8/2013 |
| WO | 2013138343 A1 | 9/2013 |
| WO | 2013138346 A1 | 9/2013 |
| WO | 2013166385 A1 | 11/2013 |
| WO | 2013166408 A1 | 11/2013 |
| WO | 2013166498 A1 | 11/2013 |
| WO | 2014020210 A1 | 2/2014 |
| WO | 2014047439 A1 | 3/2014 |
| WO | 2014066775 A1 | 5/2014 |
| WO | 2014152959 A1 | 9/2014 |
| WO | 2014160884 A1 | 10/2014 |
| WO | 2015057554 A1 | 4/2015 |
| WO | 2015066444 A1 | 5/2015 |
| WO | 2015085234 A1 | 6/2015 |
| WO | 2015085251 A1 | 6/2015 |
| WO | 2015191616 A1 | 12/2015 |
| WO | 2018093924 A1 | 5/2018 |
| WO | 2019182960 A1 | 9/2019 |

OTHER PUBLICATIONS

Kitagawa et al., "Convenient Synthesis of Amides, Esters, and Thioesters Using 2,2'-Oxalyldi(2,3-Dihydro-3-Oxobenzisosulfonazole)", Chemical and Pharmaceutical Bulletin, vol. 37, No. 12, Jan. 1, 1989, pp. 3225-3228.
Application No. PCT/US2019/056591, International Preliminary Report on Patentability, Mailed on Apr. 29, 2021, 10 pages.
Application No. PCT/US2019/056591, International Search Report and Written Opinion, Mailed on Feb. 20, 2020, 13 pages.
Yadav et al., "Pd-Catalysed Carbonylative Annulation of Salicylaldehydes with Benzyl Chlorides Using N-Formylsaccharin as a Co Surrogate", New Journal of Chemistry, vol. 42, No. 19, Jan. 1, 2018, pp. 16281-16286.
EP Application No. EP19872797.6, "Extended European Search Report", Sep. 28, 2022, 10 pages.
European Patent Application No. 19872797.6, Communication pursuant to Article 94(3) EPC mailed May 26, 2023, 4 pages.
"HBI to Treat Delayed Graft Function in Kidney Transplant", Available online at: https://www.sbir.gov/sbirsearch/detail/1199003, Accessed from Internet Feb. 14, 2018, 3 pages.
Abdel-Zaher et al., "The Interrelationship Between Gasotransmitters and Lead-induced Renal Toxicity in Rats", Toxicology Letters, Aug. 2019, pp. 39-50.
Abe et al., "High-pressure Carbon Monoxide Preserves Rat Kidney Grafts From Apoptosis and Inflammation", Laboratory Investigation, vol. 97, Apr. 2017, pp. 468-477.
Ahmad et al., "Carbon Monoxide Inhibits Sprouting Angiogenesis and Vascular Endothelial Growth Factor Receptor-2 Phosphorylation", Thrombosis and Haemostasis, vol. 113, No. 2, Aug. 2015, pp. 329-337.

Antony et al., "Fluorescein Analogue Xanthene-9-Carboxylic Acid: A Transition-Metal-Free CO Releasing Molecule Activated by Green Light", Organic Letters, vol. 15, No. 17, Aug. 19, 2013, pp. 4552-4555.
Araujo, "HO-1 and CO: Fighters vs Sickle Cell Disease?", Blood, vol. 122, Oct. 2013, pp. 2535-2536.
Astete et al., "Synthesis and Characterization of PLGA Nanoparticles", Journal of Biomaterials Science, Polymer Edition, vol. 17, No. 3, Jan. 2006, pp. 247-289.
Balkwill et al., "Inflammation and cancer: back to Virchow?", Lancet, vol. 357, Feb. 2001, pp. 539-545.
Belcher et al., "Oral Carbon Monoxide Therapy in Murine Sickle Cell Disease: Beneficial Effects on Vaso-occlusion, Inflammation and Anemia", PLoS One, vol. 13, No. 10, Oct. 2018, 11 pages.
Bhattacharyya et al., "Oxidative Stress: An Essential Factor in the Pathogenesis of Gastrointestinal Mucosal Diseases.", Physiological Reviews, vol. 94, 2014, pp. 329-354.
Bijjem et al., "Pharmacological Activation of Heme Oxygenase (Ho)-1/carbon Monoxide Pathway Prevents the Development of Peripheral Neuropathic Pain in Wistar Rats", Naunyn-Schmiedeberg's Archives of Pharmacology, vol. 386, Jan. 2013, pp. 79-90.
Bonelli et al., "Heme Oxygenase-1 End-products Carbon Monoxide and Biliverdin Ameliorate Murine Collagen-induced Arthritis", Clinical and Experimental Rheumatology, vol. 30, Jan. 2012, pp. 73-78.
Botros et al., "Interaction Between Endogenously Produced Carbon Monoxide and Nitric Oxide in Regulation of Renal Afferent Arterioles", American Journal of Physiology-Heart and Circulatory, Dec. 2006, pp. H2772-2778.
Boussif et al., "A Versatile Vector for Gene and Oligonucleotide Transfer Into Cells in Culture and in Vivo: Polyethylenimine", Proceedings of the National Academy of Sciences of the United States of America, vol. 92, Aug. 1995, pp. 7297-7301.
Brune et al., "Inhibition of Platelet Aggregation by Carbon Monoxide is Mediated by Activation of Guanylate Cyclase", Molecular Pharmacology, vol. 32, No. 4, Oct. 1987, pp. 497-504.
Carcolé et al., "Treatment with a Heme Oxygenase 1 Inducer Enhances the Antinociceptive Effects of μ-Opioid, δ-Opioid, and Cannabinoid 2 Receptors during Inflammatory Pain", Journal of Pharmacology and Experimental Therapeutics, vol. 351, Oct. 2014, pp. 224-232.
Carmona et al., "One-pot Preparation of a Novel Co-releasing Material Based on a Co-releasing Molecule@metal-organic Framework System", Chemical Communications, vol. 53, 2017, pp. 6581-6584.
Castany et al., "The Role of Carbon Monoxide on the Antinociceptive Effects and Expression of Cannabinoid 2 Receptors During Painful Diabetic Neuropathy in Mice", Psychopharmacology, Jun. 2016, pp. 2209-2219.
Chang et al., "Heme Oxygenase-2 Protects against Lipid Peroxidation-Mediated Cell Loss and Impaired Motor Recovery after Traumatic Brain Injury", The Journal of Neuroscience, vol. 23, No. 9, May 1, 2003, pp. 3689-3696.
Chaves-Ferreira et al., "Spontaneous CO Release from RuII(CO)2-Protein Complexes in Aqueous Solution, cells, and mice", Angewandte Chemie, vol. 54, 2015, pp. 1172-1175.
Che et al., "The Role of Gaseous Molecules in Traumatic Brain Injury: An Updated Review", Frontiers in Neuroscience, vol. 12, Jun. 2018, 9 pages.
Chen et al., "Clicking 1,2,4,5-Tetrazine and Cyclooctynes with Tunable Reaction Rates", Chemical Communications, vol. 48, No. 12, Feb. 7, 2012, pp. 1736-1738.
Chen et al., "Effects of Carbon Monoxide Releasing Molecule-liberated Co on Severe Acute Pancreatitis in Rats", Cytokine, vol. 49, Jan. 2010, pp. 15-23.
Cheng et al., "Therapeutic Potential of Heme Oxygenase-1/carbon Monoxide System Against Ischemia-reperfusion Injury", Current Pharmaceutical Design, Jul. 2017, pp. 3884-3898.
Choi et al., "Dual Effects of Carbon Monoxide on Pericytes and Neurogenesis in Traumatic Brain Injury", Nature Medicine, vol. 22, Sep. 2016, pp. 1335-1341.

(56) References Cited

OTHER PUBLICATIONS

Chora et al., "Heme Oxygenase-1 and Carbon Monoxide Suppress Autoimmune Neuroinflammation", The Journal of Clinical Investigation, vol. 117, Feb. 2007, pp. 438-447.
Clark et al., "Cardioprotective Actions by a Water-Soluble Carbon Monoxide-Releasing Molecule", Circulation Research, vol. 93, Jul. 2003, 7 pages.
Coburn et al., "Enhancement by Phenobarbital and Diphenylhydrantoin of Carbon Monoxide Production in Normal Man", New England Journal of Medicine, vol. 283, Sep. 1970, pp. 512-515.
Correa-Costa et al., "Carbon Monoxide protects the Kidney through the Central Circadian clock and CD39", Proceedings of the National Academy of Sciences of the United States of America, vol. 115, Mar. 2018, pp. E2302-E2310.
Coussens et al., "Inflammation and Cancer", Nature, vol. 420, No. 6917, Dec. 19, 2002, pp. 1-18.
Davidge et al., "Carbon Monoxide-releasing Antibacterial Molecules Target Respiration and Global Transcriptional Regulators", The Journal of Biological Chemistry, vol. 284, Feb. 13, 2009, pp. 4516-4524.
Diring et al., "Light Responsive Metal-Organic Frameworks as Controllable Co-releasing Cell Culture Substrates", Chemical Science, vol. 8, 2017, pp. 2381-2386.
Dolinay et al., "Inhaled Carbon Monoxide Confers Antiinflammatory Effects Against Ventilator-Induced Lung Injury", American Journal of Respiratory and Critical Care Medicine, vol. 170, May 2004, pp. 613-620.
Durante et al., "Role of Carbon Monoxide in Cardiovascular Function", Journal of Cellular and Molecule Medicine, vol. 10, No. 3, Jul. 2006, pp. 672-686.
Fan et al., "Carbon Monoxide: A Gas That Modulates Nociception", Journal of Neuroscience Research, vol. 89, Jun. 2011, pp. 802-807.
Fujihara et al., "Ruthenium-Catalyzed Ring-Closing Metathesis Accelerated by Long-Range Steric Effect.", Chemical Communications, vol. 47, No. 34, Sep. 2011, pp. 9699-9701.
Fujisaki et al., "Donor Pretreatment With Carbon Monoxide Prevents Ischemia/reperfusion Injury Following Heart Transplantation in Rats", Medical Gas Research, vol. 6, No. 3, Oct. 2016, pp. 122-129.
Fukuda et al., "Induction of Heme Oxygenase-1 (Ho-1I) After Traumatic Brain Injury in the Rat", Neuroscience Letters, vol. 199, Sep. 1995, pp. 127-130.
Garcia-Gallego et al., "Carbon-Monoxide-Releasing Molecules for the Delivery of Therapeutic CO In Vivo", Angewandte Chemie International Edition, vol. 53, 2014, 9712-9721.
Godai et al., "Heme Oxygenase-1 Inducer and Carbon Monoxide-releasing Molecule Enhance the Effects of Gabapentinoids by Modulating Glial Activation During Neuropathic Pain in Mice", PAIN Reports, vol. 3, No. 5, Sep. 2018, pp. 1-10.
Gomperts et al., "The Role of Carbon Monoxide and Heme Oxygenase in the Prevention of Sickle Cell Disease Vaso-occlusive Crises", American Journal of Hematology, vol. 92, Jan. 2017, pp. 569-582.
Gou et al., "The Role of Gaseous Neurotransmitters in the Antinociceptive Effects of Morphine During Acute Thermal Pain", European Journal of Pharmacology, vol. 737, Aug. 2014, pp. 41-46.
Grangeiro et al., "Heme Oxygenase/carbon Monoxide-biliverdin Pathway May Be Involved in the Antinociceptive Activity of Etoricoxib, a Selective Cox-2 Inhibitor", Pharmacological Reports, Dec. 2011, pp. 112-119.
Grivennikov et al., "Immunity, Inflammation, and Cancer", Cell, vol. 140, No. 6, Mar. 2010, pp. 883-899.
Hanto et al., "Intraoperative Administration of Inhaled Carbon Monoxide Reduces Delayed Graft Function in Kidney Allografts in Swine", American Journal of Transplantation, vol. 10, Nov. 2010, pp. 2421-2430.
Hegazi et al., "Carbon Monoxide Ameliorates Chronic Murine Colitis Through a Heme Oxygenase 1—Dependent Pathway", Journal of Experimental Medicine, vol. 202, No. 12, Dec. 2005, pp. 1703-1713.
Heinemann et al., "Carbon Monoxide-Physiology, Detection and Controlled Release", Chemical Communications, vol. 50, No. 28, Apr. 11, 2014, pp. 3644-3660.
Hervera et al., "Carbon Monoxide Reduces Neuropathic Pain and Spinal Microglial Activation by Inhibiting Nitric Oxide Synthesis in Mice", Plos One, vol. 7, No. 8, Aug. 22, 2012, pp. 1-10.
Hervera et al., "Treatment with Carbon Monoxide-releasing Molecules and an HO-1 Inducer Enhances the Effects and Expression of μ-Opioid Receptors during Neuropathic Pain", Anesthesiology, vol. 118, May 2013, pp. 1180-1197.
Holditch et al., "Recent Advances in Models, Mechanisms, Biomarkers, and Interventions in Cisplatin-Induced Acute Kidney Injury", International Journal of Molecular Sciences, vol. 20, No. 3011, Jun. 2019, pp. 1-25.
Hou et al., "Effect of Corm-2 on Atherosclerosis in Experimental Periodontitis of Rats", Shanghai journal of stomatology, vol. 23, Oct. 2014, pp. 531-538.
Inaba et al., "Design of Biomaterials for Intracellular Delivery of Carbon Monoxide.", Biomaterials Science, vol. 3, 2015, pp. 1423-1438.
Jeney et al., "Control of Disease Tolerance to Malaria by Nitric Oxide and Carbon Monoxide", Cell Reports, vol. 8, Jul. 10, 2014, pp. 126-136.
Ji et al., "Click and Fluoresce: A Bioorthogonally Activated Smart Probe for Wash-Free Fluorescent Labeling of Biomolecules", The Journal of Organic Chemistry, vol. 82, No. 3, Feb. 3, 2017, pp. 1471-1476.
Ji et al., "Click and Release: A Chemical Strategy toward Developing Gasotransmitter Prodrugs by Using an Intramolecular Diels-Alder Reaction", Angewandte Chemie International Edition, vol. 55, Dec. 19, 2016, p. 15846-15851.
Ji et al., "Toward Carbon Monoxide-Based Therapeutics: Critical Drug Delivery and Developability Issues", Journal of Pharmaceutical Sciences, vol. 105, No. 2, Feb. 2016, pp. 406-416.
Jurga et al., "Treatment With a Carbon Monoxide-releasing Molecule (Corm-2) Inhibits Neuropathic Pain and Enhances Opioid Effectiveness in Rats", Pharmacological Reports, vol. 68, No. 1, Jan. 2016, pp. 206-213.
Kim et al., "Therapeutic Aspects of Carbon Monoxide in Cardiovascular Disease", International Journal of Molecular Sciences, vol. 19, No. 2381, Aug. 2018, pp. 1-12.
Kourti et al., "Repurposing Old Carbon Monoxide-releasing Molecules Towards the Anti-angiogenic Therapy of Triple-negative Breast Cancer", Oncotarget, vol. 10, No. 10, Feb. 2019, pp. 1132-1148.
Krimen et al., "Acetic Formic Anhydride", Organic Syntheses, 1970, 3 pages.
Kueh et al., "Norborn-2-en-7-ones as Physiologically-Triggered Carbon Monoxide-Releasing Prodrugs", Chemical Science, vol. 8, 2017, pp. 5454-5459.
Kukowska-Latallo et al., "Efficient Transfer of Genetic Material Into Mammalian Cells Using Starburst Polyamidoamine Dendrimers", Proceedings of the National Academy of Sciences of the United States of America, vol. 93, May 1996, pp. 4897-4902.
Lee et al., "Carbon Monoxide Activates Autophagy via Mitochondrial Reactive Oxygen Species Formation", American Journal of Respiratory Cell and Molecular Biology, vol. 45, Mar. 2011, pp. 867-873.
Lim et al., "A Self-Destroying Polycationic Polymer: Biodegradable Poly(4-hydroxy-IL-proline ester)", Journal of the American Chemical Society, vol. 121, No. 24, Jun. 5, 1999, pp. 5633-5639.
Lim et al., "Cationic Hyperbranched Poly(amino ester): A Novel Class of DNA Condensing Molecule with Cationic Surface, Biodegradable Three-Dimensional Structure, and Tertiary Amine Groups in the Interior", Journal of the American Chemical Society, vol. 123, Feb. 16, 2001, pp. 2460-2461.
Liu et al., "Effect of the Haeme Oxygenase-1/endogenous Carbon Monoxide System on Atherosclerotic Plaque Formation In Rabbits", Cardiovascular Journal of Africa, vol. 21, No. 5, Oct. 2010, pp. 257-261.
Liu et al., "Effects of Induction/Inhibition of Endogenous Heme Oxygenase-1 on Lipid Metabolism, Endothelial Function, and Atherosclerosis in Rabbits on a High Fat Diet", Journal of Pharmacological Sciences, vol. 118, 2012, pp. 14-24.

(56) References Cited

OTHER PUBLICATIONS

Liu et al., "Lesional Accumulation of Heme Oxygenase-1+ Microglia/macrophages in Rat Traumatic Brain Injury", Neuro Report, vol. 24, No. 6, Apr. 17, 2013, pp. 281-286.
Liu et al., "Prevention of Atherosclerotic Plaque Development by Modulating Heme Oxygenase-1-endogenous Carbon Monoxide System in Rabbit Model", Chinese Journal of Pathology, vol. 40, Issue 6, Jun. 2011, pp. 397-402.
MacGarvey et al., "Activation of Mitochondrial Biogenesis by Heme Oxygenase-1-mediated NF-E2-Related Factor-2 Induction Rescues Mice from Lethal *Staphylococcus aureus* Sepsis", American Journal of Respiratory and Critical Care Medicine, vol. 185, No. 8, Feb. 2012, pp. 851-861.
Makhija et al., "Cytokine Storm in Acute Pancreatitis", Journal of Hepato-Biliary-Pancreatic Surgery, Oct. 2002, pp. 401-410.
Mathiowitz et al., "Polyanhydride Microspheres as Drug Carriers. II. Microencapsulation by Solvent Removal", Journal of Applied Polymer Science, vol. 35, Feb. 1988, pp. 755-774.
Mayr et al., "Effects of Carbon Monoxide Inhalation during Experimental Endotoxemia in Humans", American Journal of Respiratory and Critical Care Medicine, vol. 171, Feb. 2005, pp. 354-360.
Méndez-Lara et al., "Administration of CORM-2 Inhibits Diabetic Neuropathy but Does Not Reduce Dyslipidemia in Diabetic Mice", PLos One, Oct. 4, 2018,.
Morita et al., "Carbon Monoxide Controls the Proliferation of Hypoxic Vascular Smooth Muscle Cells", Journal of Biological Chemistry, vol. 272, No. 52, Dec. 1997, pp. 32804-32809.
Morita , "Heme Oxygenase and Atherosclerosis", Arteriosclerosis, Thrombosis, and Vascular Biology, Sep. 2005, pp. 1786-1795.
Motterlini et al., "Biological Signaling by Carbon Monoxide and Carbon Monoxide-Releasing Molecules (CO-RMs).", American Journal of Physiology-Cell Physiology, vol. 312, 2017, pp. C302-C313.
Motterlini et al., "The Therapeutic Potential of Carbon Monoxide", Nature Reviews Drug Discovery, vol. 9, Sep. 2010, pp. 728-743.
Muller et al., "Solid Lipid Nanoparticles (SLN) for Controlled Drug Delivery—A Review of the State of the Art", European Journal of Pharmaceuticals and Biopharmaceuticals, vol. 50, No. 1, Jul. 2000, pp. 161-177.
Murray et al., "Synthesis and Characterization of Monodisperse Nanocrystals and Close-packed Nanocrystal Assemblies", Annual Review of Material Science, vol. 30, Aug. 2000, pp. 545-610.
Nagao et al., "Carbon Monoxide-bound Hemoglobin Vesicles Ameliorate Multiorgan Injuries Induced by Severe Acute Pancreatitis in Mice by Their Anti-inflammatory and Antioxidant Properties", International Journal of Nanomedicine, vol. 11, 2016, pp. 5611-5620.
Nakao et al., "Carbon Monoxide Inhalation Protects Rat Intestinal Grafts from Ischemia/Reperfusion Injury", The American Journal of Pathology, vol. 163, Oct. 2003, pp. 1587-1598.
Nakao et al., "Protection Against Ischemia/Reperfusion Injury in Cardiac and Renal Transplantation with Carbon Monoxide, Biliverdin and Both", American Journal of Transplantation, vol. 5, Feb. 2005, pp. 282-291.
Nakao et al., "Protective Effect of Carbon Monoxide Inhalation for Cold-preserved Small Intestinal Grafts", Surgery, vol. 134, Aug. 2003, pp. 285-292.
Neto et al., "Protection of Transplant-induced Renal Ischemia-Reperfusion Injury With Carbon Monoxide", American Journal of Physiology-Renal Physiology, vol. 287, Aug. 2004, pp. F979-F989.
Nikam et al., "Diverse Nrf2 Activators Coordinated to Cobalt Carbonyls Induce Heme Oxygenase-1 and Release Carbon Monoxide in Vitro and in Vivo", Journal of Medicinal Chemistry, vol. 59, 2016, pp. 756-762.
Odian , "Principles of Polymerization", John Wiley & Sons, Fourth Edition, Jan. 2004,.
Otterbein et al., "Carbon Monoxide Has Anti-Inflammatory Effects Involving the Mitogen-Activated Protein Kinase Pathway", Nature Medicine, vol. 6, No. 4, Apr. 2000, pp. 422-428.

Pamplona et al., "Heme Oxygenase-1 and Carbon Monoxide Suppress the Pathogenesis of Experimental Cerebral Malaria", Nature Medicine, vol. 13, No. 6, Jun. 2007, pp. 703-710.
Pan et al., "Organic CO Prodrugs Activated by Endogenous ROS", Organic Letters, vol. 20, Jan. 2018, pp. 8-11.
Pan et al., "Organic CO Prodrugs: Structure-CO-Release Rate Relationship Studies", Chemistry—A European Journal, vol. 23, No. 41, Jul. 4, 2017, pp. 9838-9845.
Paolicelli et al., "Surface-modified PLGA-Based Nanoparticles That Can Efficiently Associate and Deliver Virus-like Particles", Nanomedicine, vol. 5, No. 6, Aug. 2010, pp. 843-853.
Pellegrino et al., "On the Development of Colloidal Nanoparticles towards Multifunctional Structures and their Possible Use for Biological Applications", Small, vol. 1, No. 1, Jan. 2005, pp. 48-63.
Pena et al., "A Novel Carbon Monoxide-Releasing Molecule Fully Protects Mice from Severe Malaria", Antimicrobial Agents and Chemotherapy, Mar. 2012, pp. 1281-1290.
Peng et al., "Visible-Light Activatable Organic CO-Releasing Molecules (PhotoCORMs) that Simultaneously Generate Fluorophores", Organic & Biomolecular Chemistry, vol. 11, No. 13, 2013, pp. 6671-6674.
Petros et al., "Strategies in the Design of Nanoparticles for Therapeutic Applications", Nature Reviews, vol. 9, Aug. 2010, pp. 615-627.
Rayburn et al., "Anti-Inflammatory Agents for Cancer Therapy", Molecular and Cellular Pharmacology, 2009, pp. 29-43.
Reis et al., "Nanoencapsulation I. Methods for Preparation of Drug-loaded Polymeric Nanoparticles", Nanomedicine: Nanotechnology, Biology, and Medicine, vol. 2, No. 1, Apr. 2006, pp. 8-21.
Romao et al., "Developing Drug Molecules for Therapy with Carbon Monoxide", Chemical Society Reviews, vol. 41, 2012, pp. 3571-3583.
Roxburgh , "Cancer and Systemic Inflammation: Treat the Tumour and Treat the Host", British Journal of Cancer, vol. 110, Mar. 2014, pp. 1409-1412.
Ryter et al., "Heme Oxygenase-1/Carbon Monoxide: From Basic Science to Therapeutic Applications", Physiological Reviews, vol. 86, Apr. 2006, pp. 583-650.
Sato et al., "Carbon Monoxide Generated by Heme Oxygenase-1 Suppresses the Rejection of Mouse-to-Rate Cardiac Transplants", The Journal of Immunology, vol. 166, Mar. 2001, pp. 4185-4194.
Schallner et al., "Microglia Regulate Blood Clearance in Subarachnoid Hemorrhage by Heme Oxygenase-1", The Journal of Clinical Investigation, vol. 125, Jul. 2015, pp. 2609-2625.
Schatzschneider , "Novel Lead Structures and Activation Mechanisms for CO-Releasing Molecules (CORMs)", British Journal of Pharmacology, vol. 172, 2015, pp. 1638-1650.
Severin et al., "Time Evolution of Methotrexate-induced Kidney Injury: a Comparative Study Between Different Biomarkers of Renal Damage in Rats", Clinical and Experimental Pharmacology and Physiology, Sep. 2019, pp. 828-836.
Sheikh et al., "An Anti-Inflammatory Role for Carbon Monoxide and Heme Oxygenase-1 in Chronic Th2-Mediated Murine Colitis", Journal of Immunology, May 2011, pp. 5506-5513.
Siow et al., "Heme Oxygenase-carbon Monoxide Signalling Pathway in Atherosclerosis: Anti-atherogenic Actions of Biliverdin and Carbon Monoxide?", Cardiovascular Research, Feb. 1999, pp. 385-394.
Song et al., "Carbon Monoxide Induces Cytoprotection in Rat Orthotopic Lung Transplantation via Anti-Inflammatory and Anti-Apoptotic Effects", The American Journal of Pathology, vol. 163, Jul. 2003, pp. 231-242.
Soni et al., "Beneficial Effects of Carbon Monoxide-releasing Molecule-2 (Corm-2) on Acute Doxorubicin Cardiotoxicity in Mice: Role of Oxidative Stress and Apoptosis", Toxicology and Applied Pharmacology, vol. 253, May 2011, pp. 70-80.
Soni et al., "Mechanism(s) Involved in Carbon Monoxide-releasing Molecule-2-mediated Cardioprotection During Ischaemia-reperfusion Injury in Isolated Rat Heart", Indian Journal of Pharmaceutical Sciences, 2012, pp. 281-291.

(56) References Cited

OTHER PUBLICATIONS

Southam et al., "A Thiol-Reactive Ru(II) Ion, not CO Release, Underlies the Potent Antimicrobial and Cytotoxic Properties of CO-Releasing Molecule-3", Redox Biology, vol. 18, Jun. 2018, pp. 114-123.

Steiger et al., "Prevention of Colitis by Controlled Oral Drug Delivery of Carbon Monoxide", Journal of Controlled Release, vol. 239, Oct. 2016, pp. 128-136.

Suliman et al., "A New Activating Role for Co in Cardiac Mitochondrial Biogenesis", Journal of Cell Science, vol. 120, No. 2, Jan. 2007, pp. 299-308.

Suliman et al., "The CO/HO System Reverses Inhibition of Mitochondrial Biogenesis and Prevents Murine Doxorubicin Cardiomyopathy", Journal of Clinical Investigation, Dec. 2007, pp. 3730-3741.

Sun et al., "Carbon Monoxide Ameliorates Hepatic Ischemia/Reperfusion Injury Via Sirtuin 1-Mediated Deacetylation of High-Mobility Group Box 1 in Rats", Liver Transplantation, Jan. 14, 2017, pp. 510-526.

Taguchi et al., "Biomimetic Carbon Monoxide Delivery Based on Hemoglobin Vesicles Ameliorates Acute Pancreatitis in Mice via the Regulation of Macrophage and Neutrophil Activity", Drug Delivery, vol. 25, No. 1, Jan. 2018, pp. 1266-1274.

Takagi et al., "Carbon Monoxide Liberated from Carbon Monoxide-Releasing Molecule Exerts an Anti-inflammatory Effect on Dextran Sulfate Sodium-Induced Colitis in Mice", Digestive Diseases and Sciences, vol. 56, Jun. 2011, pp. 1663-1671.

Takagi et al., "Inhalation of Carbon Monoxide Ameliorates Collagen-induced Arthritis in Mice and Regulates the Articular Expression of IL-1β and MCP-1", Inflammation, vol. 32, Apr. 2009, pp. 83-88.

Takagi et al., "Inhalation of Carbon Monoxide Ameliorates TNBS-Induced Colitis in Mice Through the Inhibition of TNF-a Expression", Digestive Diseases and Sciences, vol. 55, Oct. 2010, pp. 2797-2804.

Tavares et al., "The Bactericidal Activity of Carbon Monoxide-Releasing Molecules against Helicobacter pylori", PLoS One, vol. 8, Dec. 2013, 9 pages.

Trachootham et al., "Targeting Cancer Cells by ROS-Mediated Mechanisms: A Radical Therapeutic Approach?", Nature Reviews, vol. 8, No. 7, Jul. 2009, pp. 579-591.

Tran et al., "Overview of the Manufacturing Methods of Solid Dispersion Technology for Improving the Solubility of Poorly Water-Soluble Drugs and Application to Anticancer Drugs", Pharmaceutics, vol. 11, Mar. 2019, 26 pages.

Trindade et al., "Nanocrystalline Semiconductors: Synthesis, Properties, and Perspectives", Chemistry of Materials, vol. 13, Nov. 2001, pp. 3843-3858.

Uddin et al., "Carbon Monoxide Attenuates Dextran Sulfate Sodium-Induced Colitis via Inhibition of GSK-3β Signaling", Oxidative Medicine and Cellular Longevity, Nov. 2013,.

Uddin et al., "Carbon Monoxide Releasing Molecule-2 Protects Mice Against Acute Kidney Injury Through Inhibition of ER Stress", The Korean Journal of Physiology & Pharmacology, Sep. 2018, pp. 567-575.

Uhrich et al., "Polymeric Systems for Controlled Drug Release", Chemical Reviews, vol. 99, Nov. 1999, pp. 3181-3198.

Upadhyay et al., "Carbon monoxide releasing molecule A-1 attenuates acetaminophen-mediated hepatotoxicity and improves survival of mice by induction of Nrf2 and related genes", Toxicology and Applied Pharmacology, vol. 360, Dec. 2018, pp. 99-108.

Wang et al., "A Click-and-Release Approach to CO Prodrugs", Chemical Communications, vol. 50, No. 100, Oct. 31, 2014, pp. 15890-15893.

Wang et al., "Carbon Monoxide Improves Neurologic Outcomes by Mitochondrial Biogenesis after Global Cerebral Ischemia Induced by Cardiac Arrest in Rats", International Journal of Biological Sciences, vol. 12, 2016, pp. 1000-1009.

Wang et al., "Carbon Monoxide-Releasing Molecule-2 Inhibits Connexin 43-Hemichannel Activity in Spinal Cord Astrocytes to Attenuate Neuropathic Pain", Journal of Molecular Neuroscience, vol. 63, Aug. 2017, pp. 58-69.

Wegiel et al., "Carbon Monoxide Expedites Metabolic Exhaustion to Inhibit Tumor Growth", Cancer Research, vol. 73, Dec. 2013, pp. 7009-7021.

Xue et al., "Carbon Monoxide-based Therapy Ameliorates Acute Pancreatitis via TLR4 Inhibition", The Journal of Clinical Investigation, vol. 124, Jan. 2014, pp. 437-447.

Zauner et al., "Polylysine-Based Transfection Systems Utilizing Receptor-Mediated Delivery", Advanced Drug Delivery Reviews, vol. 30, Mar. 1998, pp. 97-113.

Zhang et al., "Nanoparticles in Medicine: Therapeutic Applications and Developments", Clinical Pharmacology & Therapeutics, vol. 83, No. 5, May 2008, pp. 761-769.

Zhang et al., "Pharmaceutical Dispersion Techniques for Dissolution and Bioavailability Enhancement of Poorly Water-Soluble Drugs", Pharmaceutics, vol. 10, No. 3, Jun. 2018,.

Zhao et al., "Carbon Monoxide Releasing Molecule-2 Attenuated Ischemia/reperfusion-induced Apoptosis in Cardiomyocytes via a Mitochondrial Pathway", Molecular Medicine Reports, vol. 9, Feb. 2014, pp. 754-762.

Zheng et al., "Enrichment-Triggered Prodrug Activation Demonstrated Through Mitochondria-Targeted Delivery of Doxorubicin and Carbon Monoxide", Nature Chemistry, vol. 10, No. 7, Jul. 2018, pp. 787-794.

Zhou et al., "Protective Effect of Antiapoptosis Potency of Prolonged Preservation by Desiccation Using High-Pressure Carbon Monoxide on Isolated Rabbit Hearts", Transplantation Proceedings, vol. 47, Nov. 2015, pp. 2746-2751.

Breslow et al., "Hydrophobic Effects on Simple Organic Reactions in Water.", Accounts of Chemical Research, vol. 24, 1991, pp. 159-164.

Chakraborty et al., "Design Strategies to Improve the Sensitivity of Photoactive Metal Carbonyl Complexes (Photocorms) to Visible Light and Their Potential as CO-Donors to Biological Targets", Accounts of Chemical Research, vol. 47, 2014, pp. 2603-2611.

Delacruz et al., "Click, Release, and Fluoresce: A Chemical Strategy for a Cascade Prodrug System for Codelivery of Carbon Monoxide, a Drug Payload, and a Fluorescent Reporter", Organic Letters, vol. 20, 2018, pp. 897-900.

Eguchi et al., "Synthesis and Cycloaddition Reactions of Homoadamantano[4,5-c]cyclopentadienones. A Facile Route to [4,5]-fused Homoadamantanobenzene Derivatives", The Journal of Organic Chemistry, vol. 52, 1987, pp. 496-500.

Ji et al., "An Esterase-activated Click and Release Approach to Metal-free Co-prodrugs", Chemical Communications, vol. 53, Jul. 2017, pp. 8296-8299.

Ji et al., "ph-sensitive Metal-free Carbon Monoxide Prodrugs With Tunable and Predictable Release Rates", Chemical Communications, vol. 53, Aug. 2017, pp. 9628-9631.

Liu et al., "Rational Design of a Robust Fluorescent Probe for the Detection of Endogenous Carbon Monoxide in Living Zebrafish Embryos and Mouse Tissue", Angewandte Chemie International Edition, vol. 56, Oct. 2017, pp. 13489-13492.

McLean et al., "Sulfite Species Enhance Carbon Monoxide Release From CO-releasing Molecules: Implications for the Deoxymyoglobin Assay of Activity", Analytical Biochemistry, vol. 427, No. 1, Aug. 2012, pp. 36-40.

Meng et al., "Classification of Solid Dispersions: Correlation To (i) Stability and Solubility (ii) Preparation and Characterization Techniques", vol. 41, No. 9, Drug Development and Industrial Pharmacy, Apr. 8, 2015, pp. 1401-1415.

Michel et al., "A Reaction-based Fluorescent Probe for Selective Imaging of Carbon Monoxide in Living Cells Using a Palladium-mediated Carbonylation", Journal of the American Chemical Society, vol. 134, No. 38, Sep. 2012, pp. 15668-15671.

Nguyen et al., "Macromolecular and Inorganic Nanomaterials Scaffolds for Carbon Monoxide Delivery: Recent Developments and Future Trends", ACS Biomaterials Science and Engineering, vol. 1, Sep. 2015, pp. 895-913.

(56) References Cited

OTHER PUBLICATIONS

Palao et al., "Transition-Metal-Free CO-Releasing BODIPY Derivatives Activatable by Visible to NIR Light as Promising Bioactive Molecules", Journal of the American Chemical Society, vol. 138, Dec. 23, 2015, pp. 126-133.
Palomo et al., "Diels-Alder Cycloaddition in Protein Chemistry", European Journal of Organic Chemistry, Nov. 2010, pp. 6303-6314.
Lazarus et al., "Sense and Release: A Thiol-Responsive Flavonol-Based Photonically Driven Carbon Monoxide-Releasing Molecule That Operates via a Multiple-Input and Logic Gate", Journal of the American Chemical Society, vol. 139, No. 28, Jul. 2017, pp. 9435-9438.
Starenki et al., "Mitochondria-targeted Nitroxide, Mito-cp, Suppresses Medullary Thyroid Carcinoma Cell Survival in Vitro and in Vivo", The Journal of Clinical Endocrinology and Metabolism, vol. 98, Mar. 2013, pp. 1529-1540.
Tantillo et al., "Reaction Mechanisms: Part (ii) Pericyclic Reactions", Annual Reports on the Progress of Chemistry Section "B" Organic Chemistry, vol. 102, 2006, pp. 269-289.
Wood , "Carbon Monoxide—A Potential Therapy for Traumatic Brain Injury?", Nature Reviews Neurology, vol. 12, Oct. 2016,.
Zhang et al., "Synthesis of an Extremely Crowded Naphthalene via a Stable Norbornadienone", Journal of the American Chemical Society, vol. 123, Nov. 2001, pp. 10919-10926.
Journal of the Chemical Society, Chemical Communications, 1987, vol. 5, 1987, pp. 317-318.
Fujii et al., "Purines. XLVIII. Syntheses and Proton Nuclear Magnetic Resonance Study of 2-Deuterioadenines Substituted or Unsubstituted at the 9-Position and of Their N-Oxygenated Derivatives", Chemical & Pharmaceutical Bulletin, 1991*, vol. 39(2), Feb. 1991, pp. 301-308.
JP2021-521469, "Office Action", Nov. 9, 2023, 9 pages.
Konishi et al., "Formic Acid Derivatives as Practical Carbon Monoxide Surrogates for Metal-Catalyzed Carbonylation Reactions", Synlett, 2014*, vol. 25(14), 2014, pp. 1971-1986.
Yazawa et al., "A New Formylation Reagent: 4-Formyl-2-Methyl-1,3,4-Thiadiazolin-5-Thione", Tetrahedron Letters, 1985*, vol. 26(31), 1985, pp. 3703-3706.
EP19872797.6 , "Office Action", Aug. 17, 2023, 3 pages.
EP19872797.6, "Intention to Grant", Apr. 8, 2024, 9 pages.
JP2021-521469, "Office Action", Mar. 25, 2024, 5 pages.

* cited by examiner

CARBON MONOXIDE PRODRUGS FOR THE TREATMENT OF MEDICAL DISORDERS

CROSS-REFERENCE TO RELATED APPLICATIONS

This application is a continuation of International Pat. Appl. No. PCT/US2019/056591, filed Oct. 16, 2019, which claims the benefit of U.S. Provisional Pat. Appl. No. 62/746,410, filed Oct. 16, 2018, and U.S. Provisional Pat. Appl. No. 62/825,677, filed Mar. 28, 2019, which applications are incorporated by reference in their entireties.

FIELD OF THE INVENTION

The invention provides organic compounds that release carbon monoxide under physiological conditions and their use in the treatment of medical disorders, including inflammatory, pain, and dermatological disorders.

BACKGROUND OF THE INVENTION

Carbon monoxide (CO) is a colorless, odorless, and tasteless gas that is toxic and potentially lethal to hemoglobin-containing animals when exposure levels are above 35 ppm in the air. While high concentrations of CO is known to be toxic, in recent years researchers have discovered that CO is also a member of the gasotransmitter family of signaling molecules and its importance is on par with nitric oxide (NO) and hydrogen sulfide ($H_2S$). CO is constantly produced in the human body during the catabolism of heme by the action of heme oxygenases (HO), including the inducible HO-1 and the constitutively-expressed HO-2 and HO-3. The human body produces on average in the range of 0.07 mL of CO per hour by these enzymatic processes (see Coburn, R. F. "Enhancement by Phenobarbital and Diphenylhydrantoin of Carbon Monoxide Production in Normal Man" New England Journal of Medicine 1970, 283:512-515).

Initially viewed as merely a waste by-product of heme catabolism, CO has been found to play an important role in modulating various physiological processes. At low levels typically present in vivo, CO induces vasodilation (see Morita, T. et al. "Carbon Monoxide Controls the Proliferation of Hypoxic Vascular Smooth Muscle Cells" Journal of Biological Chemistry 1997, 272:32804-32809; Durante, W. et al. "Role of carbon monoxide in cardiovascular function" Journal of Cellular and Molecule Medicine 2006, 10:672-686) and inhibits platelet aggregation by activating soluble guanylyl cyclase (see Brune, B. et al. "Inhibition of platelet aggregation by carbon monoxide is mediated by activation of guanylate cyclase" Molecular Pharmacology 1987, 32:497-504). CO also plays a role in the regulation of inflammation (see Otterbein, L. E. et al. "Carbon monoxide has anti-inflammatory effects involving the mitogen-activated protein kinase pathway" Nature Medicine 2000, 6:422), mitochondrial biogenesis (see Suliman, H. B. et al. "A new activating role for CO in cardiac mitochondrial biogenesis" Journal of Cell Science 2007, 120:299-308), and autophagy (see Lee, S-J. et al. "Carbon Monoxide Activates Autophagy via Mitochondrial Reactive Oxygen Species Formation" American Journal of Respiratory Cell and Molecular Biology 2011, 45:867-873), in addition to other processes.

The broad array of biological effects of CO is exemplified in beneficial therapeutic effects observed upon administration of gaseous CO in disease models such as acute lung injury (see Dolinay, T. et al. "Inhaled Carbon Monoxide Confers Anti-inflammatory Effects Against Ventilator-Induced Lung Injury" American Journal of Respiratory and Critical Care Medicine 2004, 170:613-620), acetaminophen-induced liver damage (see Zheng, Y. et al. "Enrichment-triggered prodrug activation demonstrated through mitochondria-targeted delivery of doxorubicin and carbon monoxide" Nature Chemistry 2018, 10:787-794), colitis (see Ji, X. et al. "Click and Release: A Chemical Strategy Toward Developing Gasotransmitter Prodrugs by Using an Intramolecule Diels-Alder Reaction" Angewandte Chemie International Edition 2016, 55:15846-15851), sepsis (see MacGarvey, N. C. et al. "Activation of Mitochondrial Biogenesis by Heme Oxygenase-1-mediated NF-E2-related Factor-2 Induction Rescues Mice from Lethal *Staphylococcus aureus* Sepsis" American Journal of Respiratory and Critical Care Medicine 2012, 185:851-861), and organ transplantation (see Sato, K. et al. "Carbon Monoxide Generated by Heme Oxygenase-1 Suppresses the Rejection of Mouse-to-Rate Cardiac Transplants" The Journal of Immunology 2001, 166:4185-4194; and Song, R. et al. "Carbon Monoxide Induces Cytoprotection in Rat Orthotopic Lung Transplantation via Anti-Inflammatory and Anti-Apoptotic Effects" The American Journal of Pathology 2003, 163:231-242).

While the therapeutic use of CO gas has been explored, its administration is plagued by its lack of portability, difficulties in controlling dosage and tailoring it to specific patient's needs, and a strong dependence on the patient's respiratory rate to deliver precise amounts (see Ji, X. and Wang, B. "Strategies toward Organic Carbon Monoxide Prodrugs" Accounts of Chemical Research 2018, 51:1377-1385).

These problems have led researchers to develop CO-releasing molecules that can be used easily to administer formulations (see Ji, X. et al. "Toward CO-base Therapeutics: Critical Drug Delivery and Developability Issues" Journal of Pharmaceutical Science 2016, 105:406-416). Many early developed CO-releasing molecules were immobilized carbonyls as metal complexes that released CO upon exposure to light or water (see Ji. X.; Wang, B. "Strategies towards Organic Carbon Monoxide Prodrugs" *Acc. Chem. Res.* 2018, 51, 1377-85; and references cited therein).

However, these molecules are often viewed as undesirable for pharmaceutical applications due to the potential toxicity of the residual metals (see Motterlini R. et al. "The therapeutic potential of carbon monoxide" Nature Reviews Drug Discovery 2010, 9:728-743). There are also organic molecules that release CO upon exposure to light, but light-controlled release is not suitable for systemic application as a treatment option.

In WO 2015/191616 and WO 2018/093924, Binghe Wang and coworkers disclosed organic prodrugs that release CO in vivo and ex vivo upon completion of an intramolecular Diels-Alder reaction.

Due to the therapeutic importance of carbon monoxide and problems with current delivery methods, there is a clear need for the development of new ways to administer CO to patients in need thereof.

SUMMARY OF THE INVENTION

The present invention provides carbon monoxide prodrugs, compositions and their uses and manufacture for the treatment of medical disorders, including inflammatory, pain, and dermatological disorders. In one aspect, the present invention provides compounds for the treatment of neuropathic pain, a disorder significantly in need of novel effective therapies. The compounds described herein release therapeutic amounts of carbon monoxide under physiological conditions and thus have beneficial effects in medical disorders that have been shown to benefit from the administration of gaseous carbon monoxide, including inflammatory and pain disorders and particularly neuropathic pain. The use of these compounds allows administration of carbon monoxide by controlled and conventional dosing and does not require the use of special equipment and careful monitoring as with gaseous carbon monoxide. Additionally, the compounds provided herein do not contain expensive or toxic heavy metals to release CO gas. These compounds release carbon monoxide spontaneously under physiological conditions with concomitant release of small molecule by-products, most of which have known safety profiles or are known as sufficiently non-toxic for administration.

In another aspect, the present invention provides a highly advantageous solid dispersion formulation comprising a selected compound of the present invention for the systemic release of CO, adhered to activated charcoal. As described in Example 12, a solid dispersion formulation comprising activated charcoal and Compound 5 releases the CO from the compound within minutes. The activated charcoal also has the added benefit of retaining drug byproducts, such as saccharin and/or acesulfame, which lowers their systemic exposure.

In one aspect, compounds are described of Formula I, Formula II, and Formula III, or pharmaceutically acceptable salts and/or compositions thereof, that release carbon monoxide under physiological conditions for the treatment of medical disorders such as inflammatory, pain disorders, and inflammatory dermatological disorder, for example, acne vulgaris.

In one aspect, a compound is provided of Formula I:

(I)

or a pharmaceutically acceptable salt thereof;
wherein A is selected from:

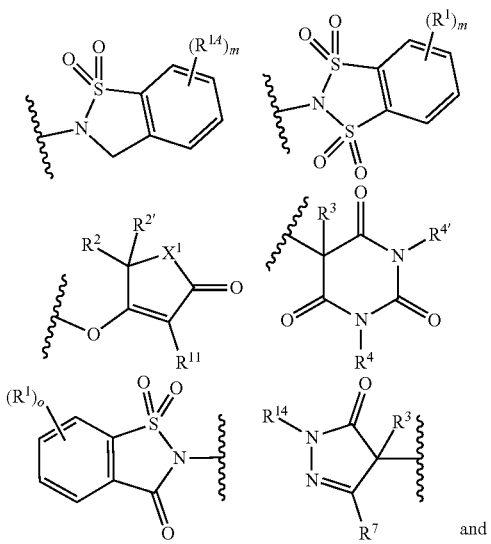

and

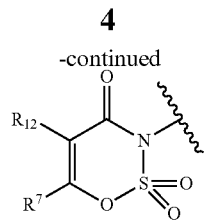

$R^1$ is independently selected at each occurrence from halogen, hydroxyl, alkyl, haloalkyl, alkoxy, haloalkoxy, aryl, heteroaryl, thiol, thioalkyl, —(C=O)$R^S$, —O(C=O)$R^S$, cyano, —SO$_3$H, —(P=O)(OH)$_2$, —O(P=O)(OH)$_2$, and nitro;

or in an alternative embodiment, $R^1$ is azido;

$R^{14}$ is independently selected at each occurrence from halogen, hydroxyl, alkyl, haloalkyl, alkoxy, haloalkoxy, aryl, heteroaryl, thiol, —(C=O)$R^S$, —O(C=O)$R^S$, cyano, —SO$_3$H, —(P=O)(OH)$_2$, —O(P=O)(OH)$_2$, and nitro;

$R^S$ is selected from hydrogen, alkyl, haloalkyl, alkoxy, amino, alkylamino, dialkylamino, aryl, and heteroaryl;

m is independently selected from 0, 1, 2, 3, or 4;

o is selected from 1, 2, 3, or 4;

$R^2$ and $R^{2'}$ are independently selected from hydrogen, alkyl, haloalkyl, aryl, and heteroaryl;

$X^1$ is —C($R^5$)($R^{5'}$)—, —N($R^{5''}$)—, —O—, or —S—;

$R^3$ is independently selected at each occurrence from halogen, alkyl, haloalkyl, aryl, heteroaryl, and

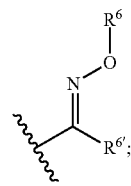

$R^4$ and $R^{4'}$ are independently alkyl;

$R^5$ and $R^{5'}$ are independently selected from hydrogen, halogen, hydroxyl, alkyl, haloalkyl, aryl, and heteroaryl;

$R^{5''}$ is selected from hydrogen, alkyl, aryl, and heteroaryl;

$R^6$ and $R^{6'}$ are independently selected from hydrogen, alkyl, haloalkyl, aryl, and heteroaryl;

$R^7$ is independently selected at each occurrence from hydrogen, alkyl, haloalkyl, aryl, and heteroaryl;

or in an alternative embodiment, $R^7$ is azido;

$R^{11}$ is selected from hydrogen, halogen, alkyl, haloalkyl, aryl, and heteroaryl;

$R^{12}$ is selected from hydrogen, halogen, alkyl, haloalkyl, aryl, and heteroaryl;

or in an alternative embodiment, $R^{12}$ is azido; and $R^{14}$ is selected from hydrogen, alkyl, aryl, and heteroaryl.

In another aspect, a novel compound is provided of Formula II:

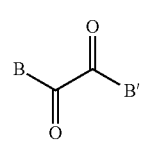

(II)

or a pharmaceutically acceptable salt thereof;

wherein:

B is selected from:

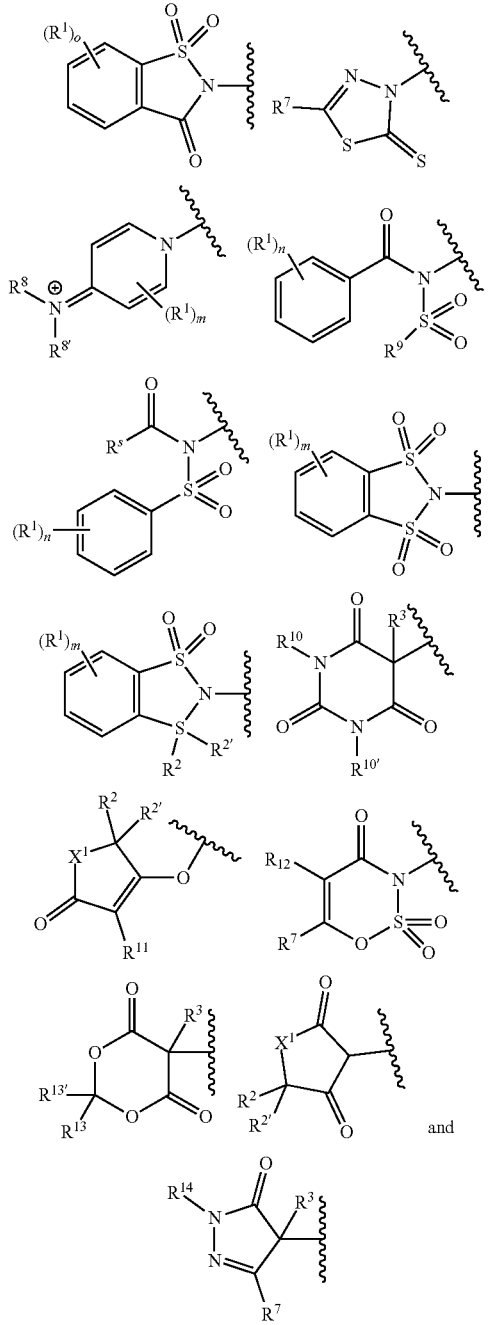

B' is selected from:

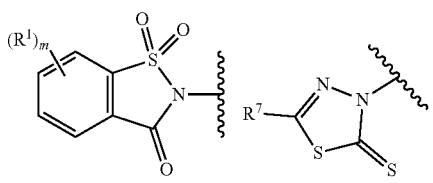

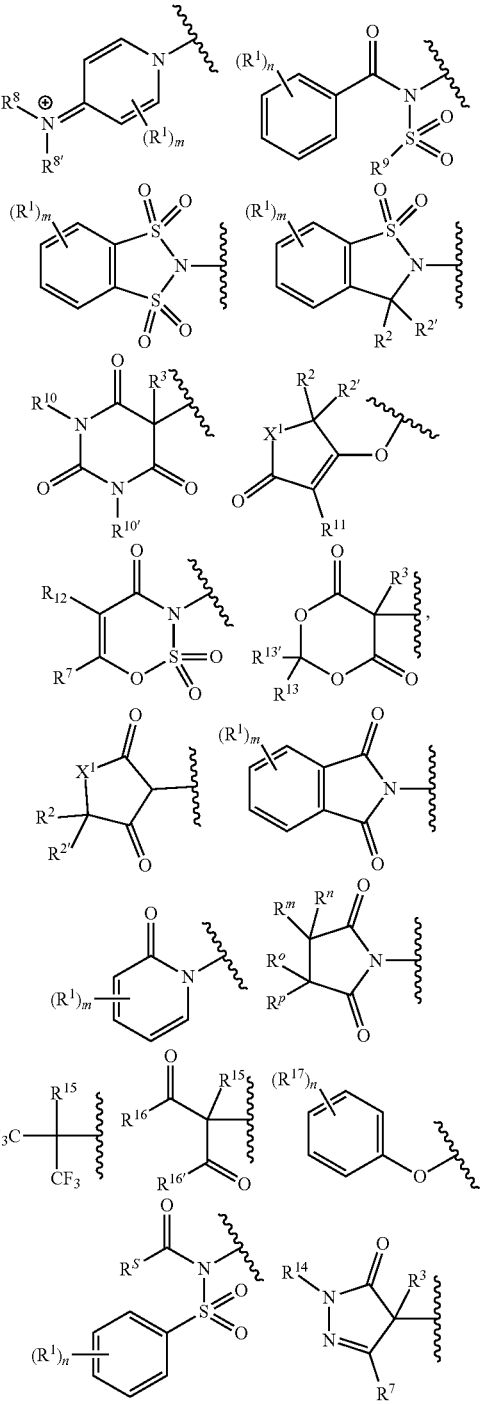

n is independently selected at each occurrence from 0, 1, 2, 3, 4, and 5;

$R^8$ and $R^{8'}$ are independently selected from alkyl and aryl;

$R^9$ is selected from alkyl, haloalkyl, aryl, and heteroaryl;

$R^{10}$ and $R^{10'}$ are independently selected from alkyl, aryl, and heteroaryl;

$R^{13}$ and $R^{13'}$ are independently selected from hydrogen, alkyl, haloalkyl, aryl, and heteroaryl;

$R^{15}$ is independently selected at each occurrence from hydrogen, halogen, alkyl, haloalkyl, aryl, and heteroaryl;

$R^{16}$ and $R^{16'}$ are independently selected at each occurrence from alkyl, haloalkyl, aryl, heteroaryl, alkoxy, haloalkoxy, aryloxy, heteroaryloxy, amino, alkylamino, and dialkylamino;

$R^{17}$ is selected from halogen, haloalkyl, and nitro;

$R^m$, $R^n$, $R^o$, and $R^p$ are independently selected from hydrogen, halogen, hydroxyl, alkyl, haloalkyl, alkoxy, haloalkoxy, aryl, and heteroaryl;

and all other variables are defined herein.

In another aspect, a novel compound is provided of Formula III:

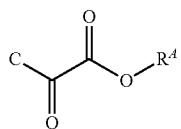

(III)

or a pharmaceutically acceptable salt thereof;
wherein:
$R^4$ is selected from hydrogen, alkyl, haloalkyl, aryl, and heteroaryl;
C is selected from:

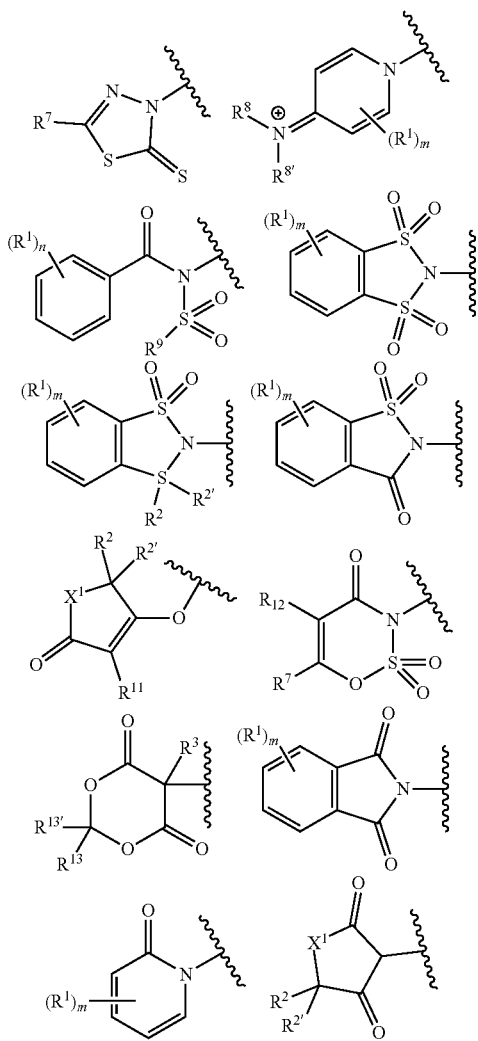

and all other variables are defined herein.

In another aspect, a pharmaceutical composition is provided comprising a compound of Formula I, Formula II, or Formula III, or its pharmaceutically acceptable salt, in a pharmaceutically acceptable carrier.

In another aspect, a method is provided for the treatment of a medical disorder in a subject, for example a human, that can be treated with carbon monoxide comprising administering to the subject an effective amount of a compound of Formula IV:

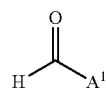

(IV)

or a pharmaceutically acceptable salt thereof;
wherein $A^1$ is selected from:

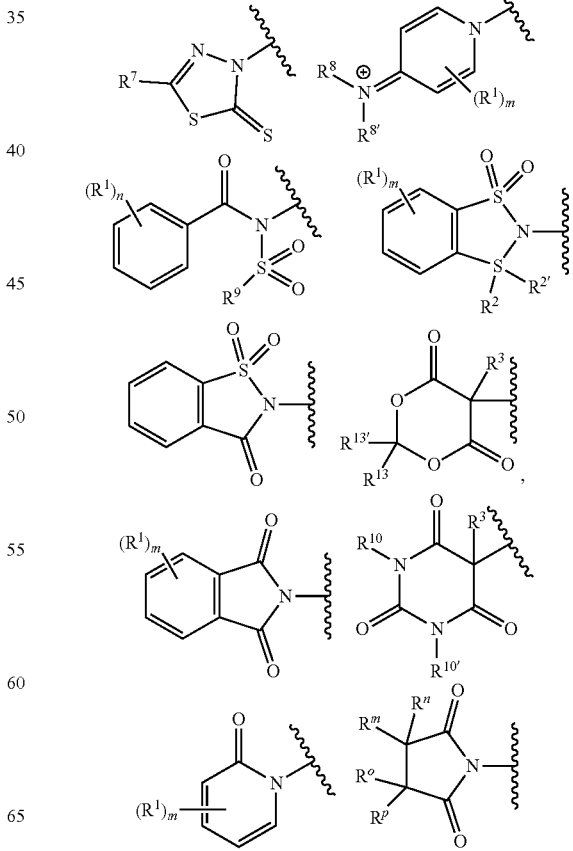

-continued

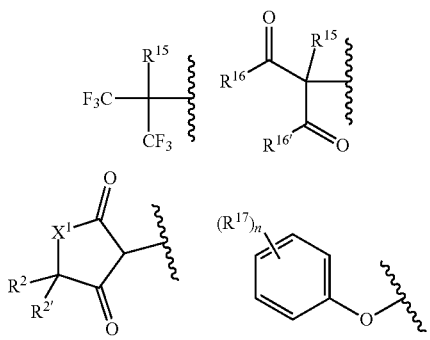

and all other variables are defined herein.

In one embodiment, the compound of Formula IV is selected from:

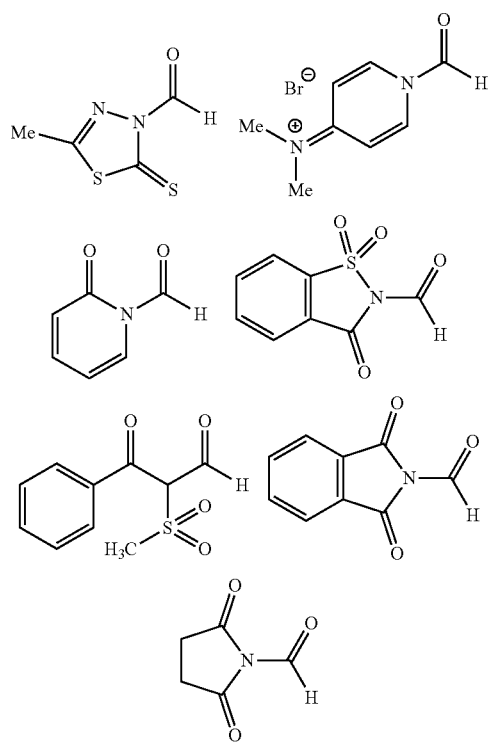

In another aspect, a method is provided for the treatment of a medical disorder in a subject, for example a human, that can be treated with carbon monoxide comprising administering to the subject an effective amount of a compound of Formula V:

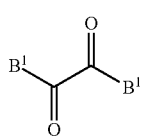

(V)

or a pharmaceutically acceptable salt thereof;

wherein $B^1$ is selected from;

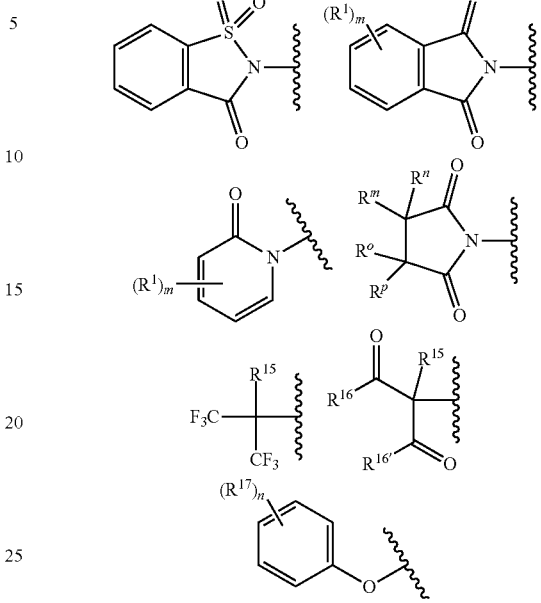

and all other variables are defined herein.

In one embodiment, the compound of Formula V is selected from:

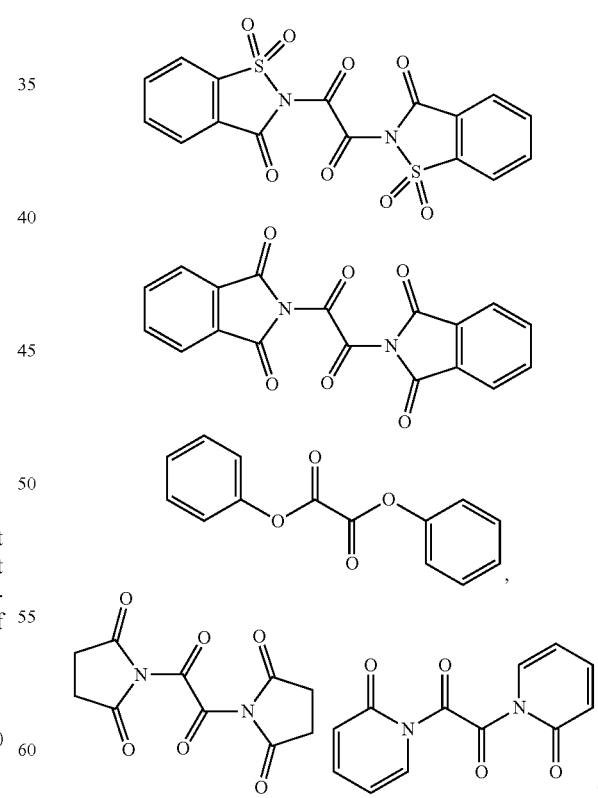

In another aspect, a method is provided for the treatment of a medical disorder in a subject, for example a human, that can be treated with carbon monoxide comprising administering to the subject an effective amount of a compound of Formula VI:

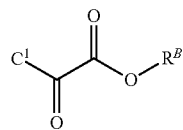
(VI)

wherein:
R$^B$ is selected from hydrogen, alkyl, haloalkyl, aryl, and heteroaryl;
C$^1$ is selected from:

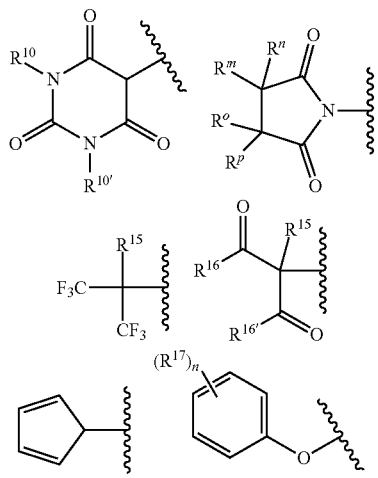

and all other variables are defined herein.

In one embodiment, the compound of Formula VI is selected from:

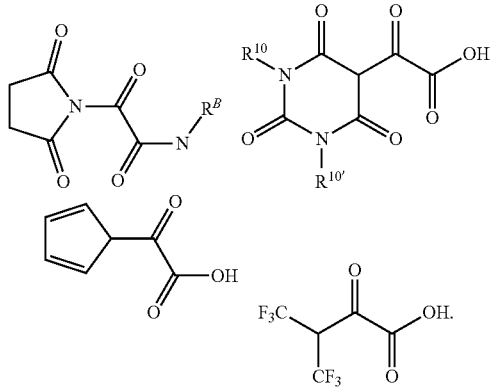

In one aspect, a method is provided for the treatment of a medical disorder in a subject, for example a human, that can be treated with carbon monoxide comprising administering to the subject an effective amount of a compound of Formula I, Formula II, Formula III, Formula IV, Formula V, or Formula VI, or a pharmaceutically acceptable salt thereof.

In another aspect, a method is provided for the treatment of neuropathic pain in a subject, for example a human, comprising administering an effective amount of a compound of Formula I, Formula II, Formula III, Formula IV, Formula V, or Formula VI, or a pharmaceutically acceptable salt thereof.

In another aspect, a method is provided for the treatment of an inflammatory disorder in a subject, for example a human, comprising administering to the subject an effective amount of a compound of Formula I, Formula II, Formula III, Formula IV, Formula V, or Formula VI, or a pharmaceutically acceptable salt thereof.

In another aspect, a method is provided for the treatment of a pain disorder in a subject, for example a human, comprising administering to the subject an effective amount of a compound of Formula I, Formula II, Formula III, Formula IV, Formula V, or Formula VI, or a pharmaceutically acceptable salt thereof.

In an alternative aspect, a method is provided for the treatment of an inflammatory dermatological disorder, for example, acne vulgaris comprising administering an effective amount of a topical composition that contains an effective amount of a compound of Formula I, Formula II, Formula III, Formula IV, Formula V, or Formula VI, or a pharmaceutically acceptable salt thereof.

In an alternative aspect, a method is provided for the treatment of an inflammatory dermatological disorder, for example, acne vulgaris comprising administering an effective amount of a topical composition that contains an effective amount of a compound of Formula VII or Formula VIII in combination with an effective amount of a compound of Formula IX:

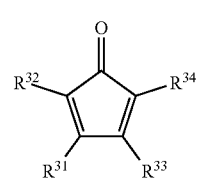
(VII)

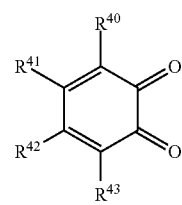
(VIII)

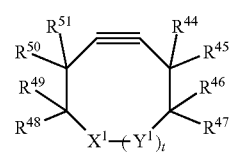
(IX)

or a pharmaceutically acceptable salt thereof, wherein:
each R$^{31}$, R$^{32}$, R$^{33}$, and R$^{34}$ is independently selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C=O)R$^{35}$, —(C=O)OR$^{36}$, and —(C=O)NR$^{37}$R$^{38}$;
or R$^{31}$ and R$^{32}$ are independently selected from the group consisting of cycloalkyl, heterocycloalkyl, aryl, and heteroaryl, and are together to form a fused tricyclic moiety which is optionally substituted with one or more R$^{39}$ moieties, wherein each R$^{39}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

each R$^{35}$, R$^{36}$, R$^{37}$, and R$^{38}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

R$^{a1}$ is independently selected at each occurrence from hydrogen, alkyl, aryl, cycloalkyl, and heteroaryl;

each R$^{40}$, R$^{41}$, R$^{42}$, and R$^{43}$ is selected from the group consisting of hydrogen, halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

each R$^{44}$, R$^{45}$, R$^{46}$, R$^{47}$, R$^{48}$, R$^{49}$, R$^{50}$, and R$^{51}$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35'}$, —(C═O)OR$^{36'}$, and —(C═O)NR$^{37'}$R$^{38'}$;

each R$^{35'}$, R$^{36'}$, R$^{37'}$, and R$^{38'}$ is independently selected from the group consisting of hydrogen, alkyl, heteroalkyl, alkenyl, heteroalkenyl, alkynyl, heteroalkynyl, cycloalkyl, heterocycloalkyl, aryl, and heteroaryl;

or R$^{44}$ or R$^{45}$ is optionally taken together R$^{46}$ or R$^{47}$ to form a fused cycloalkyl, fused heterocyclyl, fused aryl, or fused heteroaryl, each of which is optionally substituted with R$^{39'}$;

or R$^{48}$ or R$^{49}$ is optionally taken together R$^{50}$ or R$^{51}$ to form a fused cycloalkyl, fused heterocyclyl, fused aryl, or fused heteroaryl, each of which is optionally substituted with R$^{39'}$;

each R$^{39'}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

Y$^1$ is selected from the group consisting of CR$^{52a}$CR$^{52b}$, S, O, or NR$^{a1}$;

X$^1$ is selected from the group consisting of CR$^{53a}$CR$^{53b}$, S, O, or NR$^{a1}$;

wherein each R$^{52a}$, R$^{52b}$, R$^{53a}$ and R$^{53b}$ is defined as for R$^{35}$; and t is 0 or 1.

In an alternative aspect, a method is provided for the treatment of an inflammatory dermatological disorder, for example, acne vulgaris comprising administering an effective amount of a topical composition that contains an effective amount of a compound of Formula X:

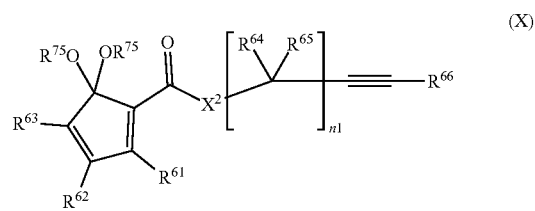

(X)

or a pharmaceutically acceptable salt thereof, wherein:

each R$^{61}$, R$^{62}$, R$^{63}$, R$^{64}$, R$^{65}$, and R$^{66}$ is independently selected from the group consisting of hydrogen, halogen, substituted or unsubstituted alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

or R$^{61}$ and R$^{62}$ are independently selected from the group consisting of cycloalkyl, heterocycloalkyl, aryl, and heteroaryl, and are together to form a fused tricyclic moiety which is optionally substituted with one or more R$^{39}$ moieties, wherein each R$^{39}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

or R$^{61}$ and R$^{62}$ are independently selected from the group consisting of cycloalkyl, heterocycloalkyl, aryl, and heteroaryl, and are together to form a fused tricyclic moiety which is optionally substituted with one or more R$^{39}$ moieties, wherein each R$^{39}$ is independently selected from the group consisting of halogen, alkyl, cycloalkyl, heterocycloalkyl, alkenyl, alkynyl, aryl, heteroaryl, alkoxy, aryloxy, hydroxyl, —N(R$^{a1}$)$_2$, —SR$^{a1}$, —S(O)R$^{a1}$, —S(O)$_2$R$^{a1}$, —OS(O)OR$^{a1}$, —OS(O)$_2$OR$^{a1}$, —OP(OR$^{a1}$)$_2$, —OP(O)HOR$^{a1}$, —OP(O)(OR$^{a1}$)$_2$, —P(O)(OR$^{a1}$)$_2$, —P(O)(OR$^{a1}$)$_2$, —ONO, —ONO$_2$, —NO$_2$, —(C═O)R$^{35}$, —(C═O)OR$^{36}$, and —(C═O)NR$^{37}$R$^{38}$;

X$^2$ is CR$^{72}$R$^{73}$, S, O, and NR$^{74}$, wherein each R$^{72}$ and R$^{73}$ is defined as for R$^{61}$, and R$^{74}$ is defined as for R$^{37}$;

each R$^{75}$ is independently selected from the group consisting of hydrogen, alkyl, cycloalkyl, heterocycloalkyl, alkenyl, alkynyl, aryl, and heteroaryl;

or two OR$^{75}$ groups are taken together to form an oxo moiety;

n1 is 1, 2, or 3;

and all other variables are as defined herein.

In an alternative aspect, a method is provided for the treatment of an inflammatory dermatological disorder, for example, acne vulgaris comprising administering an effective amount of a topical composition that contains an effective amount of a compound of Formula XI:

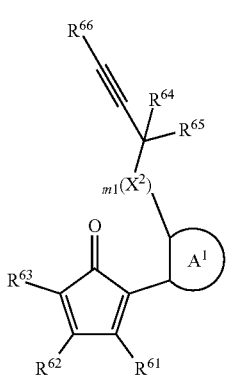

(XI)

or a pharmaceutically acceptable salt thereof, wherein:
$A^1$ is selected from the group consisting of cycloalkyl, heterocycloalkyl, aryl, and heteroaryl;
m1 is 1, 2, or 3, provided that only one of $X^2$ is S or O when m1 is 2 or 3;
and all other variables are as defined herein.

In an alternative aspect a method is provided for the treatment of an inflammatory dermatological disorder, for example, acne vulgaris comprising administering an effective amount of a topical composition that contains an effective amount of a compound of Formula XII:

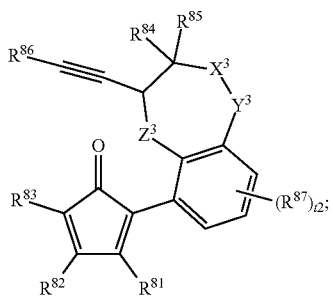

(XII)

or a pharmaceutically acceptable salt thereof, wherein:
the moiety —$X^3$—$Y^3$— is selected from the group consisting of —C(O)—O— and —O—C(O)—;
$Z^3$ is selected from the group consisting of —O— and —S—;
$R^{81}$ is selected from the group consisting of H, $C_{1-8}$ alkyl, $C_{3-8}$ cycloalkyl, $C_{6-10}$ aryl, and —C(O)$R^{81a}$;
$R^{81a}$ is selected from the group consisting of $C_{1-8}$ alkyl, $C_{3-8}$ cycloalkyl, $C_{6-10}$ aryl, 3- to 8-membered heterocyclyl, 5- to 12-membered heteroaryl, —N$R^{81b}R^{81c}$, and —O$R^{81b}$;
$R^{81b}$ and $R^{81c}$ are independently selected from H, $C_{1-8}$ alkyl, and $C_{3-8}$ cycloalkyl;
$R^{82}$ and $R^{83}$ are independently selected from $C_{6-10}$ aryl, or $R^{82}$ and $R^{83}$ are optionally taken together to form a fused tricyclic moiety;
$R^{84}$, $R^{85}$, and $R^{86}$ are independently selected from the group consisting of H and $C_{1-6}$ alkyl;
each $R^{81}$, $R^{82}$, $R^{83}$, $R^{84}$, $R^{85}$, and $R^{86}$ are optionally and independently substituted with one or more $R^{87}$;
each $R^{87}$ is selected from the group consisting of $C_{1-4}$ alkyl, halogen, —CN, —O$R^{a2}$, —C(O)$R^{b2}$, —C(O)O$R^{a2}$, —OC(O)$R^{b2}$, —N($R^{a2}$)$_2$, —N$R^{a2}$C(O)$R^{b2}$, —C(O)N($R^{a2}$)$_2$, —S(O)$R^{b2}$, —S(O)$_2R^{b2}$, —S(O)$_2$O$R^{a2}$, —S(O)$_2$N($R^{a2}$)$_2$, and —N$R^{a2}$S(O)$_2R^{b2}$;
each $R^{a2}$ is independently selected from the group consisting of H and $C_{1-4}$ alkyl;
each $R^{b2}$ is $C_{1-4}$ alkyl; and
t2 is 0, 1, 2, or 3.

An important additional aspect of the invention is a pharmaceutical formulation that comprises at least one CO-releasing molecule of the present invention adhered or adsorbed to a solid carrier, such as a solid dispersion, for example activated charcoal or a polymeric or non-polymeric solid that has suitable properties to adhere to adsorb the compounds of the present invention in a stable form. In one aspect, the CO-releasing compound is a compound of Formula I through VI or Formula X through XII or a pharmaceutically acceptable salt thereof. In one aspect, the CO-releasing compounds are compounds of Formula VII or VIII in combination with a compound of Formula IX or a pharmaceutically acceptable salt thereof.

This solid dispersion pharmaceutical formulation is advantageous over other pharmaceutical formulations for the administration of CO-releasing compounds because it releases the CO quickly while limiting the amount of systemic exposure to unnecessary drug byproducts. In one embodiment, a compound of the present invention is adsorbed onto a solid material, for example, activated charcoal, and following administration, the CO is released and the activated charcoal continues to adsorb the drug byproducts, inhibiting their systemic release. In one embodiment, the solid dispersion formulation is suitable for oral delivery, and is for example, a pill or a tablet.

In one embodiment, the solid dispersion formulation comprises activated charcoal. In one embodiment, the solid dispersion formulation comprises polymeric materials, for example, polyvinylpyrrolidone or polyvinylpyrrolidone/vinyl acetate copolymer. In one embodiment, the solid dispersion comprises an additional excipient selected from starch, talc powder, cellulose, sodium carboxymethylcellulose, and magnesium stearate. In one embodiment, the solid dispersion formulation is a tablet or a capsule. In one embodiment, the solid dispersion formulation is a controlled release formulation.

In one embodiment, the ratio between the CO-releasing compound of the present invention to the solid carrier by weight is 1 to not more than about 35, 1 to not more than about 30, 1 to not more than about 25, 1 to not more than about 20, 1 to not more than about 15, 1 to not more than about 10, 1 to not more than about 5, 1 to not more than about 2.5, or 1 to not more than about 1. In one embodiment, the ratio between the CO-releasing compound of the present invention and the solid carrier is not more than about 12 to 1, not more than about 10 to 1, not more than about 9 to 1, not more than about 8 to 1, not more than about 7 to 1, not more than about 6 to 1, not more than about 5 to 1, not more than about 4 to 1, not more than about 3 to 1, or not more than about 2 to 1.

In one embodiment, the ratio between the CO-releasing compound of the present invention to the solid carrier by weight is 1 to less than about 35, 1 to less than about 30, 1 to less than about 25, 1 to less than about 20, 1 to less than about 15, 1 to less than about 10, 1 to less than about 5, 1 to less than about 2.5, or 1 to less than about 1. In one embodiment, the ratio between the CO-releasing compound of the present invention and the solid carrier is less than about 12 to 1, less than about 10 to 1, less than about 9 to 1, less than about 8 to 1, less than about 7 to 1, less than about 6 to 1, less than about 5 to 1, less than about 4 to 1, less than about 3 to 1, or less than about 2 to 1.

In one embodiment, the solid dispersion formulation exhibits a carbon monoxide release yield of at least about 99%, at least about 95%, at least about 90%, at least about 85%, at least about 80%, at least about 75%, at least about 70%, at least about 65%, at least about 60%, at least about 55%, at least about 50%, at least about 40%, at least about 30%, at least about 20%, or at least about 10% after administration in a subject in need thereof. In one embodiment, the solid dispersion formulation exhibits a carbon monoxide release yield of at least 75%.

In one embodiment, the solid dispersion formulation retains up to about 99%, up to about 98%, up to about 95%, up to about 90%, up to about 85%, up to about 75%, up to about 65%, up to about 60%, up to about 50%, or up to about 40% of the drug byproducts after administration in a subject in need thereof. In one embodiment, the drug byproduct is saccharin and approximately 98% of the saccharin is retained in the solid dispersion formulation after administration in a subject in need thereof.

In another aspect of the present invention, a topical formulation for the treatment of an inflammatory dermatological disorder, for example, acne vulgaris is provided comprising an effective amount of a compound of Formula I-VI or X-XII and a topically acceptable carrier, wherein the topically acceptable carrier is substantially anhydrous. In some embodiments, the topically acceptable carrier can be selected from an oleaginous base, an aliphatic base including mineral oil, an absorption base, and a silicon base, or a combination thereof.

In another aspect, a topical formulation for the treatment of an inflammatory dermatological disorder, for example, acne vulgaris is provided comprising an effective amount of a compound of Formula VII or VIII in combination with an effective amount of a compound of Formula IX and a topically acceptable carrier, wherein the topically acceptable carrier is substantially anhydrous.

In another aspect, a topical product for the treatment of an inflammatory dermatological disorder, for example, acne vulgaris is provided comprising a first formulation and a second activating formulation wherein carbon monoxide is released upon mixing of the first formulation and the second activating formulation. The first formulation comprises an effective amount of a compound of Formula I-VI or X-XII and a topically acceptable carrier that is substantially anhydrous. The second activating formulation can be hydrous. The first formulation and the second activating formulation are kept physically separated until application on the skin wherein the first formulation and the second activating formulation are mixed when applied or just before application to the skin and wherein carbon monoxide is released upon mixing of the first formulation and the second activating carrier. In some embodiments, the second activating formulation further comprises an emulsifier.

In one embodiment, the composition used in the methods described herein require substantially anhydrous (for example, less than about 5%, 4%, 3%, 2%, 1%, 0.5%, or 0.25% by weight of water or alcohol or a combination thereof), carrier for stability of the carbon monoxide releasing compounds contained therein for long term storage and handling.

In one embodiment, at least one hydrogen within a compound of Formula I, Formula II, Formula III, Formula IV, Formula V, Formula VI, Formula VII, Formula VIII, Formula IX, Formula X, Formula XI, or Formula XII is replaced with a deuterium. In one aspect, the deuterium is at a location of metabolism.

Thus, the present invention includes at least the following features:

(a) a compound of Formula I, Formula II, or Formula III as described herein or a pharmaceutically acceptable salt thereof;

(b) a compound of Formula I, Formula II, or Formula III as described herein, or a pharmaceutically acceptable salt thereof, for use in the treatment of a medical disorder that can be treated with carbon monoxide;

(c) a pharmaceutical composition comprising an effective amount of a compound of Formula I, Formula II, or Formula III as described herein, or its pharmaceutically acceptable salt, in a pharmaceutically acceptable carrier;

(d) a method for the treatment of a medical disorder that can be treated with carbon monoxide comprising administering an effective amount of a compound of Formula I, Formula II, or Formula III, Formula IV, Formula V, or Formula VI, or a pharmaceutically acceptable salt thereof, optionally in a pharmaceutically acceptable carrier, to a subject in need thereof;

(e) a method for the treatment of neuropathic pain comprising administering an effective amount of a compound of Formula I, Formula II, or Formula III, Formula IV, Formula V, or Formula VI, or a pharmaceutically acceptable salt thereof, optionally in a pharmaceutically acceptable carrier, to a subject in need thereof, (f) a method for the treatment of a pain disorder comprising administering an effective amount of a compound of Formula I, Formula II, or Formula III, Formula IV, Formula V, or Formula VI, or a pharmaceutically acceptable salt thereof, optionally in a pharmaceutically acceptable carrier, to a subject in need thereof;

(g) a method for the treatment of an inflammatory disorder comprising administering an effective amount of a compound of Formula I, Formula II, or Formula III, Formula IV, Formula V, or Formula VI, or a pharmaceutically acceptable salt thereof, optionally in a pharmaceutically acceptable carrier, to a subject in need thereof, (h) a compound of Formula I, Formula II, or Formula III, Formula IV, Formula V, or Formula VI, or a pharmaceutically acceptable salt thereof, optionally in a pharmaceutically acceptable carrier, for use to treat a medical disorder that can be treated with carbon monoxide in a host in need thereof, (i) a compound of Formula I, Formula II, or Formula III, Formula IV, Formula V, or Formula VI, or a pharmaceutically acceptable salt thereof, optionally in a pharmaceutically acceptable carrier, for use to treat neuropathic pain in a host in need thereof;

(j) a compound of Formula I, Formula II, or Formula III, Formula IV, Formula V, or Formula VI, or a pharmaceutically acceptable salt thereof, optionally in a pharmaceutically acceptable carrier, for use to treat a pain disorder in a host in need thereof;

(k) a compound of Formula I, Formula II, or Formula III, Formula IV, Formula V, or Formula VI, or a pharmaceutically acceptable salt thereof, optionally in a pharmaceutically acceptable carrier, for use to treat an inflammatory disorder in a host in need thereof, (l) the use of compound of Formula I, Formula II, or Formula III, Formula IV, Formula V, or Formula VI, or a pharmaceutically acceptable salt thereof, optionally in a pharmaceutically acceptable carrier, in the manufacture of a medicament for the treatment of a medical disorder that can be treated with carbon monoxide in a host in need thereof;

(m) the use of a compound of Formula I, Formula II, or Formula III, Formula IV, Formula V, or Formula VI, or a pharmaceutically acceptable salt thereof, optionally in a pharmaceutically acceptable carrier, in the manufacture of a medicament for the treatment of neuropathic pain in a host in need thereof;

(n) the use of a compound of Formula I, Formula II, or Formula III, Formula IV, Formula V, or Formula VI, or a pharmaceutically acceptable salt thereof, optionally in a pharmaceutically acceptable carrier, in the manufacture of a medicament for the treatment of a pain disorder in a host in need thereof, (o) the use of a compound of Formula I, Formula II, or Formula III, Formula IV, Formula V, or Formula VI, or a pharmaceutically acceptable salt thereof, optionally in a pharmaceutically acceptable carrier, in the manufacture of a medicament for the treatment of an inflammatory disorder in a host in need thereof, (p) a method for the treatment of an inflammatory dermatological disorder comprising administering an effective amount of a compound of Formula I through Formula VI or Formula X through Formula XII, or a pharmaceutically acceptable salt thereof, optionally in a pharmaceutically acceptable carrier, to a subject in need thereof, (q) a compound of Formula I through Formula VI or Formula X through Formula XII, or a pharmaceutically acceptable salt thereof, optionally in a pharmaceutically acceptable carrier, for use to treat an inflammatory dermatological disorder in a host in need thereof;

(r) the use of a compound of Formula I through Formula VI or Formula X through Formula XII, or a pharmaceutically acceptable salt thereof, optionally in a pharmaceutically acceptable carrier, in the manufacture of a medicament for the treatment of an inflammatory dermatological disorder in a host in need thereof;

(s) a method for the treatment of an inflammatory dermatological disorder comprising administering an effective amount of a compound of Formula VII or Formula VIII in combination with a compound of Formula IX, or independently a pharmaceutically acceptable salt thereof, optionally in a pharmaceutically acceptable carrier, to a subject in need thereof;

(t) a compound of Formula VII or Formula VIII in combination with a compound of Formula IX, or independently a pharmaceutically acceptable salt thereof, optionally in a pharmaceutically acceptable carrier, for use to treat an inflammatory dermatological disorder in a host in need thereof, (u) the use of a compound of Formula VII or Formula VIII in combination with a compound of Formula IX, or independently a pharmaceutically acceptable salt thereof, optionally in a pharmaceutically acceptable carrier, in the manufacture of a medicament for the treatment of an inflammatory dermatological disorder in a host in need thereof;

(v) any of the embodiments (p)-(u) wherein the inflammatory dermatological disorder is acne vulgaris;

(w) a topical formulation comprising a compound of Formula I through Formula VI or Formula X through Formula XII or its pharmaceutically acceptable salt and a topically acceptable carrier;

(x) a topical formulation comprising a compound of Formula I through Formula VI or Formula X through Formula XII in combination with a compound of Formula IX and a topically acceptable carrier;

(y) a topical formulation as used in embodiments (w)-(x), wherein the compound or its pharmaceutically acceptable salt, is a mixture of enantiomers or diastereomers (as relevant), including as a racemate or including at least one atom that is isotopically enriched; and (z) a topical formulation as used in embodiments (w)-(x) wherein the compound is in enantiomerically or diastereomerically (as relevant) enriched form, including as an isolated enantiomer or diastereomer (i.e. greater than 85, 90, 95, 97, or 99% pure).

(aa) a compound as used in embodiments (a)-(z), or its pharmaceutically acceptable salt, as a mixture of enantiomers or diastereomers (as relevant), including as a racemate or including at least one atom that is isotopically enriched;

(bb) a compound as used in embodiments (a)-(z) in enantiomerically or diastereomerically (as relevant) enriched form, including as an isolated enantiomer or diastereomer (i.e., greater than 85, 90, 95, 97, or 99% pure); and (cc) a process for the preparation of a therapeutic product that contains an effective amount of a compound of Formula I through Formula XIII, or a pharmaceutically acceptable salt thereof, (dd) a solid dispersion formulation comprising a compound of Formula I through Formula VI or Formula X through Formula XII, or its pharmaceutically acceptable salt;

(ee) a solid dispersion formulation comprising a compound of Formula VII or Formula VIII in combination with a compound of Formula IX, or its pharmaceutically acceptable salt;

(ff) the solid dispersion formulation of embodiment (ee) wherein the compound of Formula VII or Formula VIII is administered in a separate solid dispersion formulation than the compound of Formula IX wherein the host receives the benefit of both active agents acting in a concerted biological manner;

(gg) the solid dispersion formulation of any one of embodiment (dd)-(ff) comprising activated charcoal;

(hh) the solid dispersion formulation of any one of embodiments (dd)-(gg) comprising a polymeric material;

(ii) the solid dispersion formulation of any one of embodiments (dd)-(hh) comprising an additional excipient selected from starch, talc powder, cellulose, sodium carboxymethylcellulose, and magnesium stearate;

(jj) the solid dispersion formulation of any one of embodiments (dd)-(ii) in a capsule or tablet; and (kk) the solid dispersion formulation of any one of embodiments (dd)-(jj) in a controlled release formulation.

(ll) a formulation for topical delivery comprising a first formulation comprising a compound of Formula I-VI or X-XII and a topically acceptable carrier that is substantially anhydrous and a second activating formulation wherein carbon monoxide is released upon mixing of the first formulation and the second activating formulation.

(mm) the formulation of (ll) wherein the second activating agent comprises an emulsifier;

(nn) the formulation of (ll) or (mm) wherein the second activating agent is hydrous.

DETAILED DESCRIPTION OF THE INVENTION

I. Definitions

Figure 1:
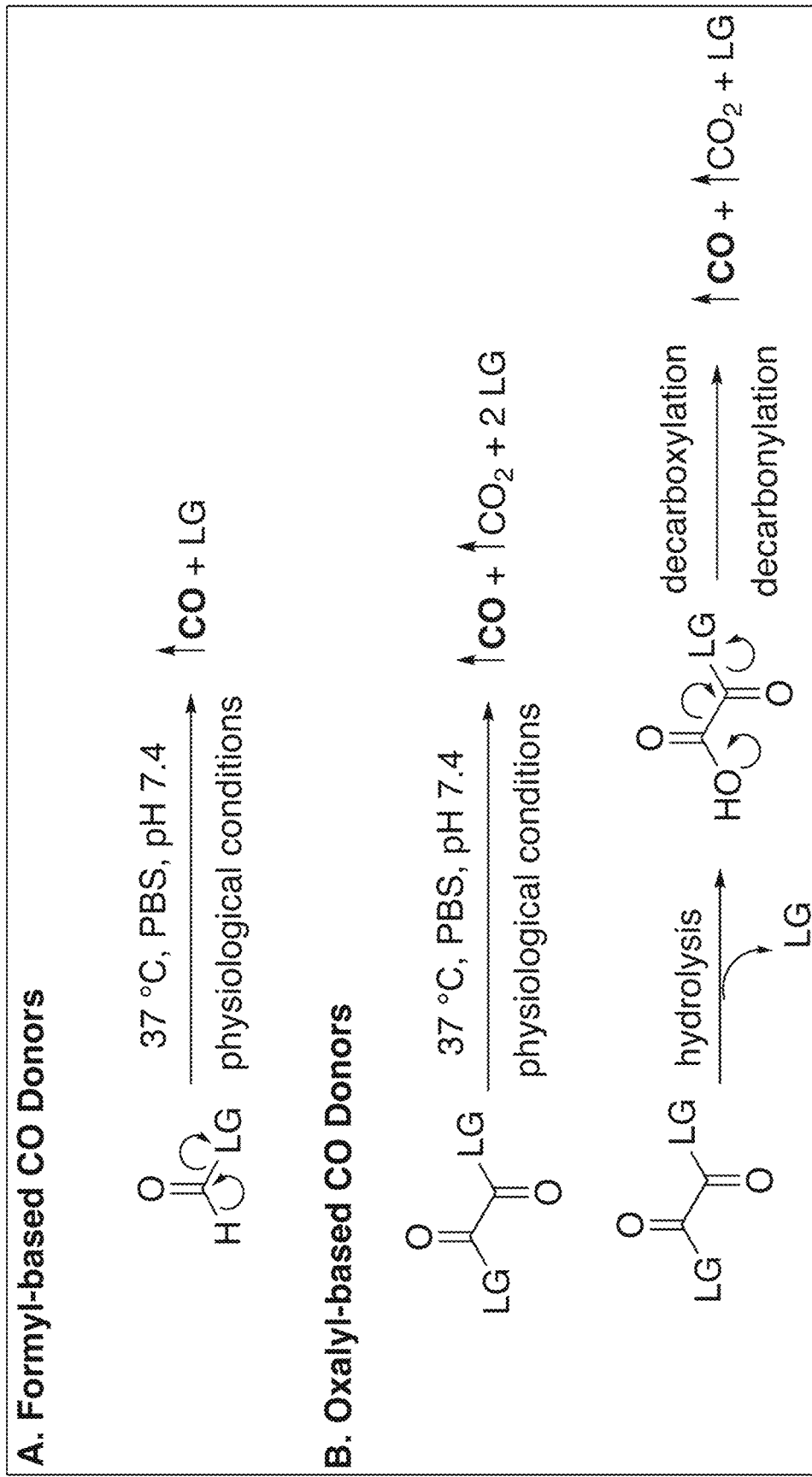
FIG. 1 is a chemical scheme that shows the mechanism of release of carbon monoxide from the compounds described herein under physiological conditions.

Compounds are described using standard nomenclature. Unless defined otherwise, all technical and scientific terms used herein have the same meaning as is commonly understood by one of skill in the art to which the invention belongs.

The terms "a" and "an" do not denote a limitation of quantity, but rather denote the presence of at least one of the referenced item. The term "or" means "and/or". Recitation of ranges of values merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of example, or exemplary language (e.g. "such as"), is intended merely to better illustrate the invention and does not pose a limitation on the scope of the invention unless otherwise claimed.

A dash ("-") that is not between two letters or symbols is used to indicate a point of attachment for a substituent. For example, —(C=O)NH$_2$ is attached through the carbon of the keto (C=O) group.

"Alkyl" is a branched or straight chain saturated aliphatic hydrocarbon group. In one non-limiting, preferred embodiment, the alkyl group generally contains from 1 to about 12 carbon atoms, from 1 to about 8 carbon atoms, from 1 to about 6 carbon atoms, or from 1 to about 4 carbon atoms. In certain embodiments, the alkyl is $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, or $C_1$-$C_{10}$. In one embodiment, the alkyl group contains from about 1 to about 50 carbon atoms or from about 1 to about 36 carbon atoms. For example, the term $C_1$-$C_6$alkyl as used herein indicates a straight chain or branched alkyl group having from 1, 2, 3, 4, 5, or 6 carbon atoms and is intended to mean that each of these are described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentance, 3-methylpentane, 2,2-dimethylbutane, and 2,3-dimethylbutane. In some embodiments, the alkyl group is optionally substituted as defined herein.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "alkyl" is "substituted alkyl"

When a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, etc. can all be considered to include the cyclic forms of alkyl, unless unambiguously excluded by context.

For example, "cycloalkyl" is an alkyl group that forms or includes a ring. When composed of two or more rings, the rings may be joined together in a fused fashion. Non-limiting examples of typical cycloalkyl groups include cyclopropyl, cyclobutyl, cyclopentyl, cyclohexyl, cycloheptyl, and cyclooctyl.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic system ("$C_6$-$C_{14}$aryl"). In some embodiments, an aryl group has 6 ring carbon atoms ("$C_6$aryl"; e.g., phenyl). In some embodiments, an aryl group has 10 ring carbon atoms ("$C_{10}$aryl"; e.g., naphthyl such as 1-naphthyl and 2-naphthyl). In some embodiments, an aryl group has 14 ring carbon atoms ("$C_{14}$aryl"; e.g., anthracyl). "Aryl" also includes ring systems wherein the aryl ring, as defined above, is fused with one or more cycloalkyl or heterocycloalkyl groups wherein the point of attachment is on the aryl ring, and in such instances, the number of carbon atoms continue to designate the number of carbon atoms in the aryl ring system. The one or more fused cycloalkyl or heterocycloalkyl groups can be 4 to 7 or 5 to 7-membered cycloalkyl or heterocycloalkyl groups that optionally contain 1, 2, or 3 heteroatoms independently selected from nitrogen, oxygen, phosphorous, sulfur, silicon, and boron. In one non-limiting embodiment, aryl groups are pendant. An example of a pendant ring is a phenyl group substituted with a phenyl group. In some embodiments, the aryl group is optionally substituted as defined herein.

In one embodiment "aryl" is a 6-carbon aromatic group (phenyl).

In one embodiment "aryl" is a 10-carbon aromatic group (napthyl).

In one embodiment "aryl" is a 6-carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

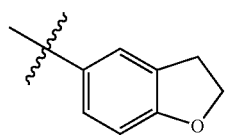 [SMILES: *c1ccc2c(c1)CCO2]

is an "aryl" group.

However,

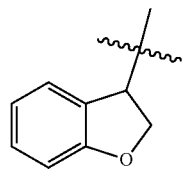 [SMILES: *C1COc2ccccc21]

is a "heterocycle" group.

In one embodiment "aryl" is a 6-carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

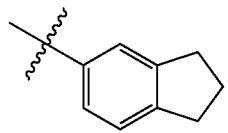

is an "aryl" group.

However,

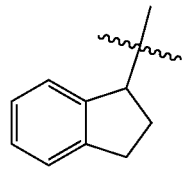 [SMILES: *C1CCc2ccccc21]

is a "cycloalkyl" group.

In one embodiment "aryl" is "substituted aryl".

In one embodiment "heteroaryl" is a 5-membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

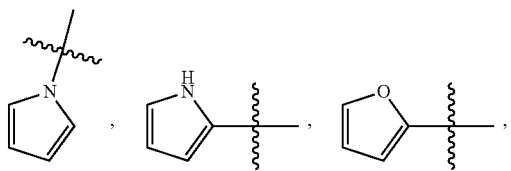

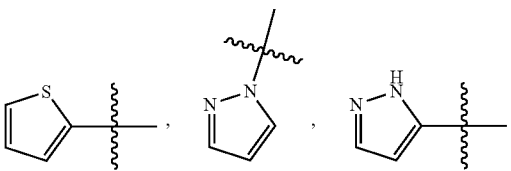

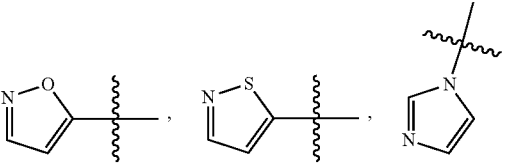

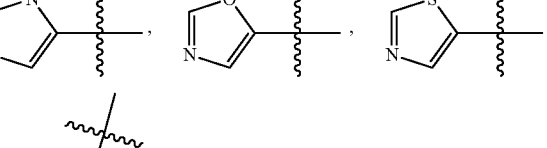

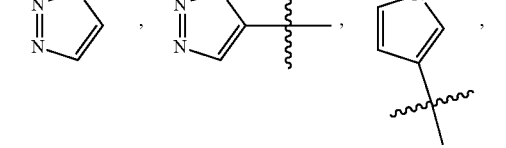

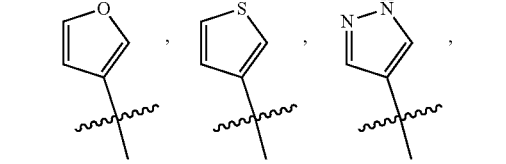

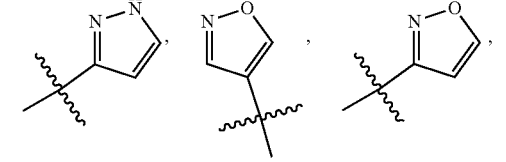

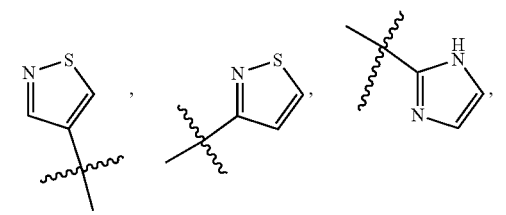

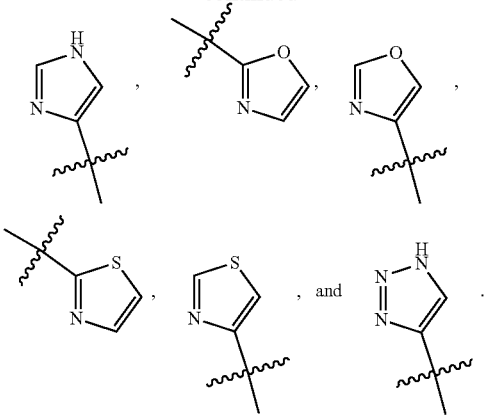

In one embodiment "heteroaryl" is a 6-membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

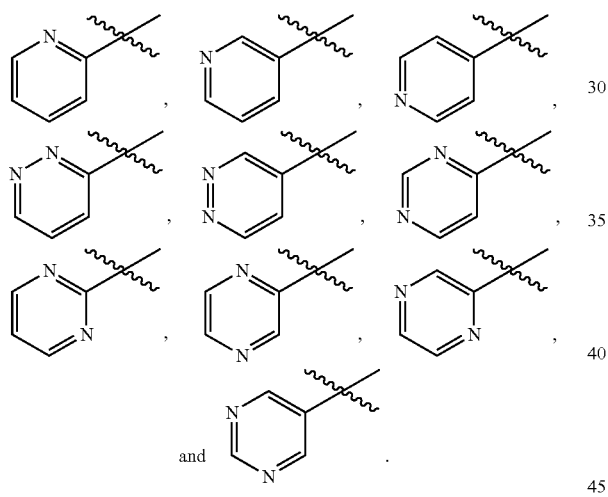

In one embodiment "heteroaryl" is a 9-membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

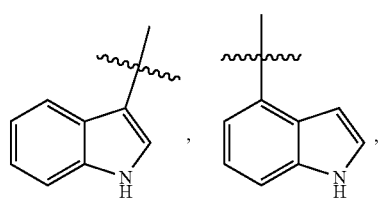

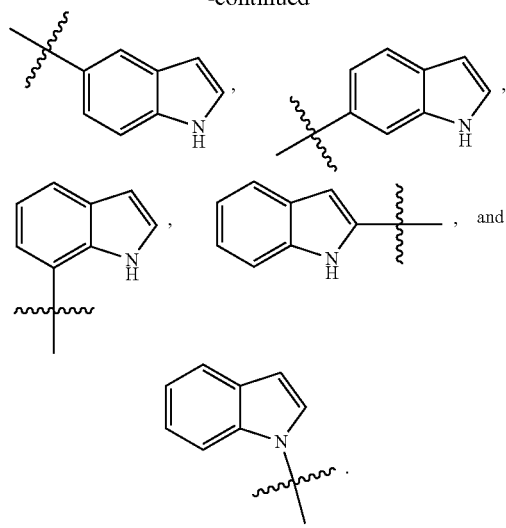

Additional non-limiting examples of "heteroaryl" groups that are bicyclic include:

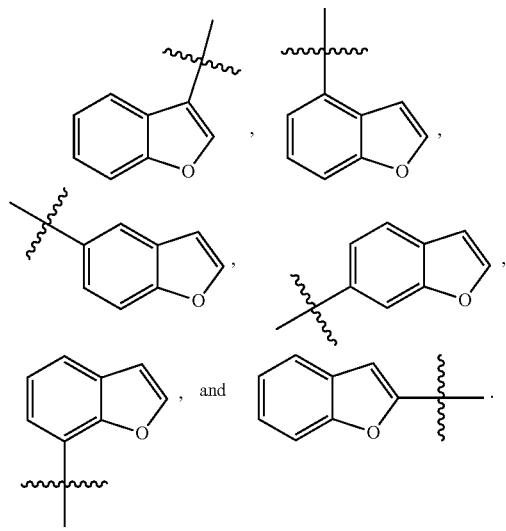

Additional non-limiting examples of "heteroaryl" groups that are bicyclic include:

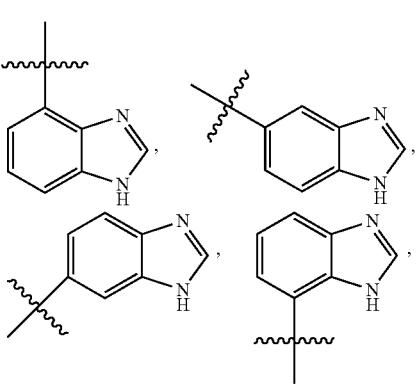

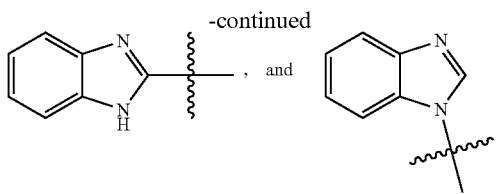

In one embodiment "heteroaryl" is a 10-membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

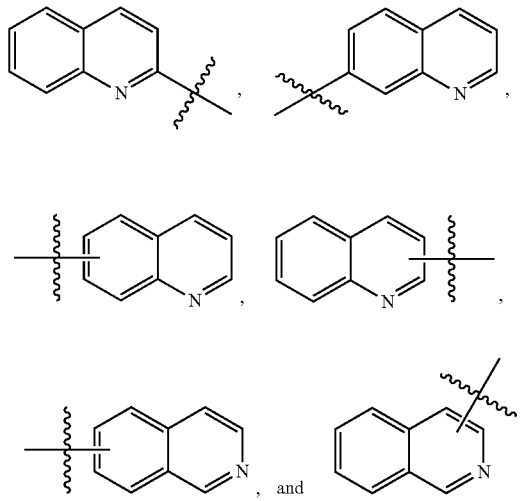

In one embodiment "heteroaryl" is "substituted heteroaryl".

"Halo" and "Halogen" is fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

Non-limiting examples of "haloalkyl" include:

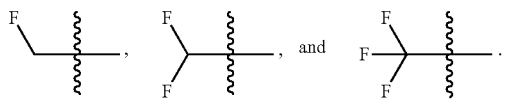

Additional non-limiting examples of "haloalkyl" include:

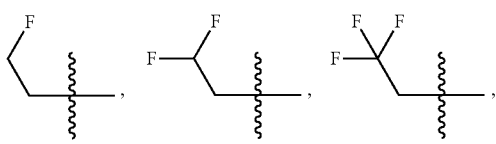

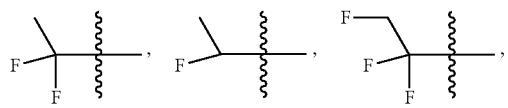

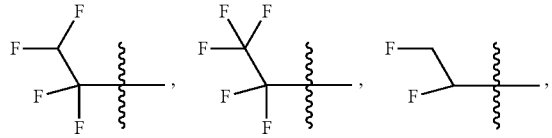

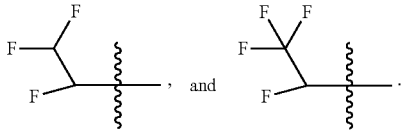

Additional non-limiting examples of "haloalkyl" include:

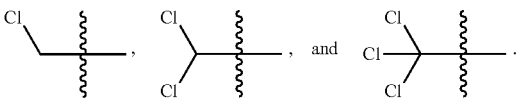

Additional non-limiting examples of "haloalkyl" include:

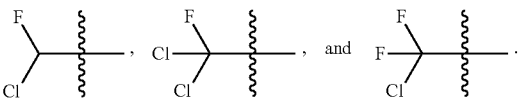

"Alkoxy" is alkyl group as defined above covalently bounds through an oxygen bridge (—O—). Examples of alkoxy include, but are not limited to, methoxy, ethoxy, n-propoxy, isopropoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. "Haloalkoxy" indicates a haloalkyl group as defined herein attached through an oxygen bridge (—O—).

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein means an amount which provides a therapeutic or prophylactic benefit. "Parenteral" administration of a pharmaceutical composition includes, e.g., subcutaneous (s.c.), intravenous (i.v.), intramuscular (i.m.), intrasternal injection, or infusion techniques.

To "treat" a disease as the term is used herein means to reduce the frequency or severity of at least one sign or symptom of a disease or disorder experienced by a subject (i.e. palliative treatment) or to decrease a cause or effect of the disease or disorder (i.e. disease-modifying treatment).

As used herein, "pharmaceutical compositions" are compositions comprising at least one active agent and at least one other substance, such as a carrier. "Pharmaceutical combinations" are combinations of at least two active agents which may be combined in a single dosage form or provided together in separate dosage forms with instructions that the active agents are to be used together to treat any disorder described herein.

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders specifically described herein. Typically, the host is a human. A "host" may alternatively refer to for example, a mammal, primate (e.g. human), cow, sheep, goat, horse, dog, cat, rabbit, rat, mice, fish, bird, and the like.

A "therapeutically effective amount" of a pharmaceutical composition/combination of this invention means an amount effective, when administered to a host, to provide a therapeutic benefit such as an amelioration of symptoms or reduction or diminution of the disease itself.

The compounds in any of the Formulas described herein may be in the form of a racemate, enantiomer, mixture of enantiomers, diastereomer, mixture of diastereomers, tautomer, N-oxide, or other isomers, such as a rotamer, as if each is specifically described unless specifically excluded by context.

The present invention includes compounds of Formula I, Formula II, Formula III, Formula IV, Formula V, Formula VI, Formula VII, Formula VIII, Formula IX, Formula X, Formula XI, or Formula XII with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{17}O$, $^{18}O$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete.

Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of one or more hydrogen atoms for a deuterium atoms can be provided in any of Formula I, Formula II, Formula III, Formula IV, Formula V, Formula VI, Formula VII, Formula VIII, Formula IX, Formula X, Formula XI, or Formula XII. In one non-limiting embodiment, the substitution of a hydrogen atom for a deuterium atom occurs within a group selected from any of R, $R^1$, $R^2$, $R^3$, $R^4$, $R^5$, $R^6$, $R^7$, $R^1$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{31}$, $R^{32}$, $R^{33}$, $R^{34}$, $R^{35}$, $R^{36}$, $R^{37}$, $R^{38}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{35'}$, $R^{36'}$, $R^{37'}$, $R^{38'}$, $R^{39'}$, $R^{61}$, $R^{62}$, $R^{63}$, $R^{64}$, $R^{65}$, $R^{66}$, $R^{72}$, $R^{73}$, $R^{74}$, $R^{75}$, $R^{a1}$, and $R^X$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compounds of the present invention may form a solvate with solvents. Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. Additional non-limiting examples of solvents are dimethyl acetamide and N-methyl-2-pyrrolidine. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

As used herein, "pharmaceutically acceptable salt" is a derivative of the disclosed compound in which the parent compound is modified by making inorganic or organic, non-toxic, acid or base addition salts thereof. The salts of the present compounds can be synthesized from a parent compound that contains a basic or acidic moiety by conventional chemical methods.

Generally, such salts can be prepared by reacting free acid forms of these compounds with a stoichiometric amount of the appropriate base (such as Na, Ca, Mg, or K hydroxide, carbonate, bicarbonate, or the like), or by reactive free base forms of these compounds with a stoichiometric amount of the appropriate acid. Such reactions are typically carried out in a variety of solvents or solvent mixtures which are compatible with the compound. Generally, non-aqueous media like ether, ethyl acetate, ethanol, isopropanol, or acetonitrile are typical, where practical. Salts of the present compounds further include solvates of the compound and the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic organic acids. For example, conventional non-toxic acid salts include the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17$^{th}$ 20 ed., Mack Publishing Company, Easton, Pa., p. 1418 (1985).

II. Compounds of Formula I, Formula II, and Formula III

A compound is provided in the present invention of Formula I, Formula II, or Formula III, or a pharmaceutically acceptable salt thereof, optionally in a pharmaceutically acceptable carrier to form a pharmaceutical composition.

In some embodiments, a compound of Formula I is provided:

(I)

or a pharmaceutically acceptable salt thereof;
wherein A is defined as above.

In some embodiments of Formula I, the compound has a chemical structure of Formula Ia:

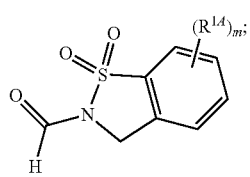

(Ia)

wherein $R^{1A}$ and m are defined as above. In one embodiment of Formula Ia, m is 0.

In some embodiments of Formula I, the compound has a chemical structure of Formula Ib:

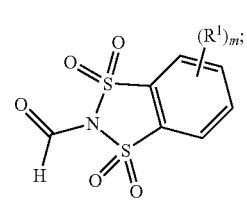

(Ib)

wherein $R^1$ and m are defined as above. In one embodiment of Formula Ib, m is 0.

In some embodiments of Formula I, the compound has a chemical structure of Formula Ic:

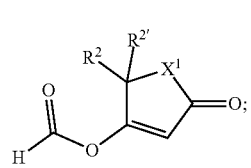

(Ic)

wherein $X^1$, $R^2$, and $R^{2'}$ are defined as above. In some embodiments of Formula Ic, $X^1$ is $CH_2$. In some embodiments of Formula Ic, $X^1$ is O. In some embodiments of Formula Ic, $X^1$ is S. In some embodiments of Formula Ic, $X^1$ is NH. In some embodiments of Formula Ic, $R^2$ and $R^{2'}$ are both hydrogen.

In some embodiments of Formula the compound has a chemical structure of Formula Id:

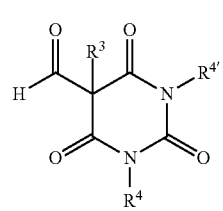

(Id)

wherein $R^3$, $R^4$, and $R^{4'}$ are defined as above. In some embodiments of Formula Id, $R^4$ and $R^{4'}$ are both methyl. In some embodiments of Formula Id, $R^3$ is methyl. In some embodiments of Formula Id, $R^3$ is —(C═N—OCH$_3$)—CH$_3$.

In some embodiments of Formula I, the compound has a chemical structure of Formula Ie:

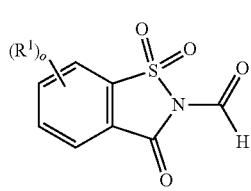

(Ie)

wherein R¹ and o are defined as above. In some embodiments of Formula Ie, $R^1$ is methyl. In some embodiment of Formula Ie, o is 1.

In some embodiments of Formula I, the compound has a chemical structure of Formula If:

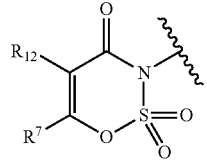

(If)

wherein $R^7$ and $R^{12}$ are defined as above. In some embodiments of Formula If, $R^7$ is methyl. In some embodiments of Formula If, $R^{12}$ is hydrogen.

In some embodiments of Formula I, the compound has a chemical structure of Formula Ig:

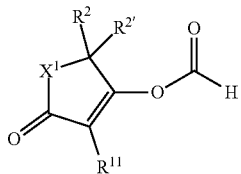

(Ig)

wherein $R^2$, $R^{2'}$, $R^{11}$, and $X^1$ are defined as above. In some embodiments of Formula Ig, $X^1$ is $CH_2$. In some embodiments of Formula Ig, $X^1$ is O. In some embodiments of Formula Ig, $X^1$ is S. In some embodiments of Formula Ig, $X^1$ is NH. In some embodiments of Formula Ig, $R^2$ and $R^{2'}$ are both hydrogen. In some embodiments of Formula Ig, $R^2$ and $R^{2'}$ are both methyl. In some embodiments of Formula Ig, $R^{11}$ is methyl. In some embodiments of Formula Ig, $R^{11}$ is hydrogen.

In some embodiments of Formula I, the compound has a chemical structure of Formula Ih:

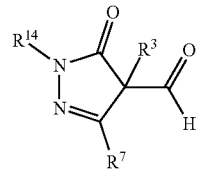

(Ih)

wherein $R^3$, $R^7$, and $R^{14}$ are defined as above.

In some embodiments of Formula Ih, $R^3$ is methyl. In some embodiments of Formula Ih, $R^7$ is methyl. In some embodiments of Formula Ih, $R^{14}$ is methyl. In some embodiments of Formula Ih, $R^{14}$ is phenyl. In some embodiments of Formula Ih, $R^{14}$ is hydrogen.

In some embodiments, a compound of Formula II is provided:

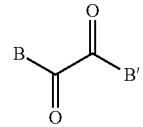

(II)

or a pharmaceutically acceptable salt thereof;
wherein B and B' are defined as above.

In some embodiments, the compound has a chemical structure of Formula IIa:

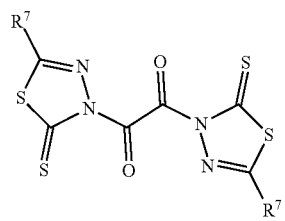

(IIa)

Wherein $R^7$ is defined as above. In one embodiment of Formula IIa, $R^7$ is methyl.

In some embodiments of Formula II, Formula IIb:

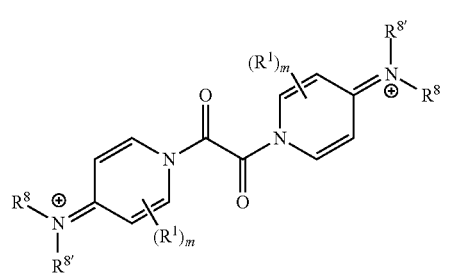

(IIb)

wherein $R^1$, m, $R^8$, and $R^{8'}$ are defined as above. In some embodiments of Formula IIb, m is 0. In some embodiments of Formula IIb, $R^8$ and $R^{8'}$ are both methyl.

In some embodiments of Formula II, the compound has a chemical structure of Formula IIc:

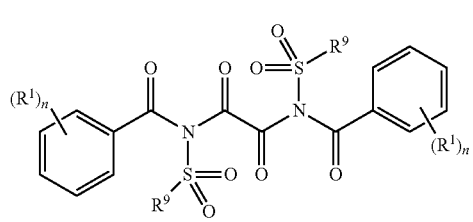

(IIc)

wherein $R^1$ and n are defined as above. In some embodiments of Formula IIc, $R^9$ is methyl. In some embodiments of Formula IIc, $R^9$ is phenyl. In some embodiments of Formula IIc, n is 0.

In some embodiments of Formula II, the compound has a chemical structure of Formula IId:

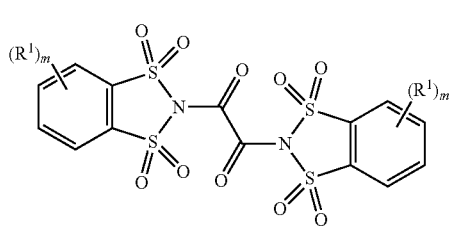

(IId)

wherein $R^1$ and m are defined as above. In one embodiment of Formula IId, m is 0.

In some embodiments of Formula II, the compound has a chemical structure of Formula IIe:

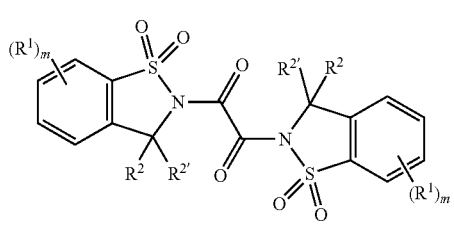

(IIe)

wherein $R^1$, m, $R^2$, and $R^{2'}$ are defined as above. In some embodiments of Formula IIe, m is 0. In some embodiments of Formula IIe, $R^2$ and $R^{2'}$ are both hydrogen.

In some embodiments of Formula II, the compound has a chemical structure of Formula IIf:

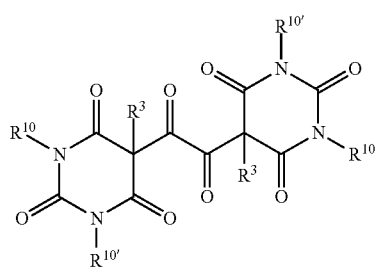

(IIf)

wherein $R^3$, $R^{10}$, and $R^{10'}$ are defined as above. In some embodiments of Formula IIf, $R^3$ is methyl. In some embodiments of Formula IIf, $R^3$ is —(C=N—OCH$_3$)—CH$_3$. In some embodiments of Formula IIf, $R^{10}$ and $R^{10'}$ are both methyl. In some embodiments of Formula IIf, $R^{10}$ and $R^{10'}$ are both hydrogen.

In some embodiments of Formula II, the compound has a chemical structure of Formula IIg:

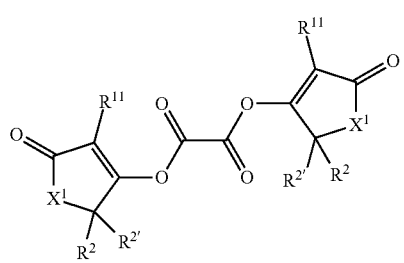

(IIg)

wherein $X^1$, $R^2$, $R^{2'}$ and $R^{11}$ are defined as above. In some embodiments of Formula IIg, $X^1$ is CH$_2$. In some embodiments of Formula IIg, $X^1$ is O. In some embodiments of Formula IIg, $X^1$ is S. In some embodiments of Formula IIg, $X^1$ is NH. In some embodiments of Formula IIg, $R^2$ and $R^{2'}$ are both hydrogen. In some embodiments of Formula IIg, $R^{11}$ is hydrogen.

In some embodiments of Formula II, the compound has a chemical structure of Formula IIh:

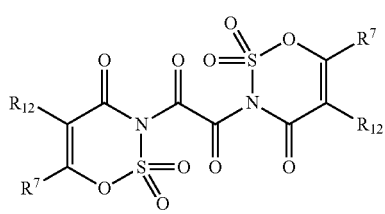

(IIh)

Wherein $R^7$ and $R^{12}$ are defined as above. In some embodiments of Formula IIh, $R^7$ is methyl. In some embodiments of Formula IIh, $R^{12}$ is hydrogen.

In some embodiments of Formula II, the compound has a chemical structure of Formula IIi:

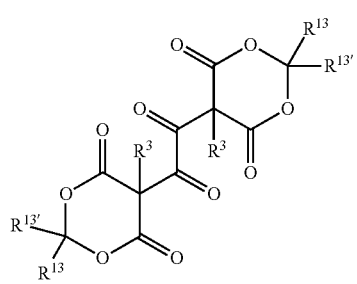

(IIi)

wherein $R^3$, $R^{13}$, and R are defined as above. In some embodiments of Formula IIi, $R^{13}$ and $R^{13'}$ are both methyl. In some embodiments of Formula IIi, $R^3$ is methyl. In some embodiments of Formula IIi, $R^3$ is —(C=N—OCH$_3$)—CH$_3$.

In some embodiments of Formula II, the compound has a chemical structure of Formula IIj:

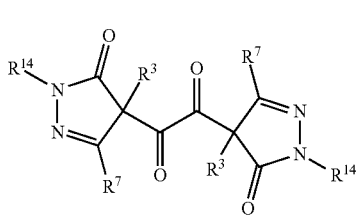

(IIj)

wherein $R^3$, $R^7$, and $R^{14}$ are defined as above. In some embodiments of Formula IIj, $R^3$ is methyl. In some embodiments of Formula IIj, $R^{13}$ is methyl. In some embodiments of Formula IIj, $R^7$ is methyl.

In some embodiments of Formula II, the compound has a chemical structure of Formula IIk:

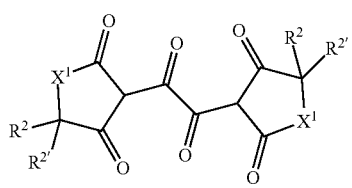
(IIk)

Wherein $R^2$, $R^{2'}$, and $X^1$ are defined as above. In some embodiments of Formula IIk, $R^2$ and $R^{2'}$ are both hydrogen. In some embodiments of Formula IIk, $X^1$ is —$CH_2$—. In some embodiments of Formula IIk, $X^1$ is O. In some embodiments of Formula IIk, $X^1$ is NH. In some embodiments of Formula IIk, $X^1$ is S.

In some embodiments of Formula II, the compound has a chemical structure of Formula IIl:

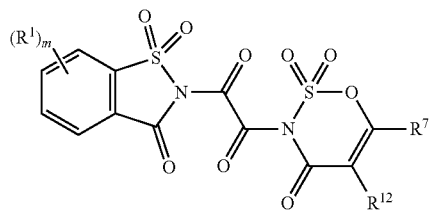
(IIl)

wherein $R^1$, $R^7$, $R^{12}$, and m are defined as above. In some embodiments of Formula IIl, m is 0. In some embodiments of Formula IIl, $R^7$ is methyl. In some embodiments of Formula IIl, $R^{12}$ is hydrogen.

In some embodiments of Formula II, the compound has a chemical structure of Formula IIm:

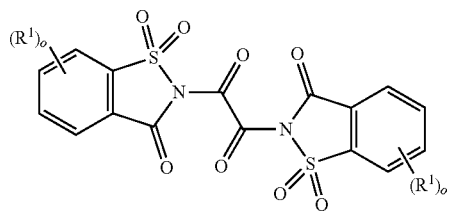
(IIm)

wherein $R^1$ and o are defined as above.

In some embodiments of Formula II, the compound has a chemical structure of Formula IIn:

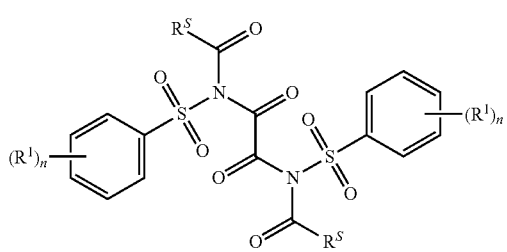
(IIn)

Wherein $R^1$, $R^S$, and n are defined as above.

In some embodiments, a compound of Formula III is provided:

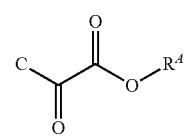
(III)

or a pharmaceutically acceptable salt thereof;
wherein C and $R^4$ are defined as above.

In some embodiments of Formula III, the compound has a chemical structure of Formula IIIa:

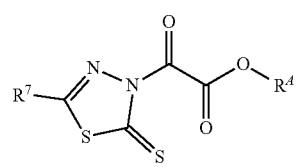
(IIIa)

wherein $R^7$ and $R^4$ are defined as above. In some embodiments of Formula IIIa, $R^7$ is methyl. In some embodiments of Formula IIIa, $R^4$ is hydrogen. In some embodiments of Formula IIIa, $R^4$ is methyl. In some embodiments of Formula IIIa, $R^4$ is phenyl.

In some embodiments of Formula III, the compound has a chemical structure of Formula IIIb:

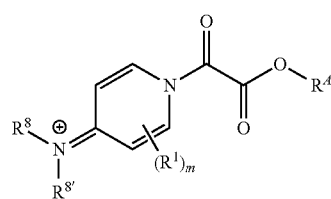
(IIIb)

wherein $R^1$, m, $R^8$, $R^{8'}$, and $R^4$ are defined as above. In some embodiments of Formula IIIb, m is 0. In some embodiments of Formula IIIb, $R^8$ and $R^{8'}$ are both methyl. In some embodiments of Formula IIIb, $R^4$ is methyl. In some embodiments of Formula IIIb, $R^4$ is phenyl.

In some embodiments of Formula III, the compound has a chemical structure of Formula IIIc:

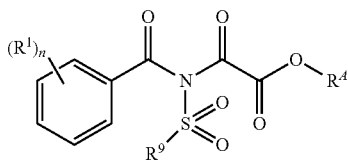
(IIIc)

wherein $R^1$, n, $R^9$, and $R^4$ are defined as above. In some embodiments of Formula IIIc, n is 0. In some embodiments of Formula IIIc, $R^9$ is methyl. In some embodiments of Formula IIIc, $R^9$ is phenyl. In some embodiments of Formula IIIc, $R^4$ is methyl. In some embodiments of Formula IIIc, $R^4$ is phenyl.

In some embodiments of Formula III, the compound has a chemical structure of Formula IIId:

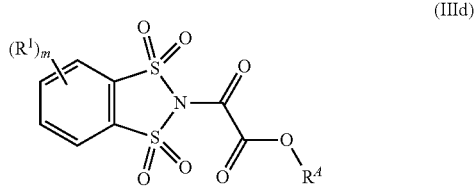

(IIId)

wherein $R^1$, m, and $R^4$ are defined as above. In some embodiments of Formula IIId, m is 0. In some embodiments of Formula IIId, $R^4$ is methyl. In some embodiments of Formula IIId, $R^4$ is phenyl.

In some embodiments of Formula III, the compound has a chemical structure of Formula IIIe:

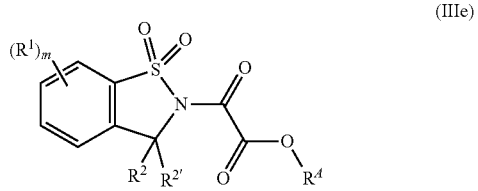

(IIIe)

wherein $R^1$, m, $R^2$, $R^{2'}$, and $R^4$ are defined as above. In some embodiments of Formula IIIe, m is 0. In some embodiments of Formula IIIe, both $R^2$ and $R^{2'}$ are methyl. In some embodiments of Formula IIIe, $R^4$ is methyl. In some embodiments of Formula IIIe, $R^4$ is phenyl.

In some embodiments of Formula III, the compound has a chemical structure of Formula IIIf:

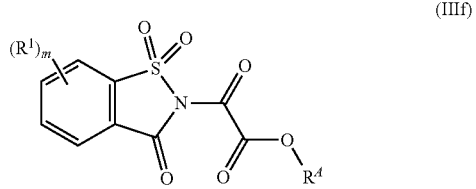

(IIIf)

wherein $R^1$, m, and $R^4$ are defined as above. In some embodiments of Formula IIIf, m is 0. In some embodiments of Formula IIIf, $R^4$ is methyl. In some embodiments of Formula IIIf, $R^4$ is phenyl.

In some embodiments of Formula III, the compound has a chemical structure of Formula IIIg:

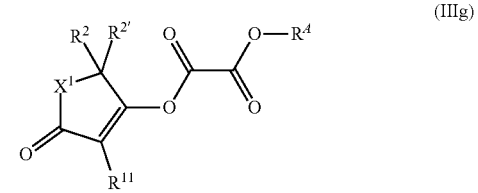

(IIIg)

wherein $R^2$, $R^{2'}$, $R^{11}$, and $R^4$ are defined as above. In some embodiments of Formula IIIg, $X^1$ is $CH_2$. In some embodiments of Formula IIIg, $X^1$ is O. In some embodiments of Formula IIIg, $X^1$ is S. In some embodiments of Formula IIIg, $X^1$ is NH. In some embodiments of Formula IIIg, $R^2$ and $R^{2'}$ are both hydrogen. In some embodiments of Formula IIIg, $R^{11}$ is hydrogen. In some embodiments of Formula IIIg, $R^4$ is methyl. In some embodiments of Formula IIIg, $R^4$ is phenyl.

In some embodiments of Formula III, the compound has a chemical structure of Formula IIIh:

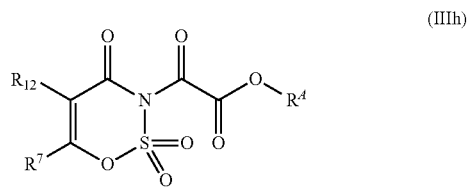

(IIIh)

wherein $R^7$, $R^{12}$, and $R^4$ are defined as above. In some embodiments of Formula IIIh, $R^7$ is methyl. In some embodiments of Formula IIIh, $R^7$ is hydrogen. In some embodiments of Formula IIIh, $R^4$ is methyl. In some embodiments of Formula IIIh, $R^4$ is phenyl. In some alternative embodiments of Formula IIIh, $R^7$ is methyl and $R^{12}$ is hydrogen.

In some embodiments of Formula III, the compound has a chemical structure of Formula IIi:

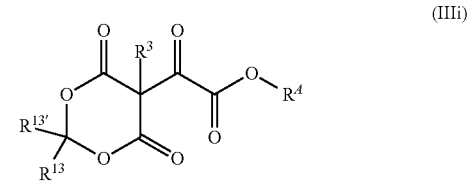

(IIIi)

wherein $R^3$, $R^{13}$, $R^{13'}$, and $R^4$ are defined as above. In some embodiments of Formula IIi, $R^3$ is methyl. In some embodiments of Formula IIIi, $R^3$ is —(C=N—OCH$_3$)—CH$_3$. In some embodiments of Formula IIIi, $R^{13}$ and $R^{13'}$ are both methyl. In some embodiments of Formula IIi, $R^4$ is methyl. In some embodiments of Formula IIIi, $R^4$ is phenyl.

In some embodiments of Formula III, the compound has a chemical structure of Formula IIIj:

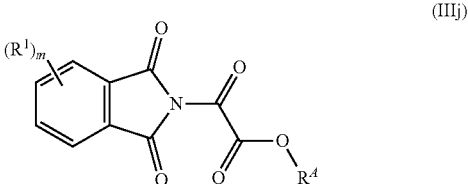

(IIIj)

wherein $R^1$, m, and $R^4$ are defined as above. In some embodiments of Formula IIIj, m is 0. In some embodiments of Formula IIIj, $R^4$ is methyl. In some embodiments of Formula IIIj, $R^4$ is phenyl.

In some embodiments of Formula III, the compound has a chemical structure of Formula IIIk:

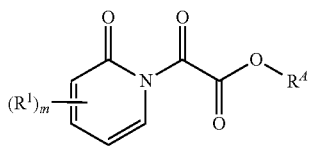

(IIIk)

wherein $R^1$, m, and $R^4$ are defined as above. In some embodiments of Formula IIIk, m is 0. In some embodiments of Formula IIIk, $R^4$ is methyl. In some embodiments of Formula IIIk, $R^4$ is phenyl.

In some embodiments of Formula III, the compound has a chemical structure of Formula IIII:

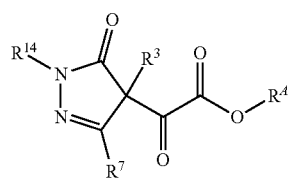

(IIII)

wherein $R^3$, $R^7$, $R^{14}$, and $R^4$ are defined as above. In some embodiments of Formula IIII, $R^3$ is methyl. In some embodiments of Formula IIII, $R^3$ is —(C=N—OCH$_3$)—CH$_3$. In some embodiments of Formula IIII, $R^7$ is methyl. In some embodiments of Formula IIII, $R^{14}$ is methyl. In some embodiments of Formula IIII, $R^4$ is methyl. In some embodiments of Formula IIII, $R^4$ is phenyl.

In some embodiments of Formula III, the compound has a chemical structure of Formula IIIm:

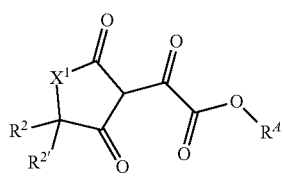

(IIIm)

Wherein $R^2$, $R^{2'}$, $R^4$, and $X^1$ are defined as above. In some embodiments of Formula IIIm, $X^1$ is CH$_2$. In some embodiments of Formula IIIm, $X^1$ is O. In some embodiments of Formula IIIm, $X^1$ is NH. In some embodiments of Formula IIIm, $X^1$ is S. In some embodiments of Formula IIIm, $R^2$ and $R^{2'}$ are both methyl. In some embodiments of Formula IIIm, $R^2$ and $R^{2'}$ are both hydrogen. In some embodiments of Formula IIIm, $R^4$ is methyl. In some embodiments of Formula IIIm, $R^4$ is phenyl.

In some embodiments of Formula III, the compound has a chemical structure of Formula IIIn:

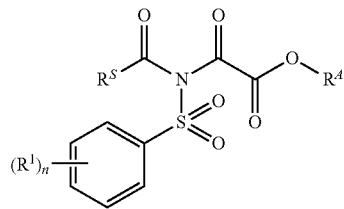

(IIIn)

wherein $R^1$, $R^S$, $R^4$, and n are defined as above.

In one embodiment of any one of Formulas I, II, or III,

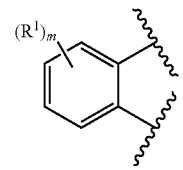

is selected from:

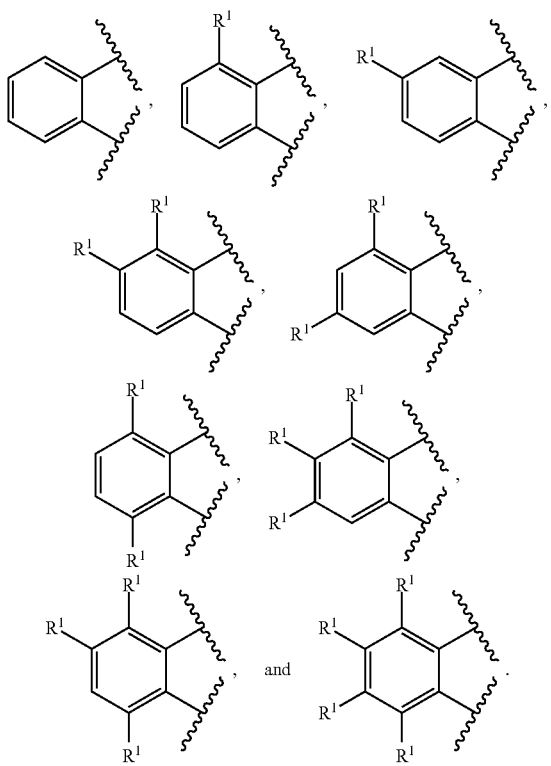

In one embodiment of any one of Formula II or III,

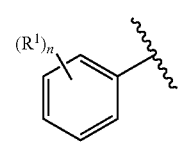

is selected from:

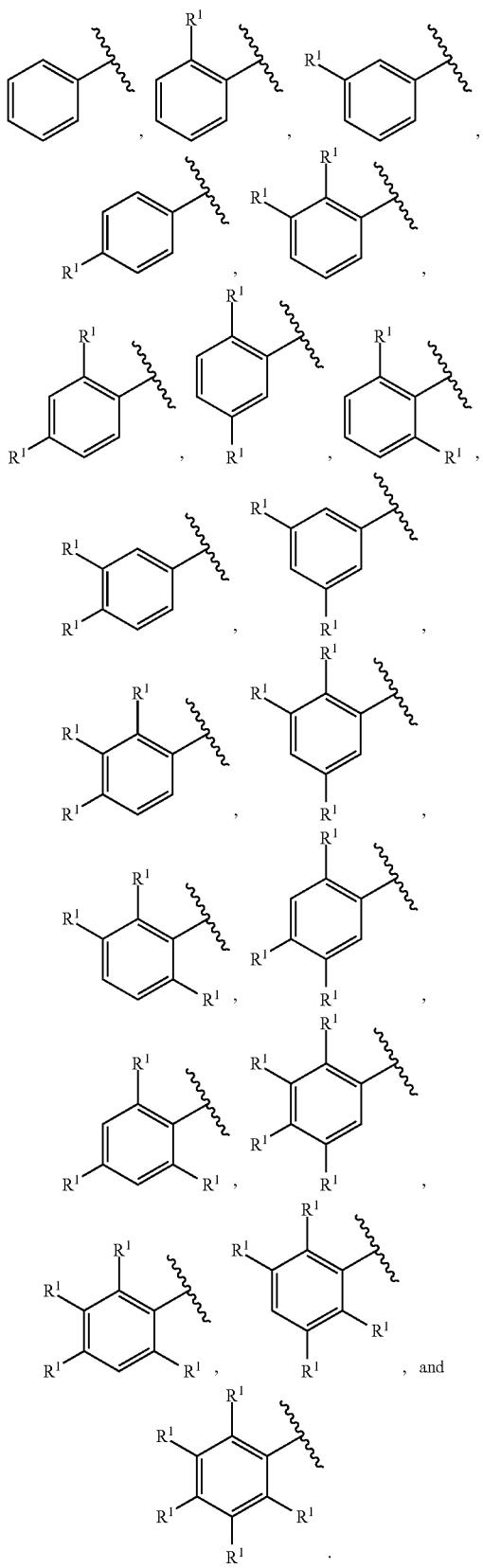

In one embodiment of any one of Formulas I, II, or III, $R^1$ is halogen. In one embodiment of any one of Formulas I, II, or III, $R^1$ is fluoro. In one embodiment of any one of Formulas I, II, or III, $R^1$ is chloro. In one embodiment of any one of Formulas I, II, or III, $R^1$ is bromo. In one embodiment of any one of Formulas I, II, or III, $R^1$ is iodo. In one embodiment of any one of Formulas I, II, or III, $R^1$ is hydroxyl. In one embodiment of any one of Formulas I, II, or III, $R^1$ is alkyl. In one embodiment of any one of Formulas I, II, or III, $R^1$ is methyl. In one embodiment of any one of Formulas I, II, or III, $R^1$ is haloalkyl. In one embodiment of any one of Formulas I, II, or III, $R^1$ is trifluoromethyl. In one embodiment of any one of Formulas I, II, or III, $R^1$ is trichloromethyl. In one embodiment of any one of Formulas I, II, or III, $R^1$ is alkoxy. In one embodiment of any one of Formulas I, II, or III, $R^1$ is methoxy. In one embodiment of any one of Formulas I, II, or III, $R^1$ is haloalkoxy. In one embodiment of any one of Formulas I, II, or III, $R^1$ is trifluoromethoxy. In one embodiment of any one of Formulas I, II, or III, $R^1$ is aryl. In one embodiment of any one of Formulas I, II, or III, $R^1$ is phenyl. In one embodiment of any one of Formulas I, II, or III, $R^1$ is naphthyl. In one embodiment of any one of Formulas I, II, or III, $R^1$ is heteroaryl. In one embodiment of any one of Formulas I, II, or III, $R^1$ is thiol. In one embodiment of any one of Formulas I, II, or III, $R^1$ is thioalkyl. In one embodiment of any one of Formulas I, II, or III, $R^1$ is thiomethyl. In one embodiment of any one of Formulas I, II, or III, $R^1$ is —$SO_3H$. In one embodiment of any one of Formulas I, II, or III, $R^1$ is —(P=O)(OH)$_2$. In one embodiment of any one of Formulas I, II, or III, $R^1$ is —(P=O)(OH)$_2$. In one embodiment of any one of Formulas I, II, or III, $R^1$ is formyl. In one embodiment of any one of Formulas I, II, or III, $R^1$ is acetyl. In one embodiment of any one of Formulas I, II, or III, $R^1$ is acetoxy. In one embodiment of any one of Formulas III, or III, $R^1$ is cyano. In one alternative embodiment of any one of Formulas III, or III, $R^1$ is an azido.

In one embodiment of any one of Formulas I, II, or III, $R^{14}$ is halogen. In one embodiment of any one of Formulas I, II, or III, $R^{14}$ is fluoro. In one embodiment of any one of Formulas I, II, or III, $R^{14}$ is chloro. In one embodiment of any one of Formulas I, II, or III, $R^{14}$ is bromo. In one embodiment of any one of Formulas I, II, or III, $R^{14}$ is iodo. In one embodiment of any one of Formulas I, II, or III, $R^{14}$ is hydroxyl. In one embodiment of any one of Formulas I, II, or III, $R^{14}$ is alkyl. In one embodiment of any one of Formulas I, II, or III, $R^{14}$ is methyl. In one embodiment of any one of Formulas I, II, or III, $R^{14}$ is haloalkyl. In one embodiment of any one of Formulas I, II, or III, $R^{14}$ is trifluoromethyl. In one embodiment of any one of Formulas I, II, or III, $R^{14}$ is trichloromethyl. In one embodiment of any one of Formulas I, II, or III, $R^{14}$ is alkoxy. In one embodiment of any one of Formulas I, II, or III, $R^{14}$ is methoxy. In one embodiment of any one of Formulas I, II, or III, $R^{14}$ is haloalkoxy. In one embodiment of any one of Formulas I, II, or III, $R^{14}$ is trifluoromethoxy. In one embodiment of any one of Formulas I, II, or III, $R^{14}$ is aryl. In one embodiment of any one of Formulas I, II, or III, $R^{14}$ is phenyl. In one embodiment of any one of Formulas I, II, or III, $R^{14}$ is naphthyl. In one embodiment of any one of Formulas I, II, or III, $R^{14}$ is heteroaryl. In one embodiment of any one of Formulas I, II, or III, $R^{14}$ is thiol. In one embodiment of any one of Formulas I, II, or III, $R^{14}$ is thioalkyl. In one embodiment of any one of Formulas I, II, or III, $R^{14}$ is thiomethyl. In one embodiment of any one of Formulas I, II, or III, $R^{14}$ is —$SO_3H$. In one embodiment of any one of Formulas I, II, or III, $R^{14}$ is —(P=O)(OH)$_2$. In one embodiment of any one of Formulas I, II, or III, $R^{14}$ is —(P=O)(OH)$_2$. In one embodiment of any one of Formulas I, II, or III, $R^{1A}$ is acetyl. In one embodiment of any one of Formulas I, II, or III, $R^{1A}$ is acetoxy. In one embodiment of any one of Formulas III, or III, $R^{1A}$ is cyano.

In one embodiment of any one of Formulas I, II, or III, $R^S$ is hydrogen. In one embodiment of any one of Formula I, II, or III, $R^S$ is methyl. In one embodiment of any one of Formula I, II, or III, $R^S$ is trifluoromethyl. In one embodiment of any one of Formula I, II, or III, $R^S$ is methoxy. In one embodiment of any one of Formula I, II, or III, $R^S$ is ethoxy. In one embodiment of any one of Formula I, II, or III, $R^S$ is —$NH_2$. In one embodiment of any one of Formula I, II, or III, $R^S$ is —$NHCH_3$. In one embodiment of any one of Formula I, II, or III, $R^S$ is —$N(CH_3)_2$. In one embodiment of any one of Formula I, II, or III, $R^S$ is phenyl. In one embodiment of any one of Formula I, II, or III, $R^S$ is heteroaryl.

In one embodiment of any one of Formulas I, II, or III, m is 0. In one embodiment of any one of Formulas I, II, or III, m is 1. In one embodiment of any one of Formulas I, II, or III, m is 2. In one embodiment of any one of Formulas I, II, or III, m is 3. In one embodiment of any one of Formulas I, II, or III, m is 4.

In one embodiment of any one of Formulas II or III, n is 0. In one embodiment of any one of Formulas II or III, n is 1. In one embodiment of any one of Formulas II or III, n is 2. In one embodiment of any one of Formulas II or III, n is 3. In one embodiment of any one of Formulas II or III, n is 4. In one embodiment of any one of Formulas II or III, n is 5.

In one embodiment of Formula I, o is 1. In one embodiment of Formula I, o is 2. In one embodiment of Formula I, o is 3. In one embodiment of Formula I, o is 4.

In one embodiment of any one of Formulas I, II, or III, $R^2$ is hydrogen. In one embodiment of any one of Formulas I, II, or III, $R^2$ is alkyl. In one embodiment of any one of Formulas I, II, or III, $R^2$ is methyl. In one embodiment of any one of Formulas I, II, or III, $R^2$ is haloalkyl. In one embodiment of any one of Formulas I, II, or III, $R^2$ is trifluoromethyl. In one embodiment of any one of Formulas I, II, or III, $R^2$ is trichloromethyl. In one embodiment of any one of Formulas I, II, or III, $R^2$ is aryl. In one embodiment of any one of Formulas I, II, or III, $R^2$ is phenyl. In one embodiment of any one of Formulas I, II, or III, $R^2$ is naphthyl. In one embodiment of any one of Formulas I, II, or III, $R^2$ is heteroaryl.

In one embodiment of any one of Formulas I, II, or III, $R^{2'}$ is hydrogen. In one embodiment of any one of Formulas I, II, or III, $R^{2'}$ is alkyl. In one embodiment of any one of Formulas I, II, or III, $R^{2'}$ is methyl. In one embodiment of any one of Formulas I, II, or III, $R^{2'}$ is haloalkyl. In one embodiment of any one of Formulas I, II, or III, $R^{2'}$ is trifluoromethyl. In one embodiment of any one of Formulas I, II, or III, $R^{2'}$ is trichloromethyl. In one embodiment of any one of Formulas I, II, or III, $R^{2'}$ is aryl. In one embodiment of any one of Formulas I, II, or III, $R^{2'}$ is phenyl. In one embodiment of any one of Formulas I, II, or III, $R^{2'}$ is naphthyl. In one embodiment of any one of Formulas I, II, or III, $R^{2'}$ is heteroaryl.

In one embodiment of any one of Formulas I, II, or III, $X^1$ is —$C(R^5)(R^{5'})$—. In one embodiment of any one of Formulas I, II, or III, $X^1$ is $CH_2$. In one embodiment of any one of Formulas I, II, or III, $X^1$ is —$N(R^{5''})$—. In one embodiment of any one of Formulas I, II, or III, $X^1$ is NH. In one embodiment of any one of Formulas I, II, or III, $X^1$ is $N(CH_3)$. In one embodiment of any one of Formulas I, II, or III, $X^1$ is O. In one embodiment of any one of Formulas I, II, or III, $X^1$ is S.

In one embodiment of any one of Formulas I, II, or III, $R^3$ is halogen. In one embodiment of any one of Formulas I, II, or III, $R^3$ is fluoro. In one embodiment of any one of Formulas I, II, or III, $R^3$ is chloro. In one embodiment of any one of Formulas I, II, or III, $R^3$ is bromo. In one embodiment of any one of Formulas I, II, or III, $R^3$ is iodo. In one embodiment of any one of Formulas I, II, or III, $R^3$ is alkyl. In one embodiment of any one of Formulas I, II, or III, $R^3$ is methyl. In one embodiment of any one of Formulas I, II, or III, $R^3$ is haloalkyl. In one embodiment of any one of Formulas I, II, or III, $R^3$ is trifluoromethyl. In one embodiment of any one of Formulas I, II, or III, $R^3$ is trichloromethyl. In one embodiment of any one of Formulas I, II, or III, $R^3$ is aryl. In one embodiment of any one of Formulas I, II, or III, $R^3$ is phenyl. In one embodiment of any one of Formulas I, II, or III, $R^3$ is naphthyl. In one embodiment of any one of Formulas I, II, or III, $R^3$ is heteroaryl. In one embodiment of any one of Formulas I, II, or III, $R^3$ is —(C=N—$OCH_3$)—$CH_3$.

In one embodiment of Formula I, $R^4$ is methyl. In one embodiment of Formula I, $R^{4'}$ is methyl.

In one embodiment of any one of Formulas I, II, or III, $R^5$ is hydrogen. In one embodiment of any one of Formulas I, II, or III, $R^5$ is halogen. In one embodiment of any one of Formulas I, II, or III, $R^5$ is fluoro. In one embodiment of any one of Formulas I, II, or III, $R^5$ is chloro. In one embodiment of any one of Formulas I, II, or III, $R^5$ is bromo. In one embodiment of any one of Formulas I, II, or III, $R^5$ is iodo. In one embodiment of any one of Formulas I, II, or III, $R^5$ is hydroxyl. In one embodiment of any one of Formulas I, II, or III, $R^5$ is alkyl. In one embodiment of any one of Formulas I, II, or III, $R^5$ is methyl. In one embodiment of any one of Formulas I, II, or III, $R^5$ is haloalkyl. In one embodiment of any one of Formulas I, II, or III, $R^5$ is trifluoromethyl. In one embodiment of any one of Formulas I, II, or III, $R^5$ is trichloromethyl. In one embodiment of any one of Formulas I, II, or III, $R^5$ is aryl. In one embodiment of any one of Formulas I, II, or III, $R^5$ is phenyl. In one embodiment of any one of Formulas I, II, or III, $R^5$ is naphthyl. In one embodiment of any one of Formulas I, II, or III, $R^5$ is heteroaryl.

In one embodiment of any one of Formulas I, II, or III, $R^{5'}$ is hydrogen. In one embodiment of any one of Formulas I, II, or III, $R^{5'}$ is halogen. In one embodiment of any one of Formulas I, II, or III, $R^{5'}$ is fluoro. In one embodiment of any one of Formulas I, II, or III, $R^{5'}$ is chloro. In one embodiment of any one of Formulas I, II, or III, $R^{5'}$ is bromo. In one embodiment of any one of Formulas I, II, or III, $R^{5'}$ is iodo. In one embodiment of any one of Formulas I, II, or III, $R^{5'}$ is hydroxyl. In one embodiment of any one of Formulas I, II, or III, $R^{5'}$ is alkyl. In one embodiment of any one of Formulas I, II, or III, $R^{5'}$ is methyl. In one embodiment of any one of Formulas I, II, or III, $R^{5'}$ is haloalkyl. In one embodiment of any one of Formulas I, II, or III, $R^{5'}$ is trifluoromethyl. In one embodiment of any one of Formulas I, II, or III, $R^{5'}$ is trichloromethyl. In one embodiment of any one of Formulas I, II, or III, $R^{5'}$ is aryl. In one embodiment of any one of Formulas I, II, or III, $R^{5'}$ is phenyl. In one embodiment of any one of Formulas I, II, or III, $R^{5'}$ is naphthyl. In one embodiment of any one of Formulas I, II, or III, $R^{5'}$ is heteroaryl.

In one embodiment of any one of Formulas I, II, or III, $R^{5''}$ is hydrogen. In one embodiment of any one of Formulas I, II, or III, $R^{5''}$ is alkyl. In one embodiment of any one of Formulas I, II, or III, $R^{5''}$ is methyl. In one embodiment of any one of Formulas I, II, or III, $R^{5''}$ is aryl. In one embodiment of any one of Formulas I, II, or III, $R^{5''}$ is phenyl. In one embodiment of any one of Formulas I, II, or III, $R^{5''}$ is naphthyl. In one embodiment of any one of Formulas I, II, or III, $R^{5''}$ is heteroaryl.

In one embodiment of any one of Formula I, II, or III, $R^6$ is hydrogen. In one embodiment of any one of Formula I, II, or III, $R^6$ is alkyl. In one embodiment of any one of Formula I, II, or III, $R^6$ is methyl. In one embodiment of any one of Formula I, II, or III, $R^6$ is haloalkyl. In one embodiment of any one of Formula I, II, or III, $R^6$ is trifluoromethyl. In one embodiment of any one of Formula I, II, or III, $R^6$ is trichloromethyl. In one embodiment of any one of Formula I, II, or III, $R^6$ is aryl. In one embodiment of any one of Formula I, II, or III, $R^6$ is phenyl. In one embodiment of any one of Formula I, II, or III, $R^6$ is naphthyl. In one embodiment of any one of Formula I, II, or III, $R^6$ is heteroaryl.

In one embodiment of any one of Formula I, II, or III, $R^{6'}$ is hydrogen. In one embodiment of any one of Formula I, II, or III, $R^{6'}$ is alkyl. In one embodiment of any one of Formula I, II, or III, $R^{6'}$ is methyl. In one embodiment of any one of Formula I, II, or III, $R^{6'}$ is haloalkyl. In one embodiment of any one of Formula I, II, or III, $R^{6'}$ is trifluoromethyl. In one embodiment of any one of Formula I, II, or III, $R^{6'}$ is trichloromethyl. In one embodiment of any one of Formula I, II, or III, $R^{6'}$ is aryl. In one embodiment of any one of Formula I, II, or III, $R^{6'}$ is phenyl. In one embodiment of any one of Formula I, II, or III, $R^{6'}$ is naphthyl. In one embodiment of any one of Formula I, II, or III, $R^{6'}$ is heteroaryl.

In one embodiment of any one of Formula I, II, or III, $R^7$ is hydrogen. In one embodiment of any one of Formula I, II, or III, $R^7$ is alkyl. In one embodiment of any one of Formula I, II, or III, $R^7$ is methyl. In one embodiment of any one of Formula I, II, or III, $R^7$ is haloalkyl. In one embodiment of any one of Formula I, II, or III, $R^7$ is trifluoromethyl. In one embodiment of any one of Formula I, II, or III, $R^7$ is trichloromethyl. In one embodiment of any one of Formula I, II, or III, $R^7$ is aryl. In one embodiment of any one of Formula I, II, or III, $R^7$ is phenyl. In one embodiment of any one of Formula I, II, or III, $R^7$ is naphthyl. In one embodiment of any one of Formula I, II, or III, $R^7$ is heteroaryl. In one alternative embodiment of any one of Formula I, II, or III, $R^7$ is an azido.

In one embodiment of any one of Formula II or III, $R^8$ is alkyl. In one embodiment of any one of Formula II or III, $R^8$ is methyl. In one embodiment of any one of Formula II or III, $R^8$ is aryl. In one embodiment of any one of Formula II or III, $R^8$ is phenyl. In one embodiment of any one of Formula II or III, $R^8$ is naphthyl.

In one embodiment of any one of Formula II or III, $R^{8'}$ is alkyl. In one embodiment of any one of Formula II or III, $R^{8'}$ is methyl. In one embodiment of any one of Formula II or III, $R^{8'}$ is aryl. In one embodiment of any one of Formula II or III, $R^{8'}$ is phenyl. In one embodiment of any one of Formula II or III, $R^{8'}$ is naphthyl.

In one embodiment of any one of Formula II or III, $R^9$ is alkyl. In one embodiment of any one of Formula II or III, $R^9$ is methyl. In one embodiment of any one of Formula II or III, $R^9$ is aryl. In one embodiment of any one of Formula II or III, $R^9$ is phenyl. In one embodiment of any one of Formula II or III, $R^9$ is naphthyl. In one embodiment of any one of Formula II or III, $R^9$ is heteroaryl.

In one embodiment of Formula II, $R^{10}$ is alkyl. In one embodiment of Formula II, $R^{10}$ is methyl. In one embodiment of Formula II, $R^{10}$ is aryl. In one embodiment of Formula II, $R^{10}$ is phenyl. In one embodiment of Formula II, $R^{10}$ is naphthyl. In one embodiment of Formula II, $R^{10}$ is heteroaryl.

In one embodiment of Formula II, $R^{10'}$ is alkyl. In one embodiment of Formula II, $R^{10'}$ is methyl. In one embodiment of Formula II, $R^{10'}$ is aryl. In one embodiment of Formula II, $R^{10'}$ is phenyl. In one embodiment of Formula II, $R^{10'}$ is naphthyl. In one embodiment of Formula II, $R^{10'}$ is heteroaryl.

In one embodiment of any one of Formula II or III, $R^{11}$ is hydrogen. In one embodiment of any one of Formula II or III, $R^{11}$ is halogen. In one embodiment of any one of Formula II or III, $R^{11}$ is fluoro. In one embodiment of any one of Formula II or III, $R^{11}$ is chloro. In one embodiment of any one of Formula II or III, $R^{11}$ is bromo. In one embodiment of any one of Formula II or III, $R^{11}$ is iodo. In one embodiment of any one of Formula II or III, $R^{11}$ is alkyl. In one embodiment of any one of Formula II or III, $R^{11}$ is methyl. In one embodiment of any one of Formula II or III, $R^{11}$ is haloalkyl. In one embodiment of any one of Formula II or III, $R^{11}$ is trifluoromethyl. In one embodiment of any one of Formula II or III, $R^{11}$ is trichloromethyl. In one embodiment of any one of Formula II or III, $R^{11}$ is aryl. In one embodiment of any one of Formula II or III, $R^{11}$ is phenyl. In one embodiment of any one of Formula II or III, $R^{11}$ is naphthyl. In one embodiment of any one of Formula II or III, $R^{11}$ is heteroaryl.

In one embodiment of any one of Formula I, II, or III, $R^{12}$ is hydrogen. In one embodiment of any one of Formula I, II, or III, $R^{12}$ is halogen. In one embodiment of any one of Formula I, II, or III, $R^{12}$ is fluoro. In one embodiment of any one of Formula I, II, or III, $R^{12}$ is chloro. In one embodiment of any one of Formula I, II, or III, $R^{12}$ is bromo. In one embodiment of any one of Formula I, II, or III, $R^{12}$ is iodo. In one embodiment of any one of Formula I, II, or III, $R^{12}$ is alkyl.

In one embodiment of any one of Formula I, II, or III, $R^{12}$ is methyl. In one embodiment of any one of Formula I, II, or III, $R^{12}$ is haloalkyl. In one embodiment of any one of Formula I, II, or III, $R^{12}$ is trifluoromethyl. In one embodiment of any one of Formula I, II, or III, $R^{12}$ is trichloromethyl.

In one embodiment of any one of Formula I, II, or III, $R^{12}$ is aryl. In one embodiment of any one of Formula I, II, or III, $R^{12}$ is phenyl. In one embodiment of any one of Formula I, II, or III, $R^{12}$ is naphthyl. In one embodiment of any one of Formula I, II, or III, $R^{12}$ is heteroaryl.

In one embodiment of any one of Formula II or III, $R^{13}$ is hydrogen. In one embodiment of any one of Formula II or III, $R^{13}$ is alkyl. In one embodiment of any one of Formula II or III, $R^{13}$ is methyl. In one embodiment of any one of Formula II or III, $R^{13}$ is methyl. In one embodiment of any one of Formula II or III, $R^{13}$ is haloalkyl. In one embodiment of any one of Formula II or III, $R^{13}$ is trifluoromethyl. In one embodiment of any one of Formula II or III, $R^{13}$ is trichloromethyl. In one embodiment of any one of Formula II or III, $R^{13}$ is aryl. In one embodiment of any one of Formula II or III, $R^{13}$ is naphthyl. In one embodiment of any one of Formula II or III, $R^{13}$ is heteroaryl.

In one embodiment of any one of Formula II or III, $R^{13'}$ is hydrogen. In one embodiment of any one of Formula II or III, $R^{13'}$ is alkyl. In one embodiment of any one of Formula II or III, $R^{13'}$ is methyl. In one embodiment of any one of Formula II or III, $R^{13'}$ is methyl. In one embodiment of any one of Formula II or III, $R^{13'}$ is haloalkyl. In one embodiment of any one of Formula II or III, $R^{13'}$ is trifluoromethyl. In one embodiment of any one of Formula II or III, $R^{13'}$ is trichloromethyl. In one embodiment of any one of Formula II or III, $R^{13'}$ is aryl. In one embodiment of any one of Formula II or III, $R^{13'}$ is naphthyl. In one embodiment of any one of Formula II or III, $R^{13'}$ is heteroaryl.

In one embodiment of any one of Formula II or III, $R^{14}$ is hydrogen. In one embodiment of any one of Formula II or III, $R^{14}$ is alkyl. In one embodiment of any one of Formula II or III, $R^{14}$ is methyl. In one embodiment of any one of Formula II or III, $R^{14}$ is aryl. In one embodiment of any one of Formula II or III, $R^{14}$ is phenyl. In one embodiment of any one of Formula II or III, $R^{14}$ is naphthyl. In one embodiment of any one of Formula II or III, $R^{14}$ is heteroaryl.

In one embodiment of Formula II, $R^{15}$ is hydrogen. In one embodiment of Formula II, $R^{15}$ is halogen. In one embodiment of Formula II, $R^{15}$ is fluoro. In one embodiment of Formula II, $R^{15}$ is chloro. In one embodiment of Formula II, $R^{15}$ is bromo. In one embodiment of Formula II, $R^{15}$ is iodo. In one embodiment of Formula II, $R^{15}$ is alkyl. In one embodiment of Formula II, $R^{15}$ is methyl. In one embodiment of Formula II, $R^{15}$ is haloalkyl. In one embodiment of Formula II, $R^{15}$ is trifluoromethyl. In one embodiment of Formula II, $R^{15}$ is trichloromethyl. In one embodiment of Formula II, $R^{15}$ is aryl. In one embodiment of Formula II, $R^{15}$ is phenyl. In one embodiment of Formula II, $R^{15}$ is naphthyl. In one embodiment of Formula II, $R^{15}$ is heteroaryl.

In one embodiment of Formula II, $R^{16}$ is alkyl. In one embodiment of Formula II, $R^{16}$ is methyl. In one embodiment of Formula II, $R^{16}$ is haloalkyl. In one embodiment of Formula II, $R^{16}$ is trifluoromethyl. In one embodiment of Formula II, $R^{16}$ is trichloromethyl. In one embodiment of Formula II, $R^{16}$ is aryl. In one embodiment of Formula II, $R^{16}$ is phenyl. In one embodiment of Formula II, $R^{16}$ is heteroaryl. In one embodiment of Formula II, $R^{16}$ is alkoxy. In one embodiment of Formula II, $R^{16}$ is methoxy. In one embodiment of Formula II, $R^{16}$ is ethoxy. In one embodiment of Formula II, $R^{16}$ is haloalkoxy. In one embodiment of Formula II, $R^{16}$ is trichloromethoxy. In one embodiment of Formula II, $R^{16}$ is aryloxy. In one embodiment of Formula II, $R^{16}$ is phenoxy. In one embodiment of Formula II, $R^{16}$ is heteroaryloxy. In one embodiment of Formula II, $R^{16}$ is amino. In one embodiment of Formula II, $R^{16}$ is alkylamino. In one embodiment of Formula II, $R^{16}$ is methylamino. In one embodiment of Formula II, $R^{16}$ is dialkylamino. In one embodiment of Formula II, $R^{16}$ is dimethylamino.

In one embodiment of Formula II, $R^{16'}$ is alkyl. In one embodiment of Formula II, $R^{16'}$ is methyl. In one embodiment of Formula II, $R^{16'}$ is haloalkyl. In one embodiment of Formula II, $R^{16'}$ is trifluoromethyl. In one embodiment of Formula II, $R^{16'}$ is trichloromethyl. In one embodiment of Formula II, $R^{16'}$ is aryl. In one embodiment of Formula II, $R^{16'}$ is phenyl. In one embodiment of Formula II, $R^{16'}$ is heteroaryl. In one embodiment of Formula II, $R^{16'}$ is alkoxy. In one embodiment of Formula II, $R^{16'}$ is methoxy. In one embodiment of Formula II, $R^{16'}$ is ethoxy. In one embodiment of Formula II, $R^{16'}$ is haloalkoxy. In one embodiment of Formula II, $R^{16'}$ is trichloromethoxy. In one embodiment of Formula II, $R^{16'}$ is aryloxy. In one embodiment of Formula II, $R^{16'}$ is phenoxy. In one embodiment of Formula II, $R^{16'}$ is heteroaryloxy. In one embodiment of Formula II, $R^{16'}$ is amino. In one embodiment of Formula II, $R^{16'}$ is alkyamino. In one embodiment of Formula II, $R^{16'}$ is methylamino. In one embodiment of Formula II, $R^{16'}$ is dialkylamino. In one embodiment of Formula II, $R^{16'}$ is dimethylamino.

In one embodiment of Formula II, $R^{17}$ is halogen. In one embodiment of Formula II, $R^{17}$ is fluoro. In one embodiment of Formula II, $R^{17}$ is chloro. In one embodiment of Formula II, $R^{17}$ is bromo. In one embodiment of Formula II, $R^{17}$ is iodo. In one embodiment of Formula II, $R^{17}$ is haloalkyl. In one embodiment of Formula II, $R^{17}$ is trifluoromethyl. In one embodiment of Formula II, $R^{17}$ is trichloromethyl. In one embodiment of Formula II, $R^{17}$ is nitro.

In one embodiment of Formula II, $R^m$ is hydrogen. In one embodiment of Formula II, $R^m$ is halogen. In one embodiment of Formula II, $R^m$ is fluoro. In one embodiment of Formula II, $R^m$ is chloro. In one embodiment of Formula II, $R^m$ is bromo. In one embodiment of Formula II, $R^m$ is iodo. In one embodiment of Formula II, $R^m$ is hydroxyl. In one embodiment of Formula II, $R^m$ is alkyl. In one embodiment of Formula II, $R^m$ is methyl. In one embodiment of Formula II, $R^m$ is haloalkyl. In one embodiment of Formula II, $R^m$ is trifluoromethyl. In one embodiment of Formula II, $R^m$ is trichloromethyl. In one embodiment of Formula II, $R^m$ is alkoxy. In one embodiment of Formula II, $R^m$ is methoxy. In one embodiment of Formula II, $R^m$ is haloalkoxy. In one embodiment of Formula II, $R^m$ is trifluoromethoxy. In one embodiment of Formula II, $R^m$ is aryl. In one embodiment of Formula II, $R^m$ is phenyl. In one embodiment of Formula II, $R^m$ is naphthyl. In one embodiment of Formula II, $R^m$ is heteroaryl.

In one embodiment of Formula II, $R^n$ is hydrogen. In one embodiment of Formula II, $R^n$ is halogen. In one embodiment of Formula II, $R^n$ is fluoro. In one embodiment of Formula II, $R^n$ is chloro. In one embodiment of Formula II, $R^n$ is bromo. In one embodiment of Formula II, $R^n$ is iodo. In one embodiment of Formula II, $R^n$ is hydroxyl. In one embodiment of Formula II, $R^n$ is alkyl. In one embodiment of Formula II, $R^n$ is methyl. In one embodiment of Formula II, $R^n$ is haloalkyl. In one embodiment of Formula II, $R^n$ is trifluoromethyl. In one embodiment of Formula II, $R^n$ is trichloromethyl. In one embodiment of Formula II, $R^n$ is alkoxy. In one embodiment of Formula II, $R^n$ is methoxy. In one embodiment of Formula II, $R^n$ is haloalkoxy. In one embodiment of Formula II, $R^n$ is trifluoromethoxy. In one embodiment of Formula II, $R^n$ is aryl. In one embodiment of Formula II, $R^n$ is phenyl. In one embodiment of Formula II, $R^n$ is naphthyl. In one embodiment of Formula II, $R^n$ is heteroaryl.

In one embodiment of Formula II, $R^o$ is hydrogen. In one embodiment of Formula II, $R^o$ is halogen. In one embodiment of Formula II, $R^o$ is fluoro. In one embodiment of Formula II, $R^o$ is chloro. In one embodiment of Formula II, $R^o$ is bromo. In one embodiment of Formula II, $R^o$ is iodo. In one embodiment of Formula II, $R^o$ is hydroxyl. In one embodiment of Formula II, $R^o$ is alkyl. In one embodiment of Formula II, $R^o$ is methyl. In one embodiment of Formula II, $R^o$ is haloalkyl. In one embodiment of Formula II, $R^o$ is trifluoromethyl. In one embodiment of Formula II, $R^o$ is trichloromethyl. In one embodiment of Formula II, $R^o$ is alkoxy. In one embodiment of Formula II, $R^o$ is methoxy. In one embodiment of Formula II, $R^o$ is haloalkoxy. In one embodiment of Formula II, $R^o$ is trifluoromethoxy. In one embodiment of Formula II, $R^o$ is aryl. In one embodiment of Formula II, $R^o$ is phenyl. In one embodiment of Formula II, $R^o$ is naphthyl. In one embodiment of Formula II, $R^o$ is heteroaryl.

In one embodiment of Formula II, $R^p$ is hydrogen. In one embodiment of Formula II, $R^p$ is halogen. In one embodiment of Formula II, $R^p$ is fluoro. In one embodiment of Formula II, $R^p$ is chloro. In one embodiment of Formula II, $R^p$ is bromo. In one embodiment of Formula II, $R^p$ is iodo. In one embodiment of Formula II, $R^p$ is hydroxyl. In one embodiment of Formula II, $R^p$ is alkyl. In one embodiment of Formula II, $R^p$ is methyl. In one embodiment of Formula II, $R^p$ is haloalkyl. In one embodiment of Formula II, $R^p$ is trifluoromethyl. In one embodiment of Formula II, $R^p$ is trichloromethyl. In one embodiment of Formula II, $R^p$ is alkoxy. In one embodiment of Formula II, $R^p$ is methoxy. In one embodiment of Formula II, $R^p$ is haloalkoxy. In one embodiment of Formula II, $R^p$ is trifluoromethoxy. In one embodiment of Formula II, $R^p$ is aryl. In one embodiment of Formula II, $R^p$ is phenyl. In one embodiment of Formula II, $R^p$ is naphthyl. In one embodiment of Formula II, $R^p$ is heteroaryl.

Representative examples of compounds of Formula I include:

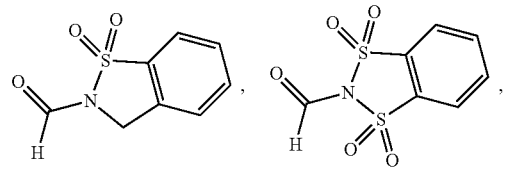

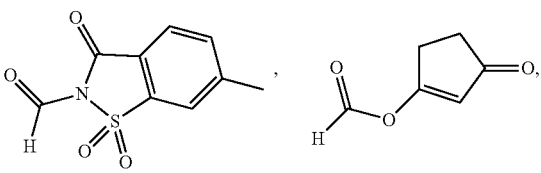

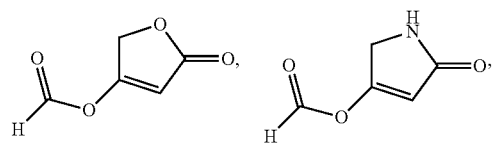

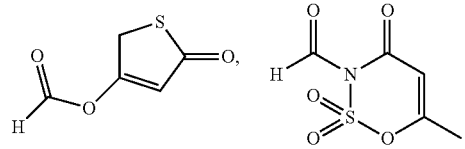

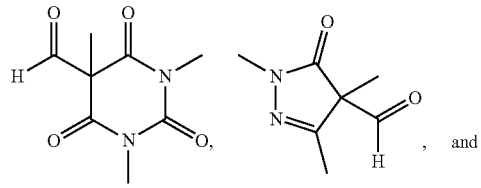

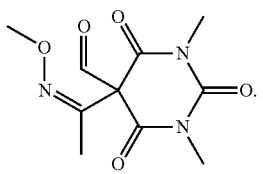

, and

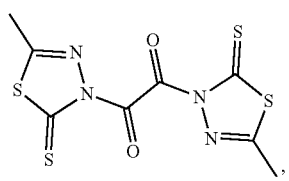

Representative examples of compounds of Formula II include:

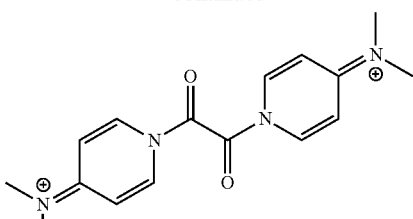

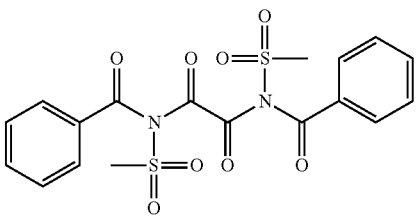

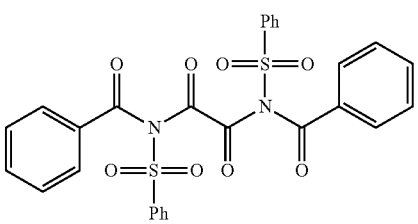

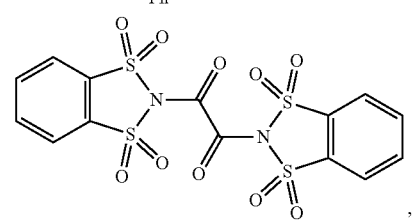

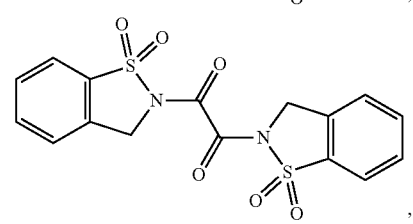

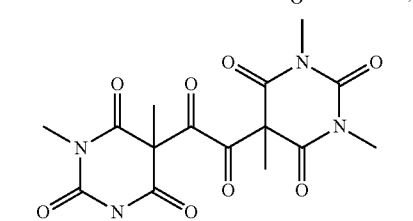

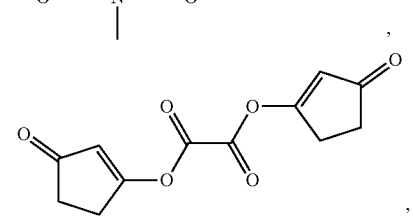

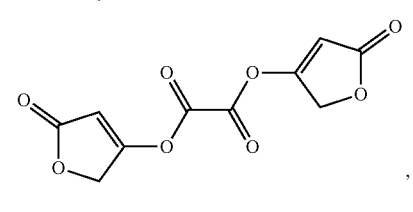

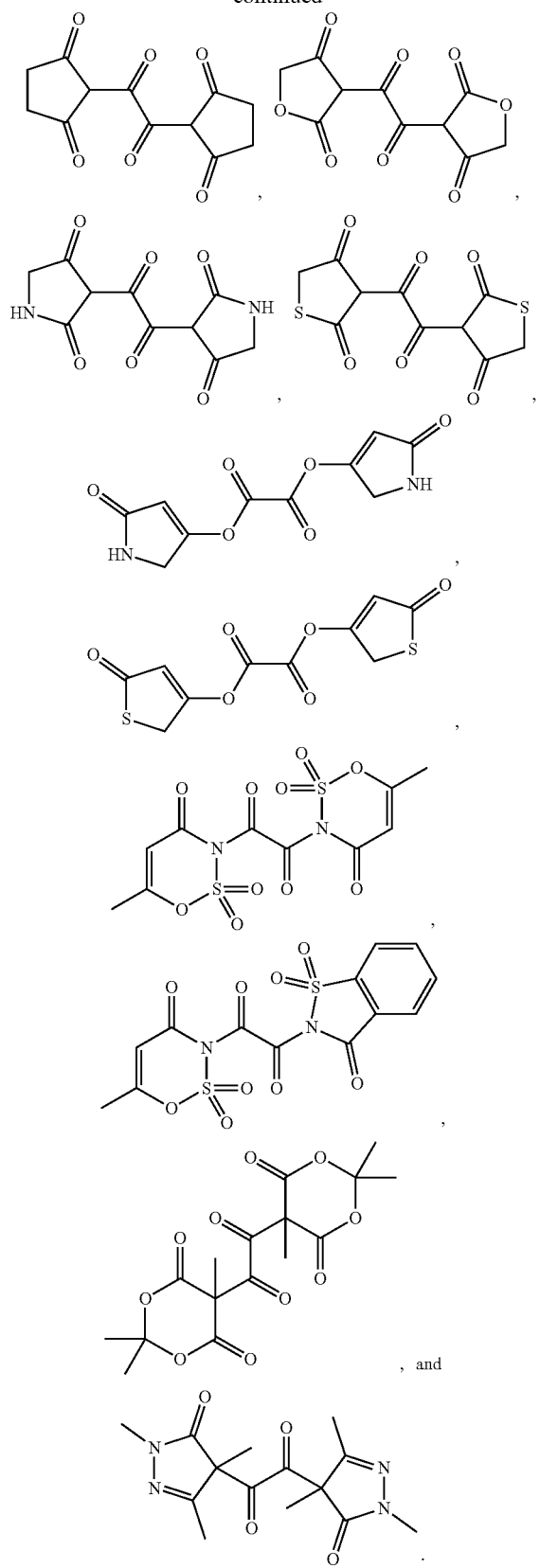
An additional representative example of Formula II includes
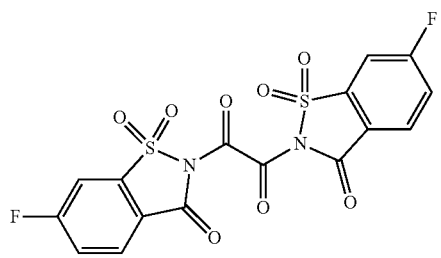 [SMILES: O=C(C(=O)N1C(=O)c2ccc(F)cc2S1(=O)=O)N1C(=O)c2ccc(F)cc2S1(=O)=O]
Representative examples of compounds of Formula III include:
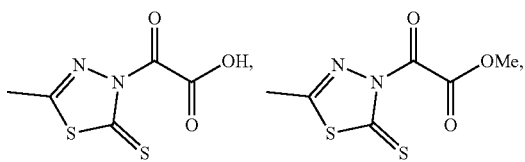
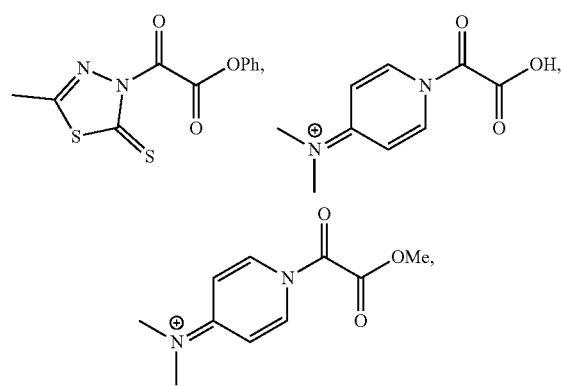

-continued
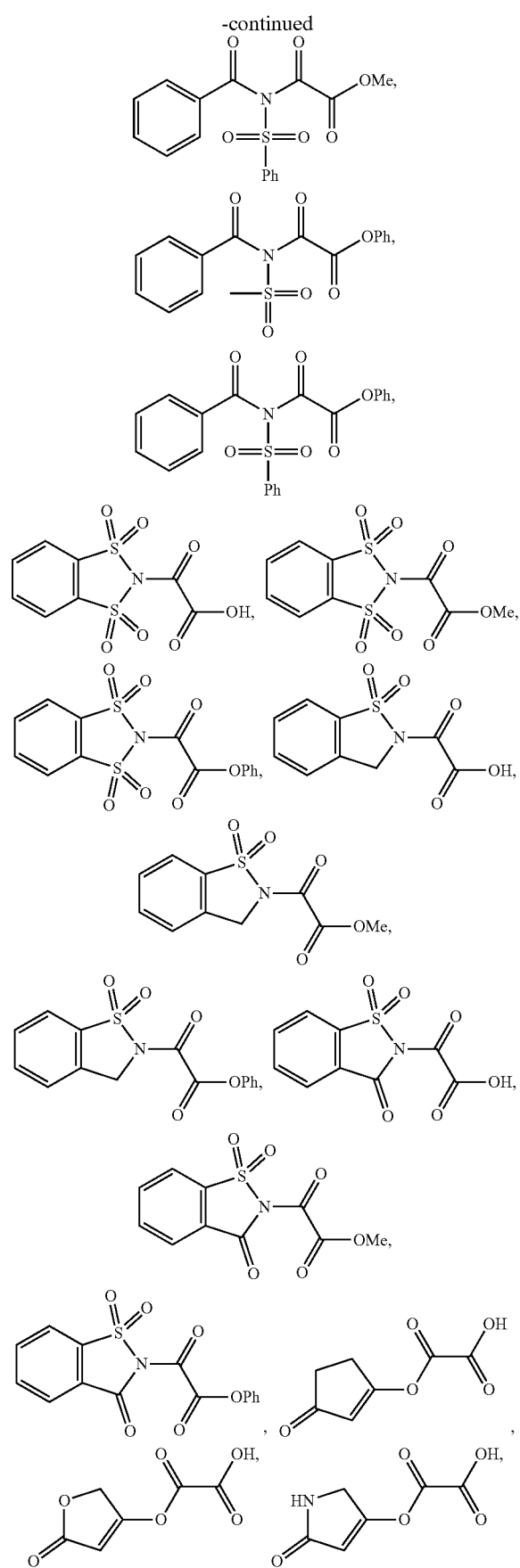
-continued
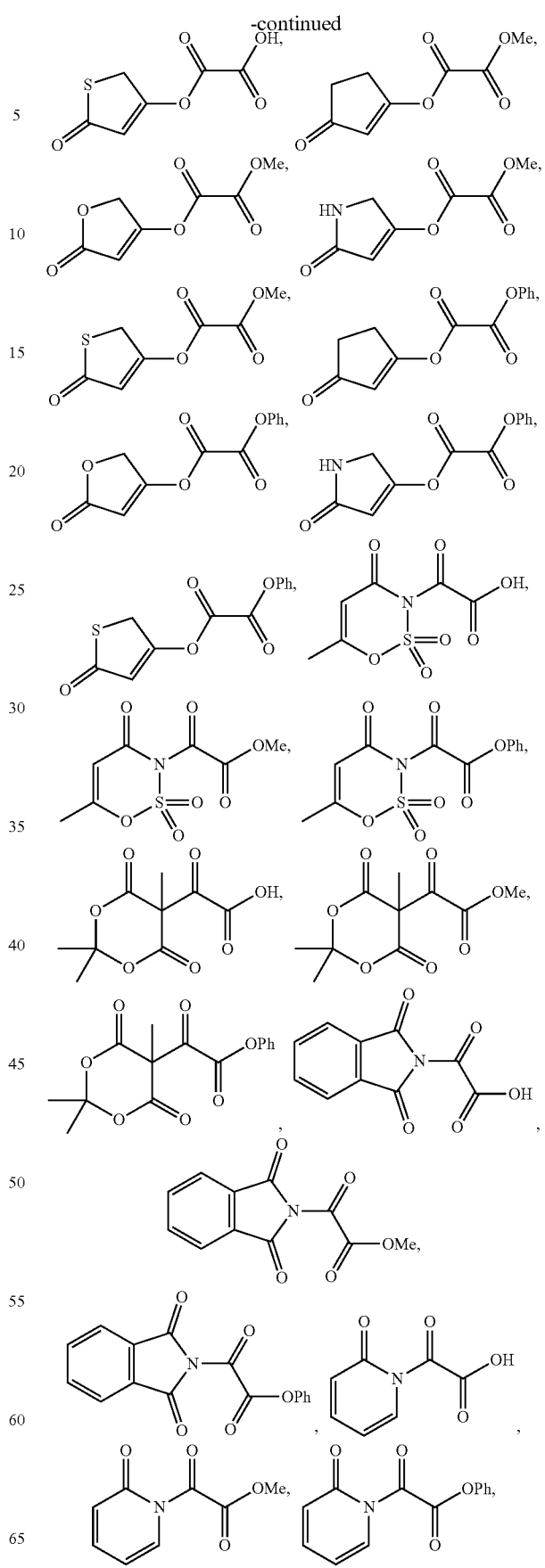

-continued

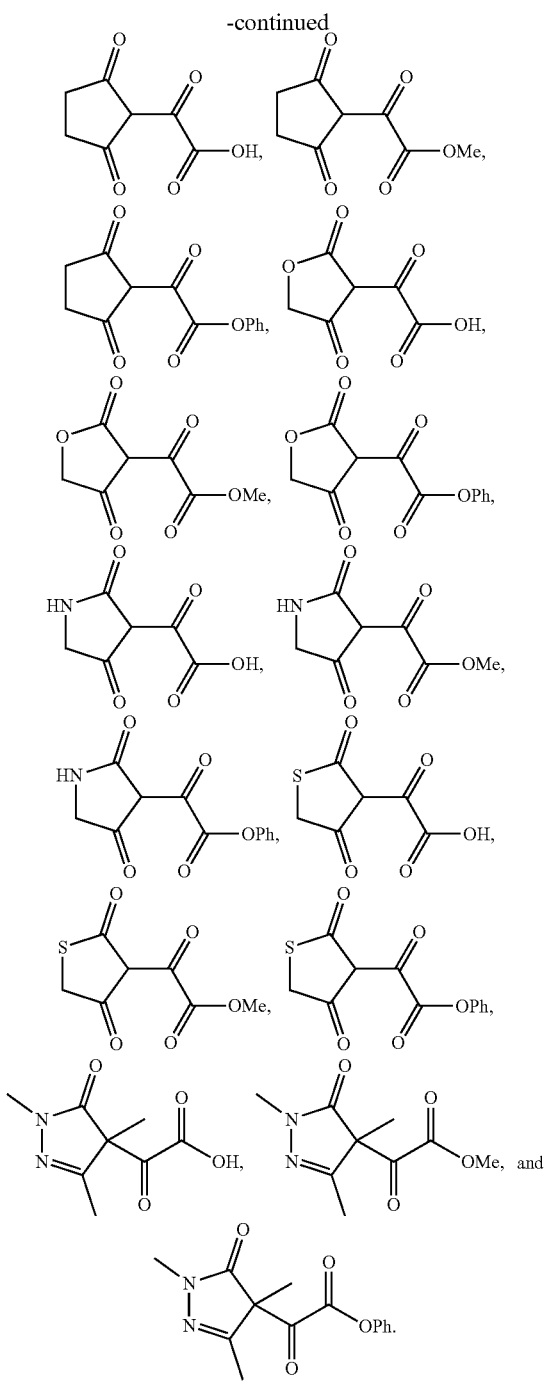

III. Compounds of Formula IV, Formula V, and Formula VI

In another aspect, the present invention also provides compounds of Formula IV, Formula V, or Formula VI, or a pharmaceutically acceptable salt or composition thereof, for use in the methods described herein.

In another aspect, a method is provided for the treatment of a medical disorder, for example an inflammatory disorder or a pain disorder, in a subject, for example a human, comprising administering to the subject an effective amount of a compound of Formula IV:

(IV)

or a pharmaceutically acceptable salt thereof, wherein $A^1$ is defined as above.

In some embodiments of Formula IV, the compound has a chemical structure of Formula IVa:

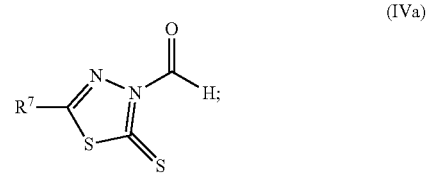

(IVa)

wherein $R^7$ is defined as above.

In one aspect of the present invention, a compound of Formula IVa is provided wherein $R^7$ is haloalkyl, aryl, or heteroaryl.

In some embodiments of Formula IV, the compound has a chemical structure of Formula IVb:

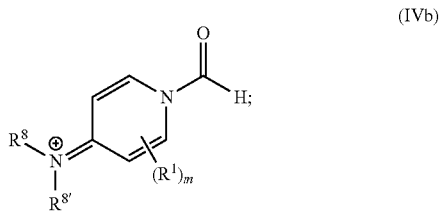

(IVb)

wherein $R^1$, $R^8$, $R^{8'}$ and m are defined as above.

In one aspect of the present invention, a compound of Formula IVb is provided wherein m is 1, 2, 3, or 4; and $R^1$, $R^8$, and $R^{8'}$ are defined as above.

In some embodiments of Formula IV, the compound has a chemical structure of Formula IVc:

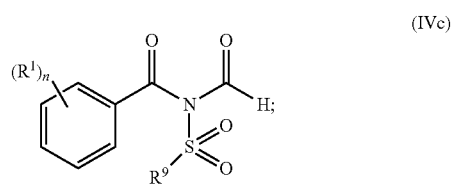

(IVc)

Wherein $R^1$, $R^9$, and n are defined as above.

In one aspect of the present invention, a compound of Formula IVc is provided wherein n is 1, 2, 3, or 4; and $R^1$ and $R^9$ are defined as above. In another aspect, a compound of Formula IVc is provided wherein $R^9$ is haloalkyl, aryl, or heteroaryl; and $R^1$ and n are defined as above.

In some embodiments of Formula IV, the compound has a chemical structure of Formula IVd:

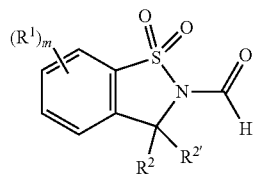

(IVd)

wherein $R^1$, $R^2$, $R^{2'}$, and m are defined as above.

In one aspect of the present invention, a compound of Formula IVd is provided wherein $R^2$ is hydrogen; and $R^1$, $R^{2'}$, and m are defined as above. In another aspect, a compound of Formula IVd is provided wherein $R^1$ is $R^{1A}$; and $R^{1A}$, $R^2$, $R^{2'}$, and m are defined as above.

In some embodiments of Formula IV, the compound has a chemical structure of Formula IVe:

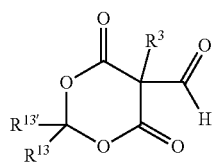

(IVe)

wherein $R^3$, $R^{13}$, and $R^{13'}$ are defined as above.

In one aspect of the present invention, a compound of Formula IVe is provided wherein $R^3$ is alkyl, haloalkyl, aryl, heteroaryl, or

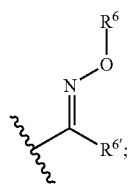

and $R^6$, $R^{6'}$, $R^{13}$, and $R^{13'}$ are defined as above.

In some embodiments of Formula IV, the compound has a chemical structure of Formula IVf:

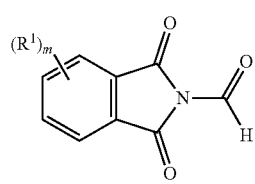

(IVf)

wherein $R^1$ and m are defined as above.

In one aspect of the present invention, a compound of Formula IVf is provided wherein m is 1, 2, 3, or 4; and $R^1$ is defined as above.

In some embodiments of Formula IV, the compound has a chemical structure of Formula IVg:

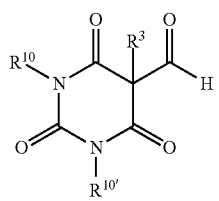

(IVg)

wherein $R^3$, $R^{10}$, and $R^{10'}$ are defined as above.

In one aspect of the present invention, a compound of Formula IVg is provided wherein $R^3$ is halogen, haloalkyl, aryl, heteroaryl, or

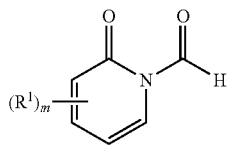

and $R^6$, $R^{6'}$, $R^{10}$, and $R^{10'}$ are defined as above.

In some embodiments of Formula IV, the compound has a chemical structure of Formula IVh:

(IVh)

wherein $R^1$ and m are defined as above.

In one aspect of the present invention, a compound of Formula IVh is provided wherein m is 1, 2, 3, or 4; and $R^1$ is hydroxyl, haloalkoxy, thiol, thioalkyl, —SO$_3$H, —(P=O)(OH)$_2$, and —O(P=O)(OH)$_2$.

In some embodiments of Formula IV, the compound has a chemical structure of Formula IVi (IVi)

wherein $R^m$, $R^n$, $R^o$, and $R^p$ are defined as above.

In some embodiments of Formula IV, the compound has a chemical structure of Formula IVj:
wherein $R^{15}$ is defined as above

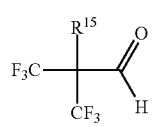

(IVj)

In some embodiments of Formula IV, the compound has a chemical structure of Formula IVk:

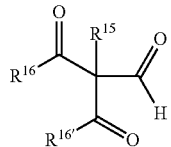

(IVk)

wherein $R^{15}$, $R^{16}$, and $R^{16'}$ are defined as above.

In some embodiments of Formula IV, the compound has a chemical structure of Formula IVl:

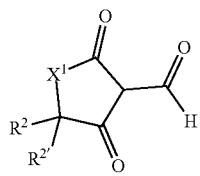

(IVl)

wherein $R^2$, $R^{2'}$, and $X^1$ are defined as above.

In some embodiments of Formula IV, the compound has a chemical structure of Formula IVm:

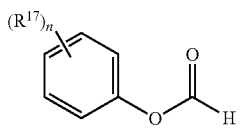

(IVm)

wherein $R^{17}$ and n are defined as above.

In another aspect, a method is provided for the treatment of a medical disorder, for example an inflammatory disorder or a pain disorder, in a subject, for example a human, comprising administering to the subject an effective amount of a compound of Formula V:

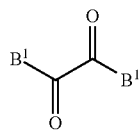

(V)

or a pharmaceutically acceptable salt thereof;
wherein $B^1$ is defined as above.

In some embodiments of Formula V, the compound has a chemical structure of Formula Va:

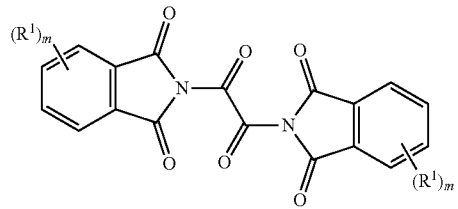

(Va)

wherein $R^1$ and m are defined as above.

In one aspect of the present invention, a compound of Formula Va is provided wherein m is 1, 2, 3, or 4; and $R^1$ is selected from $R^1$ is halogen, hydroxyl, alkyl, haloalkyl, alkoxy, haloalkoxy, aryl, heteroaryl, thiol, thioalkyl, $—SO_3H$, $—(P=O)(OH)_2$, or $—O(P=O)(OH)_2$.

In some embodiments of Formula V, the compound has a chemical structure of Formula Vb:

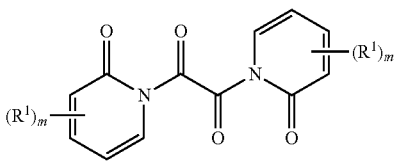

(Vb)

wherein $R^1$ and m are defined as above.

In one aspect of the present invention, a compound of Formula Vb is provided wherein m is 1, 2, 3, or 4; and $R^1$ is defined as above.

In some embodiments of Formula V, the compound has a chemical structure of Formula Vc:

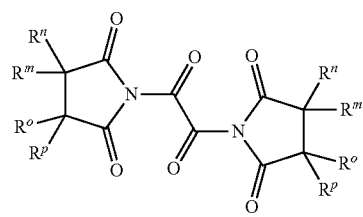

(Vc)

wherein $R^m$, $R^n$, $R^o$, and $R^p$ are defined as above.

In some embodiments of Formula V, the compound has a chemical structure of Formula Vd:

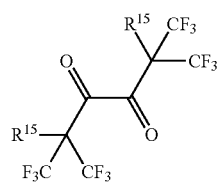

(Vd)

wherein $R^{15}$ is defined as above.

In one aspect of the present invention, a compound of Formula Vd is provided wherein $R^{15}$ is hydrogen, alkyl, haloalkyl, aryl, or heteroaryl.

In some embodiments of Formula V, the compound has a chemical structure of Formula Ve:

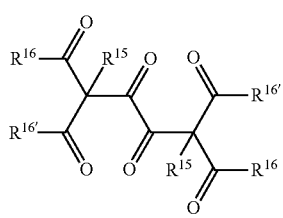

(Ve)

Wherein $R^{15}$, $R^{16}$, and $R^{16'}$ are defined as above.

In some embodiments of Formula V, the compound has a chemical structure of Formula Vf:

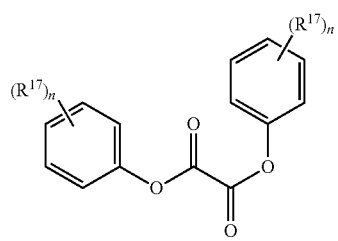

(Vf)

wherein $R^{17}$ and n are defined as above.

In another aspect, a method is provided for the treatment of a medical disorder, for example an inflammatory disorder or a pain disorder, in a subject, for example a human, comprising administering to the subject an effective amount of a compound of Formula VI:

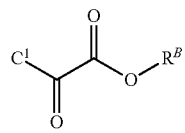

(VI)

or a pharmaceutically acceptable salt thereof;

wherein $C^1$ and $R^B$ are defined as above.

In some embodiments of Formula VI, the compound has a chemical structure of Formula VIa:

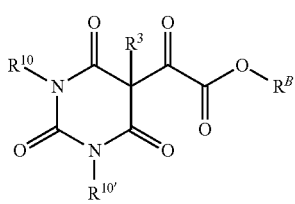

(VIa)

wherein $R^B$, $R^3$, $R^{10}$, and $R^{10'}$ are defined as above.

In one aspect of the present invention, a compound of Formula VIa is provided wherein $R^3$ is halogen, haloalkyl, aryl, heteroaryl, or

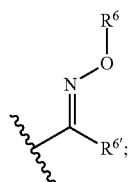

and $R^{10}$, $R^{10'}$, and $R^B$ are defined as above.

In some embodiments of Formula VI, the compound has a chemical structure of Formula VIb:

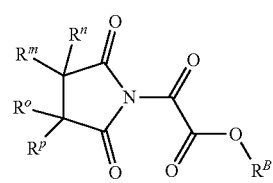

(VIb)

wherein $R^B$, $R^m$, $R^n$, $R^o$, and $R^p$ are defined as above.

In some embodiments of Formula VI, the compound has a chemical structure of Formula VIc:

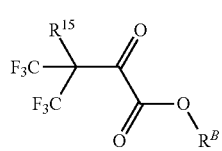

(VIc)

wherein $R^B$ and $R^{15}$ is defined as above.

In some embodiments of Formula VI, the compound has a chemical structure of Formula VId:

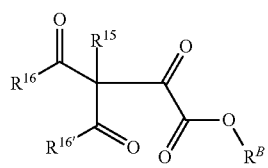

(VId)

wherein $R^B$, $R^{15}$, $R^{16}$, and $R^{16'}$ are defined as above.

In some embodiments of Formula VI, the compound has a chemical structure of Formula VIe:

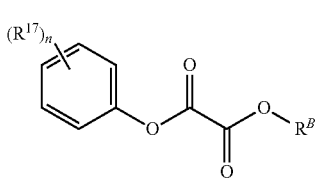

(VIe)

wherein $R^B$, $R^{17}$, and n are defined as above.

In one embodiment of any one of Formulas IV or V,

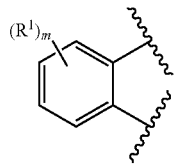

is selected from:

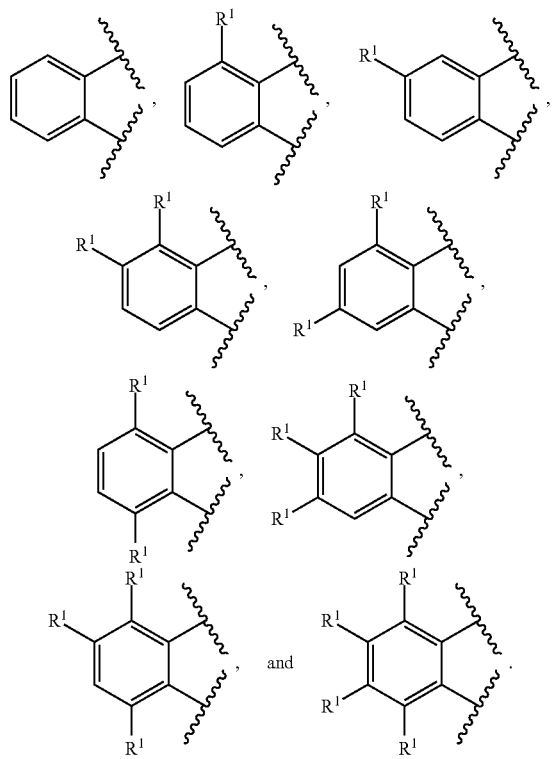

In one embodiment of any one of Formulas IV, V or VI,

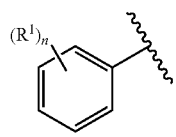

is selected from:

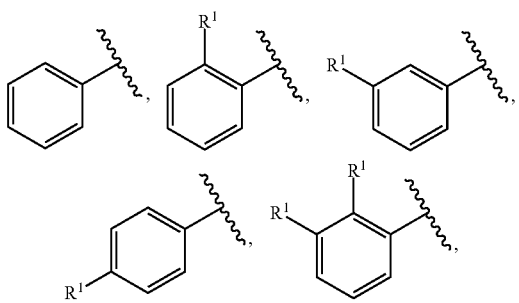

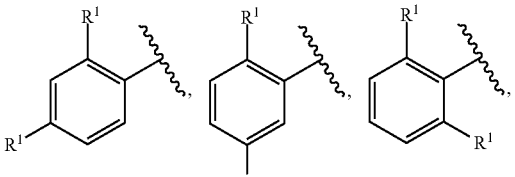

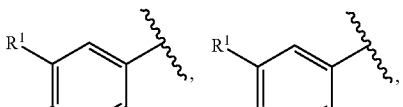

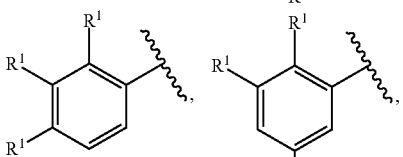

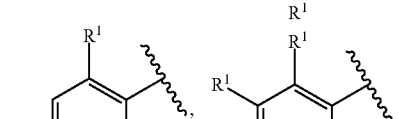

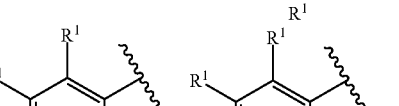

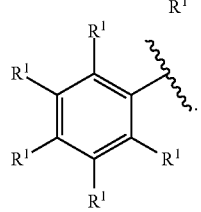

In one embodiment of any one of Formulas IV or V, $R^1$ is halogen. In one embodiment of any one of Formulas IV or V, $R^1$ is fluoro. In one embodiment of any one of Formulas IV or V, $R^1$ is chloro. In one embodiment of any one of Formulas IV or V, $R^1$ is bromo. In one embodiment of any one of Formulas IV or V, $R^1$ is iodo. In one embodiment of any one of Formulas IV or V, $R^1$ is hydroxyl. In one embodiment of any one of Formulas IV or V, $R^1$ is alkyl. In one embodiment of any one of Formulas IV or V, $R^1$ is methyl. In one embodiment of any one of Formulas IV or V, $R^1$ is haloalkyl. In one embodiment of any one of Formulas IV or V, $R^1$ is trifluoromethyl. In one embodiment of any one of Formulas IV or V, $R^1$ is trichloromethyl. In one embodiment of any one of Formulas IV or V, $R^1$ is alkoxy. In one embodiment of any one of Formulas IV or V, $R^1$ is methoxy. In one embodiment of any one of Formulas IV or V, $R^1$ is haloalkoxy. In one embodiment of any one of Formulas IV or V, $R^1$ is trifluoromethoxy. In one embodiment of any one of Formulas IV or V, $R^1$ is aryl. In one embodiment of any one of Formulas IV or V, $R^1$ is phenyl. In one embodiment of any one of Formulas IV or V, $R^1$ is naphthyl. In one embodiment of any one of Formulas IV or V, $R^1$ is heteroaryl. In one embodiment of any one of Formulas IV or V, $R^1$ is thiol. In one embodiment of any one of Formulas IV or V, $R^1$ is thioalkyl. In one embodiment of any one of Formulas IV or V, $R^1$ is thiomethyl. In one embodiment of any one of Formulas IV or V, $R^1$ is —$SO_3H$. In one embodiment of any one of Formulas IV or V, $R^1$ is —(P=O)(OH)$_2$. In one embodiment of any one of Formulas IV or V, $R^1$ is —(P=O)(OH)$_2$. In one embodiment of any one of Formulas IV or V, $R^1$ is formyl. In one embodiment of any one of Formulas IV or V, $R^1$ is acetyl. In one embodiment of any one of Formulas IV or V, $R^1$ is acetoxy. In one embodiment of any one of Formulas I II, or III, $R^1$ is cyano.

In one embodiment of any one of Formulas IV or V, $R^S$ is hydrogen. In one embodiment of any one of Formulas IV or V, $R^S$ is methyl. In one embodiment of any one of Formulas IV or V, $R^S$ is trifluoromethyl. In one embodiment of any one of Formulas IV or V, $R^S$ is methoxy. In one embodiment of any one of Formulas IV or V, $R^S$ is ethoxy. In one embodiment of any one of Formulas IV or V, $R^S$ is —$NH_2$. In one embodiment of any one of Formulas IV or V, $R^S$ is —$NHCH_3$. In one embodiment of any one of Formulas IV or V, $R^S$ is —$N(CH_3)_2$. In one embodiment of any one of Formulas IV or V, $R^S$ is phenyl. In one embodiment of any one of Formulas IV or V, $R^S$ is heteroaryl.

In one embodiment of any one of Formulas IV, V, or VI, m is 0. In one embodiment of any one of Formulas IV, V, or VI, m is 1. In one embodiment of any one of Formulas IV, V, or VI, m is 2. In one embodiment of any one of Formulas IV, V, or VI, m is 3. In one embodiment of any one of Formulas IV, V, or VI, m is 4.

In one embodiment of any one of Formulas IV or V, n is 0. In one embodiment of any one of Formulas IV or V, n is 1. In one embodiment of any one of Formulas IV or V, n is 2. In one embodiment of any one of Formulas IV or V, n is 3. In one embodiment of any one of Formulas IV or V, n is 4. In one embodiment of any one of Formulas IV or V, n is 5.

In one embodiment of any one of Formulas IV or VI, $R^2$ is hydrogen. In one embodiment of any one of Formulas IV or VI, $R^2$ is alkyl. In one embodiment of any one of Formulas IV or VI, $R^2$ is methyl. In one embodiment of any one of Formulas IV or VI, $R^2$ is haloalkyl. In one embodiment of any one of Formulas IV or VI, $R^2$ is trifluoromethyl. In one embodiment of any one of Formulas IV or VI, $R^2$ is trichloromethyl. In one embodiment of any one of Formulas IV or VI, $R^2$ is aryl. In one embodiment of any one of Formulas IV or VI, $R^2$ is phenyl. In one embodiment of any one of Formulas IV or VI, $R^2$ is naphthyl. In one embodiment of any one of Formulas IV or VI, $R^2$ is heteroaryl.

In one embodiment of any one of Formulas IV or VI, $R^{2'}$ is hydrogen. In one embodiment of any one of Formulas IV or VI, $R^{2'}$ is alkyl. In one embodiment of any one of Formulas IV or VI, $R^{2'}$ is methyl. In one embodiment of any one of Formulas IV or VI, $R^{2'}$ is haloalkyl. In one embodiment of any one of Formulas IV or VI, $R^{2'}$ is trifluoromethyl. In one embodiment of any one of Formulas IV or VI, $R^{2'}$ is trichloromethyl. In one embodiment of any one of Formulas IV or VI, $R^{2'}$ is aryl. In one embodiment of any one of Formulas IV or VI, $R^{2'}$ is phenyl. In one embodiment of any one of Formulas IV or VI, $R^{2'}$ is naphthyl. In one embodiment of any one of Formulas IV or VI, $R^{2'}$ is heteroaryl.

In one embodiment of any one of Formulas IV or VI, $X^1$ is —$C(R^5)(R^{5'})$—. In one embodiment of any one of Formulas IV or VI, $X^1$ is $CH_2$. In one embodiment of any one of Formulas IV or VI, $X^1$ is —$N(R^{5''})$—. In one embodiment of any one of Formulas IV or VI, $X^1$ is NH. In one embodiment of any one of Formulas IV or VI, $X^1$ is $N(CH_3)$. In one embodiment of any one of Formulas IV or VI, $X^1$ is O. In one embodiment of any one of Formulas IV or VI, $X^1$ is S.

In one embodiment of any one of Formulas IV or VI, $R^3$ is halogen. In one embodiment of any one of Formulas IV or VI, $R^3$ is fluoro. In one embodiment of any one of Formulas IV or VI, $R^3$ is chloro. In one embodiment of any one of Formulas IV or VI, $R^3$ is bromo. In one embodiment of any one of Formulas IV or VI, $R^3$ is iodo. In one embodiment of any one of Formulas IV or VI, $R^3$ is alkyl. In one embodiment of any one of Formulas IV or VI, $R^3$ is methyl. In one embodiment of any one of Formulas IV or VI, $R^3$ is haloalkyl. In one embodiment of any one of Formulas IV or VI, $R^3$ is trifluoromethyl. In one embodiment of any one of Formulas IV or VI, $R^3$ is trichloromethyl. In one embodiment of any one of Formulas IV or VI, $R^3$ is aryl. In one embodiment of any one of Formulas IV or VI, $R^3$ is phenyl. In one embodiment of any one of Formulas IV or VI, $R^3$ is naphthyl. In one embodiment of any one of Formulas IV or VI, $R^3$ is heteroaryl. In one embodiment of any one of Formulas IV or VI, $R^3$ is —(C=N—$OCH_3$)—$CH_3$.

In one embodiment of Formula IV, $R^7$ is hydrogen. In one embodiment of Formula IV, $R^7$ is alkyl. In one embodiment of Formula IV, $R^7$ is methyl. In one embodiment of Formula IV, $R^7$ is haloalkyl. In one embodiment of Formula IV, $R^7$ is trifluoromethyl. In one embodiment of Formula IV, $R^7$ is trichloromethyl. In one embodiment of Formula IV, $R^7$ is aryl. In one embodiment of Formula IV, $R^7$ is phenyl. In one embodiment of Formula IV, $R^7$ is naphthyl. In one embodiment of Formula IV, $R^7$ is heteroaryl.

In one embodiment of Formula IV, $R^8$ is alkyl. In one embodiment of Formula IV, $R^8$ is methyl. In one embodiment of Formula IV, $R^8$ is aryl. In one embodiment of Formula IV, $R^8$ is phenyl. In one embodiment of Formula IV, $R^8$ is naphthyl.

In one embodiment of any one of Formulas IV or VI, $R^{10}$ is alkyl. In one embodiment of any one of Formulas IV or VI, $R^{10}$ is methyl. In one embodiment of any one of Formulas IV or VI, $R^{10}$ is aryl. In one embodiment of any one of Formulas IV or VI, $R^{10}$ is phenyl. In one embodiment of any one of Formulas IV or VI, $R^{10}$ is naphthyl. In one embodiment of any one of Formulas IV or VI, $R^{10}$ is heteroaryl.

In one embodiment of any one of Formulas IV or VI, $R^{10'}$ is alkyl. In one embodiment of any one of Formulas IV or VI, $R^{10'}$ is methyl. In one embodiment of any one of Formulas IV or VI, $R^{10'}$ is aryl. In one embodiment of any one of Formulas IV or VI, $R^{10'}$ is phenyl. In one embodiment of any one of Formulas IV or VI, $R^{10'}$ is naphthyl. In one embodiment of any one of Formulas IV or VI, $R^{10'}$ is heteroaryl.

In one embodiment of Formula IV, $R^{11}$ is hydrogen. In one embodiment of Formula IV, $R^{11}$ is halogen. In one embodiment of Formula IV, $R^{11}$ is fluoro. In one embodiment of Formula IV, $R^{11}$ is chloro. In one embodiment of Formula IV, $R^{11}$ is bromo. In one embodiment of Formula IV, $R^{11}$ is iodo. In one embodiment of Formula IV, $R^{11}$ is alkyl. In one embodiment of Formula IV, $R^{11}$ is methyl. In one embodiment of Formula IV, $R^{11}$ is haloalkyl. In one embodiment of Formula IV, $R^{11}$ is trifluoromethyl. In one embodiment of Formula IV, $R^{11}$ is trichloromethyl. In one embodiment of Formula IV, $R^{11}$ is aryl. In one embodiment of Formula IV, $R^{11}$ is phenyl. In one embodiment of Formula IV, $R^{11}$ is naphthyl. In one embodiment of Formula IV, $R^{11}$ is heteroaryl.

In one embodiment of Formula IV, $R^{13}$ is hydrogen. In one embodiment of Formula IV, $R^{13}$ is alkyl. In one embodiment of Formula IV, $R^{13}$ is methyl. In one embodiment of Formula IV, $R^{13}$ is methyl. In one embodiment of Formula IV, $R^{13}$ is haloalkyl. In one embodiment of Formula IV, $R^{13}$ is trifluoromethyl. In one embodiment of Formula IV, $R^{13}$ is trichloromethyl. In one embodiment of Formula IV, $R^{13}$ is aryl. In one embodiment of Formula IV, $R^{13}$ is naphthyl. In one embodiment of Formula IV, $R^{13}$ is heteroaryl.

In one embodiment of Formula IV, $R^{13'}$ is hydrogen. In one embodiment of Formula IV, $R^{13'}$ is alkyl. In one embodiment of Formula IV, $R^{13'}$ is methyl. In one embodiment of Formula IV, $R^{13'}$ is methyl. In one embodiment of Formula IV, $R^{13'}$ is haloalkyl. In one embodiment of Formula IV, $R^{13'}$ is trifluoromethyl. In one embodiment of Formula IV, $R^{13'}$ is trichloromethyl. In one embodiment of Formula IV, $R^{13'}$ is aryl. In one embodiment of Formula IV, $R^{13'}$ is naphthyl. In one embodiment of Formula IV, $R^{13'}$ is heteroaryl.

In one embodiment of Formula IV, $R^{14}$ is hydrogen. In one embodiment of Formula IV, $R^{14}$ is alkyl. In one embodiment of Formula IV, $R^{14}$ is methyl. In one embodiment of Formula IV, $R^{14}$ is aryl. In one embodiment of Formula IV, $R^{14}$ is phenyl. In one embodiment of Formula IV, $R^{14}$ is naphthyl. In one embodiment of Formula IV, $R^{14}$ is heteroaryl.

In one embodiment of any one of Formula IV, V, or VI, $R^{15}$ is hydrogen. In one embodiment of any one of Formula IV, V, or VI, $R^{15}$ is halogen. In one embodiment of any one of Formula IV, V, or VI, $R^{15}$ is fluoro. In one embodiment of any one of Formula IV, V, or VI, $R^{15}$ is chloro. In one embodiment of any one of Formula IV, V, or VI, $R^{15}$ is bromo. In one embodiment of any one of Formula IV, V, or VI, $R^{15}$ is iodo. In one embodiment of any one of Formula IV, V, or VI, $R^{15}$ is alkyl. In one embodiment of any one of Formula IV, V, or VI, $R^{15}$ is methyl. In one embodiment of any one of Formula IV, V, or VI, $R^{15}$ is haloalkyl. In one embodiment of any one of Formula IV, V, or VI, $R^{15}$ is trifluoromethyl. In one embodiment of any one of Formula IV, V, or VI, $R^{15}$ is trichloromethyl. In one embodiment of any one of Formula IV, V, or VI, $R^{15}$ is aryl. In one embodiment of any one of Formula IV, V, or VI, $R^{15}$ is phenyl. In one embodiment of any one of Formula IV, V, or VI, $R^{15}$ is naphthyl. In one embodiment of any one of Formula IV, V, or VI, $R^{15}$ is heteroaryl.

In one embodiment of any one of Formula IV, V, or VI, $R^{16}$ is alkyl. In one embodiment of any one of Formula IV, V, or VI, $R^{16}$ is methyl. In one embodiment of any one of Formula IV, V, or VI, $R^{16}$ is haloalkyl. In one embodiment of any one of Formula IV, V, or VI, $R^{16}$ is trifluoromethyl. In one embodiment of any one of Formula IV, V, or VI, $R^{16}$ is trichloromethyl. In one embodiment of any one of Formula IV, V, or VI, $R^{16}$ is aryl. In one embodiment of any one of Formula IV, V, or VI, $R^{16}$ is phenyl. In one embodiment of any one of Formula IV, V, or VI, $R^{16}$ is heteroaryl. In one embodiment of any one of Formula IV, V, or VI, $R^{16}$ is alkoxy. In one embodiment of any one of Formula IV, V, or VI, $R^{16}$ is methoxy. In one embodiment of any one of Formula IV, V, or VI, $R^{16}$ is ethoxy. In one embodiment of any one of Formula IV, V, or VI, $R^{16}$ is haloalkoxy. In one embodiment of any one of Formula IV, V, or VI, $R^{16}$ is trichloromethoxy. In one embodiment of any one of Formula IV, V, or VI, $R^{16}$ is aryloxy. In one embodiment of any one of Formula IV, V, or VI, $R^{16}$ is phenoxy. In one embodiment of any one of Formula IV, V, or VI, $R^{16}$ is heteroaryloxy. In one embodiment of any one of Formula IV, V, or VI, $R^{16}$ is amino. In one embodiment of any one of Formula IV, V, or VI, $R^{16}$ is alkylamino. In one embodiment of any one of Formula IV, V, or VI, $R^{16}$ is methylamino. In one embodiment of any one of Formula IV, V, or VI, $R^{16}$ is dialkylamino. In one embodiment of any one of Formula IV, V, or VI, $R^{16}$ is dimethylamino.

In one embodiment of any one of Formula IV, V, or VI, $R^{16'}$ is alkyl. In one embodiment of any one of Formula IV, V, or VI, $R^{16'}$ is methyl. In one embodiment of any one of Formula IV, V, or VI, $R^{16'}$ is haloalkyl. In one embodiment of any one of Formula IV, V, or VI, $R^{16'}$ is trifluoromethyl. In one embodiment of any one of Formula IV, V, or VI, $R^{16'}$ is trichloromethyl. In one embodiment of any one of Formula IV, V, or VI, $R^{16'}$ is aryl. In one embodiment of any one of Formula IV, V, or VI, $R^{16'}$ is phenyl. In one embodiment of any one of Formula IV, V, or VI, $R^{16'}$ is heteroaryl. In one embodiment of any one of Formula IV, V, or VI, $R^{16'}$ is alkoxy. In one embodiment of any one of Formula IV, V, or VI, $R^{16'}$ is methoxy. In one embodiment of any one of Formula IV, V, or VI, $R^{16'}$ is ethoxy. In one embodiment of any one of Formula IV, V, or VI, $R^{16'}$ is haloalkoxy. In one embodiment of any one of Formula IV, V, or VI, $R^{16'}$ is trichloromethoxy. In one embodiment of any one of Formula IV, V, or VI, $R^{16'}$ is aryloxy. In one embodiment of any one of Formula IV, V, or VI, $R^{16'}$ is phenoxy. In one embodiment of any one of Formula IV, V, or VI, $R^{16'}$ is heteroaryloxy. In one embodiment of any one of Formula IV, V, or VI, $R^{16'}$ is amino. In one embodiment of any one of Formula IV, V, or VI, $R^{16'}$ is alkylamino. In one embodiment of any one of Formula IV, V, or VI, $R^{16'}$ is methylamino. In one embodiment of any one of Formula IV, V, or VI, $R^{16'}$ is dialkylamino. In one embodiment of any one of Formula IV, V, or VI, $R^{16'}$ is dimethylamino.

In one embodiment of any one of Formula IV, V, or VI, $R^{17}$ is halogen. In one embodiment of any one of Formula IV, V, or VI, $R^{17}$ is fluoro. In one embodiment of any one of Formula IV, V, or VI, $R^{17}$ is chloro. In one embodiment of any one of Formula IV, V, or VI, $R^{17}$ is bromo. In one embodiment of any one of Formula IV, V, or VI, $R^{17}$ is iodo. In one embodiment of any one of Formula IV, V, or VI, $R^{17}$ is haloalkyl. In one embodiment of any one of Formula IV, V, or VI, $R^{17}$ is trifluoromethyl. In one embodiment of any one of Formula IV, V, or VI, $R^{17}$ is trichloromethyl. In one embodiment of any one of Formula IV, V, or VI, $R^{17}$ is nitro.

In one embodiment of any one of Formula IV, V, or VI, $R'''$ is hydrogen. In one embodiment of any one of Formula IV, V, or VI, $R'''$ is halogen. In one embodiment of any one of Formula IV, V, or VI, $R'''$ is fluoro. In one embodiment of any one of Formula IV, V, or VI, $R'''$ is chloro. In one embodiment of any one of Formula IV, V, or VI, $R'''$ is bromo. In one embodiment of any one of Formula IV, V, or VI, $R'''$ is iodo. In one embodiment of any one of Formula IV, V, or VI, $R'''$ is hydroxyl. In one embodiment of any one of Formula IV, V, or VI, $R'''$ is alkyl. In one embodiment of any one of Formula IV, V, or VI, $R'''$ is methyl. In one embodiment of any one of Formula IV, V, or VI, $R'''$ is haloalkyl. In one embodiment of any one of Formula IV, V, or VI, $R'''$ is trifluoromethyl. In one embodiment of any one of Formula IV, V, or VI, $R'''$ is trichloromethyl. In one embodiment of any one of Formula IV, V, or VI, $R'''$ is alkoxy. In one embodiment of any one of Formula IV, V, or VI, $R'''$ is methoxy. In one embodiment of any one of Formula IV, V, or VI, $R'''$ is haloalkoxy. In one embodiment of any one of Formula IV, V, or VI, $R'''$ is trifluoromethoxy. In one embodiment of any one of Formula IV, V, or VI, $R'''$ is aryl. In one embodiment of any one of Formula IV, V, or VI, $R'''$ is phenyl. In one embodiment of any one of Formula IV, V, or VI, $R'''$ is naphthyl. In one embodiment of any one of Formula IV, V, or VI, $R'''$ is heteroaryl.

In one embodiment of any one of Formula IV, V, or VI, $R''$ is hydrogen. In one embodiment of any one of Formula IV, V, or VI, $R''$ is halogen. In one embodiment of any one of Formula IV, V, or VI, $R''$ is fluoro. In one embodiment of any one of Formula IV, V, or VI, $R''$ is chloro. In one embodiment of any one of Formula IV, V, or VI, $R''$ is bromo. In one embodiment of any one of Formula IV, V, or VI, $R''$ is iodo. In one embodiment of any one of Formula IV, V, or VI, $R''$ is hydroxyl. In one embodiment of any one of Formula IV, V, or VI, $R''$ is alkyl. In one embodiment of any one of Formula IV, V, or VI, $R''$ is methyl. In one embodiment of any one of Formula IV, V, or VI, $R''$ is haloalkyl. In one embodiment of any one of Formula IV, V, or VI, $R''$ is trifluoromethyl. In one embodiment of any one of Formula IV, V, or VI, $R''$ is trichloromethyl. In one embodiment of any one of Formula IV, V, or VI, $R''$ is alkoxy. In one embodiment of any one of Formula IV, V, or VI, $R''$ is methoxy. In one embodiment of any one of Formula IV, V, or VI, $R''$ is haloalkoxy. In one embodiment of any one of Formula IV, V, or VI, $R''$ is trifluoromethoxy. In one embodiment of any one of Formula IV, V, or VI, $R''$ is aryl. In one embodiment of any one of Formula IV, V, or VI, $R''$ is phenyl. In one embodiment of any one of Formula IV, V, or VI, $R''$ is naphthyl. In one embodiment of any one of Formula IV, V, or VI, $R''$ is heteroaryl.

In one embodiment of any one of Formula IV, V, or VI, $R^o$ is hydrogen. In one embodiment of any one of Formula IV, V, or VI, $R^o$ is halogen. In one embodiment of any one of Formula IV, V, or VI, $R^o$ is fluoro. In one embodiment of any one of Formula IV, V, or VI, $R^o$ is chloro. In one embodiment of any one of Formula IV, V, or VI, $R^o$ is bromo. In one embodiment of any one of Formula IV, V, or VI, $R^o$ is iodo. In one embodiment of any one of Formula IV, V, or VI, $R^o$ is hydroxyl. In one embodiment of any one of Formula IV, V, or VI, $R^o$ is alkyl. In one embodiment of any one of Formula IV, V, or VI, $R^o$ is methyl. In one embodiment of any one of Formula IV, V, or VI, $R^o$ is haloalkyl. In one embodiment of any one of Formula IV, V, or VI, $R^o$ is trifluoromethyl. In one embodiment of any one of Formula IV, V, or VI, $R^o$ is trichloromethyl. In one embodiment of any one of Formula IV, V, or VI, $R^o$ is alkoxy. In one embodiment of any one of Formula IV, V, or VI, $R^o$ is methoxy. In one embodiment of any one of Formula IV, V, or VI, $R^o$ is haloalkoxy. In one embodiment of any one of Formula IV, V, or VI, $R^o$ is trifluoromethoxy. In one embodiment of any one of Formula IV, V, or VI, $R^o$ is aryl. In one embodiment of any one of Formula IV, V, or VI, $R^o$ is phenyl. In one embodiment of any one of Formula IV, V, or VI, $R^o$ is naphthyl. In one embodiment of any one of Formula IV, V, or VI, $R^o$ is heteroaryl.

In one embodiment of any one of Formula IV, V, or VI, $R^p$ is hydrogen. In one embodiment of any one of Formula IV, V, or VI, $R^p$ is halogen. In one embodiment of any one of Formula IV, V, or VI, $R^p$ is fluoro. In one embodiment of any one of Formula IV, V, or VI, $R^p$ is chloro. In one embodiment of any one of Formula IV, V, or VI, $R^p$ is bromo. In one embodiment of any one of Formula IV, V, or VI, $R^p$ is iodo. In one embodiment of any one of Formula IV, V, or VI, $R^p$ is hydroxyl. In one embodiment of any one of Formula IV, V, or VI, $R^p$ is alkyl. In one embodiment of any one of Formula IV, V, or VI, $R^p$ is methyl. In one embodiment of any one of Formula IV, V, or VI, $R^p$ is haloalkyl. In one embodiment of any one of Formula IV, V, or VI, $R^p$ is trifluoromethyl. In one embodiment of any one of Formula IV, V, or VI, $R^p$ is trichloromethyl. In one embodiment of any one of Formula IV, V, or VI, $R^p$ is alkoxy. In one embodiment of any one of Formula IV, V, or VI, $R^p$ is methoxy. In one embodiment of any one of Formula IV, V, or VI, $R^p$ is haloalkoxy. In one embodiment of any one of Formula IV, V, or VI, $R^p$ is trifluoromethoxy. In one embodiment of any one of Formula IV, V, or VI, $R^p$ is aryl. In one embodiment of any one of Formula IV, V, or VI, $R^p$ is phenyl. In one embodiment of any one of Formula IV, V, or VI, $R^p$ is naphthyl. In one embodiment of any one of Formula IV, V, or VI, $R^p$ is heteroaryl.

Representative examples of compounds of Formula IV include:

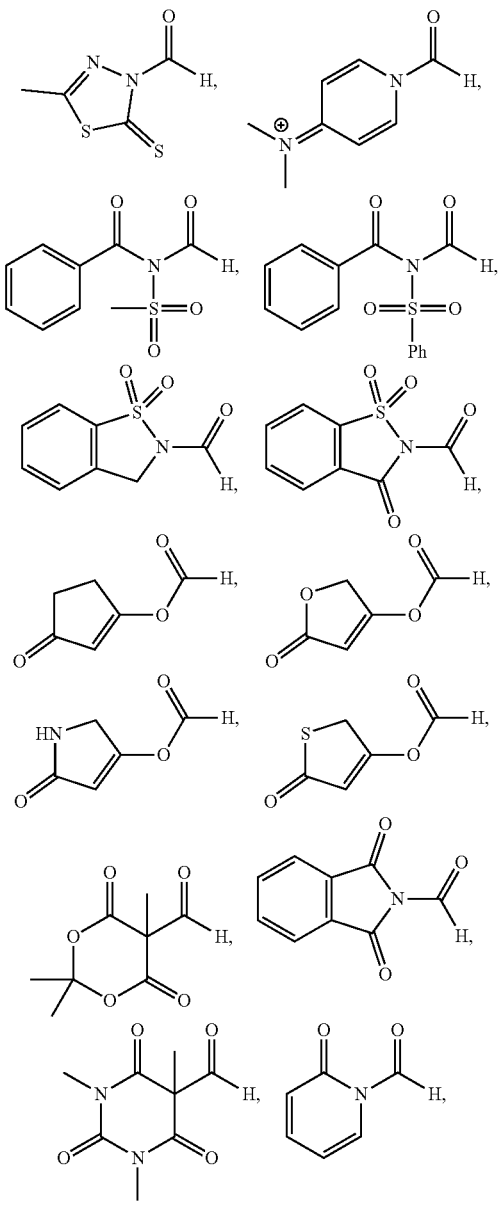

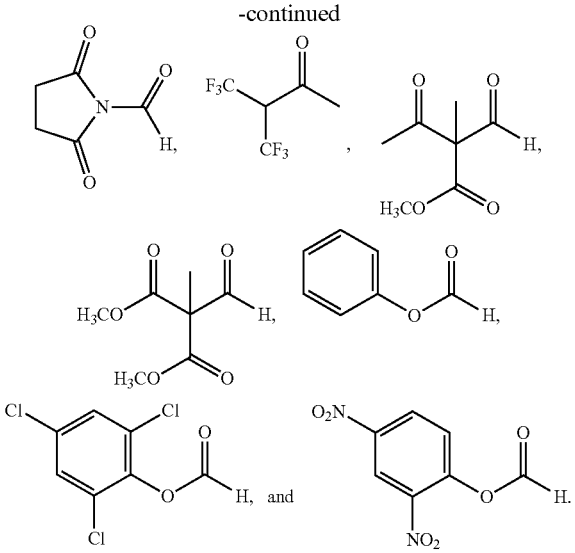
Representative examples of compound of Formula V include:
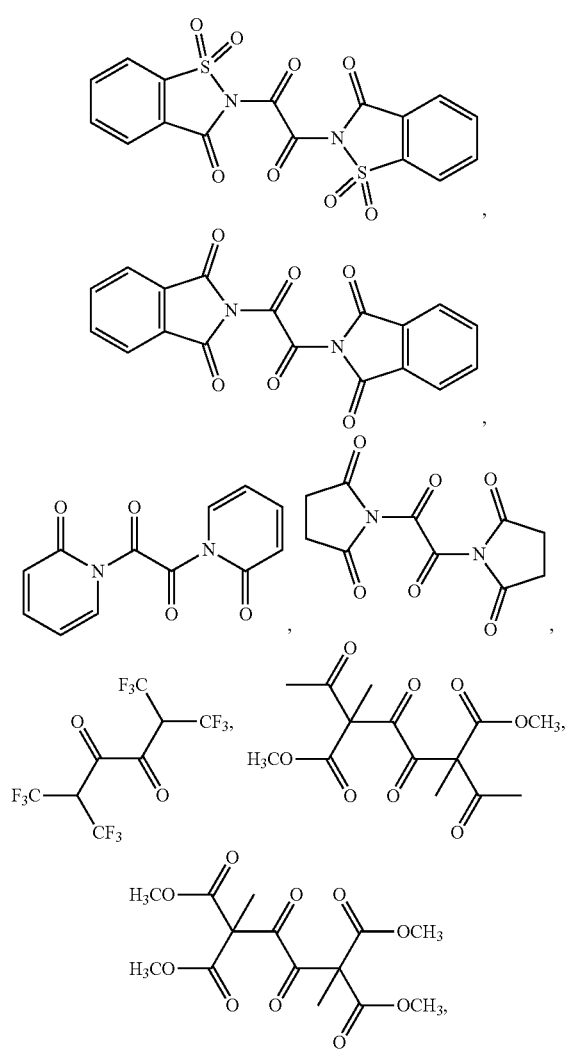
Representative examples of compounds of Formula VI include:
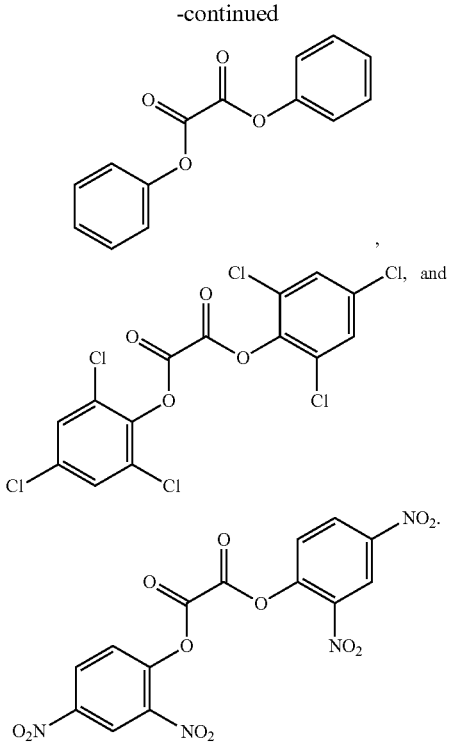

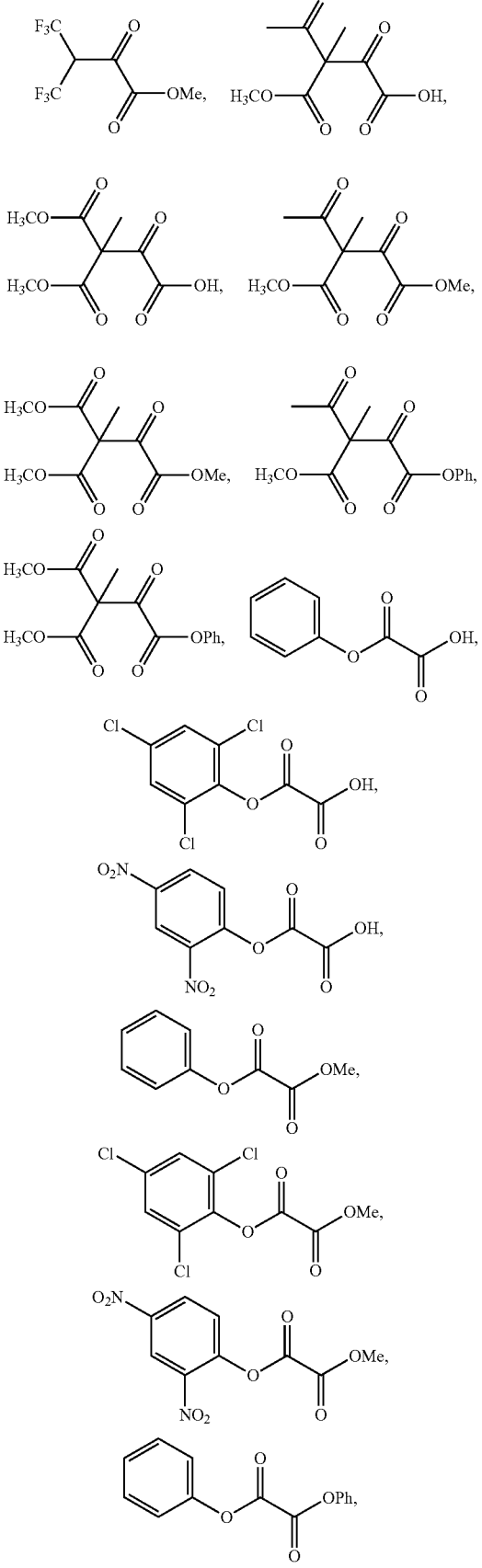

IV. Pharmaceutical Compositions

The CO-releasing compounds described herein can be administered to a host in need thereof as the neat chemical, but are more typically administered as a pharmaceutical composition that includes an effective amount for a subject, typically a human, in need of such treatment of an active compound as described herein or its pharmaceutically acceptable salt thereof. Thus, in one embodiment, the disclosure provides pharmaceutical compositions comprising an effective amount of compound or pharmaceutically acceptable salt thereof together with at least one pharmaceutically acceptable carrier for any of the uses described herein. The pharmaceutical composition may contain a compound or salt as the only active agent, or, in an alternative embodiment, the compound and at least one additional active agent.

In a typical pharmaceutical composition, the pharmaceutically acceptable carrier is anhydrous or substantially anhydrous (for example, less than about 5%, 4%, 3%, 2%, 1%, 0.5%, or 0.25% by weight of water or alcohol or a combination thereof). The pharmaceutical compositions contemplated here can optionally include a carrier. Carriers must be of sufficiently high purity and sufficiently low toxicity to render them suitable for administration to the patient being treated. The carrier can be inert, but it cannot contain quantities of water or other excipients that may adversely react with the compounds described herein. All compounds are stored and administered in a manner that prohibits exposure to moisture or other compounds it may react with. The amount of carrier employed in conjunction with the compound is sufficient to provide a practical quantity of material for administration per unit dose of the compound. Non-limiting examples of carriers include dimethylacetamide, N-methyl pyrolidone, glycol, polyethylene glycol, Tween 80, Poloxamers, and combinations thereof. An additional non-limiting example of a carrier is polypropylene glycol.

In one embodiment, the pharmaceutically acceptable carrier is a mixture of dimethylacetamide (DMA) and polyethylene glycol or a mixture of N-methyl pyrolidone (NMP) and polyethylene glycol. In one embodiment the pharmaceutically acceptable carrier is a mixture of dimethylacetamide and a water miscible solvent selected from glycol, Tween 80, and Poloxamers. In one embodiment the pharmaceutically acceptable carrier is a mixture of N-methyl pyrolidone and a water miscible solvent selected from glycol, Tween 80, and Poloxamers. In one embodiment, the ratio of solvent to the water miscible solvent is not greater than about 1:10, not greater than about 1:8, not greater than about 1:5, not greater than about 1:3, not greater than about 1:2, not greater than about 1:1, not greater than about 2:1, not greater than about 3:1, not greater than about 5:1, not greater than about 1:8, or not greater than about 1:10.

An effective amount of an active compound as described herein, or the active compound described herein either alone or in combination or alternation with, or preceded by, concomitant with or followed by an activating agent or another active agent, can be used in an amount sufficient to (a) inhibit the progression of a medical disorder described herein; (b) cause a regression of a medical disorder described herein; (c) cause a cure of a medical disorder described herein; or inhibit or prevent the development of a medical disorder described herein. Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the subject, typically a human, in need thereof, will be determined by the health care provider to achieve the desired clinical benefit.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 10 50, 75, 100, 150, 200, 250, 300, 350, 400, 450, 500, 550, 600, 650, 700, 750, 800, 900, 1000, 1100, 1200, 1250, 1300, 1400, 1500, 1600, 1700, or 1800 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent:active compound), or its salt, described herein.

In one embodiment, the pharmaceutical composition is administered in a dosage of at least about or not greater than 25, 50, 75, 100, 150, 200, 225, or 300 mg once, twice or three times a day. In one non-limiting embodiment, the dosage form is administered in a dosage of at least or not greater than 150 mg/day, 300 mg/day, 450 mg/day, 600 mg/day, 900 mg/day, 1,200 mg/day, or 1,800 mg/day. In an alternative non-limiting embodiment, the dosage form is administered in a dosage of at least or not greater than 2,000 mg/day, 3,000 mg/day, 4,000 mg/day, 5,000 mg/day, 6,000 mg/day, 7,000 mg/day, 8,000 mg/day, 9,000 mg/day, 10,000 mg/day, 11,000 mg/day, 12,000 mg/day, 13,000 mg/day, 14,000 mg/day, or 15,000 mg/day.

In an alternative non-limiting embodiment, the dosage form is administered in a dosage form based on weight of at least or not greater than 2 mg/kg, 5 mg/kg, 15 mg/kg, 30 mg/kg, 45 mg/kg, 60 mg/kg, 85 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 240 mg/kg, 250 mg/kg, 260 mg/kg, 270 mg/kg, 280 mg/kg, 290 mg/kg, 300 mg/kg, or 315 mg/kg.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Pharmaceutical compositions suitable for rectal administration are typically presented as unit dose suppositories. These may be prepared by admixing the active compound with one or more conventional solid carriers, for example, cocoa butter, and then shaping the resulting mixture.

Solid Dispersion Pharmaceutical Formulations

In another aspect of the present invention, a solid dispersion formulation is provided comprising an effective amount of a compound of Formula I through Formula VI or Formula X through Formula XII, or its pharmaceutically acceptable salt.

In one aspect of the present invention, a solid dispersion formulation is provided comprising an effective amount of a compound of Formula VII or Formula VIII in combination with a compound of Formula IX, or its pharmaceutically acceptable salt. This solid dispersion formulation can also be provided as two separate solid dispersion formulations in a manner that the host receives the benefit of both active agents acting in a concerted biological manner.

This solid dispersion formulation allows for the release of CO from the CO-releasing compounds of the present invention while retaining the drug byproducts such as saccharine and/or acesulfame. This provides for an advantageous pharmaceutical formulation that lowers the systemic exposure to unnecessary drug byproducts.

In one embodiment, the solid dispersion formulation carrier comprises activated charcoal. In one embodiment, the solid dispersion formulation carrier comprises a polymeric material. In one embodiment, the solid dispersion formulation carrier comprises activated charcoal coated with a polymeric material. In one embodiment, the solid dispersion formulation carrier comprises a surfactant. In one embodiment, the solid dispersion formulation carrier comprises an additional excipient selected from starch, talc powder, cellulose, sodium carboxymethylcellulose, and magnesium stearate.

Non-limiting examples of polymeric materials that are used in solid dispersion include poloxamers, polyvinylpyrrolidone (PVP), polyvinylpyrrolidone polyvinyl acetate (PVP-VA), hydroxypropyl methylcellulose (HPMC), ethyl cellulose, hydroxypropyl cellulose (HPC), polyethylene glycol (PEG), hydroxypropyl methylcellulose acetate succinate (HPMC AS), polyvinyl acetate, polymethacrylates, polyacrylates, crospovidone (PVP-CL), starch derivatives such as cyclodextrins, and copolymers thereof. In one embodiment, the solid dispersion comprises polyvinylpyrrolidone (PVP). In one embodiment, the solid dispersion comprises polyvinylpyrrolidone polyvinyl acetate (PVP-VA). In one embodiment, the solid dispersion formulation comprises activated charcoal and a polymeric material.

In one embodiment, the activated charcoal is granular activated charcoal. In one embodiment, the granular activated charcoal has a particle size of less than about 3 mm, less than about 2.5 mm, less than about 2 mm, less than about 1.5 mm, less than about 1 mm, less than about 0.08 mm, less than about 0.05 mm, less than about 0.03 mm, or less than about 0.01 mm.

In one embodiment, the activated charcoal is pharmaceutical grade powered activated charcoal, for example Puriss MilliporeSigma pharmaceutical grade powder. In one embodiment, the powered activated charcoal has a particle size of less than about 150 µm, less than about 140 µm, less than about 130 µm, less than about 120 µm, less than about 110 µm, less than about 100 µm, less than about 90 µm, less than about 80 µm, less than about 70 µm, less than about 60 µm, less than about 50 µm, or less than about 40 µm.

Crystalline carriers for solid dispersion formulations include sugars and polyols, such as dextrose, galactose, sucrose, mannitol, maltose, sorbitol, xylitol, isomalt, lactilol, maltilol, trihalose, glucosamine, and combinations thereof. In one embodiment, the solid dispersion formulation comprises a sugar and polymeric material, such as PEG.

In one embodiment, the solid dispersion formulation also comprises a surfactant. Typical non-limiting examples of surfactants include inulin, inutec SP1, compritol 888 ATO, gelucire 44/14, and poloxamer 407. In one embodiment, the solid dispersion formulation comprises a polymeric material and a surfactant. In one embodiment, the solid dispersion formulation comprises an organic acid, such as nicotinamide, citric acid, or succinic acid.

Preparation methods for solid dispersion formulations are well known in the art, and include solvent evaporation, melting, co-milling, co-precipitation, hot-melt extrusion, lyophilization/freeze-drying, electrospinning, and spray-drying (see Meng, F. et al. Drug Development and Industrial Pharmacy, 2015 41:9, 1401; Tran, P. et al. Pharmaceutics 2019, 11, 132; and Zhang et al. Pharmaceutics 2018, 10, 74).

In one embodiment, an active compound as described herein is administered to a patient in need thereof as a spray dried dispersion (SDD). In another embodiment, the present invention provides a spray dried dispersion (SDD) comprising a compound of the present invention and one or more pharmaceutically acceptable excipients as defined herein. In another embodiment, the SDD comprises a compound of the present invention and an additional therapeutic agent. In a further embodiment, the SDD comprises a compound of the present invention, an additional therapeutic agent, and one or more pharmaceutically acceptable excipients. In another embodiment, any of the described spray dried dispersions can be coated to form a coated tablet. In an alternative embodiment, the spray dried dispersion is formulated into a tablet but is uncoated.

In a typical embodiment, an effective amount of a compound of the present invention is adsorbed onto the solid dispersion carrier, for example activated charcoal or the polymeric materials, using a solvent evaporation method.

In one embodiment, a solid dispersion formulation is provided comprising an effective amount of a compound of Formula I through Formula VI or Formula X through Formula XII, or its pharmaceutically acceptable salt thereof and activated charcoal.

In one embodiment, a solid dispersion formulation is provided comprising an effective amount of a compound of Formula I through Formula VI or Formula X through Formula XII, or its pharmaceutically acceptable salt thereof and polvinylpyrollidone.

In one embodiment, a solid dispersion formulation is provided comprising an effective amount of a compound of Formula I through Formula VI or Formula X through Formula XII, or its pharmaceutically acceptable salt thereof and polvinylpyrollidone polyvinyl acetate.

In one embodiment, a solid dispersion formulation is provided comprising an effective amount of a compound of Formula I through Formula VI or Formula X through Formula XII, or its pharmaceutically acceptable salt thereof, activated charcoal and polvinylpyrollidone.

In one embodiment, a solid dispersion formulation is provided comprising an effective amount of a compound of Formula I through Formula VI or Formula X through Formula XII, or its pharmaceutically acceptable salt thereof, activated charcoal and polvinylpyrollidone polyvinyl acetate.

In an alternative embodiment, the present invention also includes a solid dispersion formulation comprising activated charcoal and an effective amount of a compound of Formula I through Formula VI or Formula X through Formula XII, or its pharmaceutically acceptable salt thereof for topical delivery wherein the activated charcoal is activated carbon cloth or fiber.

In one embodiment, the solid dispersion formulation contains from about 0.1% to about 0.5%, from about 0.1% to about 1.0%, from about 1.0% to about 5.0% of a compound of the present invention, from about 5.0% to about 10% of a compound of the present invention, from about 10% to about 30%, from about 30% to about 50%, from about 40% to about 60%, from about 50% to about 70%, from about 60% to about 80%, from about 70% to about 90%, or from about 80% to about 95% of a compound of the present invention. In one embodiment, the solid dispersion contains greater than 50%, greater than 60%, greater than 70%, greater than 80%, greater than 90%, greater than 95%, or more of a CO-releasing compound of the present invention.

The compounds of the present invention are adsorbed onto the carrier of the solid dispersion formulation and upon administration, the CO is released, and the carrier retains the drug byproducts, for example saccharin or acesulfame. In one embodiment, the solid dispersion formulation retains up to about 99%, up to about 98%, up to about 95%, up to about 90%, up to about 85%, up to about 75%, up to about 65%, up to about 60%, up to about 50%, or up to about 40% of the drug byproducts. In one embodiment, the drug byproduct is saccharin and approximately 98% of the saccharin is retained in the solid dispersion formulation after administration.

In one embodiment, the solid dispersion formulation exhibits a carbon monoxide release yield of at least about 99%, at least about 95%, at least about 90%, at least about 85%, at least about 80%, at least about 75%, at least about 70%, at least about 65%, at least about 60%, at least about 55%, at least about 50%, at least about 40%, at last about 30%, at least about 20%, or at least about 10% after administration in a subject in need thereof. In one embodiment, the solid dispersion formulation exhibits a carbon monoxide release yield of at least 75%.

Topical Formulations for the Treatment of Inflammatory Dermatological Disorders

In one embodiment, the CO-releasing compounds used in the present invention are formulated in a topical formulation for the treatment of an inflammatory dermatological disorder, for example acne vulgaris. Acne vulgaris is a skin disease caused in part by excessive outgrowth of *Propionibacterium acnes* bacteria and inflammation induced in response to the *P. acnes* bacteria. Acne, a common skin disease, occurs when hair follicles become clogged with dead skin cells and oil from the skin. Acne develops due to blockages that occur through increased sebum production influenced by androgens, excessive deposition of keratin in the hair follicle leading to comedo formation. The earliest pathological change involves the formation of a microcomedone due to the accumulation of skin cells in the hair follicle, which mix with oily sebum to block the follicle, a process further exacerbated by the presence of the *P. acnes* biofilm. If the microcomedone is superficial, melanin within the plug oxidizes upon exposure to air, forming a blackhead or open comedo. If the microcomedone is deeper within the hair follicle, a whitehead or closed comedo forms.

*Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically slow-growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately lives deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

While less common, *Staphylococcus epidermidis* can also cause acne. It is a Gram-positive bacterium belonging to the *Staphylococcus* Genus and the Staphylococcaceae Family that is part of the normal human flora and typically skin flora or mucosal flora. It is a facultative anaerobic bacteria and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

The presence of *P. acnes* induces skin inflammation due to the bacteria's ability to bind to toll-like receptors (TLRS), especially TLR2 and TLR4 and by altering the fatty composition of the oily sebum by oxidizing squalene. The subsequent inflammatory cascades lead to the formation of inflammatory acne lesions such as papules, pustules, or nodules. If the inflammatory reaction is very severe, the follicle will break into the dermis and subcutaneous tissue as a deep nodule, leading to local tissue destruction and scarring.

Traditionally, acne is classified as either non-inflammatory (open/closed comedones) or inflammatory (papules, pustules, or nodules). Mounting evidence indicates that inflammation exists throughout the entire duration of the acne lesion lifecycle, establishing the critical role of inflammation in the pathology of acne. In the earliest stages of acne lesion development, CD3+ T cell, CD4+ T cell, and macrophage populations are elevated, while the levels of the pro-inflammatory cytokine interleukin-1 are also upregulated. Initiation of inflammatory events have been documented even before clinical detection of acne lesions.

The present invention provides topical compositions and method for the treatment of an inflammatory dermatological disorder, for example, acne vulgaris, that include an effective amount of a carbon-monoxide ("CO") releasing compound as described herein. The CO-releasing compounds used in the compositions and methods have an anti-inflammatory and/or anti-microbial effect that helps alleviate the symptoms of acne vulgaris and/or treats the underlying overgrowth of bacteria that cause acne, for example the bacterium *Propionibacterium acnes* or *Staphylococcus epidermidis*. The present invention provides treatment options that may complement or replace those currently available in the treatment of this highly common dermatological condition. In addition, the compositions and methods described herein may actually augment the immune response against *P. acnes* or *S. epidermis* despite the reduction in inflammation.

The topical compositions and methods provide an anti-inflammatory effect due to their spontaneous release of carbon monoxide under the physiological conditions present in the skin, or when activated by a second composition.

The active CO-releasing compounds are typically sensitive to water or other agents that will attack the carbonyl under the conditions of use, such as hydroxyl groups in alcohols or potentially amines. Therefore, in a preferred embodiment, the CO-releasing compound is provided in a topical composition that is substantially anhydrous, for example, that does not contain water (or a reactive alcohol or amine) in an amount that reacts with the active agent to reduce the quantity of active agent below the effective amount needed to treat the acne. Anhydrous pharmaceutically acceptable topical materials are well known, and include silicon-based oils, aliphatic-based compositions, oleaginous materials, jellies, mineral oil, dimethicone, and other substantially anhydrous lipophilic carriers.

The active compounds described herein can be administered to a human in need thereof as a neat chemical, but are more commonly administered as a topical formulation that includes an effective amount of a compound described herein, or its pharmaceutically acceptable salt, for a human in need of treatment of an inflammatory dermatological disorder, for example, acne vulgaris.

Thus, in one embodiment, the disclosure provides topical formulations comprising an effective amount of a compound described herein, or its pharmaceutically acceptable salt, together with at least one topically acceptable carrier for any of the uses described herein. The topical formulation may contain a compound or salt as the only active ingredient, or, in an alternative embodiment, the compound and at least one additional active agent.

Additives or excipients are used as inactive ingredients in topical formulations for structuring. The main use of topical formulation additives are to control the extent of absorption of the active compound, maintaining the viscosity, improving the stability and organoleptic properties, and increasing the bulk of the formulation. The main goal of topical formulations is to confine the desired effect to the skin or within the skin. Such formulations are preferred because they are protective, emollient, and deliver the active agent to exert local activity when applied to the skin or mucous membranes.

The topical formulation contemplated herein typically includes a topically acceptable carrier. The carrier as used in the topical formulation described herein can be inert, but it cannot contain quantities of water or other excipients that may adversely react with the compounds described herein. All compounds are stored and administered in a manner that prohibits exposure to moisture or other compounds it may react with. The amount of carrier in conjunction with the compound is sufficient to provide a practical quantity of material for administration to the skin or mucous membranes of the topical formulation.

In some embodiment, the topical formulation includes a carrier selected from an oleaginous base, an absorption base, and a silicon base. Oleaginous bases are composed entirely of lipophilic materials. They are anhydrous, insoluble in water, and not easily removable with water. Oleaginous bases are inexpensive, non-reactive, nonirritating, are good emollients, have protective and occlusive properties, and are not water washable. Representative examples of oleaginous bases include hydrocarbons (such as petrolatum, paraffin wax, liquid paraffin, microcrystalline wax, plastibase, or Ceresi), vegetable oils and animal fat (such as coconut oil, bees wax, olive oil, lanolin, peanut oil, spermacetic wax, sesame oil, or almond oil), hydrogenated and sulfated oils (such as hydrogenated castor oil, hydrogenated cotton seed oil, hydrogenated soya bean oil, hydrogenated corn oil, or hydrogenated sulfated castor oils), alcohols/acids/esters (such as cetyl alcohol, stearic acid, stearyl alcohol, oleic acid, olelyl alcohol, palmitic acid, lauryl alcohol, lauraic acid, myristyl alcohol, ethyl oleate, isopropyl myristicate, or ethylene glycol), and silicones (such as dimethylpropylsiloxanes, methyl phenyl polysiloxanes, and steryl esters of dimethyl polysiloxanes).

Absorption bases are known to take up several times their own weights in water but not permit absorption of medicament from the base. The advantages of absorption bases are their protective, occlusive, and emollient properties, their ability to absorb liquids, and that they do not wash off easily so they hold the incorporated compound with sufficient contact with the skin. Representative examples of absorption bases include activating petrolatum and anhydrous lanolin.

Silicon bases typically are typically composed of siloxane oligomers, polymers, or derivatives thereof when used in skin applications. Silicone bases provide a good emollient and occlusive properties and are typically non-reactive and non-irritating, but are sometimes preferred compared to other oleaginous bases due to their breathability on the skin and their permeability to water vapor. Representative silicon bases may be composed of silicones including, but not limited to, hexamethyldisiloxane, octamethyltrisiloxane, decamethylcyclopentasiloxane, cyclopentasiloxane, cyclohexasiloxane, polydimethylsiloxane (dimethicone), hydroxy-terminated polydimethylsiloxane (dimethiconol), blends of dimethicone and dimethiconol, dimethicone crosspolymers, dimethicone crosspolymers in dimethicone, dimethicone crosspolymers in decamethylcyclopentasiloxane, blends of stearoxytrimethylsilane and stearyl alcohol, alkymethyl siloxane copolyol, silicone polyether, caprylyl methicone, trimethylsiloxysilicate, trimethylsiloxysilicate in dimethicone, C30-C45 alkyldimethylsilylpolypropylsilsesquioxane, PEG-10 dimethicone, or combinations thereof. Various silicon bases appropriate for topical applications are available from commercial suppliers, for example Dow Corning.

In another aspect, a topical product is provided comprising a first formulation and a second activating formulation. The first formulation comprises an effective amount of a compound described herein in a substantially anhydrous carrier, as defined herein and the second activating formulation is hydrous. Examples of the first formulation include and a topically acceptable carrier selected from an oleaginous base, an absorption base, and a silicone base, or a combination thereof.

In certain embodiments, the first formulation and the second activating formulation are kept physically separated until application on the skin. Alternatively, the first formulation and the second activating formulation are mixed when applied to the skin. In a different embodiment, the carbon monoxide is released upon mixing of the first formulation and the second activating formulation. This topical product allows for stable storage of the active compound in an anhydrous carrier when not in use. The mixing of the first formulation and the second activating formulation produces an emulsion that would have properties potentially more appealing to the end user when applied to the skin, while ensuring activation of the compound only once applied to the skin. In typical embodiments, the activating carrier further comprises an emulsifier to further ensure proper mixing of the first formulation and the second activating formulation.

The second activating formulation may for example comprise an aqueous solution containing an emulsifier, but more typically would comprise a type of topical formulation containing at least a portion of water or other activating component, for example a cream, a lotion, a gel, or a liniment formulation. The second activating formulation may an additional activating diluent including, but not limited to water, lower monovalent alcohols (e.g. $C_2$-$C_4$), propylene glycol, polyethylene glycol, polypropylene glycol, glycerol, butylene glycol, 1,2,3-butanetriol, sorbitol esters, 1,2,6-hexanetriol, ethanol, isopropanol, sorbitol esters, butanediol, ether propanol, ethoxylated ethers, propoxylated ethers, or combinations thereof.

The second activating formulation may contain an emulsifier to aid in the complete mixing of the two formulations upon application to the skin. These materials may be ionic or non-ionic, and are typically chosen for their ability to provide wetting, emulsification, low irritation, foam (or lack thereof), or other desired properties. Representative examples of emulsifiers include, but are not limited to: alkyl sulfates; alkyl ether sulfates; alkyl monoglyceryl ether sulfates; alkyl sulfonates; alkylaryl sulfonates; alkyl sulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; polyoxyethylene derivatives of polyol esters (1) derived from (a) a fatty acid containing from about 8 to about 22, and preferably from about 10 to about 14 carbons, and (b) a polyol selected from sorbitol, sorbitan, glucose, alpha-methyl glucoside, polyglucose having an average of about 1 to about 3 glucose residues per molecule, glycerin, pentaerythritol and mixtures thereof, (2) contains an average of from about 10 to about 120, and preferably about 20 to about 80 oxyethylene units, and (3) has an average of about 1 to about 3 fatty acid residues per mole of polyoxyethylene derivative of polyol ester; amphocarboxylates such as alkylamphoacetates; alkyl betains; amidoalkyl betaines; amidoalkyl sultaines; amphophosphates; phosphorylated imidazolines such as phosphobetaines and pyrophosphobetaines; carboxylalkyl alkyl polyamines; alklyiminodipropionates; alkylamphoglycinates; alkylamphopropionates; N-alkyl beta-aminopropionic acids; alkylpolyamino carboxylates; alkyl quaternaries; benzyl quaternaries; ester quaternaries; ethoxylated quaternaries; alkyl amines; and combinations thereof.

In one embodiment, the second activating formulation comprises a water-soluble ointment base. Water-soluble bases, also known as greaseless ointment bases, consists of water soluble ingredients such as polyethylene glycol polymer (carbowax). Polyethylene glycol is water soluble, nonvolatile, and inert. Other water-soluble bases include glyceryl monostearate, cellulose derivatives, sodium alginate, bentonite, and carbopol 934.

In one embodiment, the second activating formulation is a gel formulation. Gels are transparent or translucent semisolid preparations of one or more active ingredients in suitable activating bases. Gels may be clear or opaque. Gels are prepared by either a fusion process or a special procedure necessitated by the gelling agents, humectants, and preservatives. Gelling agents exhibit pseudoplastic properties that give the formulation a thixotropic consistency. Gelling agents are typically used in concentrations of 0.5-10% to allow for easy addition of the active drug before the gel is formed. Representative examples of agents used in gel formulations include tragacanth, fenugreek mucilage, methyl cellulose, hydroxy ethyl cellulose, hydroxy propyl cellulose, hydroxy propyl methyl cellulose, carboxy methylcellulose, carbopol, pectin, poloxamers, alginates (such as sodium, potassium, or ammonium alginates), gelatin, starch, polyvinyl alcohol, povidone, propylene glycol, and ethyldiamine tetraacetic acid.

In one embodiment, the second activating formulation is a lotion formulation. Lotions are low- to medium-viscosity preparations intended for application to unbroken skin. Lotions are applied to external skin with bare hands, a clean cloth, cotton wool or gauze. Lotions provide cooling effects to the skin by the evaporation of solvents formulated therein. Typical additives in lotion formulations include bentonite, sodium carboxymethylcellulose, alcohols, and glycerin.

In one embodiment, the second activating formulation is a cream formulation. Creams are semisolid emulsion formulation for application to the skin or mucous membranes. Creams may be formulated as water in oil (w/o) emulsions or as oil in water (o/w) emulsions. Water in oil emulsion creams are less greasy and provide good spreadability compared to ointments. Oil in water emulsion creams, often called vanishing creams, readily rub into the skin and are easily removed by water.

Water in oil emulsion formulations typically consist of an activating component, e.g. water or other activating diluent, and a hydrophobic component, e.g. a lipid, oil, or oily material. The activating component is typically dispersed, i.e. exists as small particles and droplets, within the hydrophobic component. Water in oil emulsions typically comprise from about 1% to about 98% of the dispersed activating phase and from about 1% to about 50% of the hydrophobic phase. Additives commonly used in water in oil emulsion formulations include wool fat (containing sterols, cholesterol, oxycholesterol, triterpene, or aliphatic alcohols), waxes, bivalent soaps, sorbitan esters, borax, and oleic acid. In some embodiments, the water in oil emulsion refers to a water in silicone emulsion.

Oil in water emulsion formulations typically consist of an activating component, e.g. water or other activating diluent, and a hydrophobic component, e.g. a lipid, oil, or oily material. The hydrophobic component is typically dispersed, i.e. exists as small particles and droplets, within the activating component. Water in oil emulsions typically comprise from about 1% to about 98% of the activating phase and from about 1% to about 50% of the dispersed hydrophobic phase. Additives commonly used in oil in water emulsion formulations include polysorbates (such as Tween 80, Tween 21, and Tween 40), methylcellulose, acacia, tragacanth, triethanolamine oleate, *arachis* oil, and cetostearyl alcohol.

A wide variety of optional components/ingredients may be included optionally in any of the above topical formulations including, but not limited to, absorbents, abrasives, anticaking agents, antifoaming agents, antimicrobial agents, binders, biological actives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-inflammatory agents, anti-androgens, depilation agents, desquamation agents/exfoliants, organic hydroxy acids, vitamins and derivatives thereof, and natural extracts.

Micro- and Nano-Particle Formulations

The CO-releasing compounds of the present invention can be formulated as particles, for example, microparticles or nanoparticles. In one embodiment, the particles are or include microparticles. In an alternative embodiment, the particles are or include nanoparticles. The particles can be polymeric or non-polymeric, for example, activated charcoal particles.

Common techniques that may be used for preparing particles using the compounds described herein include, but are not limited to, solvent removal, spray drying, phase inversion, coacervation, and low temperature casting. Suitable methods of particle formulation are briefly described below. Pharmaceutically acceptable excipients, including disintegrants, preservatives, and antioxidants, can optionally be incorporated into the particles during particle formation.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion.

In one embodiment, an active compound as described herein is administered to a patient in need thereof as particles formed by solvent removal. In another embodiment, the present invention provides particles formed by solvent removal comprising a compound of the present invention and one or more pharmaceutically acceptable excipients as defined herein. In another embodiment, the particles formed by solvent removal comprise a compound of the present invention and an additional therapeutic agent. In a further embodiment, the particles formed by solvent removal comprise a compound of the present invention, an additional therapeutic agent, and one or more pharmaceutically acceptable excipients. In another embodiment, any of the described particles formed by solvent removal can be formulated into a tablet and then coated to form a coated tablet. In an alternative embodiment, the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment, the present invention provides particles formed by low temperature casting comprising a compound of the present invention and one or more pharmaceutically acceptable excipients as defined herein. In another embodiment, the particles formed by low temperature casting comprise a compound of the present invention and an additional therapeutic agent. In a further embodiment, the particles formed by low temperature casting comprise a compound of the present invention, an additional therapeutic agent, and one or more pharmaceutically acceptable excipients. In another embodiment, any of the described particles formed by low temperature casting can be formulated into a tablet and then coated to form a coated tablet. In an alternative embodiment, the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and U.S. Pat. No. 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010); U.S. Pat. No. 6,632,671 to Unger Oct. 14, 2003, all incorporated herein by reference.

In one embodiment, the particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticles.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

The pharmaceutical compositions can be formulated for delayed release. Delayed release formulations can be created by coating a solid dosage form with a polymer film which is insoluble in the acidic environment of the stomach and soluble in the neutral environment of the small intestine. The delayed release dosage form can be prepared, for example, by coating a drug or a drug-containing composition with a selected coating material. The drug-containing composition may be, for example, a table for incorporation into a capsule, a table for use as an inner core in a coated core dosage form, or a plurality of drug-containing beads, particles or granules, for incorporation into either a tablet or capsule. Typical coating materials include bioerodible, gradually hydrolyzable, gradually water-soluble, or enzymatically degradable polymers. The coating materials may be polymers typically used when creating enteric coatings. Enteric polymers, as understood by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Examples of coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropyl methyl cellulose phthalate, methyl cellulose, ethyl cellulose, cellulose acetate, cellulose acetate phthalate, cellulose acetate trimellitate and carboxymethylcellulose sodium; acrylic acid polymers and copolymers, preferably formed from acrylic acid, methyacrylic acid, methyl acrylate, ethyl acrylate, methyl methacrylate or ethyl methacrylate, and other methacrylic resins that are commercially available under the trade-name Eudragit® (Rohm Pharma, Westerstadt, Germany) including Eudragit L30D-55 and L100-55 (soluble at pH=5.5 and above), Eudragit L-100 (soluble at pH=6.0 and above), Eudragit S (soluble at pH 7.0 and above), and Eudragit NE, Eudragit RL, and Eudragit RS (water-insoluble polymers having varying permeability and expandability); vinyl polymers and copolymers such as polyvinyl pyrrolidine, vinyl acetate, vinyl acetate phthalate, vinyl acetate crotonic acid copolymer, and ethyl-vinyl acetate copolymers; enzymatically degradable polymers such as azo polymers, pectin, chitosan, amylose and guar gum; zein and shellac. Combinations of different coating materials may also be used. Multilayer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from clinical studies.

The coating composition may include conventional additives such as plasticizers, pigments, colorants, stabilizing agents, and glidants. A plasticizer is usually present to reduce the fragility of the coating and will generally represent from about 10 wt. % to about 50 wt. % relative to the dry weight of the polymer. Examples of typical plasticizers include polyethylene glycol, propylene glycol, tracetin, dimethyl phthalate, diethyl phthalate, dibutyl phthalate, dibutyl sebacate, triethyl citrate, tributyl citrate, triethyl acetate citrate, castor oil and acetylated monoglycerides. A stabilizing agent is preferably used to stabilize particles in the dispersion. Typical stabilizing agent sare non-ionic emulsifiers such as sorbitan esters, polysorbates and polyvinylpyrrolidone. Glidants are typically used to reduce sticking effects during film formation and drying, and will generally represent from about 25 wt. % to about 75 wt. % of the polymer weight in the coating solution. Representative glidants include talk, magnesium stearate and glycerol monostearates. Pigments such as titanium oxide may also be used. In some embodiments, a small quantity of an antifoaming agent such as simethicone may be added to the coating composition.

Particles, including nanoparticles and microparticle, are common for ocular delivery of drugs. Many methods and devices for drug delivery to the eye, including polymeric delivery, are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen O Y); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

V. Methods of Treatment

In one embodiment, an effective amount of Formula I through Formula VI or its salt or composition as described herein is used to treat or to prevent a medical disorder. The compounds described herein can be used to treat disorders that show improvement when gaseous carbon monoxide is administered. The compounds of the present invention release carbon monoxide in vivo, allowing for administration in a form that does not require the use of specialized equipment and allows controlled dosing. In one embodiment, the compounds of the present invention may be used to treat a disorder that has previously shown improvement when treated with gaseous carbon monoxide. In one embodiment, a method is provided comprising administering an effective amount of a compound or a pharmaceutically acceptable or composition thereof described herein to a subject, typically a human, to a medical disorder described herein.

In some embodiments, a compound of Formula I through Formula VI or a pharmaceutically acceptable salt thereof may be used to treat an inflammatory disorder. Examples of inflammatory disorder include, but are not limited to: inflammation associated with asthma; arteritis including Polyarteritis, temporal arteritis, periarteritis nodosa, and Takayasu's arteritis; arthritis including crystalline arthritis, osteoarthritis, psoriatic arthritis, gouty arthritis, reactive arthritis, rheumatoid arthritis, and Reiter's arthritis; ankylosing spondylitis; amylosis; amyotrophic lateral sclerosis; autoimmune diseases; allergies or allergic reactions; atherosclerosis; bronchitis; bursitis; chronic prostatitis; conjunctivitis; Chagas disease; chronic obstructive pulmonary disease; cermatomyositis; diverticulitis; diabetes including type I diabetes mellitus and type II diabetes mellitus; a skin condition including psoriasis, eczema, burns, dermatitis, and pruritis; endometriosis; Guillain-Barre syndrome; infection; ischaemic heart disease; Kawasaki disease; glomerulonephritis; gingivitis; hypersensitivity; headaches including migraine headaches and tension headaches; ileus including postoperative ileus and ileus during sepsis; idiopathic thrombocytopenic purpura; interstitial cystitis; a gastrointestinal disorder including peptic ulcers, regional enteritis, diverticulitis, gastrointestinal bleeding, Eosinophilic esophagitis, Eosinophilic gastritis, eosinophilic gastroenteritis, eosinophilic colitis, gastritis, diarrhea, gastroesophageal reflux disease, inflammatory bowel disease, Crohn's disease, Behcet's syndrome, ulcerative colitis, collagenous colitis, lymphocytic colitis, ischaemic colitis, diversion colitis, indeterminate colitis, microscopic colitis, chemical colitis, infectious colitis, fulminant colitis, and inflammatory bowel syndrome; lupus; multiple sclerosis, Morphea; myeasthenia gravis; myocardial ischemia; nephrotic syndrome; pemphigus vulgaris; pernicious anemia; peptic ulcers; Polymyositis; primary biliary cirrhosis; neuroinflammation including Parkinson's disease, Huntington's disease, and Alzheimer's disease; prostatitis; chronic inflammation associated with cranial radiation injury; pelvic inflammatory disease; reperfusion injury; regional enteritis; rheumatic fever; systemic lupus erythematosus; schleroderma; scierodoma; Sarcoidosis; spondyloarthopathies; Sjogren's syndrome; thyroiditis; transplantation rejection; tendonitis; trauma or injury including frostbite, chemical irritants, toxins, scarring, burns, or physical injury; vasculitis; vitiligo; and Wegener's granulomatosis.

In some embodiments, the compound of Formula I through Formula VI or a pharmaceutically acceptable salt thereof may be used to treat a pain disorder. The pain disorder may be an acute pain disorder or a chronic pain disorder. Examples of pain disorders that may be treated include, but are not limited to, inflammatory pain, postoperative pain, osteoarthritis, pain associated with metastatic cancer, trigeminal neuralgia, acute herpetic and post-herpetic neuralgia, diabetic neuropathy, causalgia, brachial plexus avulsion, occipital neuralgia, reflex sympathetic dystrophy, fibromyalgia, gout, and phantom limb pain.

In one embodiment, a method for the treatment of infection-induced inflammatory pain, including but not limited to pain induced from the flu, SARS, or a cold, in a subject is provided comprising administering an effective amount of a compound of Formula I through Formula VI or a pharmaceutically acceptable salt thereof.

In one embodiment, a method for the treatment of inflammatory pain in a subject is provided comprising administering an effective amount of a compound described herein or its pharmaceutically acceptable salt.

In one embodiment, a method for the treatment of postoperative pain in a subject is provided comprising administering an effective amount of a compound of Formula I through Formula VI or a pharmaceutically acceptable salt thereof.

In one embodiment, a method for the treatment of osteoarthritis in a subject is provided comprising administering an effective amount of a compound of Formula I through Formula VI or a pharmaceutically acceptable salt thereof.

In one embodiment, a method for the treatment of pain associated with metastatic cancer in a subject is provided comprising administering an effective amount of a compound of Formula I through Formula VI or a pharmaceutically acceptable salt thereof.

In some embodiments, the compounds of Formula I through Formula VI or a pharmaceutically acceptable salt thereof may be used to treat neuropathic pain. Neuropathic pain is pain caused by damage or disease that affects the somatosensory nervous system. Neuropathic pain is typically characterized by abnormal sensations (dysesthesia) or pain from normally non-painful stimuli (allodynia). Neuropathic pain may result from a disorder of the peripheral system or a disorder of the central nervous system, e.g. the brain or spinal cord. Central neuropathic pain is found in cases of spinal cord injury, multiple sclerosis, and stroke. Peripheral neuropathic pain can be found in patients with in diabetes (diabetic neuropathy), herpes zoster infection, HIV infection, nutritional deficiencies, exposure to toxins, remote manifestations of malignancies, immune-mediated disorders, and physical trauma to the nerve trunk. Neuropathic pain may occur in cases of cancer either due to direct compression of a tumor on peripheral nerves, or as a side effect of chemotherapy (chemotherapy-induced peripheral neuropathy), radiation or surgery.

In one embodiment, a method for the treatment of central neuropathic pain in a subject is provided comprising administering an effective amount of a compound of Formula I through Formula VI or a pharmaceutically acceptable salt thereof.

In one embodiment, a method for the treatment of peripheral neuropathic pain in a subject is provided comprising administering an effective amount of a compound of Formula I through Formula VI or a pharmaceutically acceptable salt thereof.

In one embodiment, a method for the treatment of trigeminal neuralgia in a subject is provided comprising an effective amount of a compound of Formula I through Formula VI or a pharmaceutically acceptable salt thereof.

In one embodiment, a method for the treatment of acute herpetic neuralgia in a subject is provided comprising administering an effective amount of a compound of Formula I through Formula VI or a pharmaceutically acceptable salt thereof.

In one embodiment, a method for the treatment of post-herpetic neuralgia in a subject is provided comprising administering an effective amount of a compound of Formula I through Formula VI or a pharmaceutically acceptable salt thereof.

In one embodiment, a method for the treatment of neuropathic pain associated with diabetic peripheral neuropathy in a subject is provided comprising administering an effective amount of a compound of Formula I through Formula VI or a pharmaceutically acceptable salt thereof.

In one embodiment, a method for the treatment of neuropathic pain associated with injury or trauma in a subject is provided comprising administering an effective amount of a compound of Formula I through Formula VI or a pharmaceutically acceptable salt thereof.

In one embodiment, a method for the treatment of causalgia in a subject is provided comprising administering an effective amount of a compound of Formula I through Formula VI or a pharmaceutically acceptable salt thereof.

In one embodiment, a method for the treatment of brachial plexus avulsion in a subject is provided comprising administering an effective amount of a compound of Formula I through Formula VI or a pharmaceutically acceptable salt thereof.

In one embodiment, a method for the treatment of occipital neuralgia in a subject is provided comprising administering an effective amount of a compound of Formula I through Formula VI or a pharmaceutically acceptable salt thereof.

In one embodiment, a method for the treatment of reflex sympathetic dystrophy in a subject is provided comprising administering an effective amount of a compound of Formula I through Formula VI or a pharmaceutically acceptable salt thereof.

In one embodiment, a method for the treatment of fibromyalgia in a subject is provided comprising administering an effective amount of a compound of Formula I through Formula VI or a pharmaceutically acceptable salt thereof.

In one embodiment, a method for the treatment of gout in a subject is provided comprising administering an effective amount of a compound of Formula I through Formula VI or a pharmaceutically acceptable salt thereof.

In one embodiment, a method for the treatment of phantom limb pain in a subject is provided comprising administering an effective amount of a compound of Formula I through Formula VI or a pharmaceutically acceptable salt thereof.

In one embodiment, a method for the treatment of rheumatoid arthritis in a subject is provided comprising administering an effective amount of a compound of Formula I through Formula VI or a pharmaceutically acceptable salt thereof. CO has been proven to ameliorate collagen-induced arthritis in mice (Takagi, T., et al. *Inflammation* 2009, 32, 2, 83-88; Bonelli, M., et. al. *Clin Exp Rheumatol.* 2012, 30, 1, 73-8)

In an alternative embodiment, an effective amount of a compound of Formula I through Formula VI or a pharmaceutically acceptable salt thereof is provided for an analgesic effect. CO, whether produced endogenously by HO or administered by using exogenous CO, is proven to be efficacious in animal models of nociceptive pain management (Castany, S., et al. *Psychopharmacol.* 2016, 233, 2209-2219; Fan, W., et al. *J. Neurosci. Res.* 2011, 89, 802-807; Gou, G., et al. *Eur. J. Pharmacol.* 2014, 737, 41-46) and neuropathic pain management (Hervera, A., et al. *Anesthesiology* 2013, 118, 1180-1197; Hervera, A., et al. *PLOS ONE* 2012, 7, e43693; Jurga, A. M., et al. *Pharmacolog. Rep.* 2016, 68, 206-213; Mendez-Lara, K. A., et al. *PLOS ONE* 2018, 13, e0204841; Wang, H., et al. *J. Mol. Neurosci.* 2017, 63, 58-69; Bijjem, K. R. V., et al. *Naunyn-Schmiedeberg's Arch. Pharmacol.* 2013, 386, 79-90).

Further, CO is known to synergize with opioids, cannabinoids, and gabapentinoids in pain management (Godai, K., et al. *Pain Rep.* 2018, 3, e677; Carcole, M., et al. *J Pharmacol. Exp. Therap.* 2014, 351, 224) and may be involved in the anti-nociceptive effect of some NSAIDs (Grangeiro, N. M. G., et al. *Pharmacolog. Rep.* 2011, 63, 112-119). The cytoprotective, anti-inflammation, and neuroprotective effects of CO may also be beneficial in pain management, especially nociceptive pain.

In an alternative embodiment, a method for the treatment of atherosclerosis in a subject is provided comprising administering an effective amount of a compound of Formula I through Formula VI or a pharmaceutically acceptable salt thereof. CO has been shown to attenuate animal models of atherosclerosis (Hou, M., et al. *Shanghai journal of stomatology* 2014, 23, 531-538; Liu, D. N., et al. *Cardiovasc. J. Aft.* 2010, 21, 257-262; Liu, D., et al. J. Pharmacol. Sci. 2012, 118, 14-24; Liu, D. N., et al. *Chinese journal of pathology* 2011, 40, 397-402; Durante, W., et al. *J. Cell. Mol. Med.* 2006, 10, 672-686; Morita, T. *Arterioscler. Thromb. Vasc. Biol.* 2005, 25, 1786-1795; Siow, R. C., et al. *Cardiovasc. Res.* 1999, 41, 385-394).

In an alternative embodiment, a method for the treatment of organ injuries in a subject is provided comprising administering an effective amount of a compound of Formula I through Formula VI or a pharmaceutically acceptable salt thereof. In one embodiment, the organ is selected from the kidney, heart, liver, brain, and the gastrointestinal tract.

CO has been extensively examined as a therapeutic agent for treating inflammatory conditions and in offering cytoprotection in various organ injury models including kidney (Correa-Costa, M., et al. *Proc. Natl. Acad. Sci. USA* 2018, 115, E2302; Uddin, M. J., et al. *Korean J. Physiol. Pharmacol.* 2018, 22, 567-575; Cheng, Y., et al. *Curr. Pharm. Des.* 2017, 23, 3884-3898; Abe, T., Lab. Invest. 2017, 97, 468-477), heart (Suliman, H. B., et al. *J. Clin. Invest.* 2007, 117, 3730-3741; Kim, H. H., et al. *Int. J. Mol. Sci.* 2019, 19, doi: 10.3390/ijms19082381), liver (Zheng, Y., et al. *Nature Chem.* 2018, 10, 787-794; Sun, J., et al. *Liver Transpl.* 2017, 23, 510-526; Upadhyay, K. K., et al. *Toxicology and appliedpharmacology* 2018, 360, 99-108), brain (Che, X., et al. *Front. Neurosci.* 2018, 12, 392; Choi, Y. K., et al. *Nat. Med.* 2016, 22, 1335-1341; Wang, P., et al. *Int. J. Biol. Sci.* 2016, 12, 1000-1009), and the gastrointestinal tract (Ji, X., et al. *Angew. Chem. Int. Ed. Engl.* 2016, 55, 15846-15851; Hegazi, R. A. F., et al. *J. Exp. Med.* 2005, 202, 1703; Sheikh, S. Z., et al. *J. Immunol.* 2011, 186, 5506-5513; Steiger, C., et al. *J. Control. Release* 2016, 239, 128-136; Takagi, T., et al. *Digest. Dis. Sci.* 2010, 55, 2797-2804; Takagi, T., et al. *Digest. Dis. Sci.* 2011, 56, 1663-1671; Uddin, M. J., et al. *Oxid. Med. Cell. Longev.* 2013, 2013, 210563), and others (Motterlini, R., et al. *Nat. Rev. Drug Discov.* 2010, 9, 728-743; Ji, X., et al. *J. Pharm. Sci.* 2016, 105, 406-416).

In an alternative embodiment, a method for the treatment or prevention of ischemia reperfusion injury (IRI) in a subject is provided comprising administering an effective amount of a compound of Formula I through Formula VI or a pharmaceutically acceptable salt thereof. In one embodiment, the ischemia reperfusion injury is a result of surgery or organ transplantation.

CO's efficacy has been extensively demonstrated in organ transplantation work. In multiple organ transplant studies, the data sets were similar in that they all showed that CO could prevent ischemia reperfusion injury (Hanto, D. W., et al. *Am. J. Transplant.* 2010, 10, 2421-2430; Nakao, A., et al. *Am. J. Transplant.* 2005, 5, 282-291, Neto, J. S., et al. *Am. J. Physiol. Renal. Physiol.* 2004, 287, F979-989; Nakao, A., *Surgery* 2003, 134, 285-292; Nakao, A., et al. *Am. J Pathol.* 2003, 163, 1587-1598).

In an alternative embodiment, a method for the treatment of acute kidney injury in a subject is provided comprising administering an effective amount of a compound of Formula I through Formula VI or a pharmaceutically acceptable salt thereof. In one embodiment, the acute kidney injury is a result of chemotherapy. In one embodiment, the acute kidney injury is cisplatin-induced acute kidney injury. In one embodiment, the acute kidney injury is induced by methotrexate. In one embodiment, the acute kidney infection is caused by ischemia reperfusion injury.

CO has been shown to be protective in areas such as chemotherapy-mediated injury as observed with cisplatin or methotrexate (Holditch, S. J., et al. *Int. J. Mol. Sci.* 2019, 20, doi: 10.3390/ijms20123011; Severin, M. J., et al. *Clin. Exp. Pharmacol. Physiol.* 2019, doi: 10.1111/1440-1681.13122)

and there have been extensive studies describing the biological activities of CO including as an anti-inflammatory and anti-apoptotic agent in kidney endothelial cells, hepatocytes and cardiomyocytes, as well as its pro-apoptotic effect in pathological conditions such as cancer cells, dysregulated fibroblasts, and aggressive T cells (Motterlini, R., et al. *Nat Rev Drug Discov* 2010, 9, 728-743).

In an alternative embodiment, a method to improve renal microcirculation in a subject is provided comprising administering an effective amount of a compound of Formula I through Formula VI or a pharmaceutically acceptable salt thereof. The effect of CO on renal microcirculation and reno-protective activity has been studied (Botros, F. T., et al. Am. J. Physiol. Heart Circ. Physiol. 2006, 291, H2772-2778).

In an alternative embodiment, a method for the treatment of heavy metal poisoning in a subject is provided comprising administering an effective amount of a compound of Formula I through Formula VI or a pharmaceutically acceptable salt thereof. In an animal study using rats poisoned by 100 mg/kg lead acetate, CORM-A1 treatment for 3 months restored serum urea to a similar level of the non-poisoned control group. Intracellular glutathione (GSH) of the kidney tissue was also restored to the level comparable with the non-poisoned control. Serum creatinine and malondialdehyde levels were also significantly decreased by CORM-A1 treatment compared with the poisoned group. CORM-A1 was also shown to prevent elevations of inflammatory cytokines (TNF, IL-1β) and caspase-3 (Southam, H. M., et al. *Redox Biol.* 2018, 18, 114-123). The amelioration effect of CORM-A1 was comparable with 10 mg/kg/d L-NAME and 3 mg/kg/d NaHS in all tested kidney function-related biochemical markers (Abdel-Zaher, A. O., et al. *Toxicol Lett* 2019, 310, 39-50).

In an alternative embodiment, a method to prevent chemotherapy-induced cardiotoxicity and/or sensitize cancer cells to chemotherapy in a subject is provided comprising administering an effective amount of a compound of Formula I through Formula VI or a pharmaceutically acceptable salt thereof. In one embodiment, the chemotherapy is doxorubicin. In one embodiment, the chemotherapy is cisplatin.

CO has shown to have protective effects in doxorubicin-induced cardiotoxicity and sensitizes cancer cells toward chemotherapy. It has demonstrated that low doses of CO protect the cardiomyocyte from cell death, and maintain overall cardiovascular health (Soni, H., et al. *Toxicol. Appl. Pharmacol.* 2011, 253, 70-80; Soni, H. M., et al. *Indian J. Pharm. Sci.* 2012, 74, 281-291; Suliman, H. B., et al. *J. Clin. Invest.* 2007, 117, 3730-3741; Clark, J. E., et al. *Circ. Res.* 2003, 93, e2-8; Musameh, M. D., et al. *Med. Gas. Res.* 2016, 6, 122-129; Zhao, S., et al. *Mol. Med. Rep.* 2014, 9, 754-762; Zhou, P. Y., Transplant Proc. 2015, 47, 2746-2751).

DXR cardiotoxicity is a major limiting factor of this standard-of-care drug and identification of ways to mitigate the damage by DXR could have significant implications because of the powerful cardioprotective effects of CO. CO also sensitizes cancer cells and may result in profound effects to reduce the dose and thus minimize toxicity of chemotherapy. Furthermore, existing drug resistance, especially efflux-related multi-drug resistance, is unlikely to have an impact on the effectiveness of CO-based approaches because of CO's ability to diffuse through membranes and the extremely low likelihood for CO to be an efflux substrate. CO is also known to control inflammation, which is intimately linked to cancer (Roxburgh, C. S. D., et al. *British J Cancer* 2014, 110, 1409-1412; Rayburn, E. R., et al. *Mol. Cell. Pharmacol.* 2009, 1, 29-43; Balkwill, F., et al. *Lancet* 2001, 357, 539-545; Grivennikov, S. I., et al. *Cell* 2010, 140, 883-899; Coussens, L. M.; Werb, Z. *Nature* 2002, 420, 860-867).

In an alternative embodiment, a method for the treatment of pancreatitis in a subject is provided comprising administering an effective amount of a compound of Formula I through Formula VI or a pharmaceutically acceptable salt thereof. In one embodiment, the pancreatitis is severe acute pancreatitis (SAP).

In severe acute pancreatitis (SAP), HO-1 gene expression is remarkably up-regulated in rat pancreas and liver mitigating pancreatic injury and subsequent organ injury brought about by an intense systemic inflammatory response. The protective effects of HO-1 in pancreatitis is reproduced by CO, one of its metabolites. CO delivered in different forms has been shown to be efficacious in controlling pancreatitis (Chen, P., et al. *Cytokine* 2010, 49, 15-23; Nagao, S., et al. *Internation, J. Nanomed.* 2016, 11, 5611-5620; Makhija, R., et al. *J. Hepato-Biliary-Pancr. Surg.* 2002, 9, 401-410; Xue, J.; Habtezion, *J. Clin. Investig.* 2014, 124, 437-447; Taguchi, K., et al. *Drug Delivery* 2018, 25, 1266-1274).

In an alternative embodiment, a method for the treatment of malaria in a subject is provided comprising administering an effective amount of a compound of Formula I through Formula VI or a pharmaceutically acceptable salt thereof. CO protects against severe forms of malaria associated with *Plasmodium* infection (Jeney, V., et al. *Cell Rep.* 2014, 8, 1, 126-36; Pamplona, A., et al. *Nat. Med.* 2007, 13, 6, 703-10; Pena, AC., *Antimicrob Agents Chemother.* 2012, 56, 3, 1281-90) In an alternative embodiment, a method for the treatment of traumatic brain injury in a subject is provided comprising administering an effective amount of a compound of Formula I through Formula VI or a pharmaceutically acceptable salt thereof. CO, similar to NO, acts as a second messenger and a neuromodulator. As such, CO and HO expression have been shown to promote neurogenesis in traumatic brain injury (Choi, Y K., et al. Nat Med. 2016, 22, 11, 1335-1341, Chang, E F., et. al. J Neurosci. 2003, 23, 9, 3689-96; Liu, Y., at al., Neuroreport. 2013, 24, 6, 281-6; Fukuda, K., et al. Neurosci Lett. 1995, 199, 2, 127-30; Schallner N., et. al. J Clin Invest 2015, 125, 7, 2609-2625; Wood, H., et. al., Nat Rev Neurology 2016, 12, 615; Che, X., et al., Front Neurosci 2018, 12, 392)

In an alternative embodiment, a method for the treatment of sickle cell disease in a subject is provided comprising administering an effective amount of a compound of Formula I through Formula VI or a pharmaceutically acceptable salt thereof. CO at low concentrations offers powerful cytoprotection in sickle cell disease (Belcher, J., et. al., Plos One 2018, 13, 10, e0205194; Gomperts, E., et al., Am J Hematol 2017, 92, 6, 569-582; Araujo, J., Blood, 2013, 122, 15, 2535-2536) In an alternative embodiment, a method for the treatment of autoimmune neuroinflammation in a subject is provided comprising administering an effective amount of a compound of Formula I through Formula VI or a pharmaceutically acceptable salt thereof. HO-1 expression or exogenous administration of CO suppresses the pathologic outcome of autoimmune neuroinflammation (Chora, A., et al., *J Clin Invest* 2007, 117, 2, 438-447)

In an alternative embodiment, a method for the treatment of angiogenesis in a subject is provided comprising administering an effective amount of a compound of Formula I through Formula VI or a pharmaceutically acceptable salt thereof. Exposure of mice CO has been shown to inhibit vascular endothelial growth factor (VEGF)-induced angiogenesis (Ahmad, S., et al., Thromb Haemost 2015, 113, 2, 329-37; Kourti, M., et. al., *Oncotarget*, 2019, 10, 10, 1132-1148)

In an alternative embodiment, a method for the treatment of a metabolic disorder in a subject is provided comprising administering an effective amount of a compound of Formula I through Formula VI or a pharmaceutically acceptable salt thereof. In one embodiment, the metabolic disorder is selected from Familial hypercholesterolemia, Gaucher disease, Hunter syndrome, Krabbe disease, Maple syrup urine disease, Metachromatic leukodystrophy, Mitochondrial encephalopathy, lactic acidosis, stroke-like episodes (MELAS), Niemann-Pick, Phenylketonuria (PKU), *Porphyria*, Tay-Sachs disease, and Wilson's disease.

In one embodiment, an active compound or its salt or composition as described herein may be provided in combination or alternation with or preceded by, concomitant with or followed by, an effective amount of at least one additional therapeutic agent, for example, for treatment of a disorder listed herein. Non-limiting examples of additional active agents for such combination therapy are provided below. Described below and herein generally, whenever any of the terms referring to an active compound or its salt or composition as described herein are used, it should be understood that pharmaceutically acceptable salt, prodrugs, or compositions are considered included, unless otherwise state or inconsistent with the text.

In one embodiment, an active compound or its salt or composition as described herein may be used in combination or alternation with a non-steroidal anti-inflammatory drug (NSAID). Representative examples of NSAIDs that may be used include, but are not limited to, aspirin, diflunisal, salicyclic acid and other salicylates, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celecoxib, rofecoxib, valdecoxib, parecoxib, lumiracoxib, etoricoxib, firocoxib, nimesulide, clonixin, licofelone, and h-harpagide.

In one embodiment, an active compound or its salt or composition as described herein may be used in combination or alternation with a corticosteroid. Representative examples of corticosteroids include, but are not limited to, hydrocortisone, methylprednisolone, prednisolone, prednisone, triamcinolone, amcinonide, budesonide, desonide, fluocinolone acetonide, fluocinonide, halcinonide, triamcinolone acetonide, beclometasone, betamethasone, dexamethasone, fluocortolone, halonetasone, mometasone, alclometasone dipropionate, betamethasone dipropionate, betamethasone valerate, clobetasol propionate, clobetasone butyrate, fluprednidene acetate, mometasone furoate, ciclesonide, cortisone acetate, hydrocortisone aceponate, hydrocortisone acetate, hydrocortisone buteprate, hydrocortisone butyrate, hydrocortisone valerate, prenicarbate, and tixocortol pivalate.

In one embodiment, an active compound or its salt or composition as described herein may be used in combination or alternation with an opioid. Representative examples of opioids include, but are not limited to, codeine, fentanyl, hydrocodone, hydromorphone, meperidine, methadone, morphine, oxycodone, alfentanil, remifentanil, sufentanil, etorphine, carfentanil, buprenorphine, pentazocine, propoxyphene, tapentadol, tramadol, butorphanol, and nalbuphine.

In one embodiment, an active compound or its salt or composition as described herein may be used in combination or alternation with a tricyclic antidepressant, for example nortriptyline or amitriptyline.

In one embodiment, an active compound or its salt or composition as described herein may be used in combination or alternation with duloxetine.

In one embodiment, an active compound or its salt or composition as described herein may be used in combination or alternation with an antiepileptic medication, for example gabapentin, regabalin, or sodium valproate.

VI. Methods for the Treatment of an Inflammatory Dematological Disorder

An effective amount of a selective CO-releasing compound of the present invention or its salt or composition as described herein can also be used to treat or prevent an inflammatory dermatological disorder, for example, acne vulgaris that is due to any bacteria that causes such acne, including *P. acnes* and *S. epidermis*. In one embodiment, a method is provided comprising administering to a human an effective amount of a compound or its pharmaceutically acceptable salt or composition either alone or in combination with an effective amount of an additional active agent, for example an antibiotic or anti-inflammatory agent, to treat acne vulgaris.

Acne vulgaris severity may be classified as mild, moderate, or severe. Mild acne is classically defined by the presence of clogged skin follicle (known as comedones) limited to the face with occasional inflammatory lesions. Moderate acne occurs when a higher number of inflammatory papules and pustules occur on the face, with some being found on the trunk of the body. Severe acne occurs when nodules are the characteristic facial lesions and involvement of the trunk is extensive.

The present method includes identifying a target portion of skin affected with an inflammatory dermatological disorder, for example, acne vulgaris, in need of treatment and applying a compound or its salt or composition as described herein to the target portion of skin. In some instances, the target portion of skin may not appear to be suffering from the inflammatory dermatological disorder, i.e. the compound or its salt or composition as described herein may be used as a preventative therapy for the inflammatory dermatological disorder. The compound or its salt or composition may be applied to the target skin portion and, if desired, to the surrounding skin at least once a day, twice a day, or on a more frequent daily basis during the treatment period. Typically, the compound or its salt or composition is applied in the morning and/or in the evening before bed.

The treatment period is ideally sufficient time for the active compound to reduce or eliminate the appearance of the inflammatory dermatological disorder, for example, acne vulgaris on the target portion of skin. The treatment period may last for at least 1 week, about two weeks, about 4 weeks, about 8 weeks, or about 12 weeks. The treatment period may extend over multiple months (about 3-12 months) or multiple years. The step of applying the compound or its salt or composition may be accomplished by localized application, i.e. by applying to the targeted area while minimizing delivery to skin surfaces where treatment is not desired, or by applying more generally or broadly to one or more skin surfaces.

*Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically slow-growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately lives deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

*Staphylococcus epidermidis* is a Gram-positive bacterium belonging to the *Staphylococcus* Genus and the Staphylococcaceae Family that is part of the normal human flora and typically skin flora or mucosal flora. It is a facultative anaerobic bacteria and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

In one embodiment, an active compound or its salt or composition as described herein may be used in combination or alternation with benzoyl peroxide. In the skin follicle, benzoyl peroxide kills *P. acnes* by oxidizing its proteins through the formation of oxygen free radicals and benzoic acid. These radicals are believed to interfere with the bacterium's metabolism and ability to make proteins. Additionally, benzoyl peroxide is mildly effective at breaking down comedones and inhibiting inflammation. In one embodiment, an active compound or its salt is formulated in combination with benzoyl peroxide in a topical formulation as described herein.

In one embodiment, an active compound or its salt or composition as described herein may be used in combination or alternation with a retinoid. Retinoids are medications which reduce inflammation, normalize the follicle cell life cycle, and reduce sebum production. They are structurally related to vitamin A. The retinoids appear to influence the cell life cycle in the follicle lining; this helps prevent the accumulation of skin cells within the hair follicle that can create a blockage. Frequently used topical retinoids include adapalene, isotretinoin, retinol, tazarotene, and tretinoin. In one embodiment, an active compound or its salt is formulated in combination with a retinoid in a topical formulation as described herein.

In one embodiment, an active compound or its salt or composition as described herein may be used in combination or alternation with an antibiotic. Antibiotics are frequently applied to the skin or taken orally to treat acne and are thought to work due to their antimicrobial activity against *P. acnes* and their ability to reduce inflammation. Commonly used antibiotics, either applied to the skin or taken orally, include clindamycin, erythromycin, metronidazole, sulfacetamide, and tetracyclines such as doxycycline and minocycline. Other representative topical antibiotics include bacitracin, polymycin b, neomycin, retapamulin, mupirocin, pramoxine, gentamicin, mafenide, and ozenoxacin. The compounds described herein are particularly effective in combination with antibiotics due to their potentiation of the antimicrobial effect of the antibiotic.

In one embodiment, an active compound or its salt is formulated in combination with an antibiotic in a topical formulation as described herein.

In one embodiment, an active compound or its salt or composition as described herein may be used in combination or alternation with azelaic acid. Azelaic acid is thought to be an effective acne treatment due to its ability to reduce skin cell accumulation in the follicle, along with its antibacterial and anti-inflammatory properties. In one embodiment, an active compound or its salt is formulated in combination with an antibiotic in a topical formulation as described herein.

In one embodiment, an active compound or its salt or composition as described herein may be used in combination or alternation with salicyclic acid. Salicyclic acid is a topically applied beta-hydroxy acid that has keratolytic properties in addition to stopping bacterial reproduction. In one embodiment, an active compound or its salt is formulated in combination with salicyclic acid in a topical formulation as described herein.

In one embodiment, an active compound or its salt or composition as described herein may be used in combination or alternation with niacinamide. Niacinamide can improve acne by decreasing inflammation, suppressing sebum production, and promoting wound healing. In one embodiment, an active compound or its salt is formulated in combination with salicyclic acid in a topical formulation as described herein.

VI. Process of Preparation of Compounds of the Present Invention

The compounds described herein can be prepared by methods known to those skilled in the art. In one non-limiting example, the disclosed compounds can be made using the routes provided below.

General Routes of Synthesis

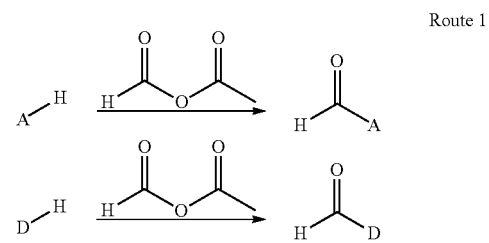

Route 1

In some embodiments, a compound of Formula I or Formula IV can be formed by the methods shown in Route 1. A compound of Formula I can be synthesized by reacting A-H with acetic formic anhydride. Similarly, a compound of Formula IV can be synthesized by reacting D-H with acetic formic anhydride. Acetic formic anhydride can be formed by reacting acetic anhydride with formic acid at 0° C. or by reacting sodium formate with acetyl chloride in anhydrous diethyl ether at 23-27° C. (see Krimen, L. I. Organic Syntheses 1970, 50:1). Similar reagents to acetic formic anhydride may be substituted as would be known to those having skill in the art.

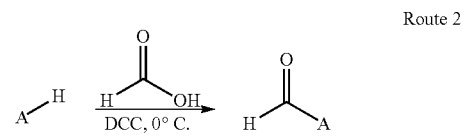

Route 2

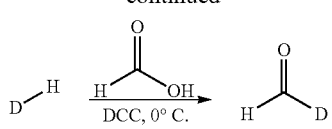

In other embodiments, a compound of Formula I or Formula IV can be synthesized by the methods shown in Route 2. A compound of Formula I can be synthesized by reacting A-H with formic acid and N,N'-dicyclohexylcarbodiimide (DCC) at 0° C. Similarly, a compound of Formula IV can be synthesized by reacting D-H with formic acid and DCC at 0° C. Reagents similar to DCC may be substituted as would be known to those having skill in the art.

Route 3

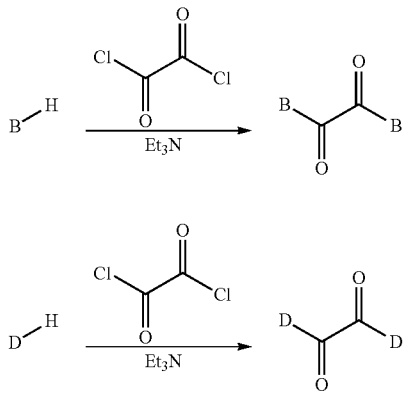

In other embodiments, a compound of Formula II or Formula V can be synthesized by the methods shown in Route 3. A compound of Formula II can be formed by reacting at least two equivalents of B—H with one equivalent of oxalyl chloride in the presence of triethylamine. Alternatively, Formula II can also be synthesized from salts of B—H without the need for bases such as triethylamine. Similarly, a compound of Formula V can be synthesized by reacting at least two equivalents of D-H with one equivalent of oxalyl chloride in the presence of triethylamine. Reagents similar to triethylamine, for example diisopropyl ethyl amine or sodium carbonate, may be substituted as would be known to those having skill in the art. In one embodiment, the reaction is conducted at 0° C. and allowed to warm to room temperature.

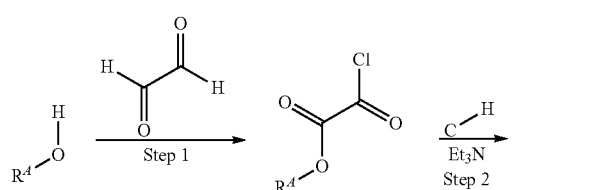
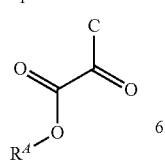

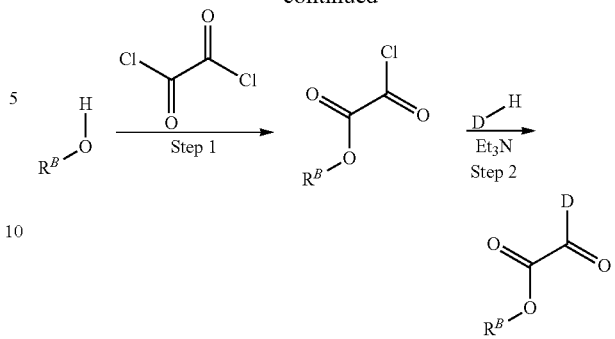

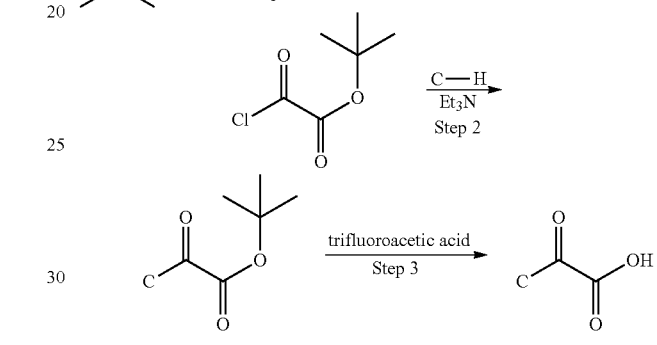

In other embodiments, a compound of Formula III or Formula VI can be synthesized by the methods shown in Route 4. A compound of Formula III is synthesized by reacting about one equivalent of $R^A$—OH with about one equivalent of oxalyl chloride to provide crude $R^A$—O—(C=O)—(C=O)—Cl, which is then reacted with about one equivalent of C—H in the presence of triethylamine. Similarly, a compound of Formula VI is synthesized by reacting about one equivalent of $R^A$—OH with about one equivalent of oxalyl chloride to provide crude $R^A$—O—(C=O)—(C=O)—Cl, which is then reacted with about one equivalent of D-H in the presence of triethylamine. To make compounds with $R^A$ being H, oxalyl chloride is reacted first with tert-butanol to provide crude tBu-O—(C=O)—(C=O)—Cl, which is then reacted with about one equivalent of C—H in the presence of triethylamine. Then tert-butyl group is removed using trifluoroacetic acid.

EXPERIMENTAL EXAMPLES OF THE PRESENT INVENTION

Reactions were carried out under nitrogen atmosphere using glassware that was previously oven-dried overnight with magnetic stirring unless otherwise indicated. Unless otherwise noted, all reagents were obtained from commercial suppliers (Sigma Aldrich, VWR International, and Oakwood Chemicals) and used without further purification. Thin layer chromatography was performed on glass-backed silica gel TLC plates using mixtures of hexanes/ethyl acetate as eluent, and using either UV light, iodine powder, or potassium permanganate stain for visualization. Column chromatography was done using Silica Flash P60 silica gel (230-400 mesh). $^1$H and $^{13}$C NMR spectra were recorded on Bruker-400 spectrometers (400 MHz and 100 MHz, respectively). Chemical shifts were reported in ppm relative to residual solvent peaks (67.26 for $^1$H, 77.1 for $^{13}$C, CHCl$_3$/CDCl$_3$) and (62.49 for $^1$H, and 39.1 for $^{13}$C, DMSO/DMSO-d$_6$). Data are reported as follows: bs=broad singlet, s=singlet, d=doublet, t=triplet, q=quartet, m=multiplet, dd=doublet of doublets, ddd=doublet of doublet of doublets, ddt=doublet of doublets of triplets, td=triplet of doublets; coupling constants in Hz; integration. Accurate mass measurements were acquired at the Mass Spectrometry Facilities at Georgia State University. For spectrophotometric studies, Shimadzu PharmaSpec UV-1700 was used as UV-Vis spectrophotometer; while Shimadzu RF-5301PC fluorimeter was used for fluorescent studies. Agilent 7820A with TCD detector was used for CO and CO$_2$ quantification.

Example 1. Synthesis of 3-Oxobenzo[d]isothiazole-2(3H)-carbaldehyde 1,1-dioxide (1)

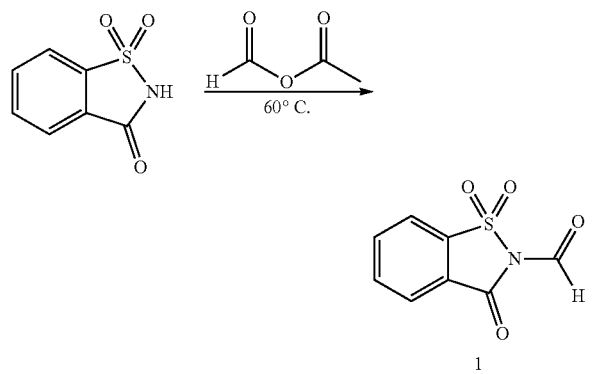

A mixture of formic acid (1.21 g, 26.3 mmol) and acetic anhydride (2.67 g, 26.2 mmol) was heated to 55° C. for 2 hours, then benzo[d]isothiazol-3(2H)-one 1,1-dioxide (1.7 g, 9.3 mmol) was added in one portion. The resulting mixture was stirred at 60° C. for another 5 hours. After that, the reaction mixture was cooled to room temperature, and 20 mL of deionized water was added. The formed white precipitate was filtered and dried under vacuum to afford 3-oxobenzo[d]isothiazole-2(3H)-carbaldehyde 1,1-dioxide as a white solid (1.65 g, 84%). $^1$H NMR (400 MHz, DMSO-d$_6$) 9.15 (s, 1H), 8.35 (d, J=8.0 Hz, 1H), 8.22 (d, J=8.0 Hz, 1H), 8.14 (t, J=7.6 Hz, 1H), 8.04 (t, J=8.0 Hz, 1H).

Example 2. Synthesis of 5-Methyl-2-thioxo-1,3,4-thiadiazole-3(2H)-carbaldehyde (2)

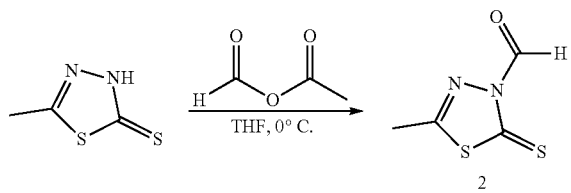

To a solution of 5-methyl-1,3,4-thiadiazole-2(3H)-thione (500 mg, 3.8 mmol) in dry THF (10 mL) was added acetic formic anhydride (670 mg, 7.6 mmol) at 0° C., and the resulting mixture was stirred for another 15 minutes and cooled to −20° C. for 2 hours. The formed precipitate was filtered to yield 5-methyl-2-thioxo-1,3,4-thiadiazole-3(2H)-carbaldehyde as a yellow needle-like crystals (480 mg, 80%). $^1$H NMR (400 MHz, DMSO-d$_6$) 9.45 (s, 1H), 2.58 (s, 3H).

Example 3. Synthesis of 2-Oxopyridine-1(2H)-carbaldehyde (3)

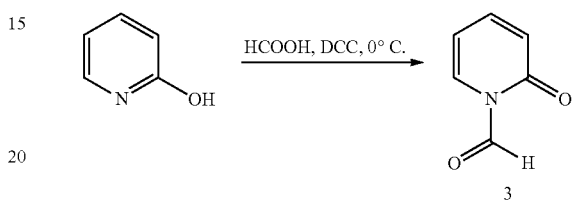

To a solution of pyridin-2-ol (1 g, 10.5 mmol) and formic acid (485 mg, 10.5 mmol) in CH$_2$C$_2$ (50 mL) was added DCC (2.27 g, 11.0 mmol) portion-wise at 0° C., and the reaction mixture was stirred for another 30 minutes at 0° C. The reaction mixture was then filtered, and the filtrate was cooled to −80° C. The formed yellowish precipitate was filtered to yield 2-oxopyridine-1(2H)-carbaldehyde (450 mg, 35%). 1H NMR (400 MHz, DMSO-d$_6$) 9.65 (s, 1H), 7.82 (d, J=8.0 Hz, 1H), 7.54 (t, J=8.0 Hz, 1H), 6.58 (d, J=8.0 Hz, 1H), 6.39 (t, J=8.0 Hz, 1H).

Example 4. Synthesis of N-(1-Formylpyridin-4(1H)-ylidene)-N-methylmethanaminium Bromide (4)

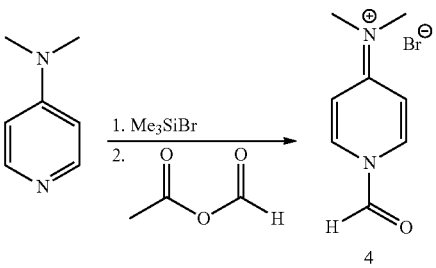

To a solution of N,N-dimethylpyridin-4-amine (600 mg, 4.92 mmol) in CH$_2$C$_2$ (10 mL) was added trimethylsilyl bromide (752 mg, 4.92 mmol) drop-wise at room temperature, and the resulting solution was stirred for another 30 minutes. Then the reaction mixture was added to a solution of 5 formic acetic anhydride (476 mg, 5.4 mmol) at −20° C. The formed white precipitate was filtered washed with CH$_2$Cl$_2$ to afford N-(1-formylpyridin-4(1H)-ylidene)-N-methylmethanaminium bromide as white solid (790 mg, 70%). $^1$H NMR (400 MHz, CD$_3$CN), 8.56 (d, J=8.0 Hz, 2H), 7.09 (d, J=8.0 Hz, 2H), 3.41 (s, 6H).

Example 5. Synthesis of 1,2-Bis(1,1-dioxido-3-oxobenzo[d]isothiazol-2(3H)-yl)ethane-1,2-dione (5)

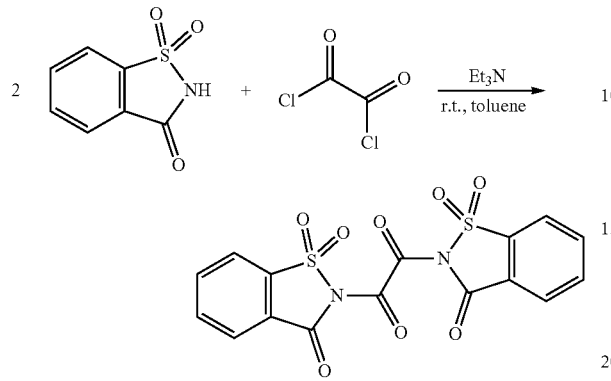

To a solution of benzo[d]isothiazol-3(2H)-one 1,1-dioxide (1 g, 5.46 mmol) and triethylamine (766 µL, 5.46 mmol) in THF was added drop-wise oxalyl chloride (190 µL, 2.73 mmol) dissolved in THF at 0° C. After the addition of oxalyl chloride, the reaction mixture stirred at room temperature for 3 hours. Then, THF was removed by rotary evaporation. The residue was dissolved in dichloromethane, washed with water (2×10 mL), saturated NaHCO$_3$(3×10 mL), and brine. The organic layer was then concentrated in the rotary evaporator at <30° C. to give white solid. The isolated solid was recrystallized in acetonitrile to yield 1,2-bis(1,1-dioxido-3-oxobenzo[d]isothiazol-2(3H)-yl)ethane-1,2-dione as a white solid. $^1$H NMR (400 MHz, CD$_3$CN) 8.13-8.22 (m, 6H), 8.01-8.05 (m, 2H). $^{13}$C NMR (100 MHz, CD$_3$CN) 159.5, 156.8, 139.8, 139.6, 137.4, 128.4, 125.2, 123.3.

Example 6. Synthesis of 2,2'-Oxalylbis(isoindoline-1,3-dione) (6)

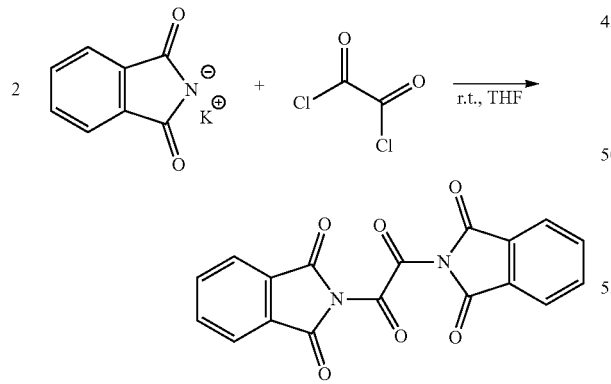

To a suspension of potassium phthalimide (200 mg, 1.08 mmol) in THF (10 mL) was added drop-wise oxalyl chloride (37.5 µL, 0.539 mmol). The reaction mixture was stirred at room temperature for 45 minutes. After 1 hour, the reaction mixture was diluted with DCM and filtered. The filtrate was concentrated in the rotavap to give 2,2'-oxalylbis(isoindoline-1,3-dione) as a white solid (260 mg, 70%).

Example 7. Synthesis of 1,2-Bis(6-methyl-2,2-dioxido-4-oxo-1,2,3-oxathiazin-3(4H)-yl)ethane-1,2-dione (7)

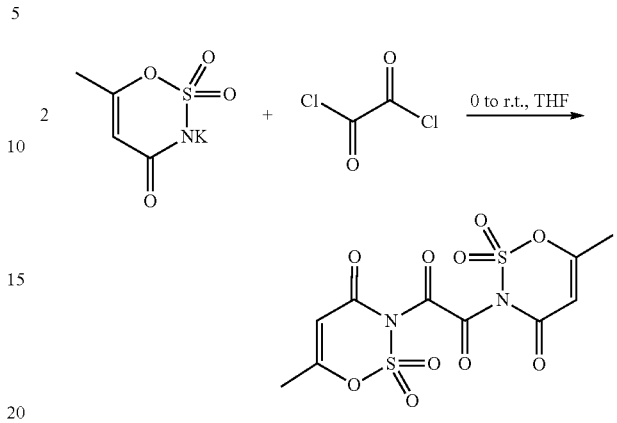

To a suspension of acesulfame potassium (1 g, 4.97 mmol) in THF (10 mL) stirring at 0° C. was added drop-wise oxalyl chloride (173 µL, 2.49 mmol) dissolved in THF (5 mL). The reaction mixture was stirred in ice-bath for 10 minutes and then stirred at room temperature for 3 hours. Then, the reaction mixture was concentrated in the rotavap. The crude residue was dissolved in DCM and washed with water (2×20 mL), sat NaHCO$_3$(2×20 mL), and brine. The organic layer was dried over Na$_2$SO$_4$ and concentrated in the rotavap to give a yellowish solid. This crude residue was suspended in diethyl ether and filtered to give 1,2-bis(6-methyl-2,2-dioxido-4-oxo-1,2,3-oxathiazin-3(4H)-yl)ethane-1,2-dione as a white solid. $^1$H NMR (400 MHz, CD$_3$CN) 6.12 (m, 1H), 2.31 (m, 3H). $^{13}$C NMR (100 MHz, CD$_3$CN) 167.9, 160.8, 156.4, 104.4, 20.4.

Example 8. Synthesis of N$^1$,N$^2$-Dibenzoyl-N$^1$,N$^2$-bis(methylsulfonyl)oxalamide (9)

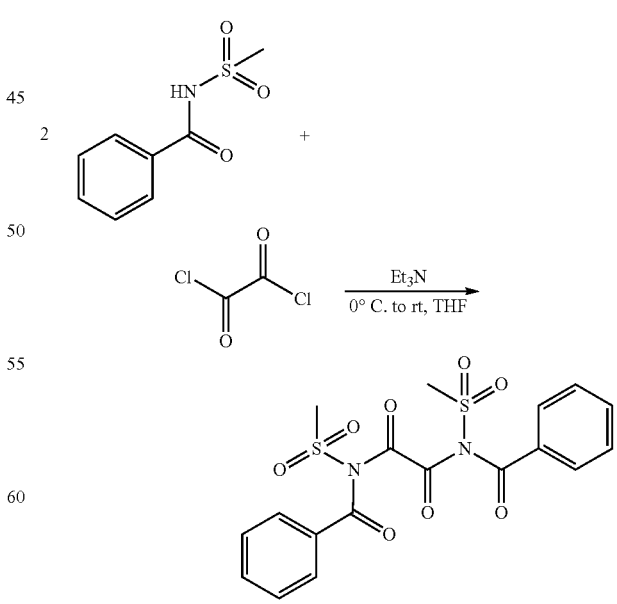

To a solution of N-(methylsulfonyl)benzamide (350 mg, 1.76 mmol) and triethylamine (247 µL, 1.76 mmol) in THF was added dropwise oxalyl chloride (61 µL, 0.88 mmol) dissolved in THF while stirring at 0° C. After the addition, the reaction mixture was stirred at room temperature. Then THF was removed by rotary evaporation. The residue was re-dissolved in dichloromethane, and washed with water (2×10 mL), saturated NaHCO$_3$ (3×10 mL), and brine. The organic layer was then concentrated in the rotary evaporator at <30° C. to give a solid. The isolated solid purified using silica gel column with dichloromethane as eluting solvent to give a white solid. $^1$H NMR (CD$_3$CN) 8.04-8.06 (2H, m), 7.77-7.81 (1H, m), 7.58-7.62 (2H, m), 3.62 (3H, s). $^{13}$C NMR (CD$_3$CN) 169.2, 137, 132.9, 131.6, 130.5, 44.5.

Example 9. Synthesis of tert-Butyl 2-(1,1-Dioxido-3-oxobenzo[d]isothiazol-2(3H)-yl)-2-oxoacetate (8) and 2-(1,1-Dioxido-3-oxobenzo[d]isothiazol-2(3H)-yl)-2-oxoacetic acid (10)

reaction mixture was diluted with dichloromethane and washed with saturated NaHCO$_3$ (2×15 mL). The organic layer was dried over sodium sulfate and concentrated in the rotavap. The residue was suspended in diethyl ether and filtered to give tert-butyl 2-(1,1-dioxido-3-oxobenzo[d]isothiazol-2(3H)-yl)-2-oxoacetate (8) as a white solid. $^1$H NMR (400 MHz, CD$_3$CN) 8.17-8.16 (m, 1H), 8.0-7.94 (m, 3H), 1.62 (s, 9H). $^{13}$C NMR (100 MHz, CD$_3$CN) 157.0, 156.8, 156.7, 138.9, 137.3, 135.5, 126.7, 124.5, 121.7, 87.2, 27.9.

To a solution of tert-butyl 2-(1,1-dioxido-3-oxobenzo[d]isothiazol-2(3H)-yl)-2-oxoacetate (8) (50 mg) in dichloromethane while stirring at 0° C. was added trifluoroacetic acid (1 mL). Then the reaction was stirred at room temperature. After 5 h, the reaction mixture was dried in the rotary evaporator to give 2-(1,1-dioxido-3-oxobenzo[d]isothiazol-2(3H)-yl)-2-oxoacetic acid (10) as a white solid. $^1$H NMR (CD$_3$CN) 8.04-8.06 (2H, m), 7.77-7.81 (1H, m), 7.58-7.62 (2H, m), 3.62 (3H, s). $^{13}$C NMR (CD$_3$CN) 169.2, 137, 132.9, 131.6, 130.5, 44.5.

Example 10. Non-limiting Example of the Present Invention

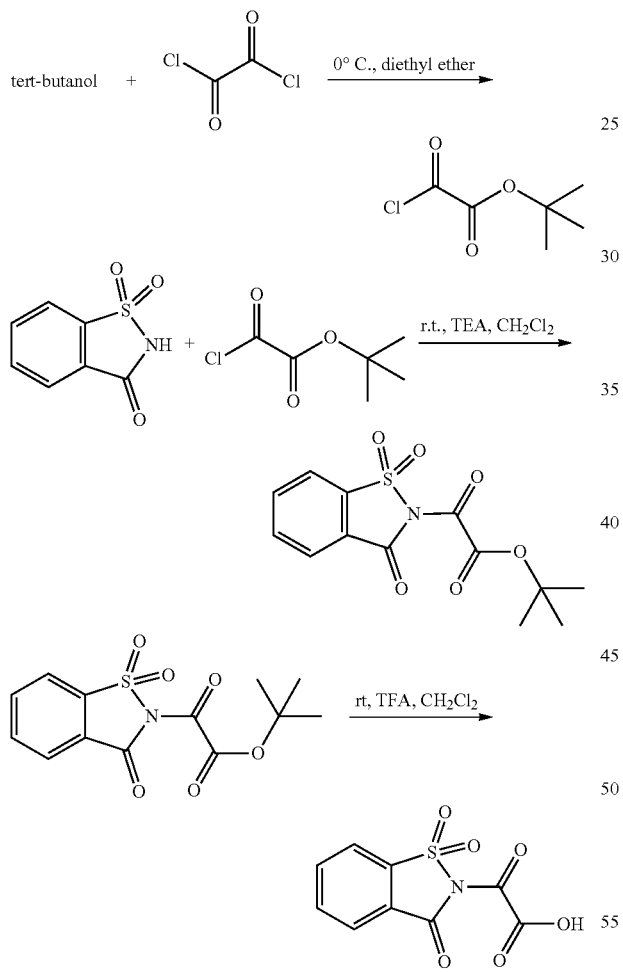

TABLE 1 illustrates non-limiting examples of the present invention

| Compound | Compound Structure |
|---|---|
| 1 | 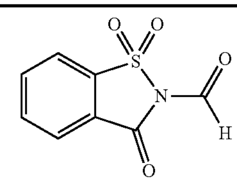 |
| 2 | 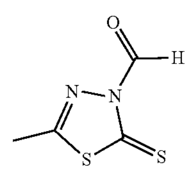 |
| 3 | 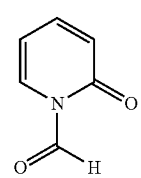 |
| 4 | 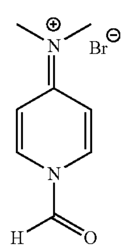 |
| 5 | 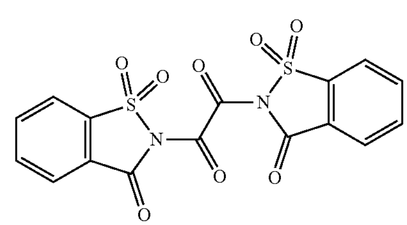 [SMILES: O=C(C(=O)N1C(=O)c2ccccc2S1(=O)=O)N1C(=O)c2ccccc2S1(=O)=O] |

To a solution of oxalyl chloride (1.8 mL) in diethyl ether (10 mL) stirred at 0° C. was added drop-wise a solution of tert-butanol (2.0 mL) in diethyl ether (3 mL). The mixture was stirred for 20 hours at room temperature, and then concentrated in the rotavap to give a crude tert-butyl 2-chloro-2-oxoacetate as a clear, colorless liquid.

The crude-butyl 2-chloro-2-oxoacetate was added dropwise to a solution of saccharin (1.3 g) and triethylamine (3.0 mL) and stirred at room temperature for 3 hours. Then the

TABLE 1-continued illustrates non-limiting examples of the present invention

| Compound | Compound Structure |
|---|---|
| 6 | 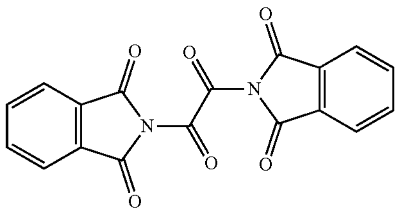 [SMILES: O=C(C(=O)N1C(=O)c2ccccc2C1=O)N1C(=O)c2ccccc2C1=O] |
| 7 | 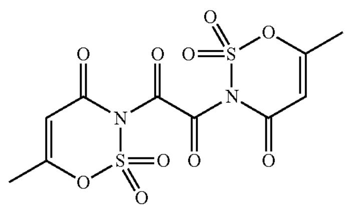 |
| 8 | 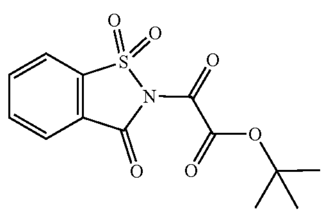 [SMILES: CC(C)(C)OC(=O)C(=O)N1C(=O)c2ccccc2S1(=O)=O] |

Example 11. Evaluation of Carbon Monoxide Release

Evaluation by the CO Fluorescent Probe COP-1

Figure 2:
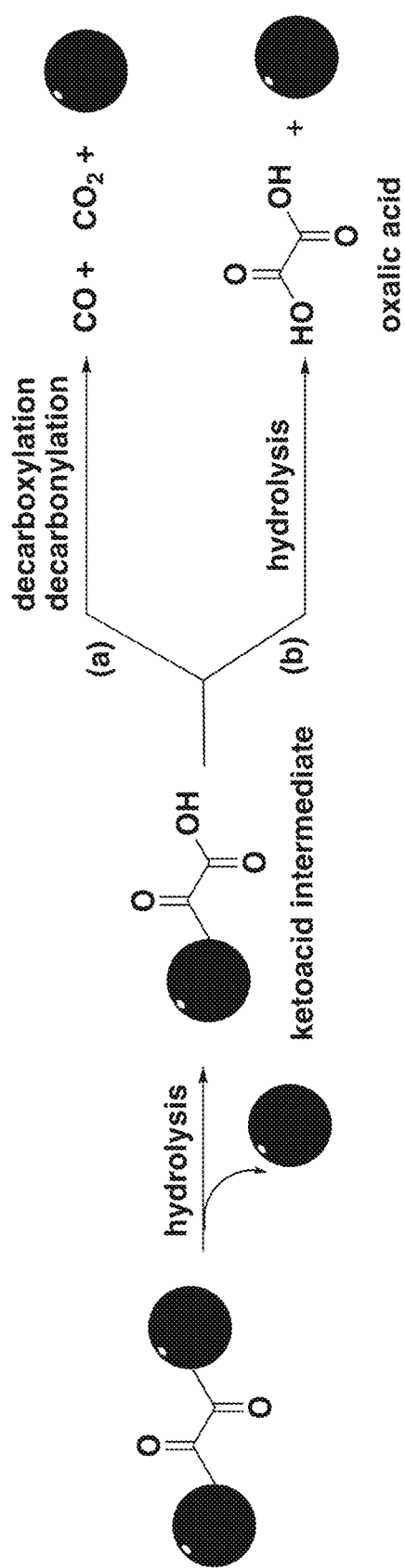
FIG. 2 is a chemical scheme showing the competing paths (the CO-generating pathway (a) and the oxalic acid generating pathway (b) by which oxalyl-based CO prodrugs can break down in aqueous solution as described in Example 11.

Oxalyl-based compound with appropriate leaving groups are susceptible to hydrolysis expelling one leaving group and generating a ketoacid intermediate (FIG. 2). CO is generated once this ketoacid intermediate undergoes a subsequent decarboxylation and decarbonylation reactions. For oxalyl chloride, this path predominates and thus form only CO, $CO_2$, and HCl when placed in water. However, when chloride leaving groups are replaced by weaker leaving groups such as saccharin, another decomposition path may compete with the CO generating path. The ketoacid intermediate can undergo hydrolysis to expel the second leaving group and form oxalic acid without CO generation. Therefore, the pKa of the leaving group must be carefully selected so that the reaction favors the CO generating path.

COP-1, a CO probe that is commonly employed in the literature to detect CO was used to evaluate the ability of different oxalyl-based compounds to release CO under aqueous solution at room temperature. Chloride was replaced with various leaving groups having different pKa values to survey the effect of pKa on CO release.

To a solution of the CO probe COP-1 (0.5 μM) in 3% DMSO in PBS, a solution of 1,2-bis(1,1-dioxido-3-oxobenzo[d]isothiazol-2(3H)-yl)ethane-1,2-dione in DMSO was added to form a 100 μM final solution concentration. The resulting mixture was incubated at 37° C., and the fluorescence emission intensity was recorded at different time points from 430-460 nm with an excitation wavelength of 475 nm.

Figure 3:
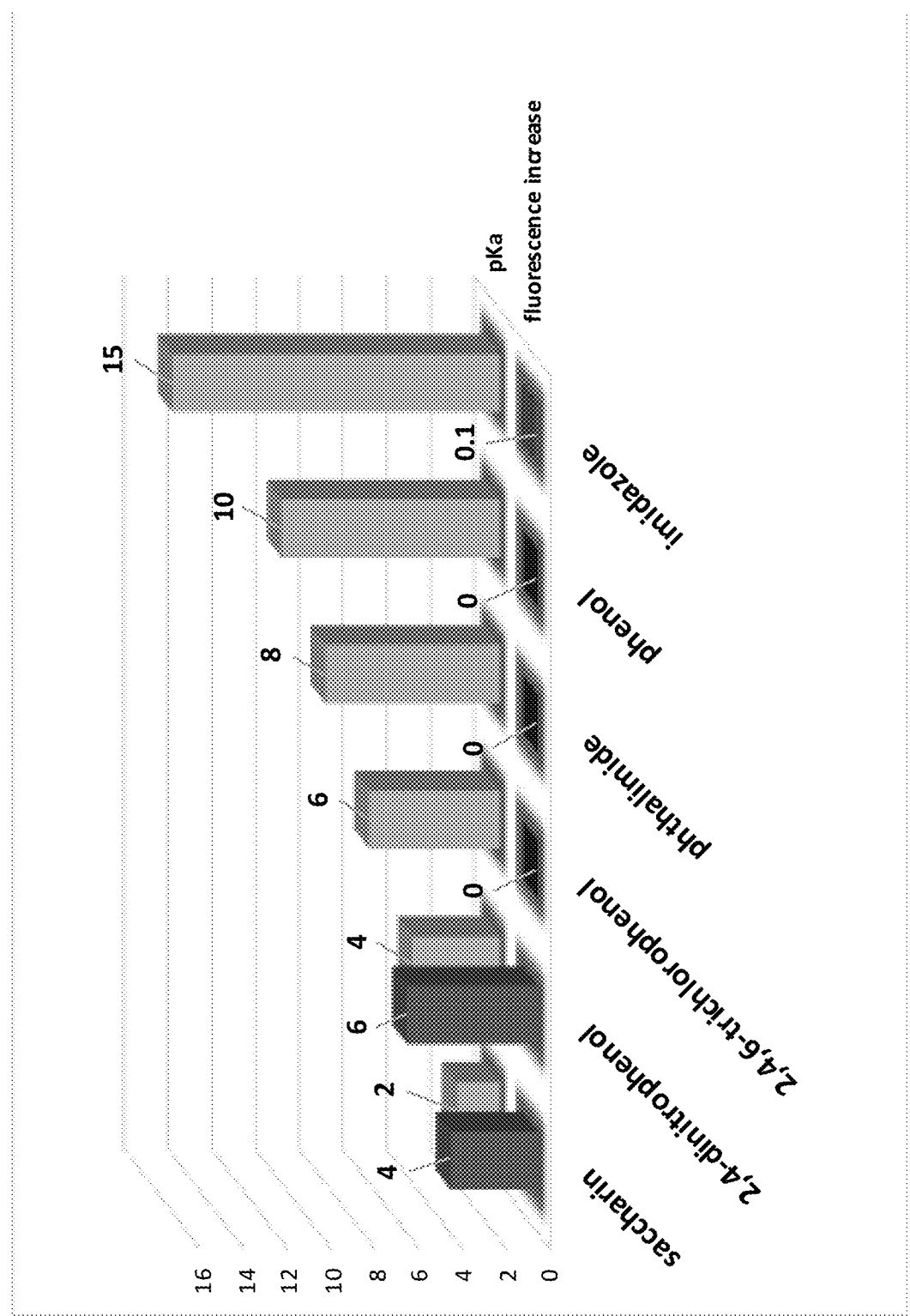
FIG. 3 is a bar graph showing the effect of the pKa of the leaving group of oxalyl-based CO prodrugs on CO releasing capability as described in Example 11. The x-axis is labeled with the various leaving groups and the y-axis is labeled to show the fluorescence increase and the pKa of the leaving group.

As shown in FIG. 3, a 4- to 6-fold increase in fluorescence turn-on intensity was observed with leaving groups having pKa lower than 4, while increasing the pKa of the leaving group to greater than 4 led to compounds incapable of CO release (except in a modest 0.1-fold increase with imidazole).

Figure 4:
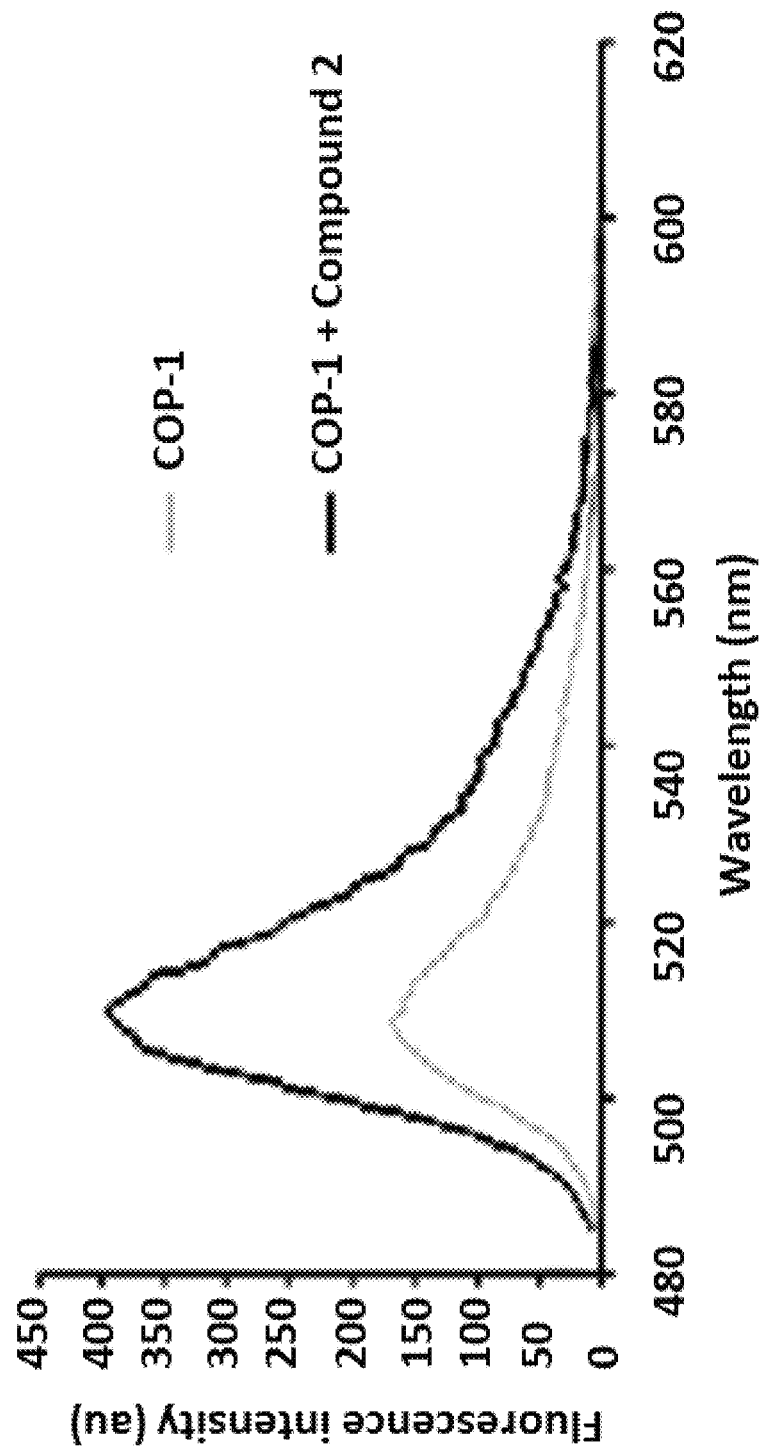
FIG. 4 is a UV-Vis fluorescence spectrum for the carbon monoxide probe COP-1 in the absence and presence of Compound 2 as described in Example 11. The x-axis shows wavelength in nanometers, and the y-axis shows the fluorescence index in atomic units.
Figure 5:
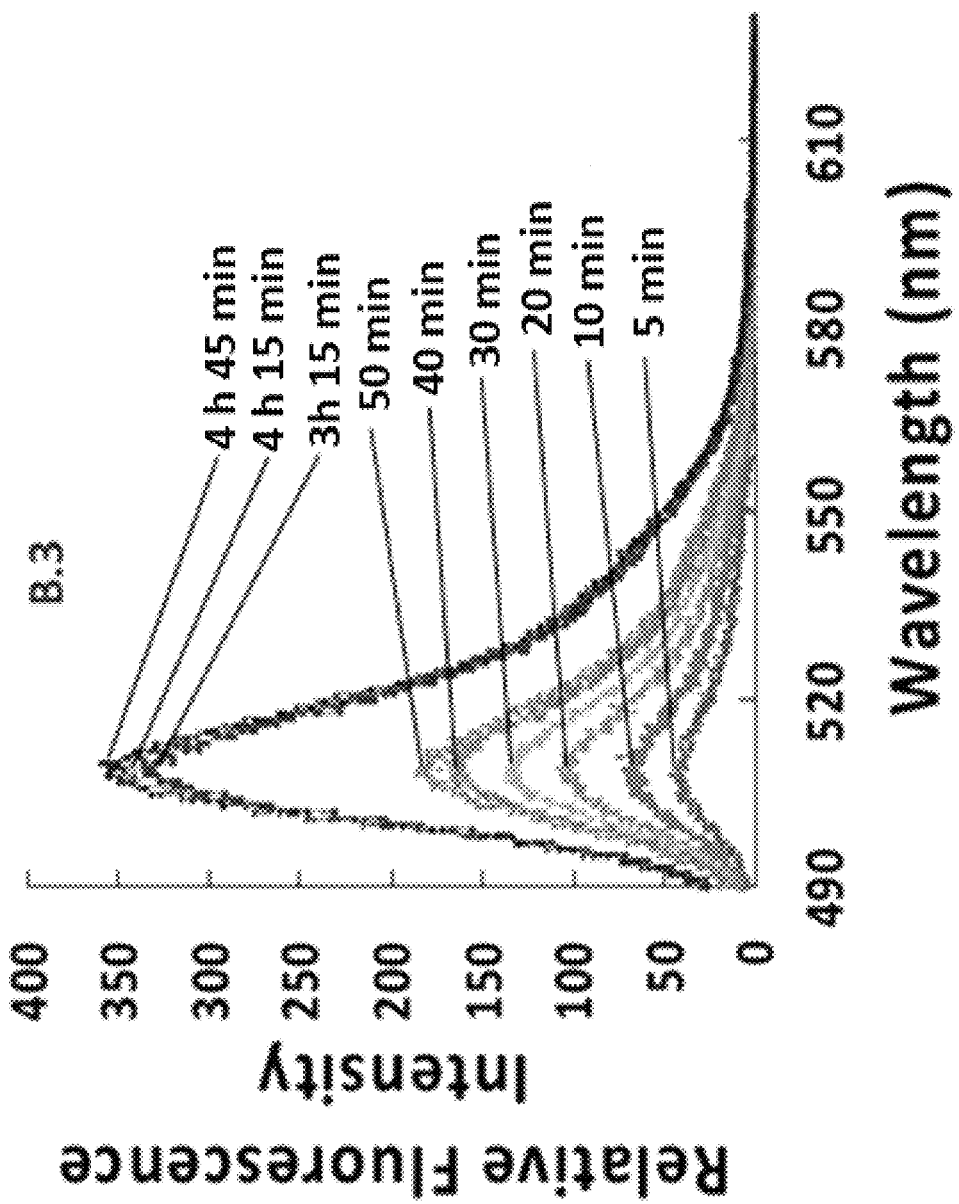
FIG. 5 is a UV-Vis fluorescence spectrum for the carbon monoxide probe COP-1 in the absence and presence of Compound 5 as described in Example 11. The x-axis shows wavelength in nanometers, and the y-axis shows the fluorescence index in atomic units.

As illustrated in FIG. 4, a 2.3-fold increase in fluorescence was observed after 10 minutes of incubation of Compound 2 with the COP-1 probe. A 4-fold increase in fluorescence intensity was observed with Compound 5 after 3 h (FIG. 5).

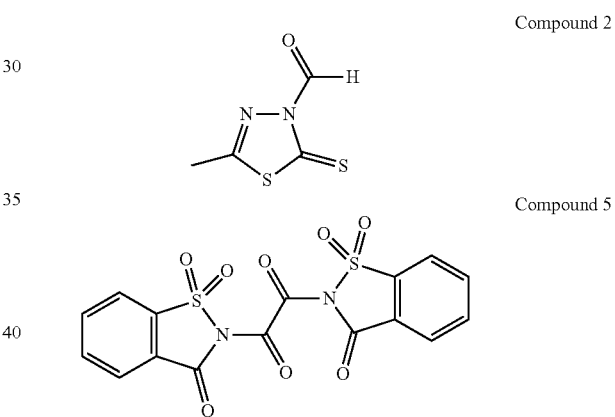

A series of oxalyl-based CO donors were examined for their response in the COP-1 fluorescence assay. As can be seen by the results in Table 2, the best CO donors were compounds that typically had a pKa less than 4.0 for the conjugate acid of the leaving group.

TABLE 2

COP-1 Fluorescence Response of Oxalyl-Based CO Donors

| Compound | pKa | COP-1 Fluorescence? |
|---|---|---|
| | 1.6 | Yes (4-fold increase) |

TABLE 2-continued

COP-1 Fluorescence Response of Oxalyl-Based CO Donors

| Compound | pKa | COP-1 Fluorescence? |
|---|---|---|
| bis(2,4-dinitrophenyl) oxalate | 4.09 | Yes (6-fold increase) |
| bis(2,4,6-trichlorophenyl) oxalate | 6.23 | No |
| N,N'-diphthalimidyl oxalamide | 8.3 | No |
| diphenyl oxalate | 10 | No |
| 1,1'-oxalyldiimidazole | 14.5 | Yes (0.1-fold increase) |

CO-Myoglobin Assay

Direct detection of carbon monoxide release was done through a "two-compartment" Mb-CO assay. The set-up was assembled by putting a small vial inside a bigger vial and sealing the system. The bigger vial contained the deoxy-Mb solution while the smaller vial contained the CO-releasing molecule in DMSO/PBS. The deoxy-IVB solution was prepared by degassing a solution of myoglobin in PBS (1 mg/mL, pH=7.4) with nitrogen for at least 20 minutes, and then converting to deoxy-MB by adding a freshly prepared solution of sodium dithionite (1 mL, 22 mg/mL). The solution of the CO-releasing molecule in DMSO was added to the inner vial containing PBS via a syringe. The whole set-up was then incubated at 37° C. After 25 minutes, the set-up was cooled in an ice-bath for 10 minutes to increase the solubility of CO gas, after which the incubated solution was immediately transferred into a cuvette for UV-Vis spectral analysis.

Figure 6A:
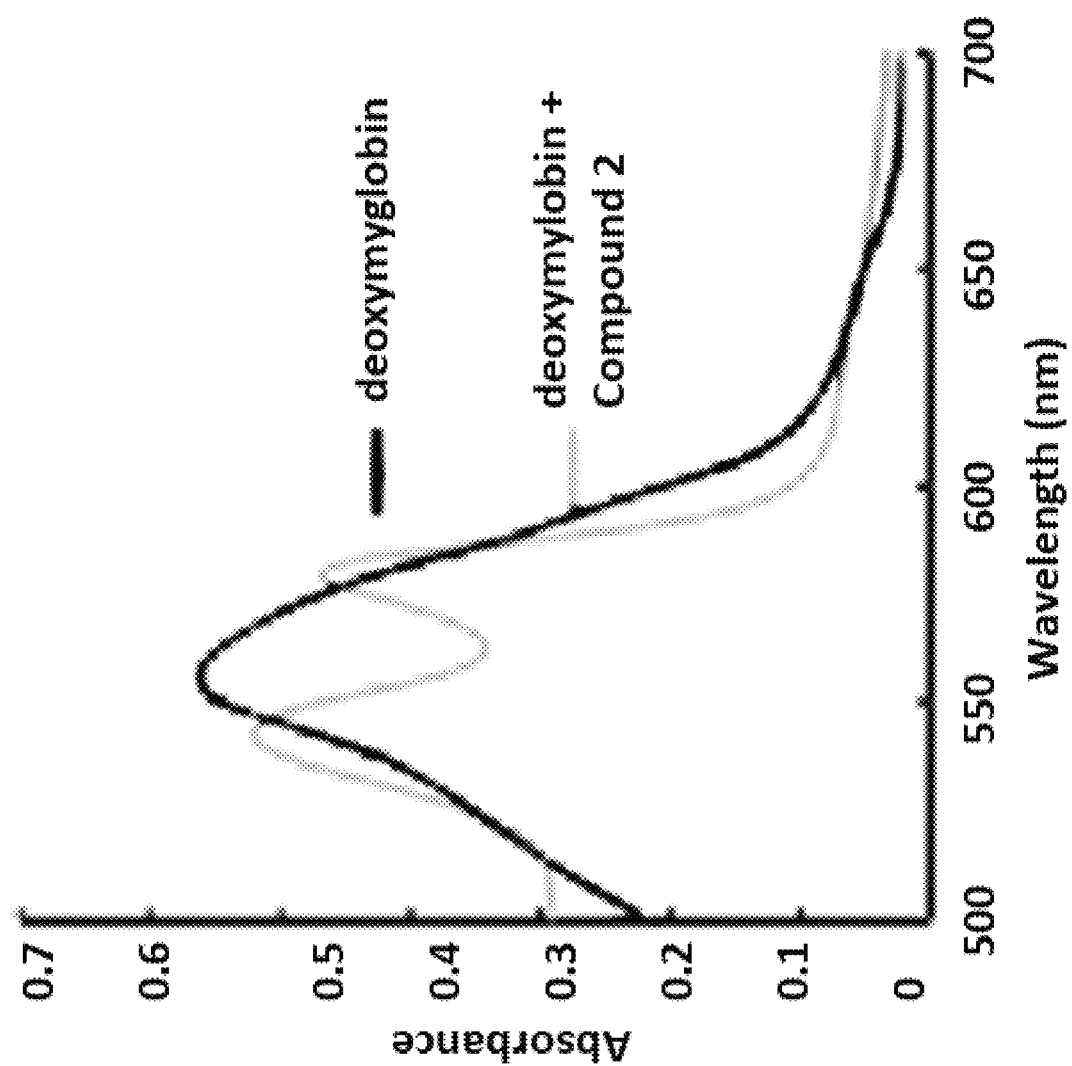
FIG. 6A is a UV-Vis absorption spectrum for deoxymyoglobin in the absence and presence of Compound 2 as described in Example 11. The x-axis is wavelength measured in nanometers, and the y-axis show the level of absorbance.
Figure 6B:
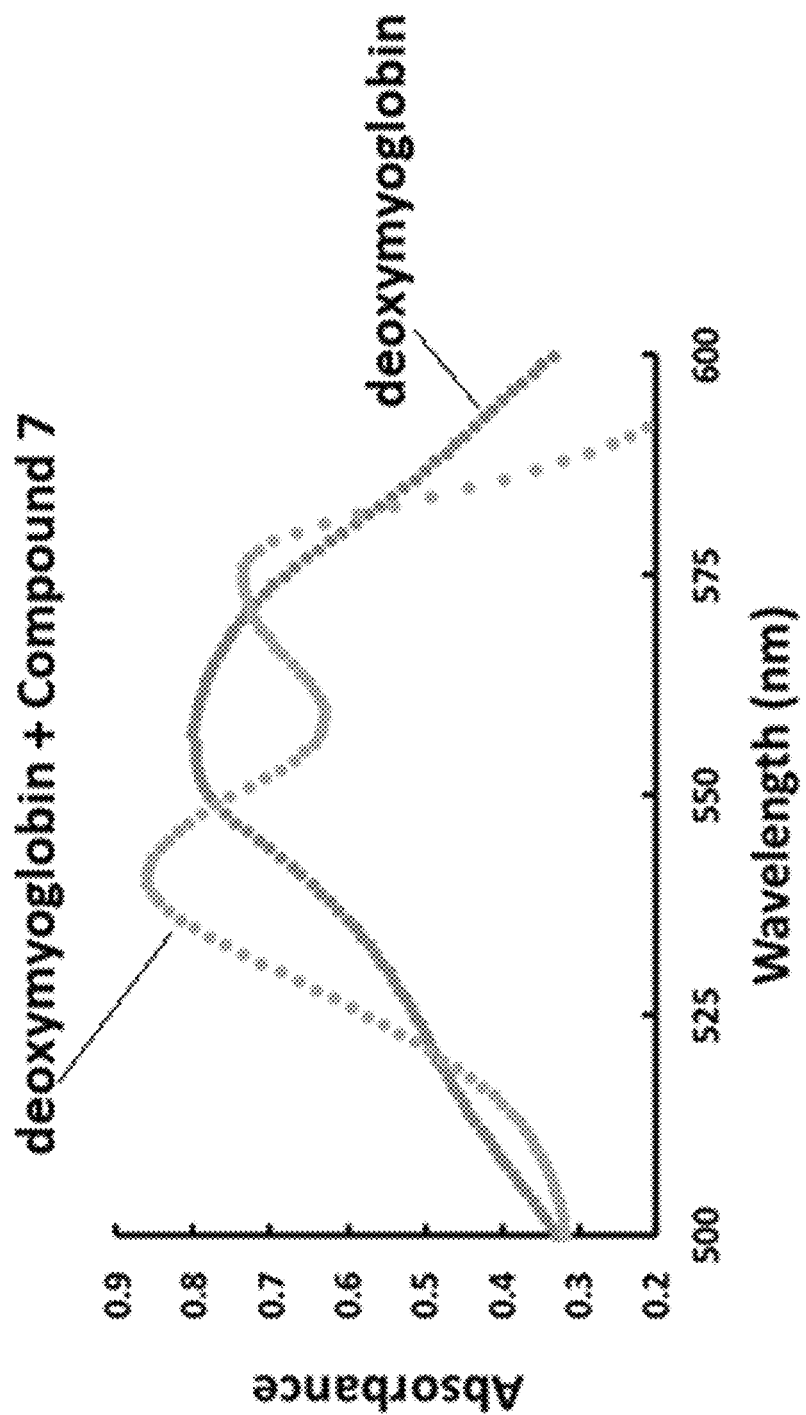
FIG. 6B is a UV-Vis absorption spectrum for deoxymyoglobin in the absence and presence of Compound 7 as described in Example 11. The x-axis is wavelength measured in nanometers, and the y-axis show the level of absorbance.
Figure 7:
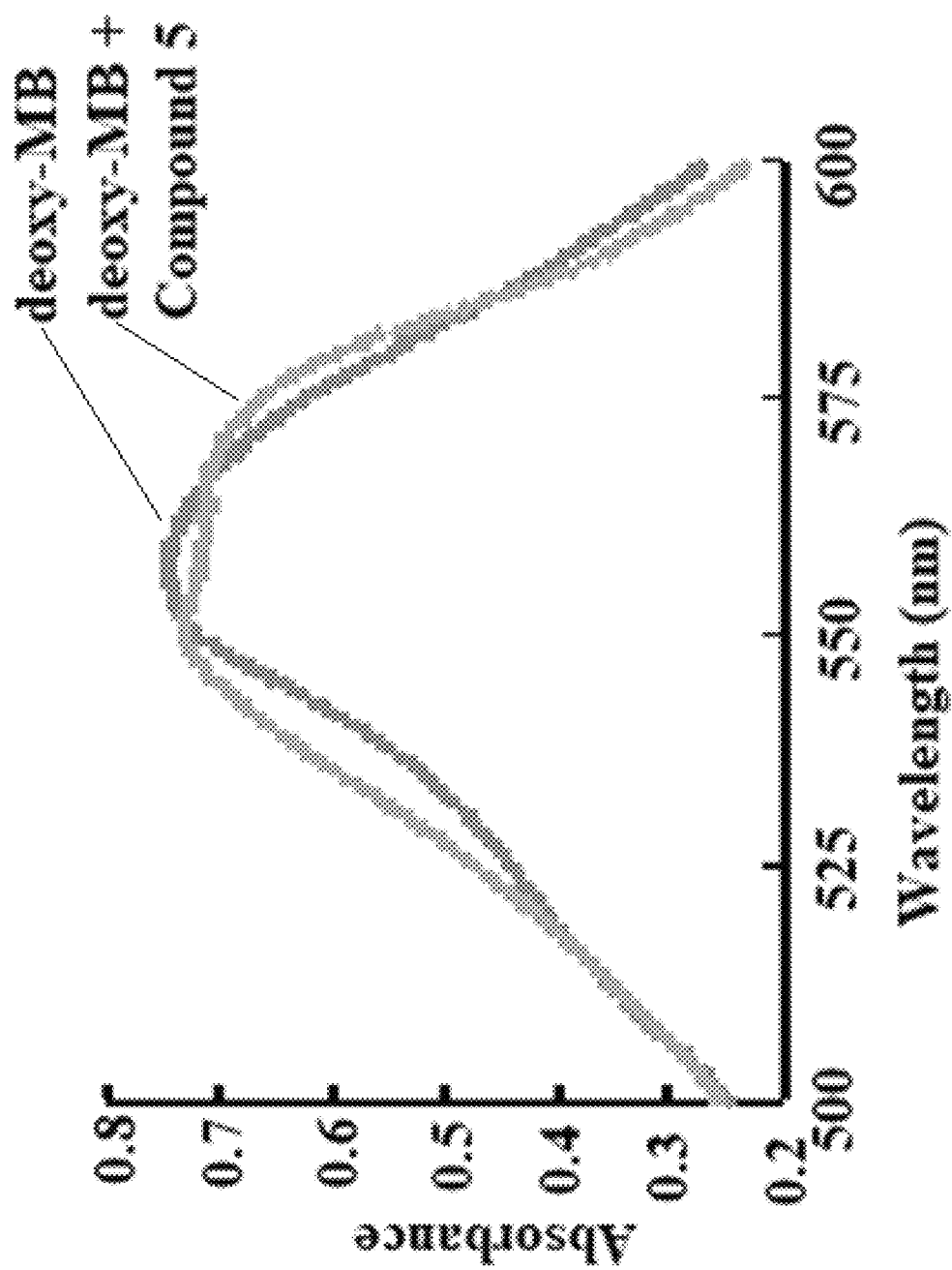
FIG. 7 is a UV-Vis absorption spectrum for deoxymyoglobin in the absence and presence of Compound 5 as described in Example 11. The x-axis is wavelength measured in nanometers, and the y-axis show the level of absorbance.

As illustrated in FIG. 6A, FIG. 6B, and FIG. 7, Compound 2, Compound 7, and Compound 5, respectively, showed the characteristic spectral signature for the formation of CO-myoglobin, confirming the release of CO from these molecules under physiological conditions.

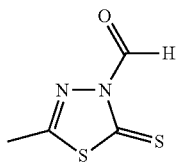

Compound 2

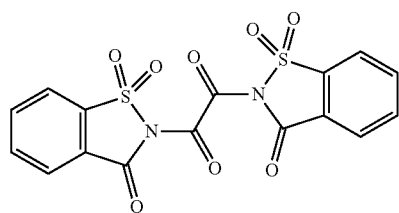

Compound 5

Compound 7

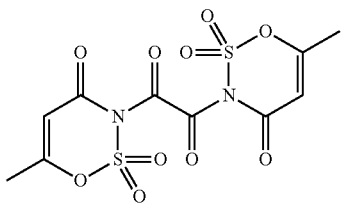

Quantitative CO Analysis

An Agilent 7820A GC System equipped with a thermal conductivity detector was used to detect and quantify CO release yield of the CO prodrugs. Using a gas tight syringe, specific volumes of the headspace of 20-mL headspace vials were sampled and transferred to the injector port maintained at 125° C. Helium was used as the carrier gas with a flow rate of 30 mL/min. Gaseous components of the headspace were separated by passing through a packed column with 60/80 Carboxen-1000 matrix support, L×O.D.×I.D. 15.0 ft (4.6 m)×⅛ in.×2.1 mm (Supelco). The column was heated 35° C. for 5 min then 225° C. at 20° C./min while the detector was held at 125° C. Under these conditions, CO had an elution time of around 7.4 minutes while $CO_2$ eluted at 13.4 minutes.

Figure 9:
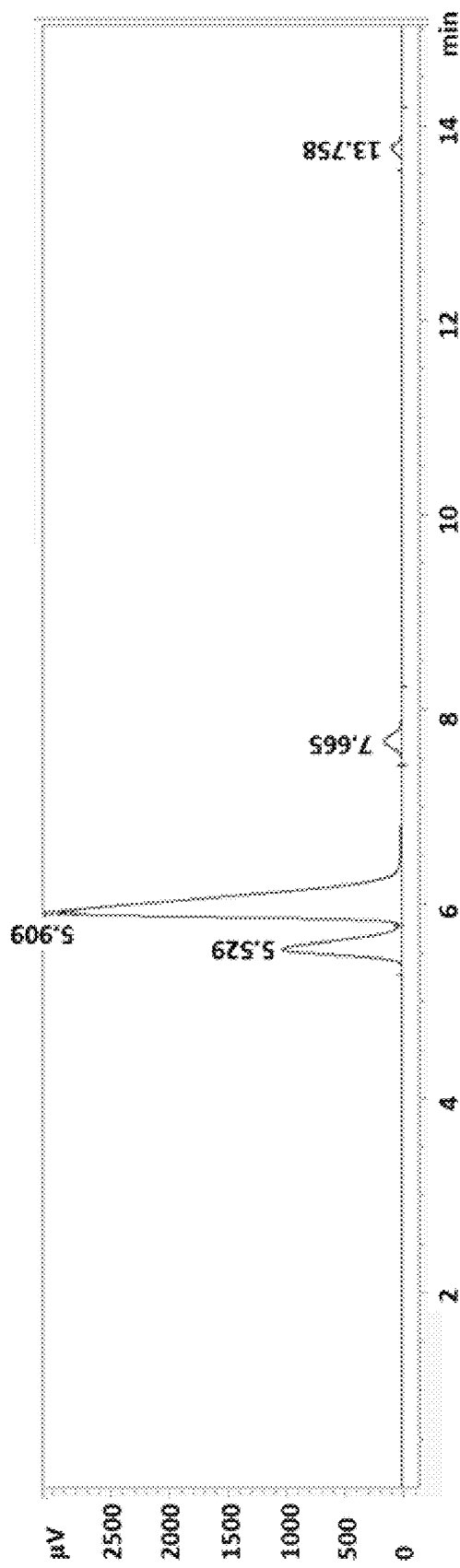
FIG. 9 is a chromatograph measuring the release of CO and $CO_2$ of Compound 5 as described in Example 5 as described in Example 11. The x-axis is time in minutes and the y-axis is intensity.
Figure 10:
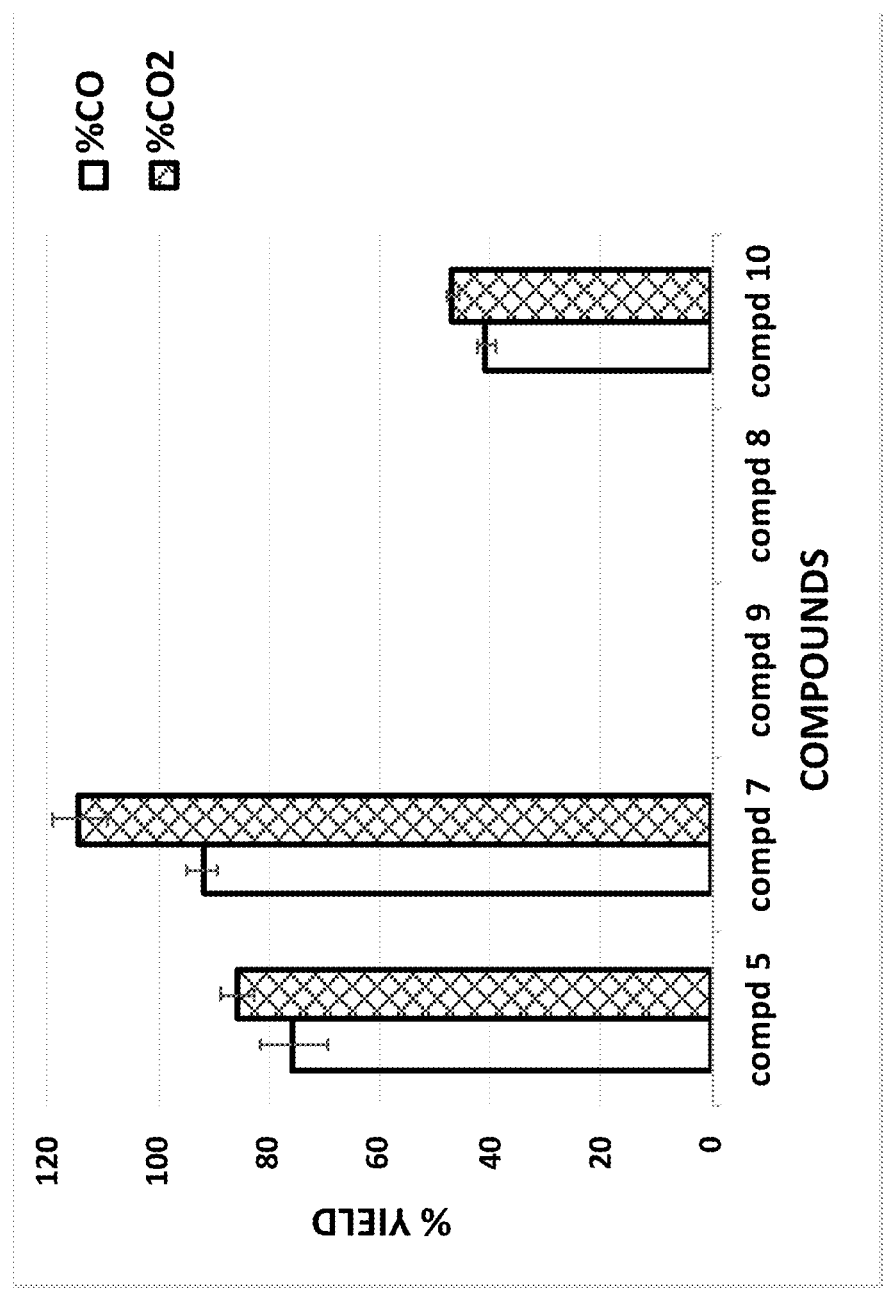
FIG. 10 is a graph of the CO and $CO_2$ yields of different compounds in $ACN:H_2O$ (4:1) at 37° C. for 1 hour as described in Example 11. The x-axis is labeled with the compound and the y-axis is the yield of CO and $CO_2$ measured in percent.

Compound 5 released 76%±6 CO and Compound 7 released 92%±3 CO when dissolved in 4 to 1 acetonitrile: water and incubated at 37° C. for 1 h (FIG. 10). FIG. 9 is the chromatogram for Compound 5. On the other hand, no CO was detected from Compound 9 probably because the second hydrolysis is much more favored compared to the CO generating path.

Compound 9

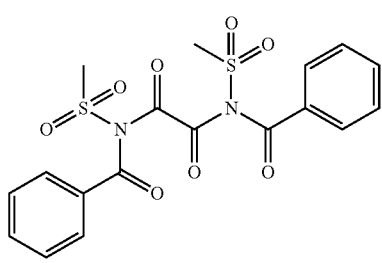

To study the requirement that a CO Compound needs to undergo hydrolysis first to unmask the ketoacid intermediate which is the source of CO, Compound 10 was synthesized from Compound 8 (Example 9 above). No CO nor $CO_2$ were detected from Compound 8 while around 40% CO and $CO_2$ were generated from Compound 10 (FIG. 10). These results suggest that installing two of saccharin groups into the oxalyl core protects from hydrolysis and favors the CO generating reaction pathway.

Compound 8

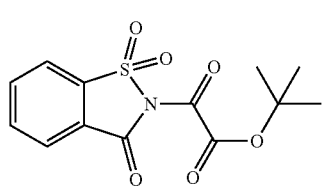

Compound 10

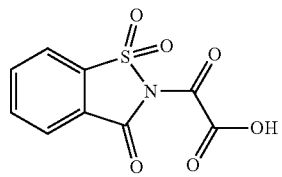

Figure 11:
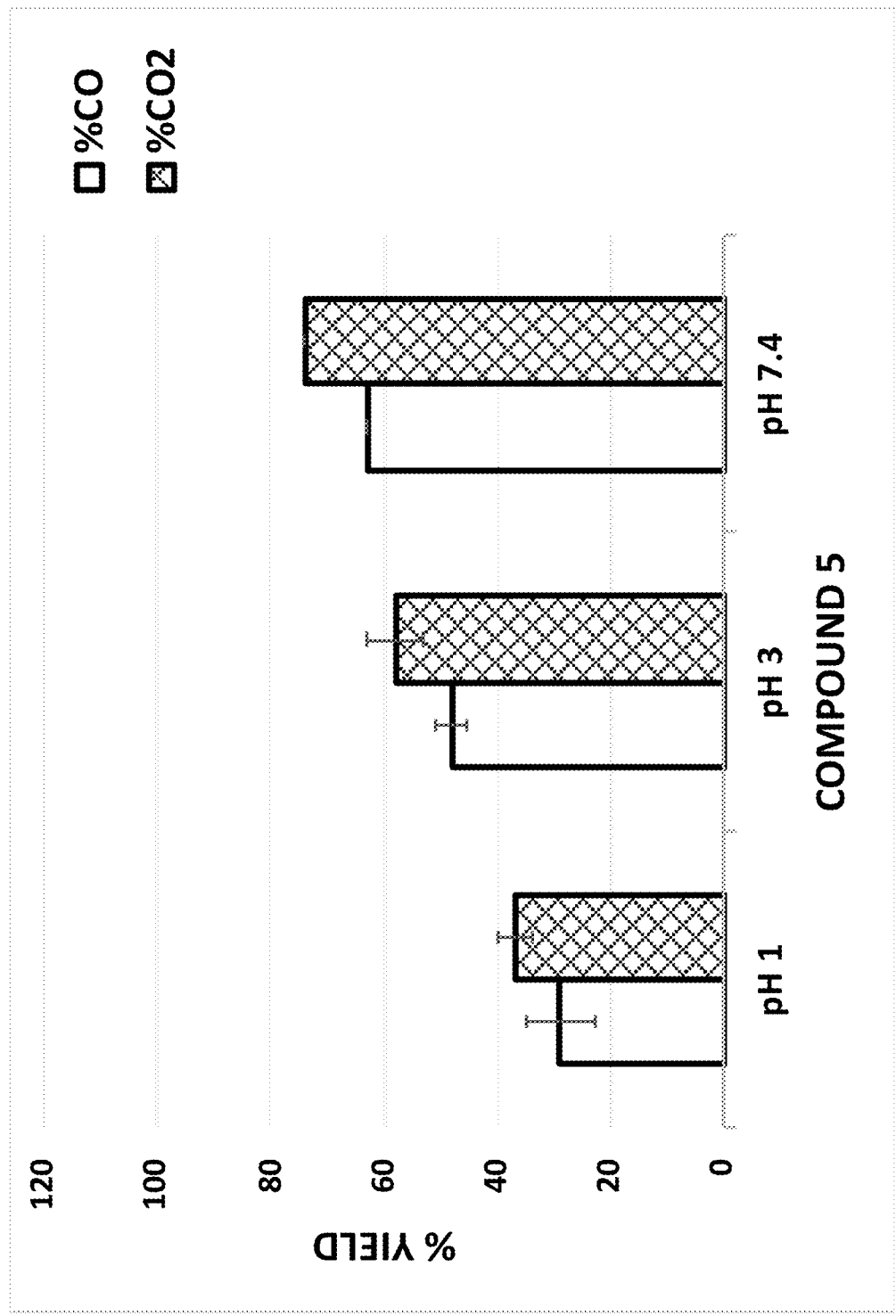
FIG. 11 is a graph showing the effect of pH on CO and $CO_2$ yield of Compound 5 in pH 1 (glycine/NaCl/HCl), pH 3 (citric acid/NaOH/HCl), and pH 7.4 (phosphate buffer) in $ACN:H_2O$ (4:1) at 37° C. for 1 hour as described in Example 11. The x-axis is labeled with the compound and the y-axis is the yield of CO and $CO_2$ measured in percent.
Figure 12:
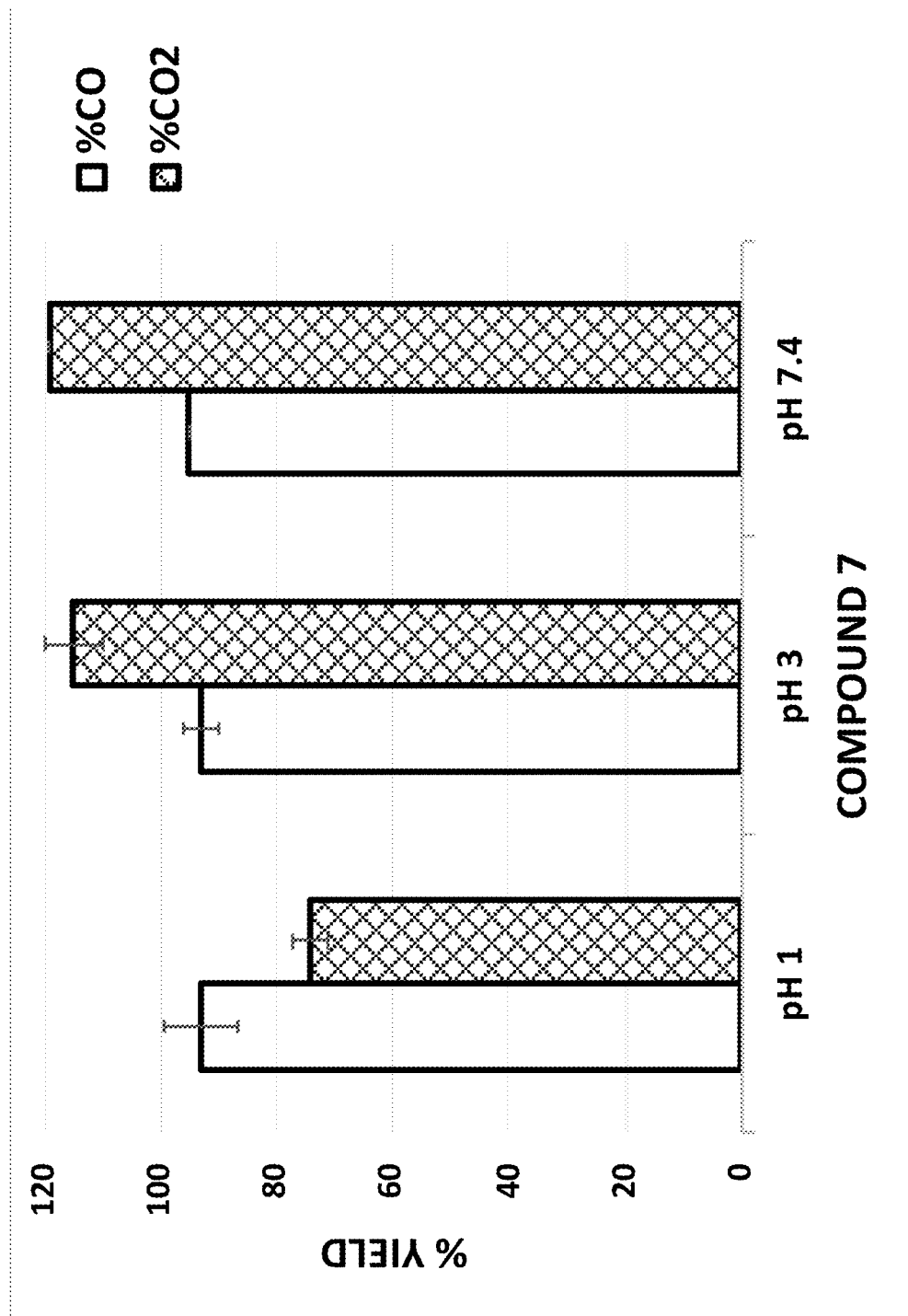
FIG. 12 is a graph showing the effect of pH on CO and $CO_2$ yield of Compound 7 in pH 1 (glycine/NaCl/HCl), pH 3 (citric acid/NaOH/HCl), and pH 7.4 (phosphate buffer) in $ACN:H_2O$ (4:1) at 37° C. for 1 hour as described in Example 11. The x-axis is labeled with the compound and the y-axis is the yield of CO and $CO_2$ measured in percent.

The effect of pH was also studied. Compound 5 CO yield decreased from 60% to 30% with decreasing pH (FIG. 11). The CO release yield for Compound 7 is pH-independent with CO yields constant at around 90% across a broad pH range (FIG. 12).

Figure 8A:
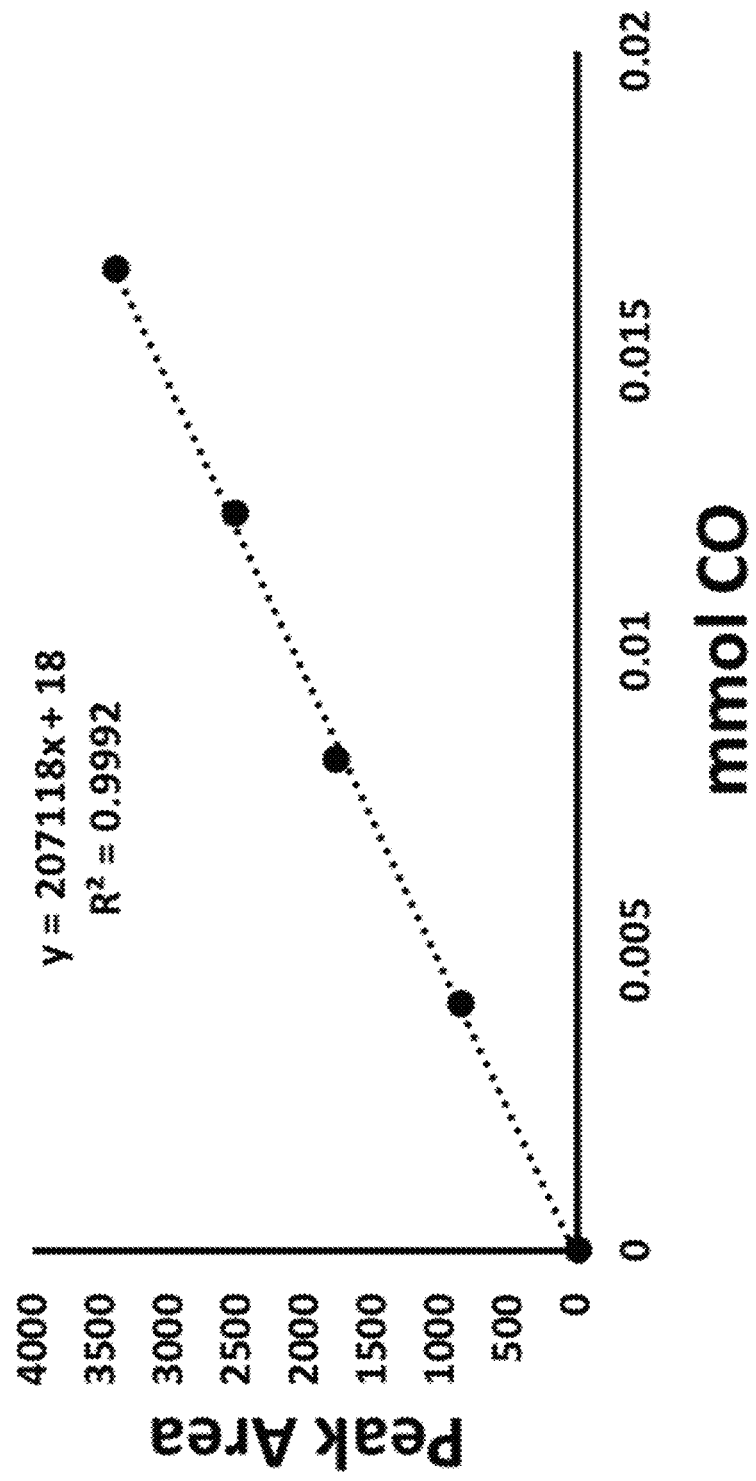
FIG. 8A is the calibration curve for CO release as described in Example 11. The x-axis is mmol CO and the y-axis is peak area of the HPLC curve.
Figure 8B:
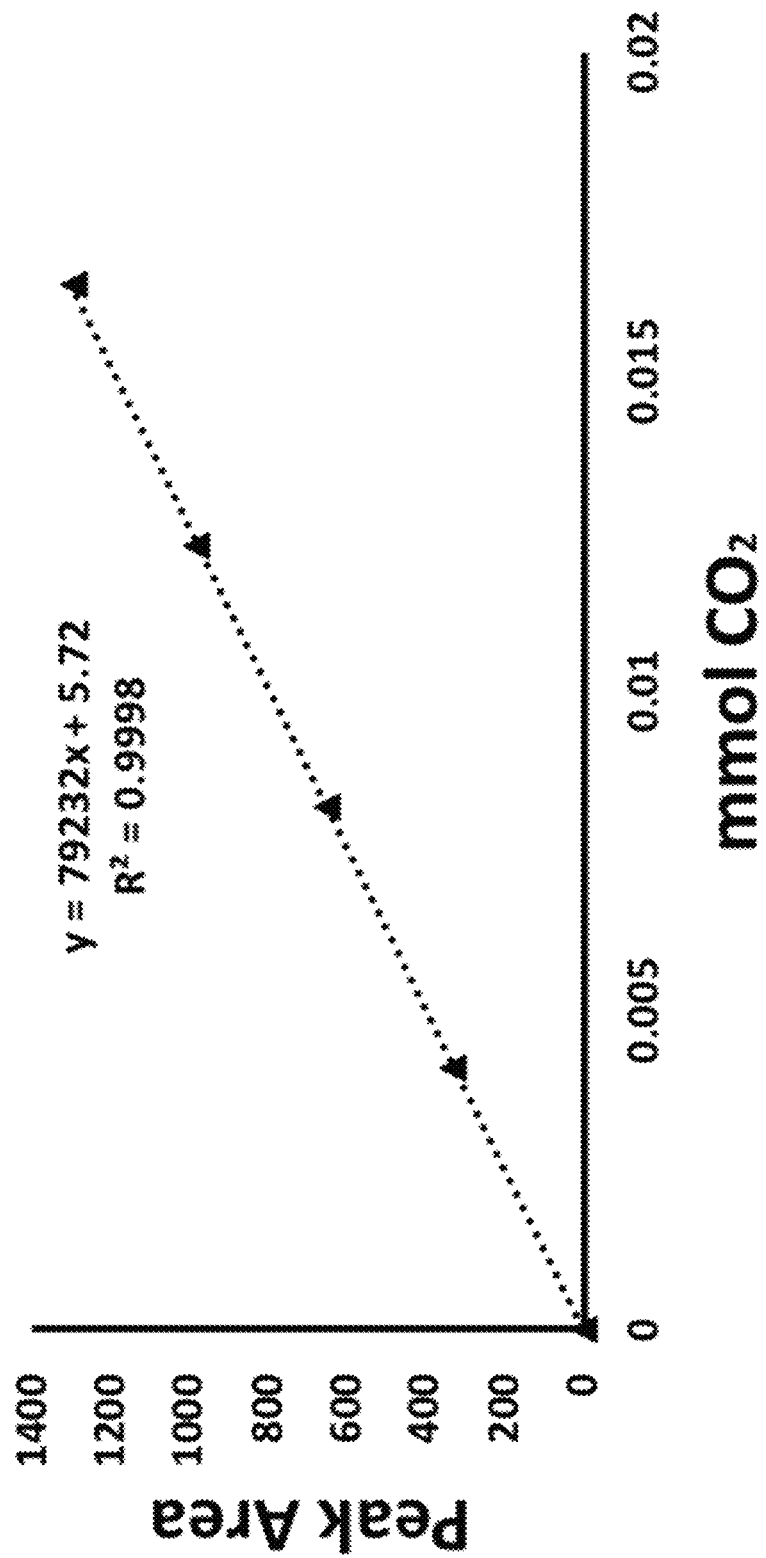
FIG. 8B is the calibration curve for $CO_2$ release as described in Example 11. The x-axis is mmol CO and the y-axis is peak area of the HPLC curve.

FIG. 8A and FIG. 8B are the calibration curves for CO and $C_{O2}$ release, respectively.

LC-MS Studies: CO Production Vs Non-CO Producing Pathways The LCMS analysis was performed on an Agilent 1200 HPLC and 3200 API triple quadrupole mass spectrometer with electrospray ionization source in a negative mode. Selected ion mode was used for the detection of ions at m/z 182 for saccharin and m/z 89 for oxalic acid. A 5 uL of sample solution (compound 5) was directly delivered to the mass spectrometer ionization source with an Agilent autosampler and HPLC by mixing with 1% ACN in water mobile phase at 200 uL/min flow rate. No column was used. Three minutes were recorded and the peak area was integrated and the peak are ratio of PA (Oxalic acid)/PA(Saccharin) vs Concentration ratio (C(Saccharine)/C(Oxalic acid) was plotted as standard curve. The linear regression equation was generated for the calculation of the ratio of unknowns.

Figure 13:
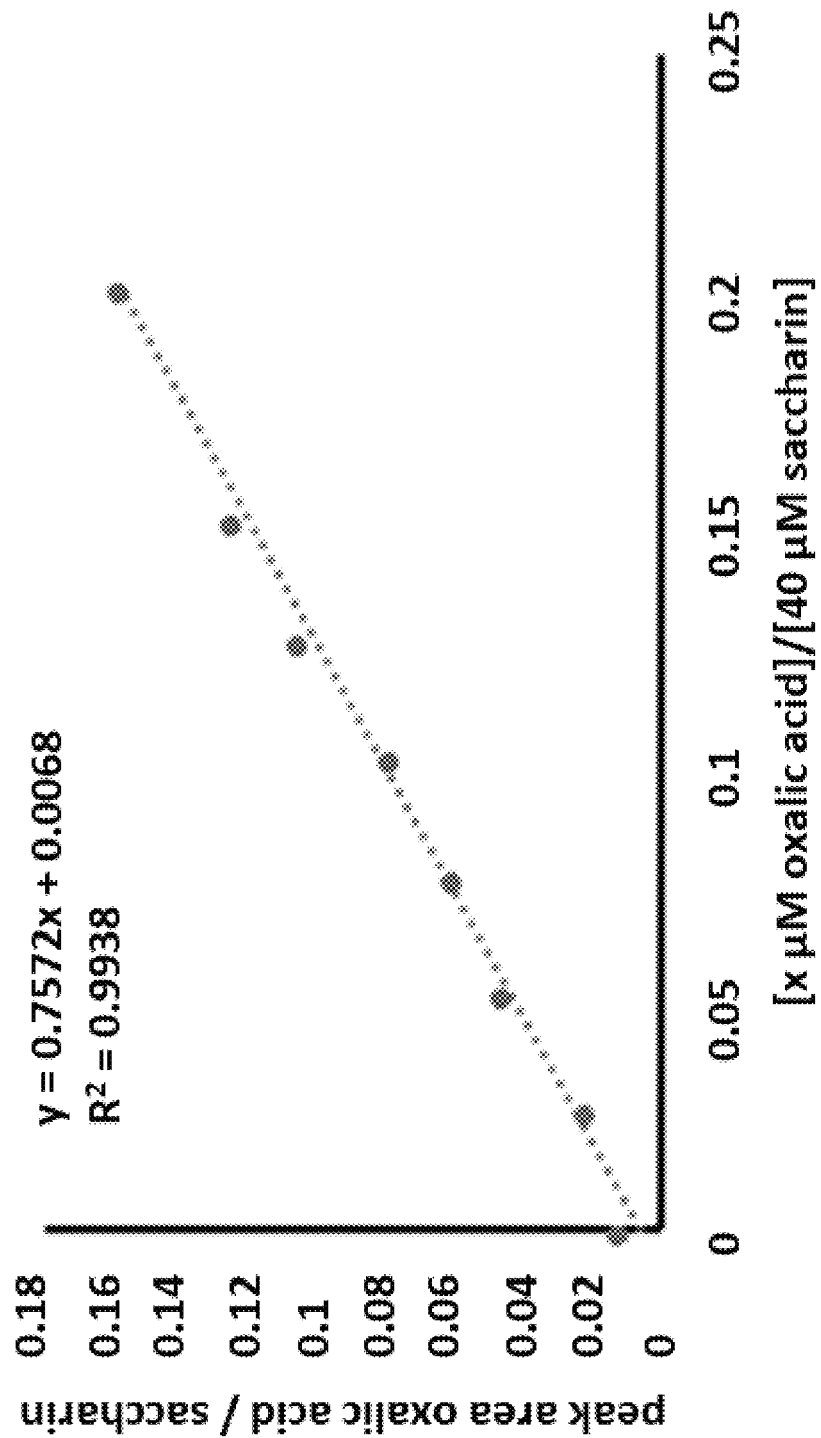
FIG. 13 is the standard curve for LC-MS determination of oxalic acid generated from Compound 5 as described in Example 11. The x-axis is the proportion of oxalic acid/saccharin measured in M and the y-axis is the peak area ratio of oxalic acid/saccharin.

Using this method, 47 μM of oxalic acid was produced from a 200-μM sample of Compound 5 (FIG. 13). Therefore, CO production is estimated to be about 75%, which agrees well with the results generated from the GC-TCD experiments (quantitative CO Analysis described above).

NMR CO Release Experiments for Formyl Compounds

Compounds 1-4 were tested for their CO release by NMR. Each compound was placed in deuterated PBS or 20% DMSO-$d_6$ in deuterated PBS. CO release yield was indirectly determined by calculating the ratio of formic acid formed as a by-product of the competing hydrolysis reaction. The CO release yields of these compounds are summarized in Table 3 below.

TABLE 3

Carbon Monoxide Release Yields of Formyl CO Donors

| Compound | Compound Structure | CO Release Yield (%) |
|---|---|---|
| 1 | 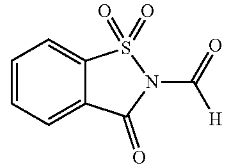 [SMILES: O=CN1C(=O)c2ccccc2S1(=O)=O] | 20 |
| 2 | 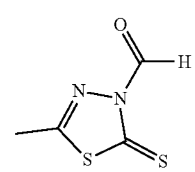 | 33 |

TABLE 3-continued

Carbon Monoxide Release Yields of Formyl CO Donors

| Compound | Compound Structure | CO Release Yield (%) |
|---|---|---|
| 3 | 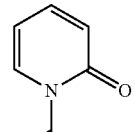 | 20 |
| 4 | 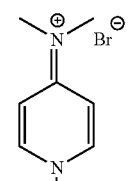 | 34 |

Figure 14:
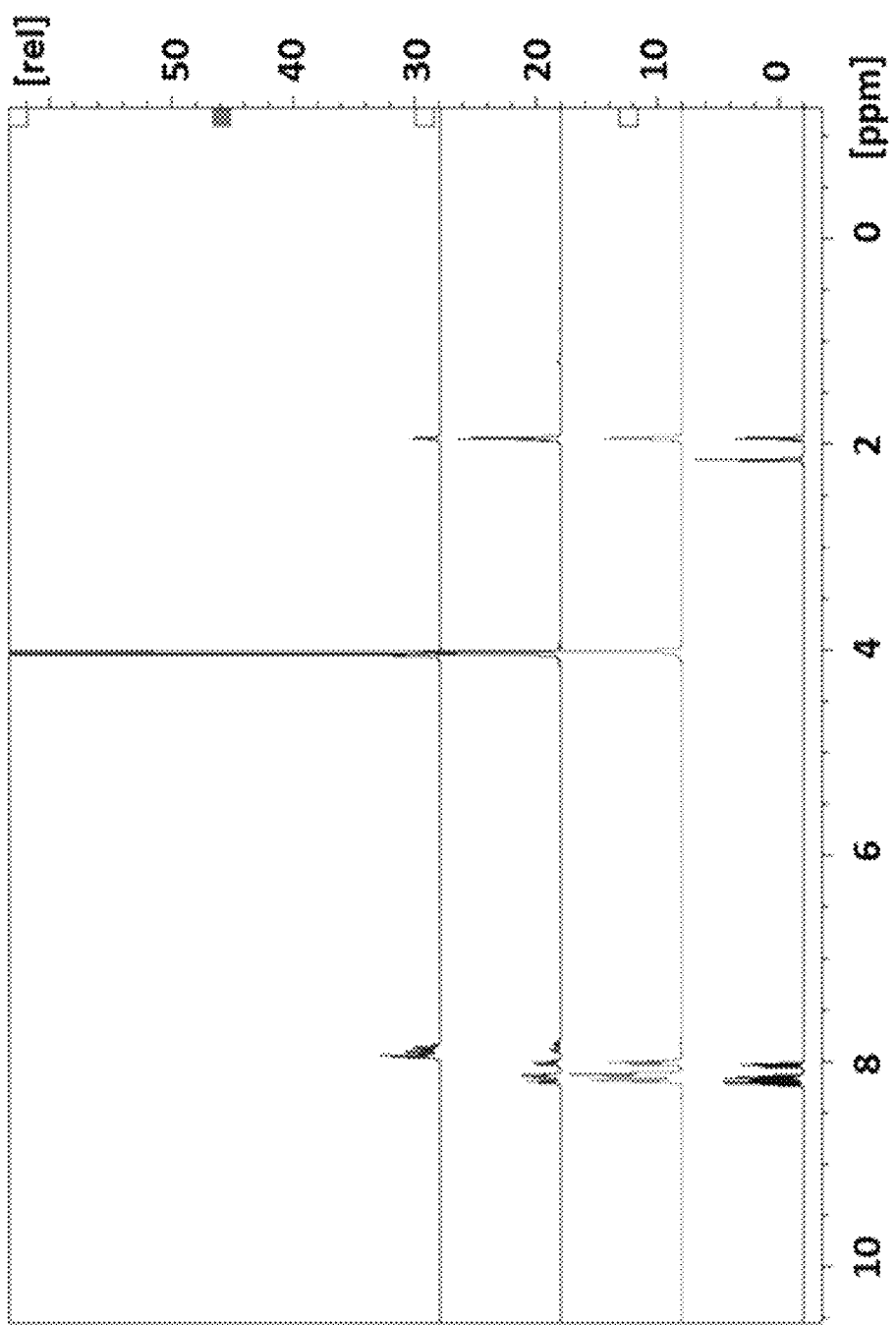
FIG. 14 is a $^1HNMR$ spectrum of the decomposition of Compound 5 as described in Example 11.
Figure 15:
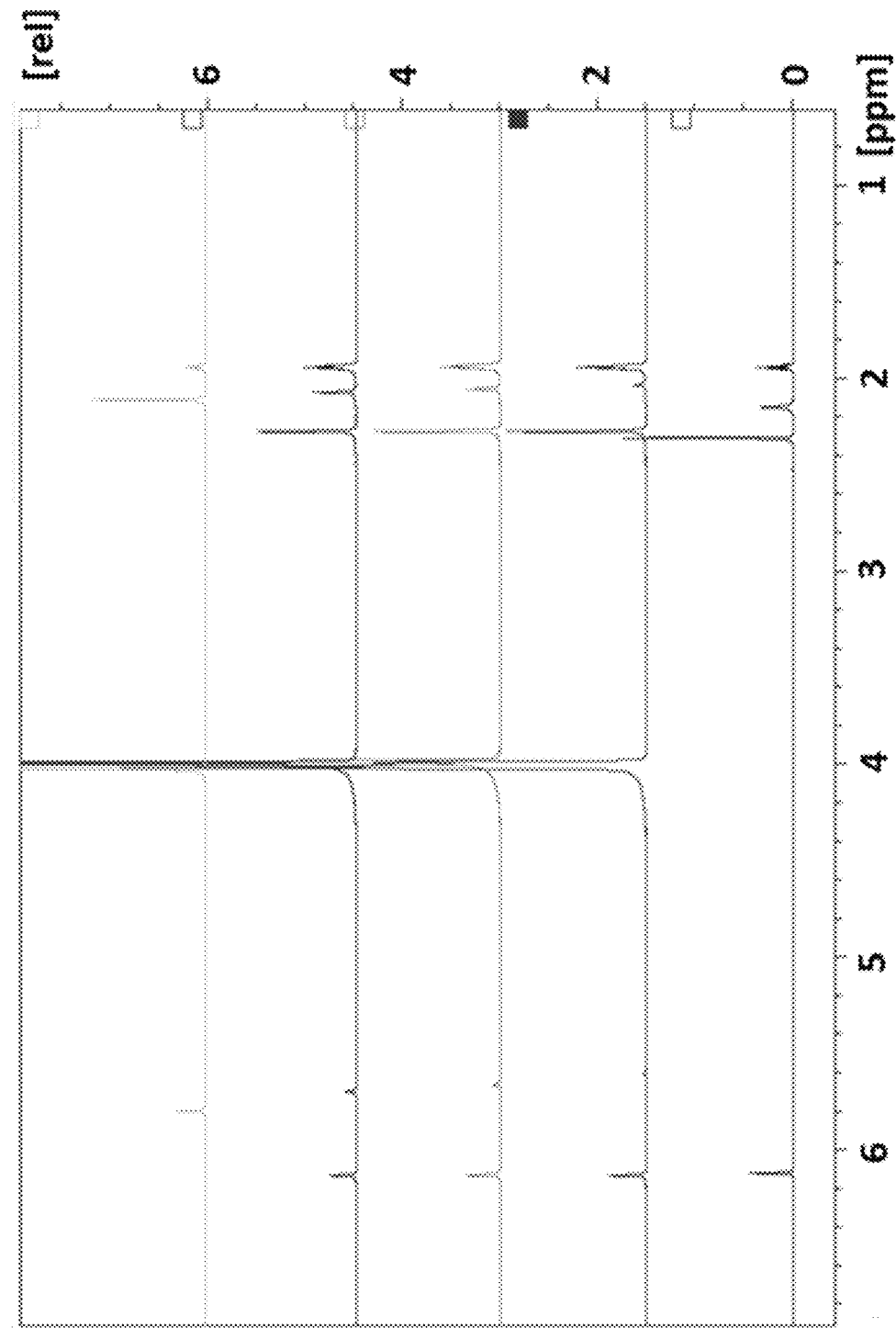
FIG. 15 is a $^1HNMR$ spectrum of the decomposition of Compound 7 as described in Example 11.

Approximately 5 mg of Compound 5 was dissolved in 450 μL of deuterated acetonitrile and a proton and carbon NMR were run. Then 250 μL of deuterated water was added to the NMR tube and a proton and carbon NMR run were run at different time points. This experiment was repeated with Compound 7. These two studies show that products after gas release are mainly the benign carriers saccharin and acesulfame. FIG. 14 is the $^1$HNMR of the decomposition of Compound 5 and FIG. 15 is the $^1$HNMR of the decomposition of Compound 7.

HPLC Kinetics Experiments

Compound 5 was tested for its rate of decomposition under physiological conditions. The followed samples were injected into the HPLC instrument i) saccharin (200 μM) dissolved in 40% acetonitrile in PBS; and b) incubated solution of the CO-releasing molecule Compound 5 dissolved in 40% acetonitrile in PBS at 37° C. at different time points. A 200 μL aliquot of incubated sample was placed inside a 0.5 mL vial followed by dilution with 200 μL of acetonitrile. The study was performed using the Shimadzu Prominence UFLC with a reversed-phase analytical column (Waters C18 3.5 μM, 4.6×100 mm) at 25° C. The flow rate was set at 1 mL/min. Gradient elution using acetonitrile and deionized water with 0.05% TFA was used to elute out the components of the sample. Elution conditions: 0-7 min 50% to 70% acetonitrile; injection volume 10 μL; detection wavelength of 254 and 280 nm. Experiments were done in triplicate.

Figure 16A:
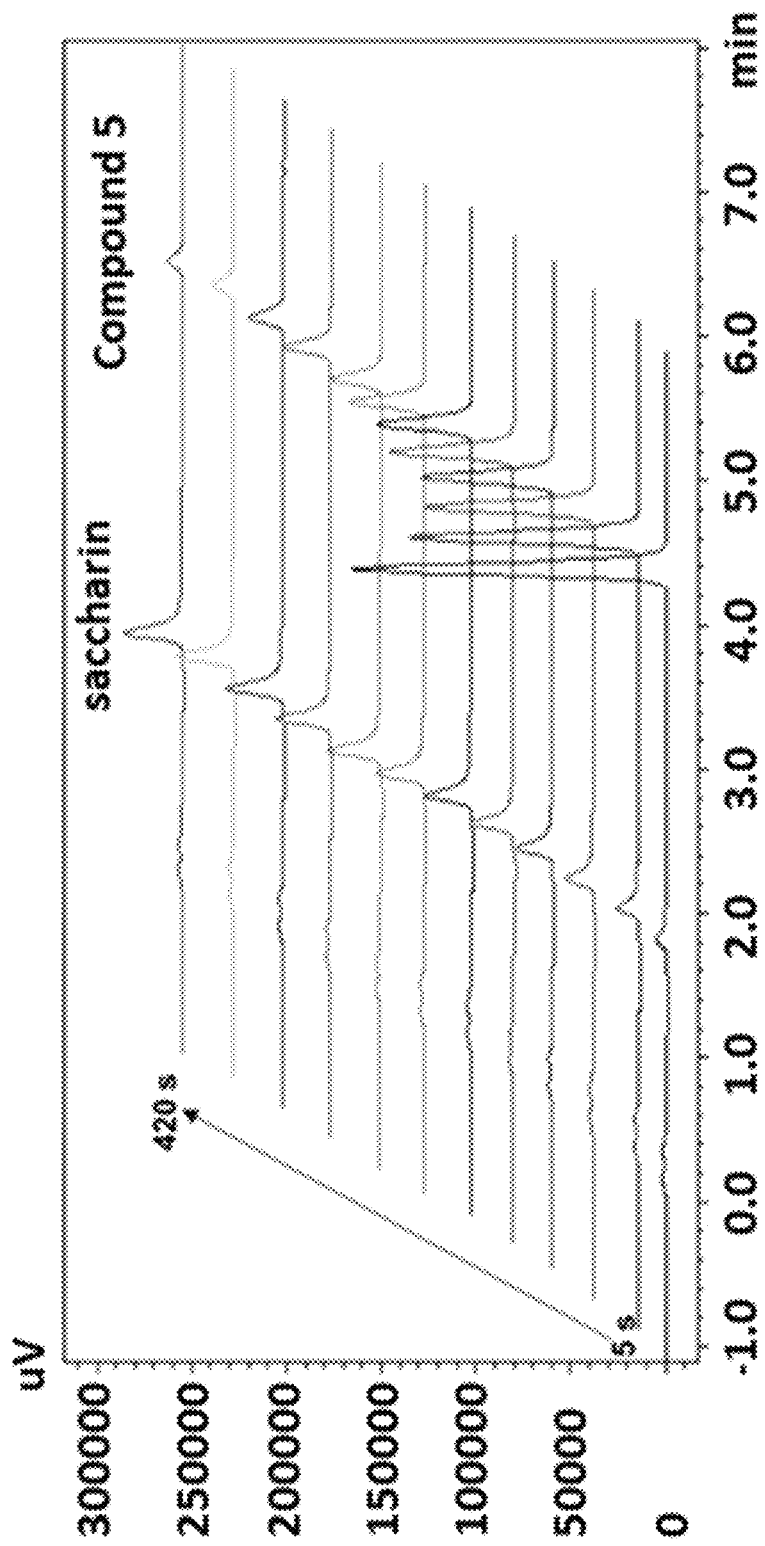
FIG. 16A is the decomposition of Compound 5 as measured by HPLC as described in Example 11. The decomposition was measured over the course of 420 seconds. The x-axis is time measured in minutes and the y-axis is UV intensity.
Figure 16B:
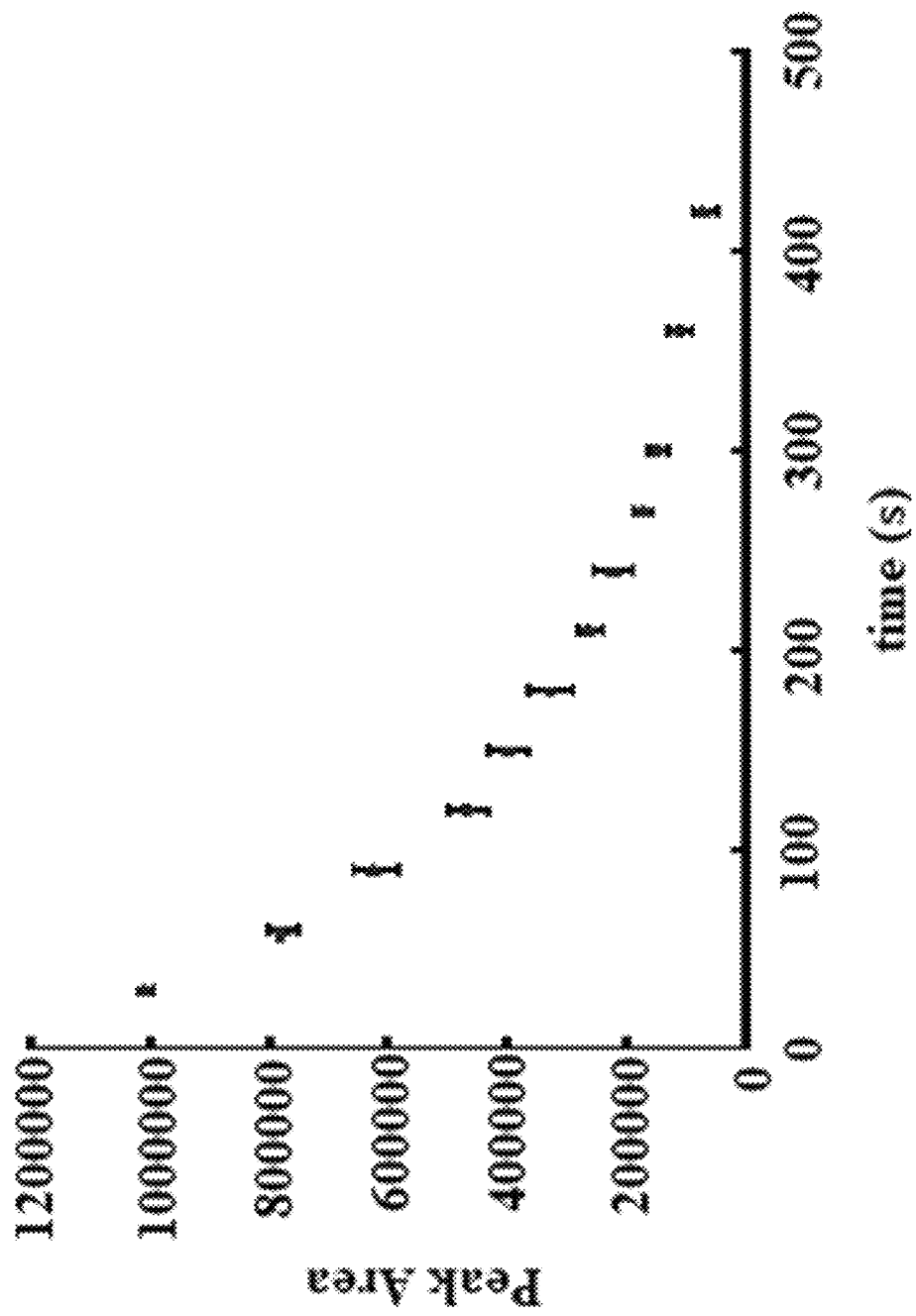
FIG. 16B is a scatter plot that shows the levels of Compound 5 in 60% PBS at 37° C. over time as measured by HPLC as described in Example 11. The x-axis is time in seconds, and the y-axis is the peak area measured by HPLC.

FIG. 16A is the decomposition profile of Compound 5 in 60% PBS. As illustrated in FIG. 16B, the half-life of Compound 5 in 60% PBS at 37° C. is 1.28±0.03 minutes. In comparison, Compound 5 is stable as a solid for at least 24 days and is stable as a solution in acetonitrile for at least seven days.

Figure 17A:
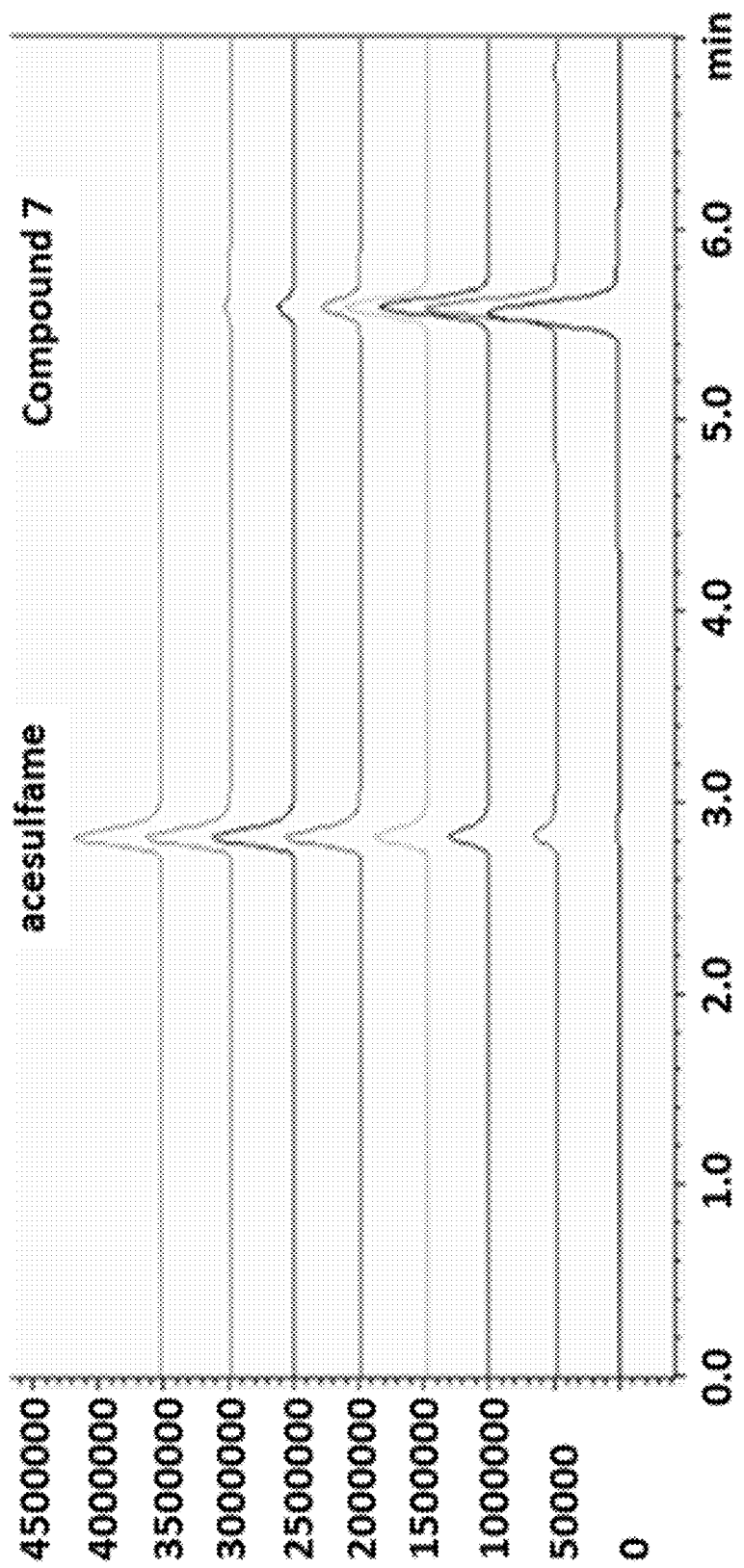
FIG. 17A is the decomposition of Compound 7 as measured by HPLC as described in Example 11. The decomposition was measured over the course of 60 minutes. The x-axis is time measured in minutes and the y-axis is UV intensity.
Figure 17B:
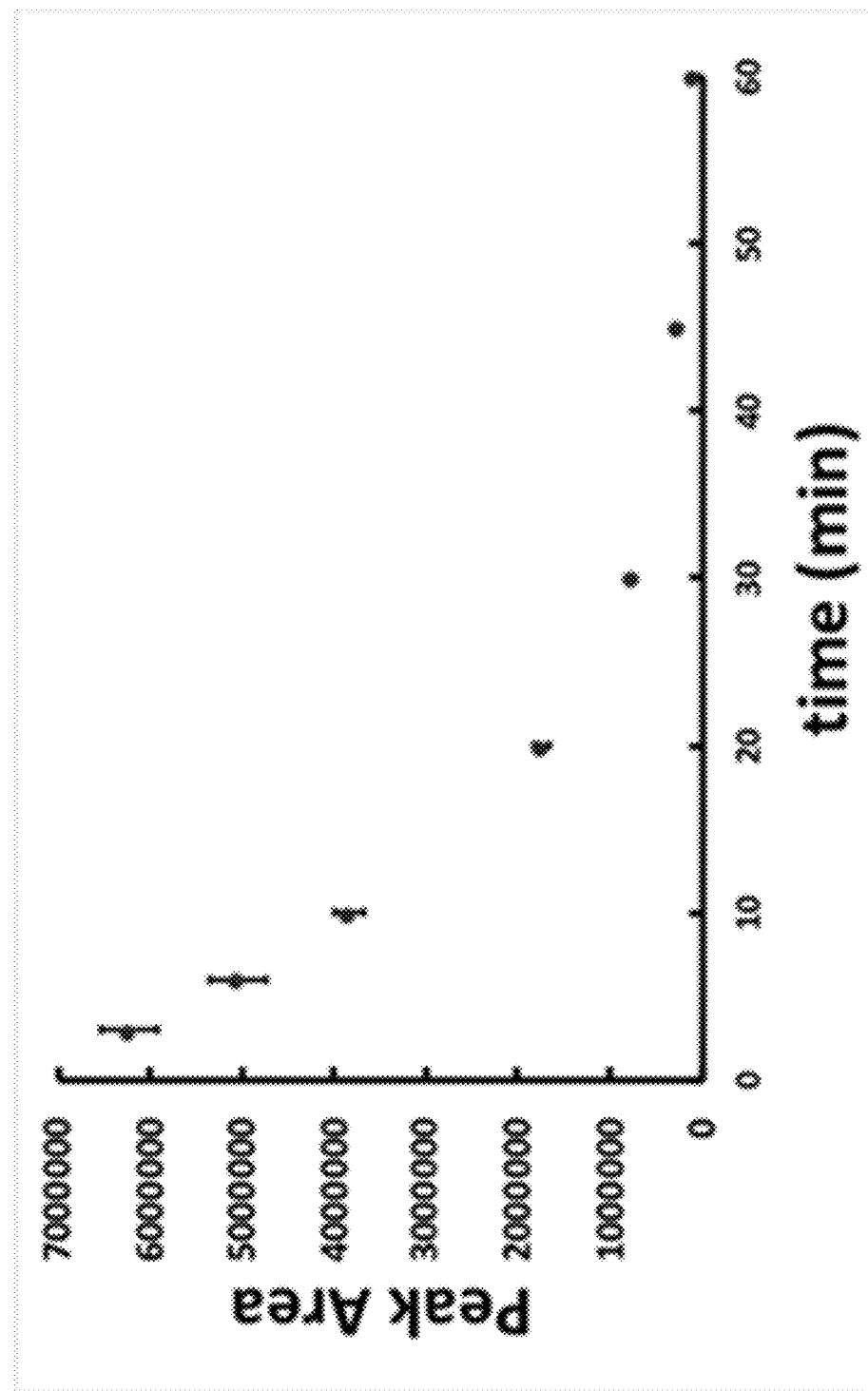
FIG. 17B is a scatter plot that shows the levels of Compound 7 in 60% PBS at 37° C. over time as measured by HPLC as described in Example 11. The x-axis is time in seconds, and the y-axis is the peak area measured by HPLC.

Compound 7 was tested in the same manner. FIG. 17A is the decomposition profile of Compound 7 in 60% PBS and FIG. 17B illustrates the half-life of Compound 7 to be 9.5±0.1 min. In FIG. 17A, the decomposition was measured from 0 to 60 minutes.

Anti-Inflammatory Assay

Figure 18A:
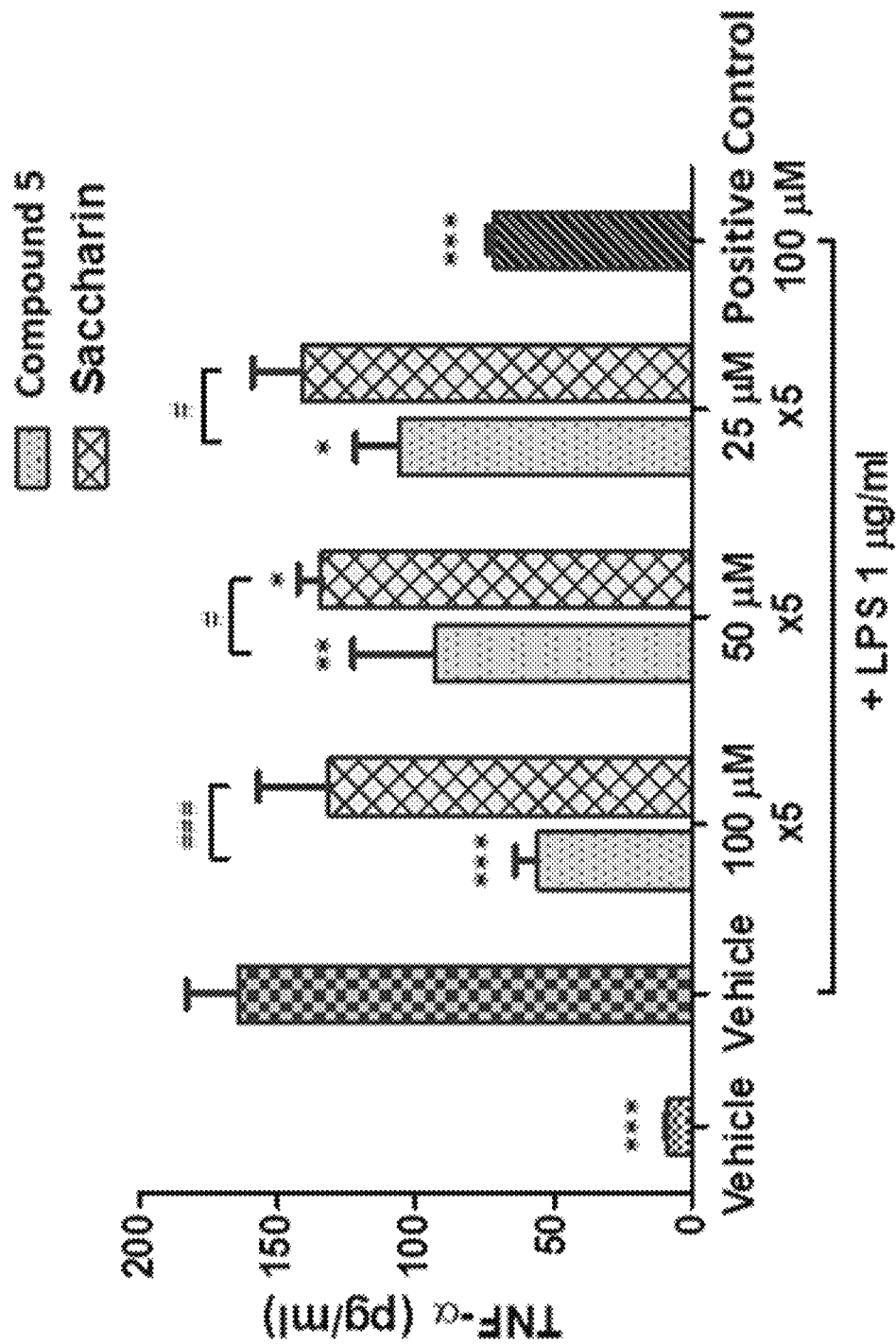
FIG. 18A is a bar graph that shows attenuation of TNF-alpha levels at different concentrations of compound 5 and the control compound saccharin as described in Example 11. The x-axis is the micromolar concentration of vehicle, control, Compound 5 or saccharin, and the x-axis is TNF-alpha levels measured in nanograms per milliliter.
Figure 18B:
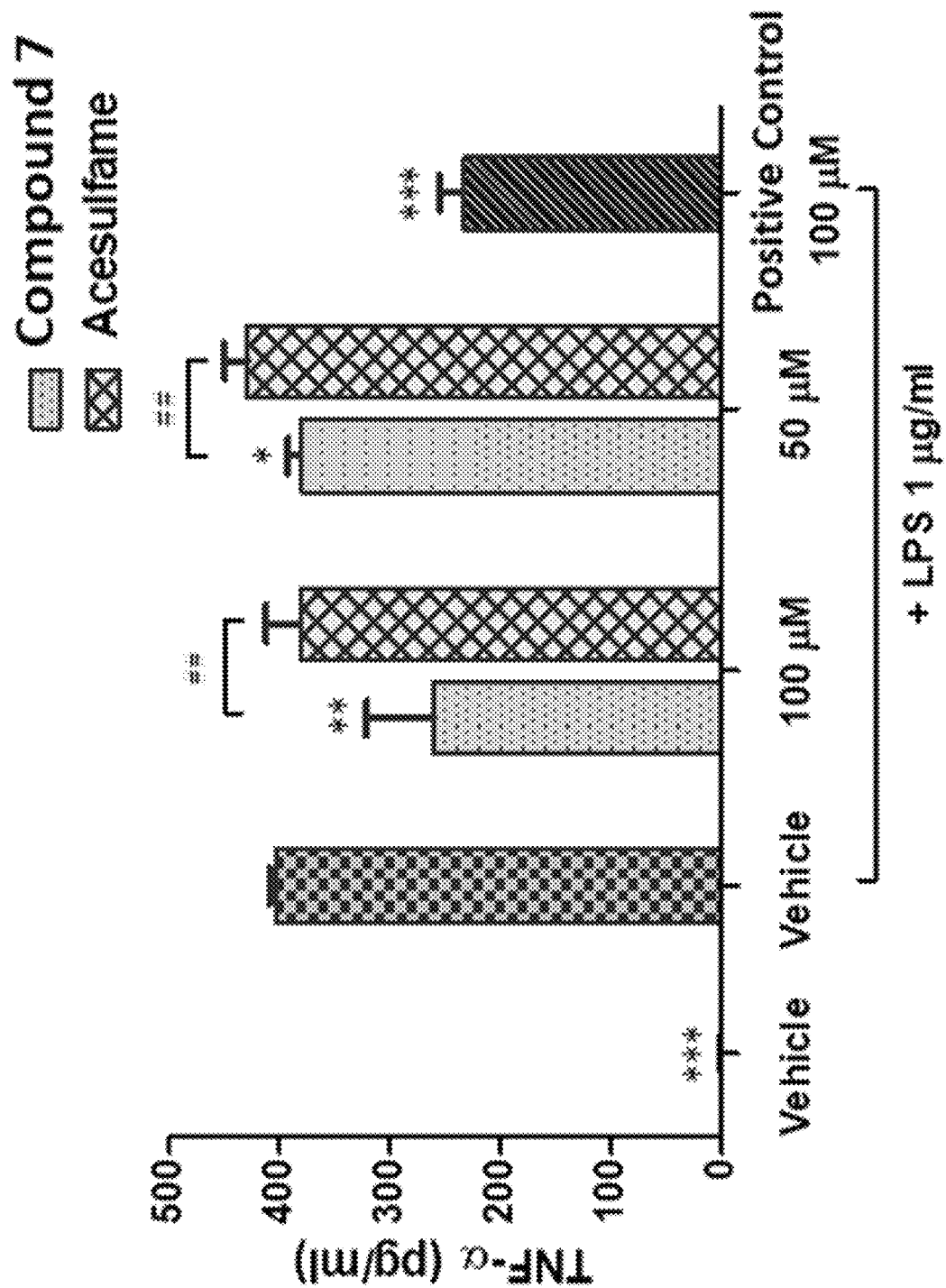
FIG. 18B is a bar graph that shows attenuation of TNF-alpha levels at different concentrations of compound 7 and the control compound acesulfame as described in Example 11. The x-axis is the micromolar concentration of vehicle, control, Compound 7 or acesulfame, and the x-axis is TNF-alpha levels measured in nanograms per milliliter.

The effect of the compounds of the present invention on CO-associated anti-inflammation activity was studied. Pro-inflammatory cytokine TNF-α in RAW264.7 cell culture upon stimulation by lipid polysaccharide (LPS) from *E. coli* was tested with ELSA assay. Results shown in FIG. 18A and FIG. 18B indicate that the pretreatment of the RAW264.7 cells with representative CO-prodrugs Compound 5 and Compound 7, respectively, inhibit LPS induced TNF-α production in a dose-dependent manner and the released product did not show anti-inflammation effect. Due to the fast release kinetics of Compound 5, a repeated dosage protocol was used. Indicated concentration of Compound 5 was added to the culture medium right before addition to the cell and the fresh-made drug loaded culture medium was changed every 1 hour 5 times. Compound 7 has a longer half-life and therefore a single addition of the drug can fulfill the anti-inflammation effect. A Total 5 hour pretreatment was used throughout the experiments and the reported CO prodrug shown below (Ji, X., et al. *Angew Chem Int Ed Engl* 2016, 55 (51), 15846-15851) was used as the positive control:

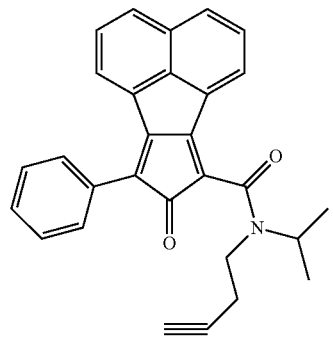 [SMILES: C#CCCN(C(=O)C1=C2C(=C(c3ccccc3)C1=O)c1cccc3cccc2c13)C(C)C]

Cytotoxicity Assay

For the CCK-8 assay, HeLa cells were cultured in DMEM (Dulbecco's Modified Eagle's Medium) supplements with 10% fetal bovine serum (MidSci; SO1520HI) and 1% penicillin-streptomycin (Sigma-Aldrich; P4333) at 37° C. with 5% $C_{O2}$. Fresh medium was replenished every other day. The cells were treated with the compounds (0-100 μM) using 1% DMSO in DMEM for 24 hours.

Figure 19:
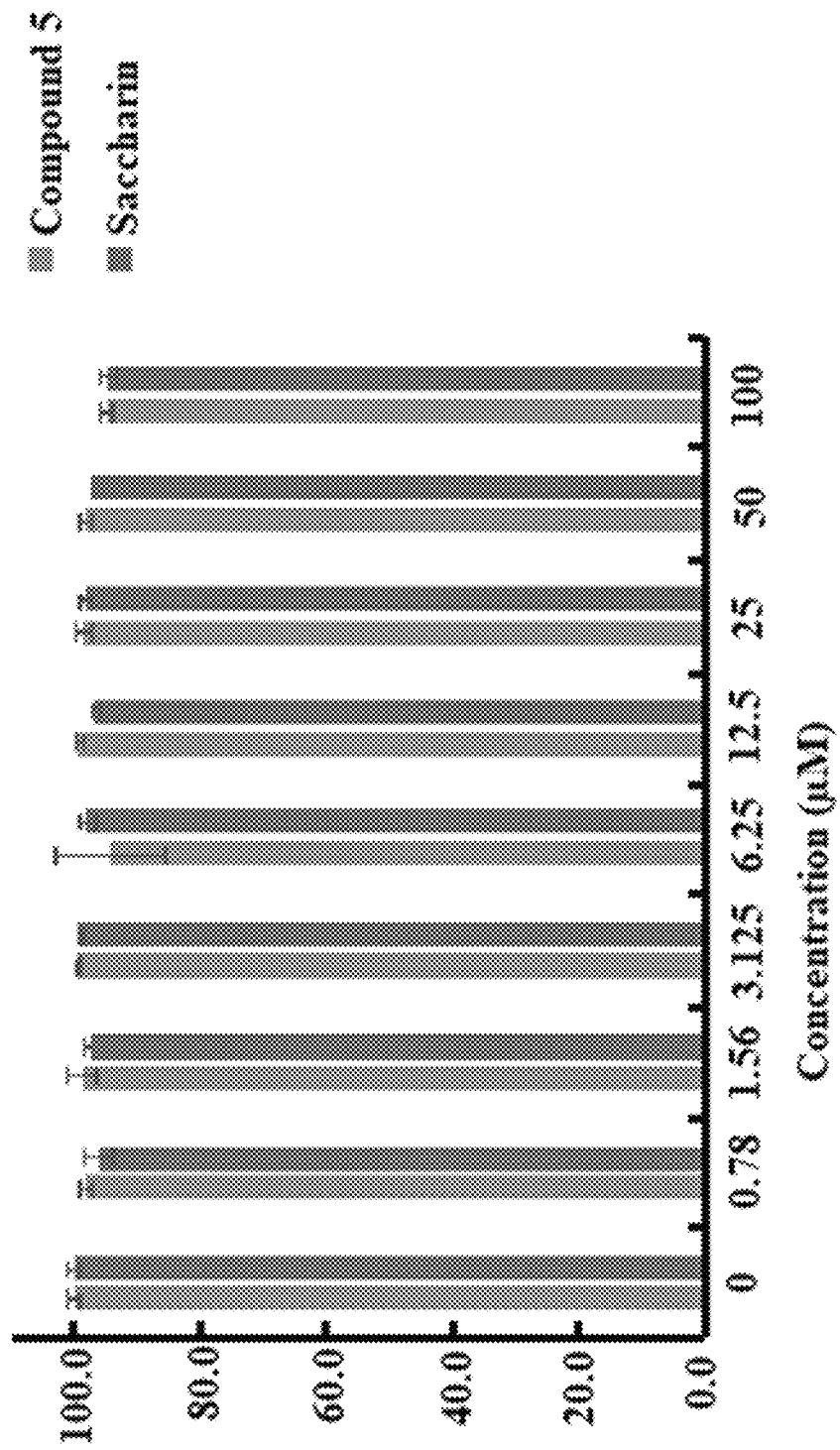
FIG. 19 is a bar graph that shows the cytotoxicity of Compound 5 in HeLa cells as compared to saccharin as described in Example 11. The x-axis is the micromolar concentration of Compound 5 or saccharin, and the x-axis is cell survival in percent.

As illustrated in FIG. 19, Compound 5 shows no toxicity to HeLa cells up to a 100 μM concentration.

Stability Study

Figure 20A:
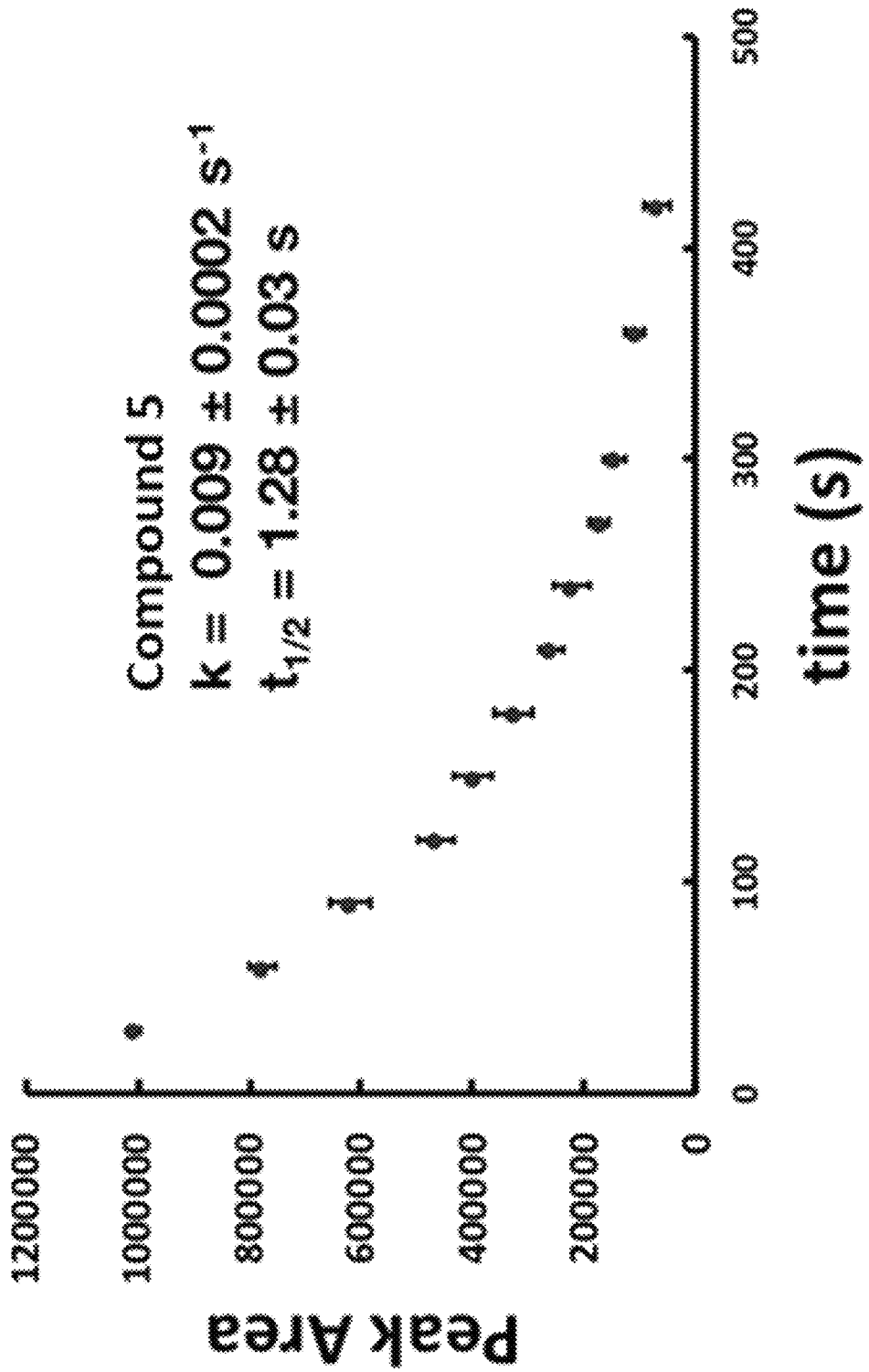
FIG. 20A is a scatter plot that shows the levels of Compound 5 in $ACN:H_2O$ (4:1) over time as measured by HPLC as described in Example 11. The x-axis is time in seconds, and the y-axis is the peak area measured by HPLC.
Figure 20B:
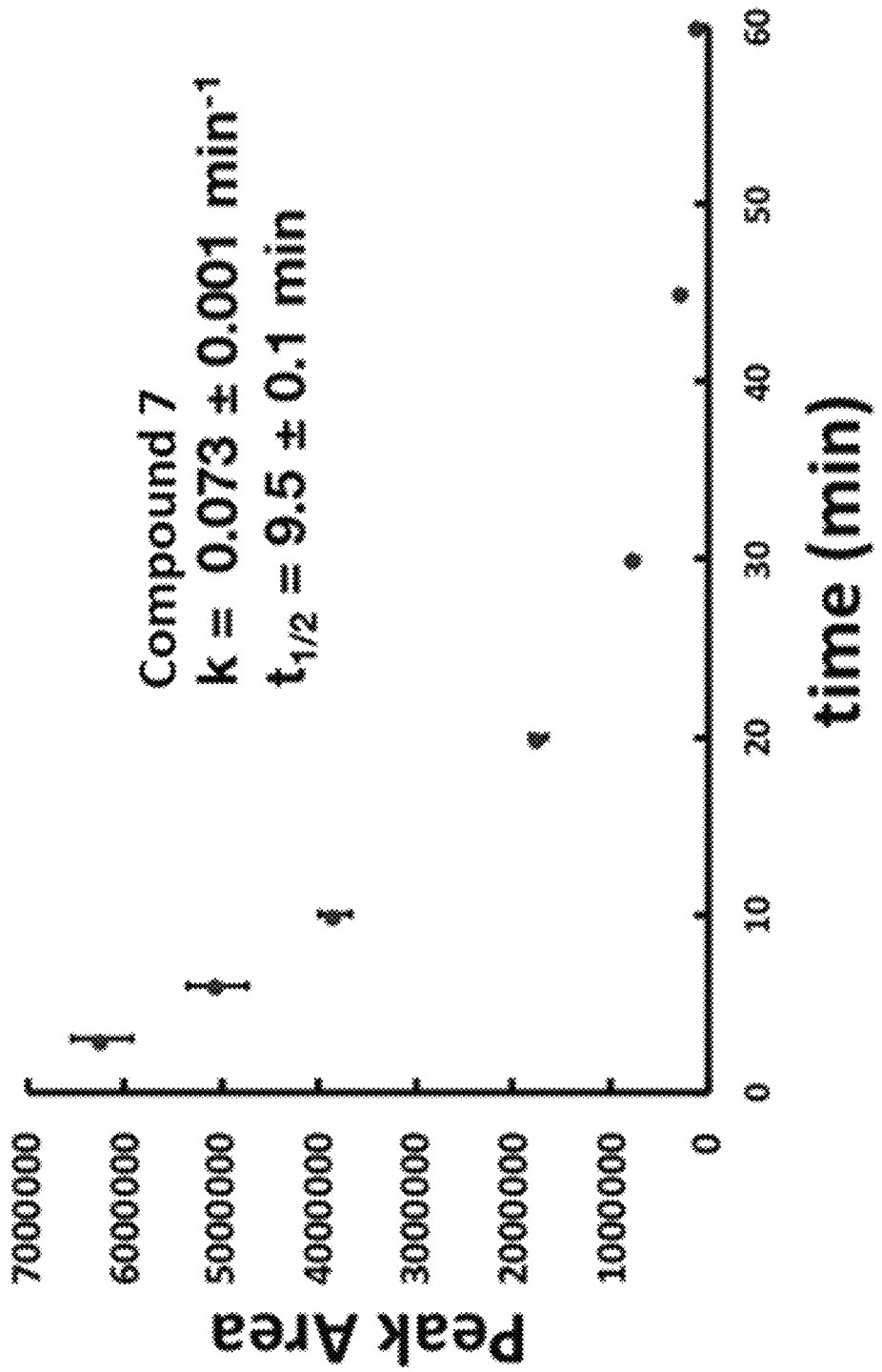
FIG. 20B is a scatter plot that shows the levels of Compound 7 in $ACN:H_2O$ (4:1) over time as measured by HPLC as described in Example 11. The x-axis is time in seconds, and the y-axis is the peak area measured by HPLC.

RP-HPLC studies revealed that Compound 5 and Compound 7 are stable as a solid for at least 24 days exposed to ambient light and temperature. These prodrugs are also stable as a solution of acetonitrile stored at room temperature for at least seven days. Kinetic experiments using HPLC revealed that the half-lives of Compound 5 (FIG. 20A) and Compound 7 (FIG. 20B) in 60% phosphate buffered saline is 1.28±0.03 min and 9.5±0.14 min, respectively.

Example 12. Formulation of Compound 5

In one embodiment, the compounds of the present invention are formulated in such a way that they can readily mix with water and yet are not exposed to water contents during storage. For drug administration, one approach is to dissolve the prodrug in an organic excipient which are miscible or partially miscible with water. Upon contact with water, CO can be released from this homogenous mixture. In one embodiment, dimethylacetamide (DMA) is used to dissolve compound 5 in DMA to form 10 mg/ml solution and this solution was further diluted by three folds with polyethylene glycol (PEG) 300. The formed mixture can be used as a liquid formulation of compound 5. N-methyl pyrolidone (NMP) can also be used in place of DMA or other non-nucleophilic solvents that miscible with water can serve as the same purpose. In the place of PEG, glycol, Tween 80, Poloxamer and other similar water miscible co-solvents can also be used. A mixture with a certain ratio of the solvent and co-solvent can be used.

Another approach is to achieve even dispersion in a solid-phase matrix. The adsorption of the saccharin-based Compound 5 on activated charcoal is described below. The various ratios and conditions that were studied are also described. In all cases, the activated charcoal was preheated at 120° C. overnight to eliminate adsorbed water. This represents an advantageous method for dispersing the agent to result in CO release under physiologically relevant aqueous conditions.

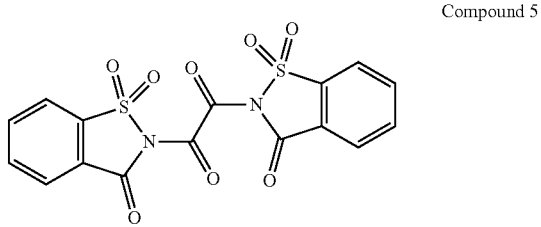 [SMILES: O=C(C(=O)N1C(=O)c2ccccc2S1(=O)=O)N1C(=O)c2ccccc2S1(=O)=O]

Compound 5

Determination of the Adsorption Ratio of Compound 5 on Activated Charcoal

Figure 21:
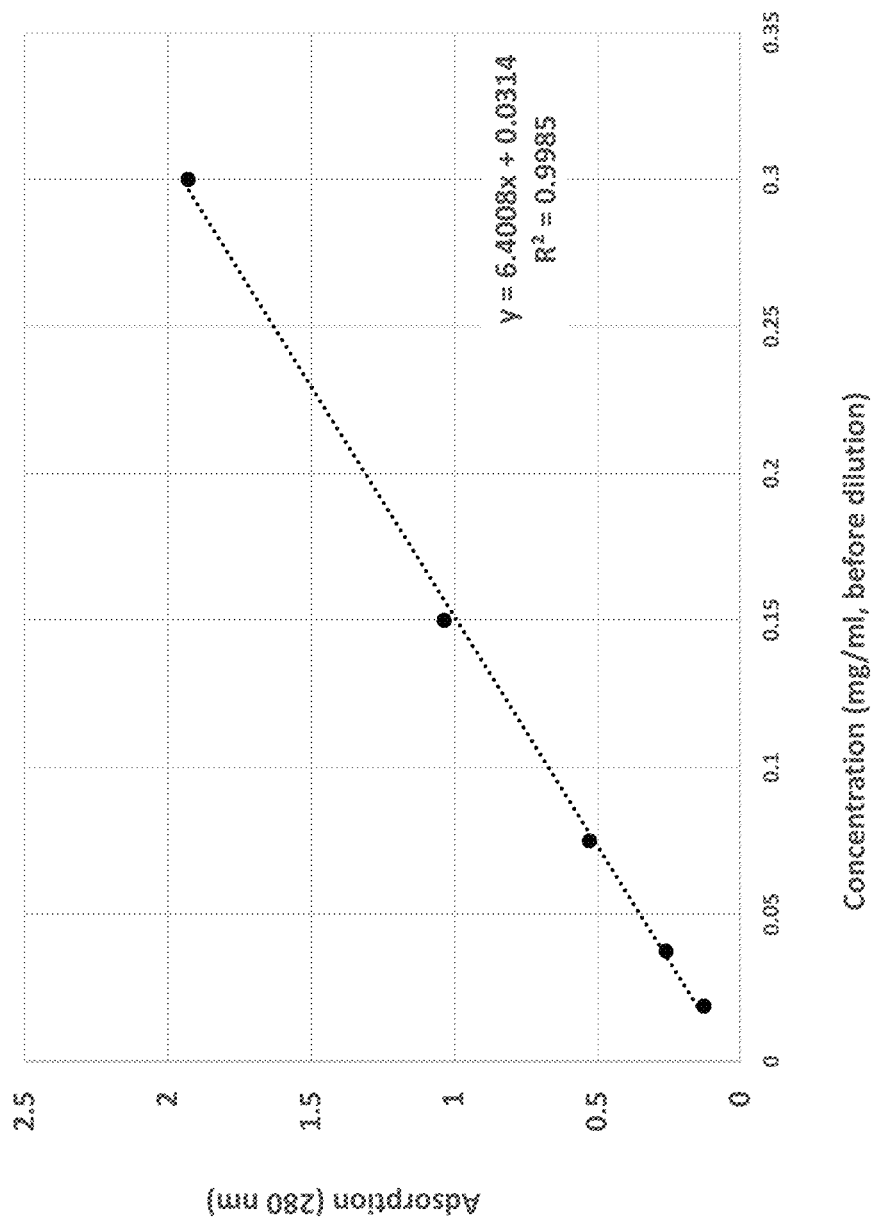
FIG. 21 is a standard curve of Compound 5 in ACN that was used to determine the adsorption capacity of Compound 5 on activated charcoal as described in Example 12. The x-axis is the concentration before dilution measured in (mg/mL) and the y-axis is adsorption measured at 280 nm.

A saturation adsorption assay was used to determine the adsorption capacity of the Compound 5 on activated charcoal. Compound 5 was dissolved in anhydrous ACN to form calibration samples with a concentration range from 0.019 to 0.3 mg/ml. The absorbance at 280 nm was measured with a UV-Vis spectrometer and plotted against the concentration to give the calibration curve (FIG. 21).

At room temperature (25° C.), 1-6 mg Compound 5 was mixed with 10 mg of activated charcoal and then 0.5 ml ACN was added. The mixture was shaken for 1 h followed by centrifuging at 12000×g for 5 min and the supernatant was diluted by 50 folds with ACN and measured with UV/Vis spectrometer at 280 nm to get the Compound 5 concentration in the supernatant. Adsorbed mass of Compound 5 was calculated by Formula I:

Adsorbed mass=(Initial mass)−0.5*(supernatant concentration)  (Formula I)

Adsorbed mass=$Y_0$+(Plateau-$Y_0$)*(1−$e^{kX}$)  (Formula II)

Figure 22:
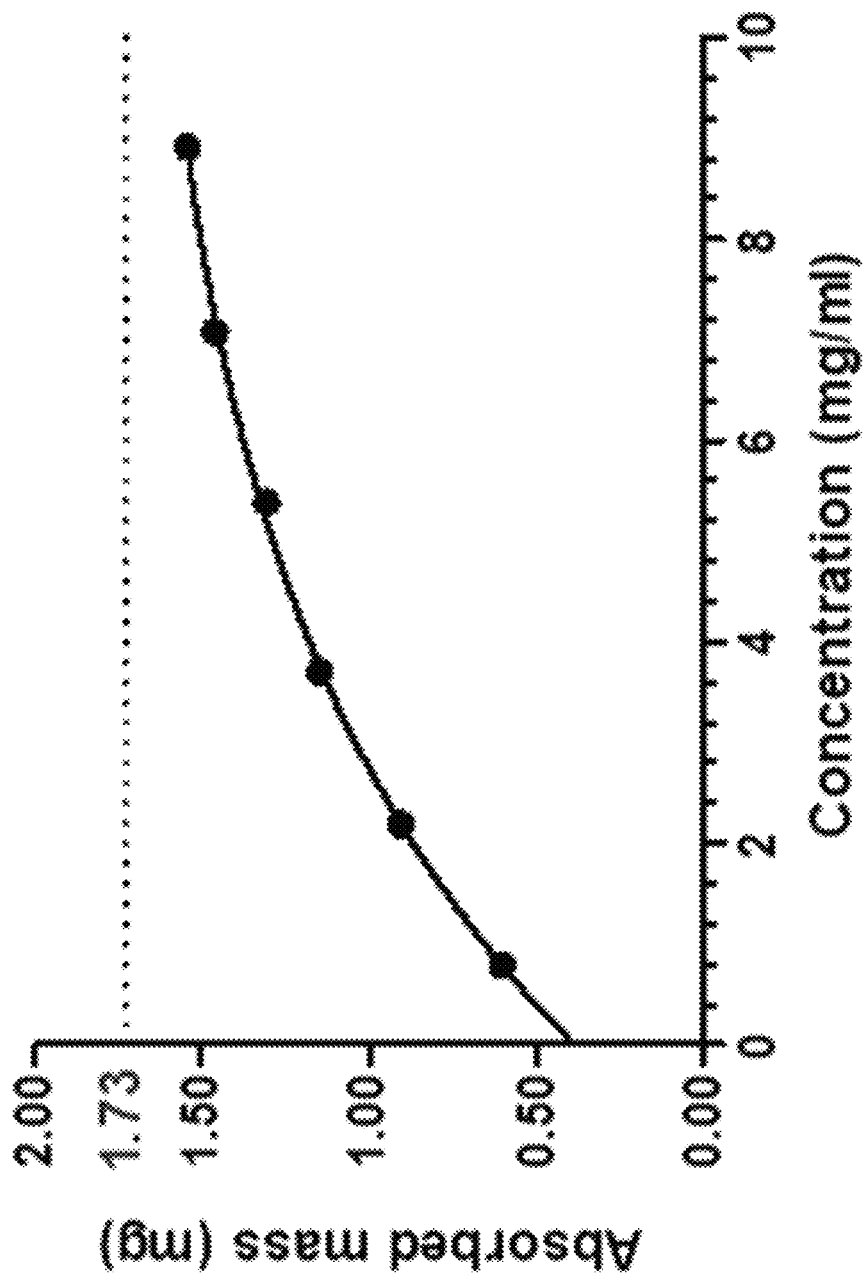
FIG. 22 is an adsorption curve of Compound 5 on activated charcoal to determine the maximum adsorption amount of Compound 5 as described in Example 12. The x-axis is concentration of Compound 5 in mg/mL and the y-axis is adsorbed mass measured in mg. The dash line at 1.73 mg represents the maximum amount that was adsorbed.

Adsorbed mass was plotted against the concentration (FIG. 22). The plateau was calculated to be 1.73 mg by Formula II, which represents the maximum adsorption amount of the Compound 5 that can be adsorbed in 10 mg activated charcoal at 25° C.

Formulation of Compound 5 with Activated Charcoal

Two typical procedures to formulate Compound 5 with activated charcoal are described below.

Method A: 10 mg Compound 5 was mixed and shaken at room temperature with 100 mg activated charcoal and 1 ml anhydrous ACN for 1 h. The mixture was concentrated under reduced pressure. The formed black powder was dried by using a lyophilizer (vacuum 1 mbar, condensation trap −70° C.) overnight to remove residual ACN. The dried black powder was used as the activated CO prodrug formulation.

Method B: 10 mg Compound 5 was mixed and shaken at room temperature with 60 mg activated charcoal and 1 ml anhydrous ACN for 1 h. The slurry was filtered and the solid was dried by using a lyophilizer (vacuum 1 mbar, condensation trap −70° C.) overnight to remove residual ACN. The dried black powder was used as the CO prodrug formulation. The actual loading is determined by gas chromatograph.

In an alternative embodiment, polyvinylpyrollidone (PVP), polyvinyl pyrollidone polyvinyl acetate (PVP-VA) are used as the excipients to make the solid dispersion. In a typical embodiment, the solvent is anhydrous and non-nucleophilic, for example ACN, THF, acetone, or methylene chloride.

Figure 23:
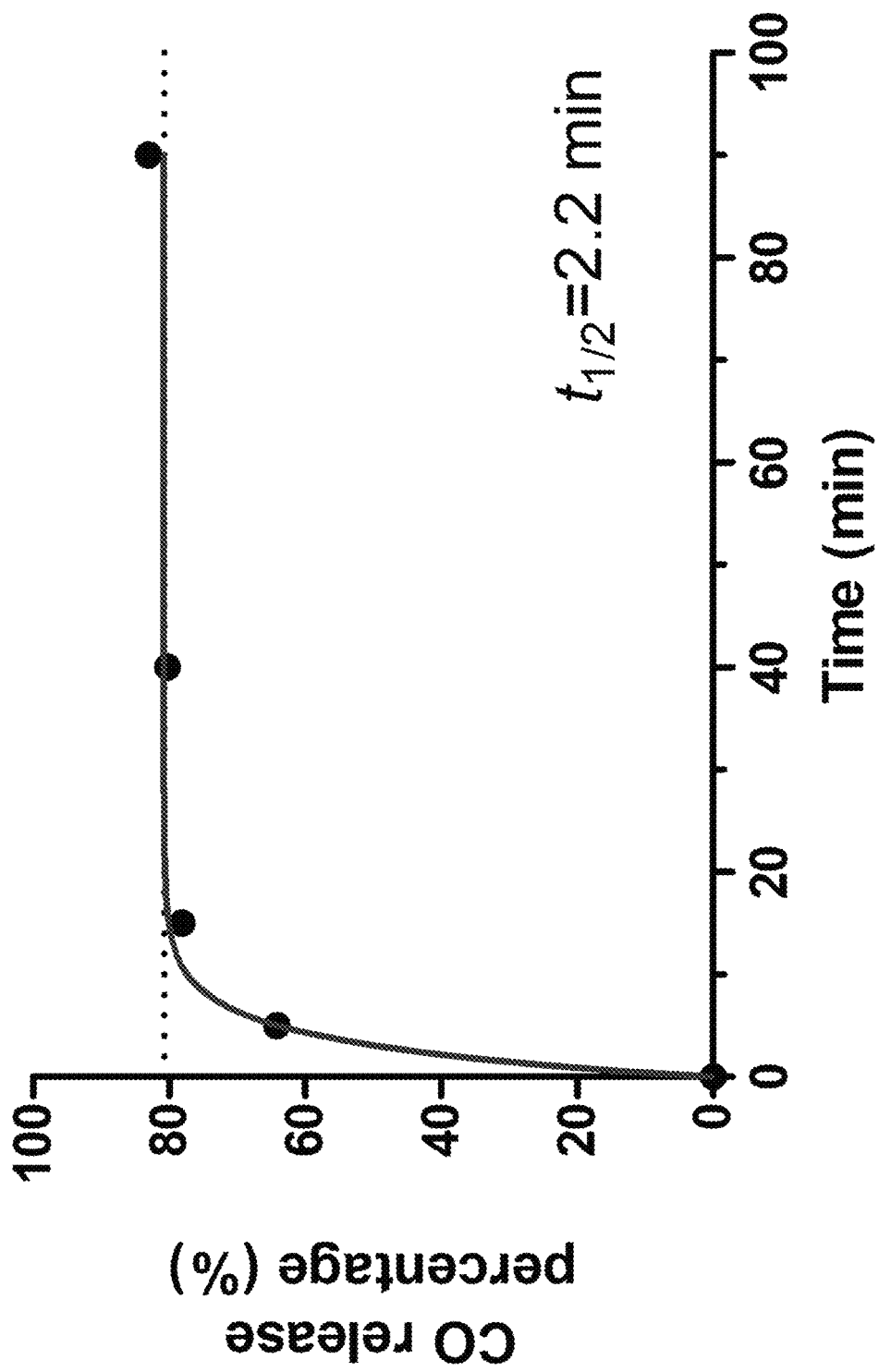
FIG. 23 is a graph of the CO release kinetic profile of Compound 5 as described in Example 12. The x-axis is time measured in minutes and the y-axis is CO release measured in percent. The dash line at 81% represents the total CO release.

Determination of CO Release Profile of the CO Prodrug Formulation on Activated Charcoal Activated charcoal comprising Compound 5 (100 mg) that was formulated by method A was put into a GC-headspace vial. PBS (3 mL) preheated to 37° C. was added and the vial was sealed and incubated at 37° C. At different time points, 250 µL of the headspace gas was withdrawn and injected to a gas chromatograph (Agilent 7820) equipped with a RESTEK packed molecular sieve column and a TCD detector. The CO release kinetic and yield were plotted (FIG. 23) based on the CO peak area and calibration curve.

The results show that by adsorption of Compound 5 on activated charcoal, the release rate was fast with a half-life of 2.2 min and the total CO release yield was 81% which was higher than using homogenous conditions in the ACN/water system.

Quantification of the Saccharin in the Supernatant after CO Release

The byproduct after CO release of Compound 5 is saccharin. Due to the adsorption effect of activated charcoal, the byproduct may still get adsorbed on activated charcoal, which could result in less systemic exposure to saccharin. Although saccharin is considered to be safe, lowering systemic absorption is still beneficial.

Figure 24:
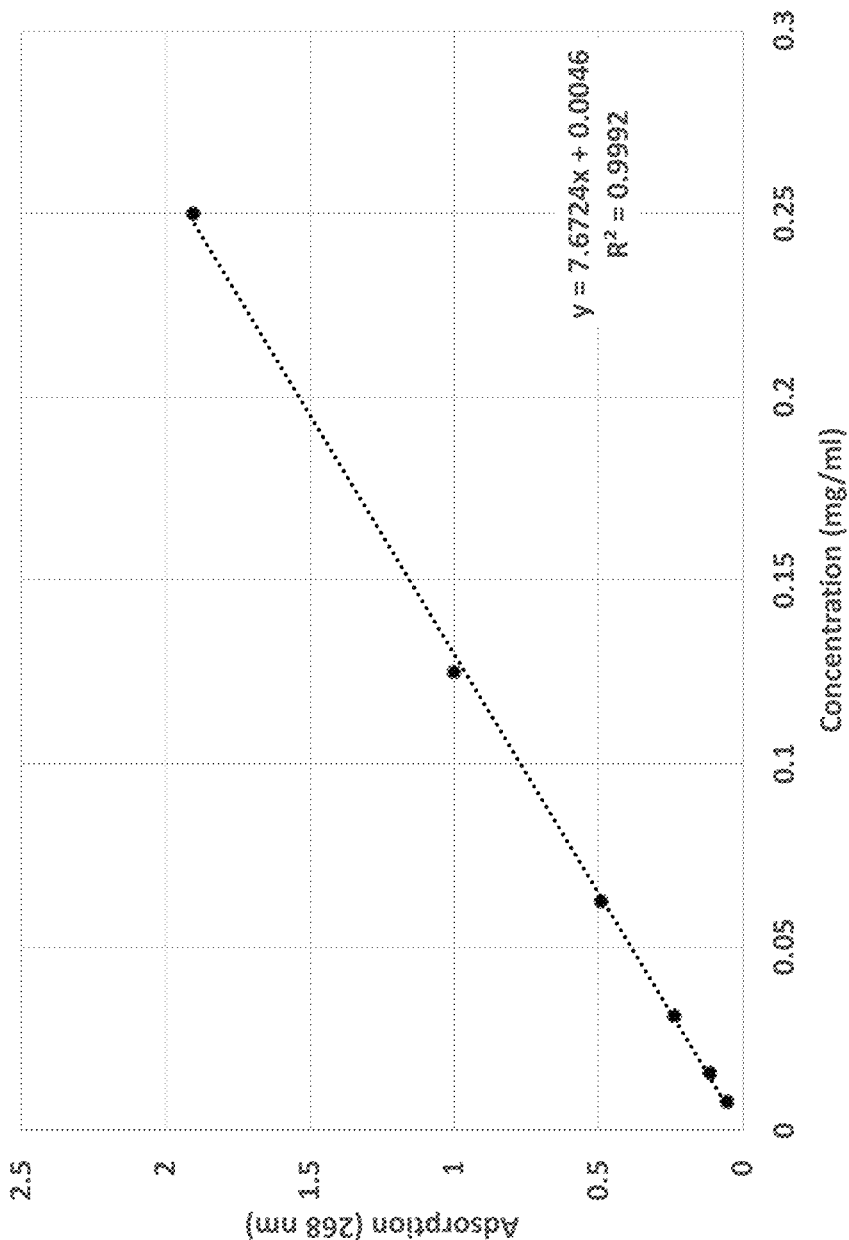
FIG. 24 is a standard curve of saccharin in the supernatant (PBS) following the adsorption of Compound 5 on activated charcoal as described in Example 12. The x-axis is concentration of saccharin measured in mg/mL and the y-axis is adsorption measured at 268 nm.
Figure 25:
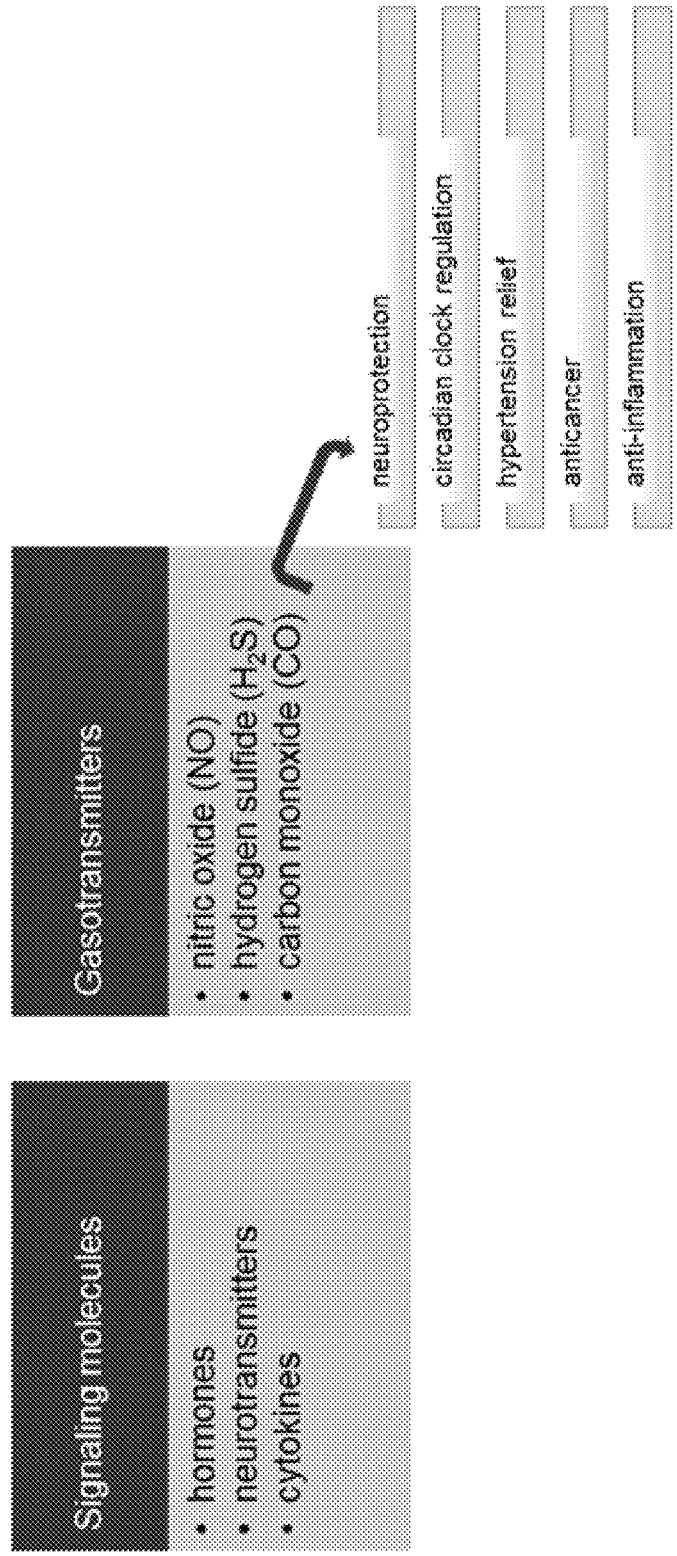
FIG. 25 is a scheme summarizing the categorization of carbon monoxide as a gasotransmitter and detailing some of the general biological effects of gasotransmitters.
Figure 26:
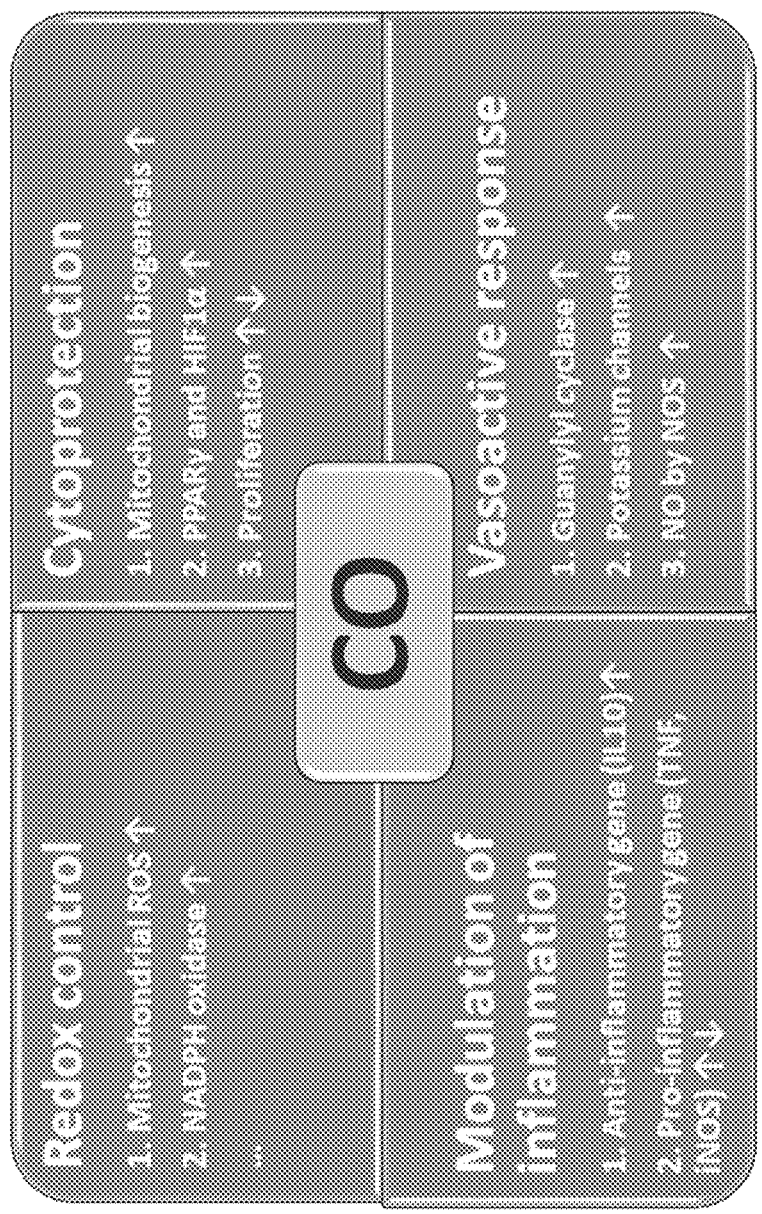
FIG. 26 is a scheme summarizing the general biological effects of carbon monoxide.
Figure 27:
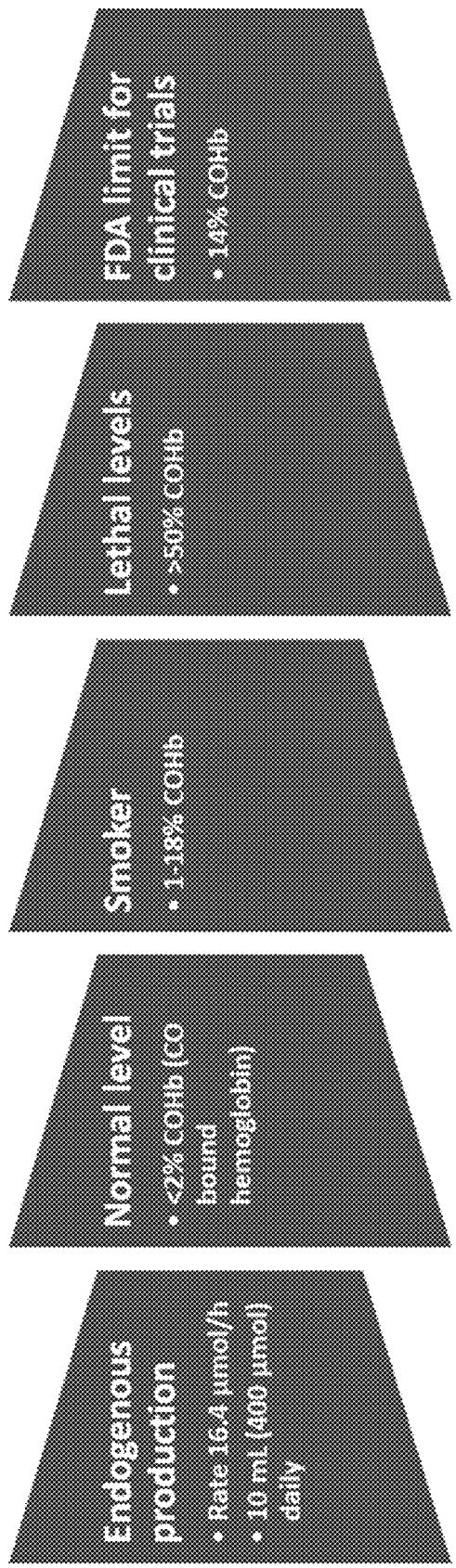
FIG. 27 is a scheme comparing the concentrations of carbon monoxide produced endogenously to the levels present in exogenous circumstances, including the lethal and FDA clinical limit levels.
Figure 28:
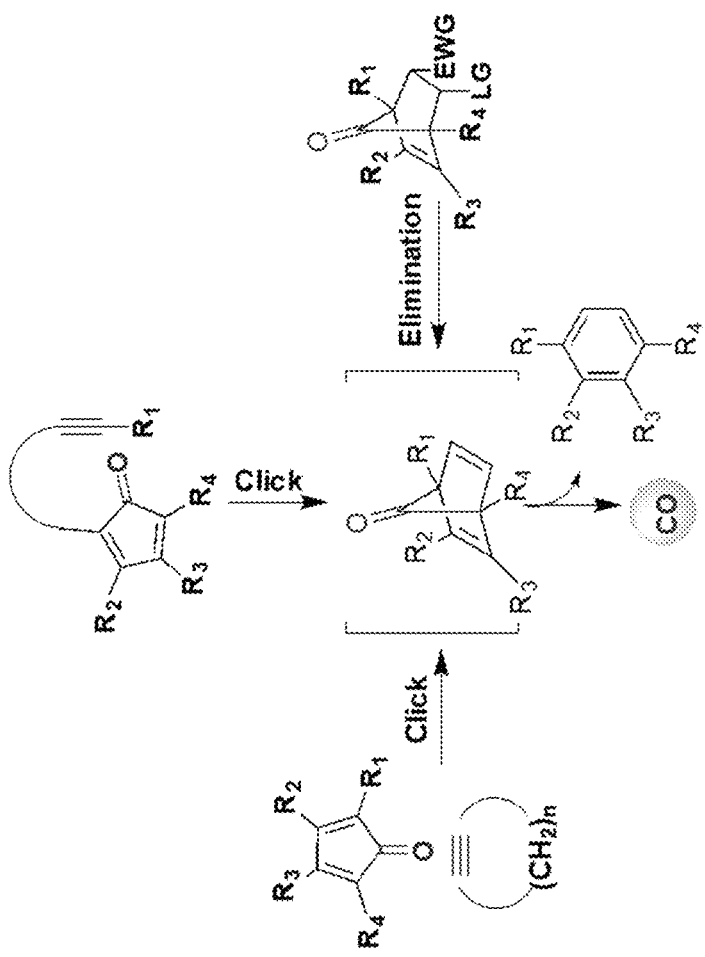
FIG. 28 is a scheme showing a representative example of the release of CO from organic carbon monoxide-releasing compounds.
Figure 29:
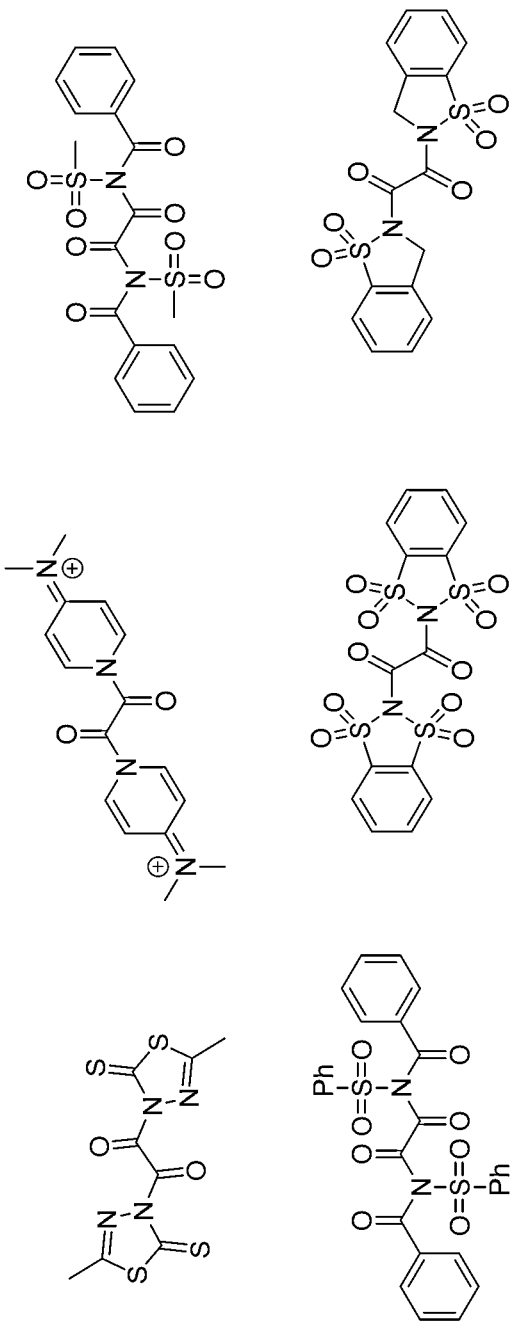
FIG. 29 are representative examples of compounds of Formula II.

The standard curve of saccharin in PBS was established with a UV spectrophotometry method by plotting adsorption at 268 nm against saccharin concentration ranging from 0.0078 to 0.25 mg/ml (FIG. 24). After CO release from the 100 mg activated charcoal comprising Compound 5 formulation (incubated at 37° C. for 4 h), the liquid phase was drawn by filtration through a 0.45 µm syringe filter and diluted by 5 folds and tested with a UV spectrometer. The Abs reading was 0.1575, which corresponded to 0.1 mg/ml concentration of the saccharin in the supernatant PBS. This only accounts for 1.5% of the total input saccharin. Therefore, the majority of the saccharin byproduct was still adsorbed on the activated charcoal used and the amount of free saccharin after CO release was greatly reduced by using this formulation approach.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modifications may be made thereto without departing from the spirit and scope of the invention as defined in the appended claims.

What is claimed is:

1. A compound of Formula II:

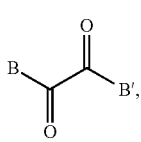

or a pharmaceutically acceptable salt thereof;
wherein B is selected from:

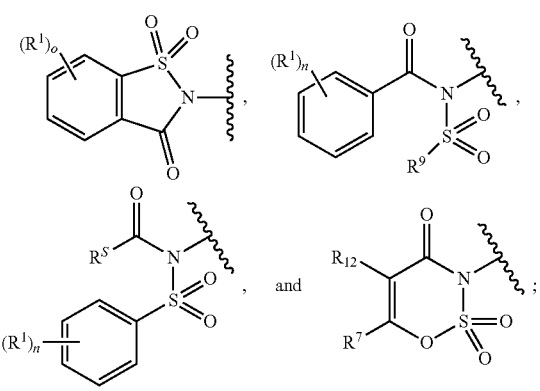

B' is selected from:

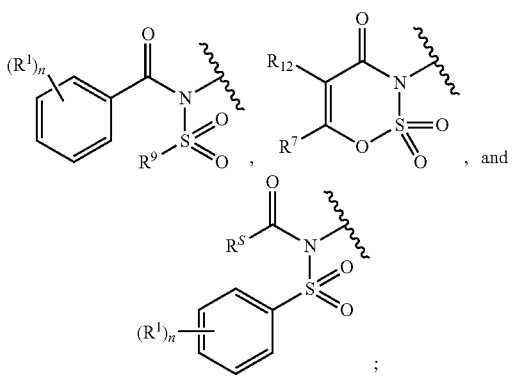

$R^1$ is independently selected at each occurrence from halogen, hydroxyl, alkyl, haloalkyl, alkoxy, haloalkoxy, aryl, heteroaryl, thiol, thioalkyl, —(C=O)$R^S$, —O(C=O)$R^S$, cyano, —SO$_3$H, —(P=O)(OH)$_2$, —O(P=O)(OH)$_2$, and nitro;

$R^7$ is independently selected at each occurrence from hydrogen, alkyl, haloalkyl, aryl, and heteroaryl;

$R^9$ is selected from alkyl, haloalkyl, aryl, and heteroaryl; and $R^{12}$ is selected from hydrogen, halogen, alkyl, haloalkyl, aryl, and heteroaryl;

$R^S$ is selected from hydrogen, alkyl, haloalkyl, alkoxy, amino, alkylamino, dialkylamino, aryl, and heteroaryl;

m is independently selected from 0, 1, 2, 3, or 4;

n is independently selected at each occurrence from 0, 1, 2, 3, 4, and 5; and o is selected from 1, 2, 3, or 4.

2. The compound of claim 1, having a formula selected from:

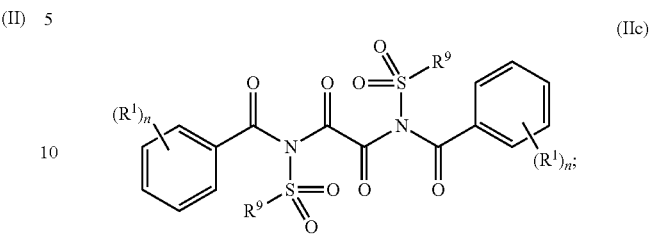

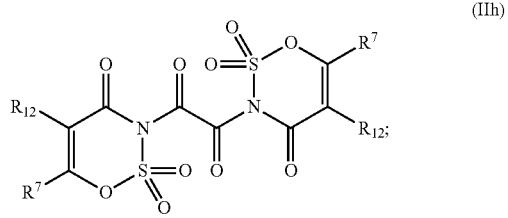

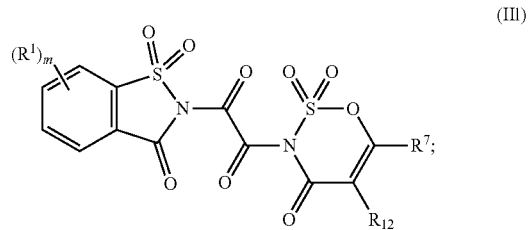

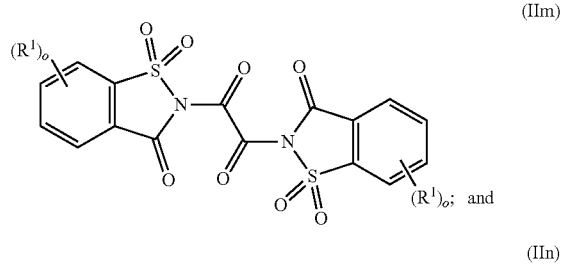

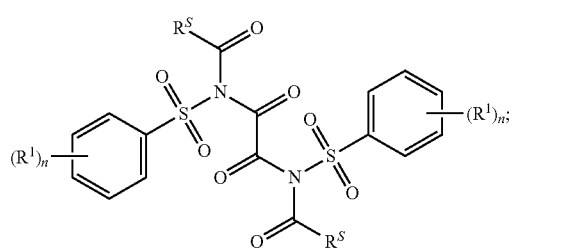

or a pharmaceutically acceptable salt thereof.

3. The compound of claim 2, which is selected from:

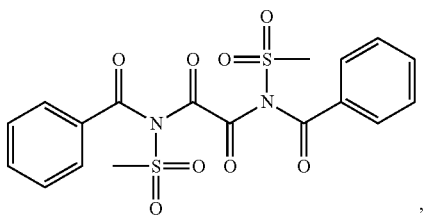

-continued

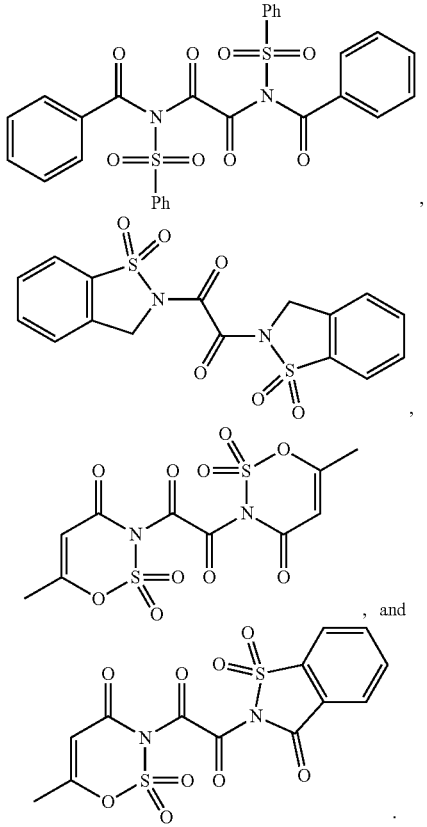

, and

4. A pharmaceutical composition comprising a compound of claim 1 in a pharmaceutically acceptable carrier.

5. The pharmaceutical composition of claim 4, wherein the composition is a solid dispersion.

6. The pharmaceutical composition of claim 5, wherein the composition comprises activated charcoal, polyvinylpyrrolidone, a polyvinylpyrrolidone/vinyl acetate copolymer, or a combination thereof.

7. A solid dispersion pharmaceutical composition comprising a compound of Formula (V):

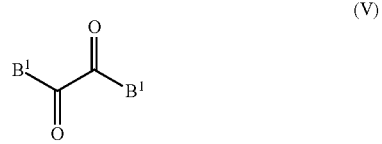

(V)

or a pharmaceutically acceptable salt thereof;

wherein $B^1$ is:

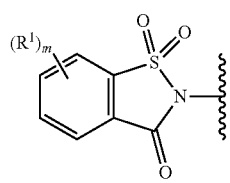

$R^1$ is independently selected at each occurrence from halogen, hydroxyl, alkyl, haloalkyl, alkoxy, haloalkoxy, aryl, heteroaryl, thiol, thioalkyl, —(C=O)$R^S$, —O(C=O)$R^S$, cyano, —SO$_3$H, —(P=O)(OH)$_2$, —O(P=O)(OH)$_2$, and nitro;

$R^S$ is selected from hydrogen, alkyl haloalkyl, alkoxy amino alkylamino, aryl, and heteroaryl; and m is independently selected from 0, 1, 2, 3, or 4.

* * * * *